US009017826B2

(12) United States Patent
Forrest et al.

(10) Patent No.: US 9,017,826 B2
(45) Date of Patent: Apr. 28, 2015

(54) VISIBLE/NEAR-INFRARED PORPHYRIN-TAPE/C60 ORGANIC PHOTODETECTORS

(75) Inventors: Stephen R. Forrest, Ann Arbor, MI (US); Jeramy D. Zimmerman, Ann Arbor, MI (US); Mark E. Thompson, Anaheim Hills, CA (US); Viacheslav Diev, Los Angeles, CA (US); Kenneth Hanson, Carrboro, NC (US)

(73) Assignees: The University of Southern California, Los Angeles, CA (US); The Regents of the University of Michigan, Ann Arbor, MI (US)

( * ) Notice: Subject to any disclaimer, the term of this patent is extended or adjusted under 35 U.S.C. 154(b) by 298 days.

(21) Appl. No.: 12/868,503

(22) Filed: Aug. 25, 2010

(65) Prior Publication Data

US 2011/0168984 A1  Jul. 14, 2011

Related U.S. Application Data

(60) Provisional application No. 61/275,156, filed on Aug. 26, 2009, provisional application No. 61/341,413, filed on Mar. 31, 2010.

(51) Int. Cl.
| | |
|---|---|
| H01L 51/46 | (2006.01) |
| H01L 51/54 | (2006.01) |
| C07D 487/22 | (2006.01) |
| C09B 47/04 | (2006.01) |
| H01L 51/00 | (2006.01) |
| H01L 27/30 | (2006.01) |

(52) U.S. Cl.
CPC ............ *C07D 487/22* (2013.01); *C09B 47/045* (2013.01); *H01L 27/305* (2013.01); *H01L 51/0058* (2013.01); *H01L 51/0077* (2013.01); *H01L 51/009* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 6,013,982 A | 1/2000 | Thompson et al. | |
| 6,087,196 A | 7/2000 | Sturm et al. | |
| 6,294,398 B1 | 9/2001 | Kim et al. | |
| 6,337,102 B1 | 1/2002 | Forrest et al. | |
| 6,468,819 B1 | 10/2002 | Kim et al. | |
| 7,230,269 B2 | 6/2007 | Rand et al. | |
| 7,279,704 B2 | 10/2007 | Walters et al. | |
| 7,375,370 B2 | 5/2008 | Forrest et al. | |
| 7,431,968 B1 | 10/2008 | Shtein | |
| 2003/0187252 A1* | 10/2003 | Osuka | 540/145 |
| 2005/0258417 A1* | 11/2005 | Minakata | 257/40 |
| 2007/0096085 A1* | 5/2007 | Rand et al. | 257/40 |
| 2007/0272918 A1* | 11/2007 | Rand et al. | 257/40 |

OTHER PUBLICATIONS

Wasielewski, M. R., Chem. Rev. 1992, 435-461.
Harriman, A., Sauvage, J.-P., Chem. Soc. Rev. 1996, 24, 41-48.
Murakami, Y., Kikuchi, J.-i., Hisaeda, Y., Hayashida, O., Chem. Rev. 1996, 96, 721-758.
Past, Present and Future. The Porphyrin Handbook; Kadish, K. M., Smith, K. M. and Guilard, R., Eds.; Academic Press: San Diego, CA, 2000; vol. 6, pp. 1-346.
Electron Transfer. The Porphyrin Handbook; Kadish, K. M., Smith, K. M. and Guilard, R., Eds.; Academic Press: San Diego, CA, 2000; vol. 8, pp. 1-205.
Perez, M. D., Borek, C., Djurovich, P. I., Mayo, E. I., Lunt, R. R., Forrest, S. R., Thompson, M. E., Adv. Mater. 2009, 21, 1517-1520.
Imahori, H., Umeyama, T., Ito, S., Acc. Chem. Res. 2009.
Liu, Y., Feng, X., Shen, P., Zhou, W., Weng, C., Zhao, B., Tan, S., Chem. Comm. 2009, 2499-2501.
Che, C.-M., Chui, S. S.-Y., Xu, Z.-X., Roy, V. A. L., Yan. J. J., Fu, W.-F., Lai, P. T., Williams, I. D., Che. Asia. J. 2008, 3, 1092-1103.
Biochemistry and Binding: Activation of Small Molecules. The Porphyrin Handbook; Kadish, K. M., Smith, K. M. and Guilard, R., Eds.; Academic Press: San Diego, CA, 2000; vol. 4, pp. 1-345.
Lu, Y., Yeung, N., Sieracki, N., Marshall, N. M., Nature, 2009, 855-862.
Doyle, M. P., Angew. Chem. Int. Ed. 2009, 48, 850-852.
Thu, H-Y., Tong, G. S-M., Huang, J-S., Chan, S. L-F., Deng, Q-H., Che, C-M., Angew. Chem. Int. Ed. 2008, 47, 9747-9751.
Medical Aspects of Porphyrins. The Porphyrin Handbook; Kalish, K. M., Smith, K. M. and Guilard, R., Eds.; Academic Press: San Diego, CA, 2003; vol. 14, pp. 1-347.
Huijser, A., Savenije, T. J., Meskers, S. C. J., Vermeulen, M. J., Siebbeles, L. D. A., J. Am. Chem. Soc. 2008, 130, 12496-12500.
Winters, M. U., Dahlstedt, E. D., Blades, H. E., Wilson, C. J., Frampton, M. J., Anderson, H. L., Albinsson, B, J. Am. Chem. Soc. 2007, 129, 4291-4297.
Siebbeles, L. D. A., Huijser, A., Savenije, T. J., J. Mater. Chem. 2009, 19, 6067-6072.
Huijser, A., Suijkerbuijk, B. M. J. M., Klein Gebbink, R, J. M., Savenije, T. J., Siebbeles, L. D. A., J. Am. Chem. Soc. 2008, 130, 2485-2492.
Beletskaya, I., Tyurin, V. S., Tsivadze, A. Yu., Guilard, R., Stern, C., Chem. Rev. 2009, 109, 1659-1713.
Fukuzumi, S., Kojima, T., J. Mater. Chem. 2008, 18, 1427-1439.
Tsuda, A., Osuka, A., Science, 2001, 293, 79-82.
Tsuda, A., Furuta, H., Osuka, A., J. Am. Chem. Soc. 2001, 123, 10304-10321.

(Continued)

*Primary Examiner* — Andrew K Bohaty
(74) *Attorney, Agent, or Firm* — Morgan, Lewis & Bockius, LLP

(57) ABSTRACT

Porphyrin compounds are provided. The compounds may further comprise a fused polycyclic aromatic hydrocarbon or a fused heterocyclic aromatic. Fused polycyclic aromatic hydrocarbon s and fused heterocyclic aromatics may extend and broaden absorption, and modify the solubility, crystallinity, and film-forming properties of the porphyrin compounds. Additionally, devices comprising porphyrin compounds are also provided. The porphyrin compounds may be used in a donor/acceptor configuration with compounds, such as $C_{60}$.

29 Claims, 20 Drawing Sheets

(56) References Cited

OTHER PUBLICATIONS

Cho, H. S., Jeong, D. H., Cho, S., Kim, D., Matsuzaki, Y., Tanaka, K., Tsuda, A., Osuka, A., J. Am. Chem. Soc. 2002, 124, 14642-14654.
Tsuda, A., Bull. Chem. Soc, Jpn., 2009, 82, 11-28.
Yamane, O., Sugiura, K-i., Miyasaka, H., Nakamura, K., Fujumoto, T., Nakamura, K., Kaneda, T., Sakata, Y., Yamashita, M., Chem. Lett. 2004, 33, 40-42.
Tanaka, M., Hayashi, S., Eu, S., Umeyama, T., Matano, Y., Imahori, H., Chem. Comm. 2007, 2069-2071.
Davis, N. K. S., Pawlicki, M., Anderson, H. L., Org. Lett. 2008, 10, 3945-3947.
Y. J. Xia, L. Wang, X. Y. Deng, D. Y. Li, X. H. Zhu, Y. Cao, *Applied Physics Letters* 2006, 89.
L. Wen, B. C. Duck, P. C. Dastoor, S. C. Rasmussen, *Macromolecules* 2008, 41, 4576.
E. Perzon, F. L. Zhang, M. Andersson, W. Mammo, O. Inganas, M. R. Andersson, *Advanced Materials* 2007, 19, 3308.
D. Tittelbachhelmrich, R. P. Steer, *Chemical Physics* 1995, 197, 99.
X. M. Jiang, R. D. Schaller, S. B. Lee, J. M. Pietryga, V. I. Klimov, A. A. Zakhidov, *Journal of Materials Research* 2007, 22, 2204.
M. S. Arnold, J. D. Zimmerman, C. K. Renshaw, X. Xu, R. R. Lunt, C. M. Austin, S. R. Forrest, *Nano Letters* 2009, 9, 3354.
A. Tsuda, H. Furuta, A. Osuka, Angewandte ChemieInternational Edition 2000, 39, 2549.
M. Kamo, A. Tsuda, Y. Nakamura, N. Aratani, K. Furukawa, T. Kato, A. Osuka, Organic Letters 2003, 5, 2079.
F. Y. Cheng, S. Zhang, A. Adronov, L. Echegoyen, F. Diederich, Chemistrya European Journal 2006, 12, 6062.
K. Kurotobi, K. S. Kim, S. B. Noh, D. Kim, A. Osuka, Angewandte ChemieInternational Edition 2006, 45, 3944.
L. A. Fendt, H. Fang, M. E. Plonska-Brzezinska, S. Zhang, F. Cheng, C. Braun, L. Echegoyen, F. Diederich, European Journal of Organic Chemistry 2007, 4659.
S. A. Lerke, B. A. Parkinson, D. H. Evans, P. J. Fagan, Journal of the American Chemical Society 1992, 114, 7807.
N. Li, B. E. Lassiter, R. R. Lunt, G. Wei, S. R. Forrest, Applied Physics Letters 2009, 94, 3.
B. P. Rand, D. P. Burk, S. R. Forrest, Physical Review B 2007, 75, 11.
M. D. Perez, C. Borek, S. R. Forrest, M. E. Thompson, Journal of the American Chemical Society 2009, 131, 9281.
Peumans, A. Yakimov, S. R. Forrest, Journal of Applied Physics 2003, 93, 3693.
S. M. Sze, Physics of Semiconductor Devices, Wiley, New York 1981.
A. Rogalski, Infrared Physics & Technology 2002, 43, 187.
J. G. Webster, The measurement, instrumentation, and sensors handbook, CRC Press published in cooperation with IEEE Press, Boca Raton, Fla. 1999.
Diev V. V. et al., "Fused Pyrene-Diporphyrins: Shifting Near-Infrared Absorption to 1.5 .mu.m and Beyond" Angewandte Chemie. International Edition, Wiley VCH Verlag, Weinheim 1NKOOOI, vol. 49, No. 32, Jul. 26, 2010, pp. 5523-5526.
Sato Hiroshi et al: "Positive Heterotropic Cooperativity for Selective Guest Binding via Electronic Communications through a Fused Zinc Porphyrin Array" Journal of the American Chemical Society, American Chemical Society LNKD, vol. 127, No. 38, Sep. 28, 2005, pp. 13086-13087.
Sato Hiroshi et al: "Cyclic dimer of a fused porphyrin Zinc complex as a novel host with two .pi.-electronically coupled binding sites" Chemical Communications—CHEMCOM, No. 18, Mar. 15, 2005, pp. 2324-2326.
Matsumoto Ryuji et al., "Ultrafast all-optical light modulation in the near infrared region by phase sensitive polymer guided wave mode geometry containing porphyrin tapes" Applied Physics Letters, AIP, American Institute of Physics, Melville, NY, US, vol. 94, No. 25, Jun. 22, 2009, pp. 253301-253301.
Ikeda, Toshiaki et al., "Synthesis of Extremely .pi.-Extended Porphyrin Tapes from Hybrid meso-meso Linked Porphyrin Arrays: An Approach Towards the Conjugation Length" Chemistry—An Asian Journal, 4(8), 1248-1256 CODEN: CAAJBIj ISSN: 1861-4728, Jun. 30, 2009, the whole document.
Ikeda, Toshiaki et al: "Synthesis of doubly strapped meso-meso-linked porphyrin arrays and triply linked conjugated porphyrin tapes" European Journal of Organic Chemistry, (14), 3193-3204, May 9, 2006, the whole document.
A. Guinier, X-ray diffraction in crystals, imperfect crystals, and amorphous bodies, W. H. Freeman, San Francisco, 1963.
Search Report and Written Opinion in corresponding to the PCT/US2010/046816 application.
A. Tsuda, Discrete Conjugated Porphyrin Tapes with an Exceptionally Small Bandgap, Adv. Mater. 2002, 14, No. 1, Jan. 4, pp. 75-79.
N. Aratani, Extremely Long, Discrete meso-meso-Coupled Porphyrin Arrays, Angew. Chem. Int. Ed. 2000, 39, No. 8, 2000, pp. 1458-1462.
A. Tsuda, Doubly meso-P-Linked Diporphyrins from Oxidation of 5,10,15-Triaryl-Substituted Nill-and Pdll-Porphyrins, Angew. Chem. Int. Ed. 2000, 39, No. 3, 2000, pp. 558-561.

\* cited by examiner

VISIBLE/NEAR-INFRARED PORPHYRIN-TAPE/C60 ORGANIC PHOTODETECTORS

CROSS-REFERENCE TO RELATED APPLICATIONS

This application claims priority to U.S. 61/275,156, filed Aug. 26, 2009, and U.S. 61/341,413, filed Mar. 31, 2010, the disclosures of which are herein expressly incorporated by reference in their entirety.

GOVERNMENT SUPPORT

This invention was made with government support under W15P7T-08-C-P409 awarded by Army/Cecom. The government has certain rights in the invention.

JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic compounds and devices comprising these compounds. More specifically, the invention relates to porphyrin oligomers and photodetectors comprising porphyrin oligomer compounds in a donor/acceptor configuration.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors.

Photosensitive optoelectronic devices convert electromagnetic radiation into electricity. Solar cells, also called photovoltaic (PV) devices, are a type of photosensitive optoelectronic device that is specifically used to generate electrical power. Another type of photosensitive optoelectronic device is a photoconductor cell. In this function, signal detection circuitry monitors the resistance of the device to detect changes due to the absorption of light. Another type of photosensitive optoelectronic device is a photodetector. In operation a photodetector is used in conjunction with a current detecting circuit which measures the current generated when the photodetector is exposed to electromagnetic radiation and may have an applied bias voltage. A detecting circuit as described herein is capable of providing a bias voltage to a photodetector and measuring the electronic response of the photodetector to electromagnetic radiation. Photosensitive devices may be used in a range of devices, including photodetectors, imaging devices, photosensors, and the like. Photosensitive devices and their fabrication and operation are further described in U.S. Pat. Nos. 7,375,370 and 7,230,269, the disclosures of which are incorporated herein in their entirety.

In addition to organic photosensitive and emissive devices, organic materials may be used in various other electronic components. For example, organic transistors may be constructed in which some or all of the materials or structures in the transistor include organic materials.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

In the context of organic materials, the terms "donor" and "acceptor" refer to the relative positions of the HOMO and LUMO energy levels of two contacting but different organic materials. This is in contrast to the use of these terms in the inorganic context, where "donor" and "acceptor" may refer to types of dopants that may be used to create inorganic n- and p-types layers, respectively. In the organic context, if the LUMO energy level of one material in contact with another is lower, then that material is an acceptor. Otherwise it is a donor. It is energetically favorable, in the absence of an external bias, for electrons at a donor-acceptor junction to move into the acceptor material, and for holes to move into the donor material.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on organic devices, and the definitions described above, can be found in U.S. Pat. No. 7,279,704, which is incorporated herein by reference in its entirety.

SUMMARY OF THE INVENTION

Porphyrin compounds are provided, the compounds having the structure:

Formula I

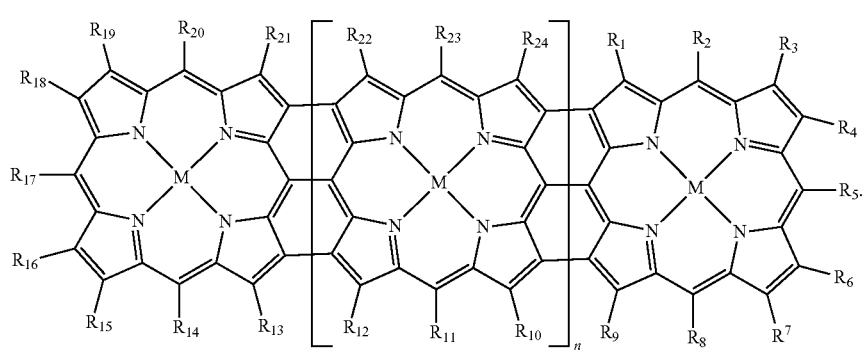

$R_1$-$R_{24}$ are independently selected from the group consisting of hydrogen, hydroxyl, halogen, chalcogen, mercapto, alkyl, fluoroalkyl, alkoxy, amino, cyano, alkenyl, alkynyl, aryl, and heteroaryl. One of $R_1$-$R_{24}$ is a fused polycyclic aromatic or a fused heterocyclic aromatic. M is a dicoordinate, tricoordinate, tetracoordinate, pentacoordinate or hexacoordinate metal ion or 2 hydrogen atoms. n is 0-100. Preferably, n is 0-5.

In one aspect, M is selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, P, As, Sb, Bi, Pr, Nd, Sm, Eu, Gd, Tb, Dy, Ho, Er, Tm, Yb, Lu, Th, U, Zn, ClAl, SnO, $SnCl_2$, Pb(OAc), and $Sn(OH)_2$. Preferably, M is Zn, Pb, Sn, ClAl, SnO, $SnCl_2$, Pb(OAc), and $Sn(OH)_2$.

In one aspect, one of $R_1$-$R_{24}$ is a fused pyrene. Preferably, one of $R_1$-$R_9$ and $R_{13}$-$R_{21}$ is a fused pyrene.

In one aspect, the compound is selected from the group consisting of:

Formula II

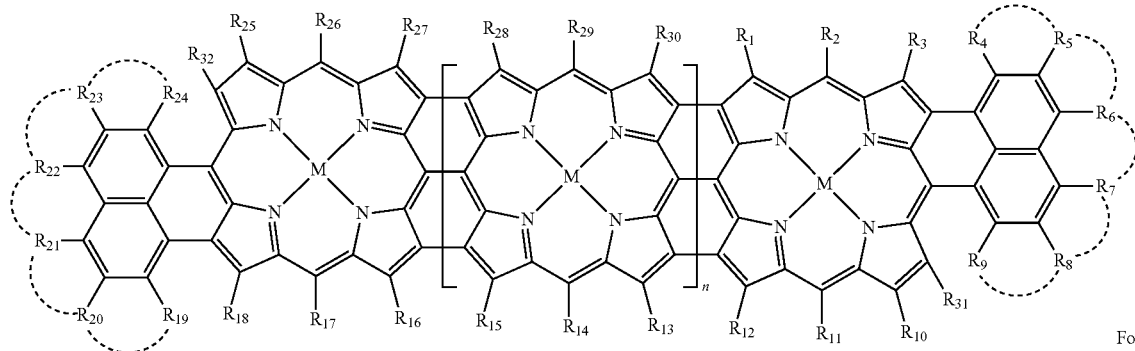

Formula III

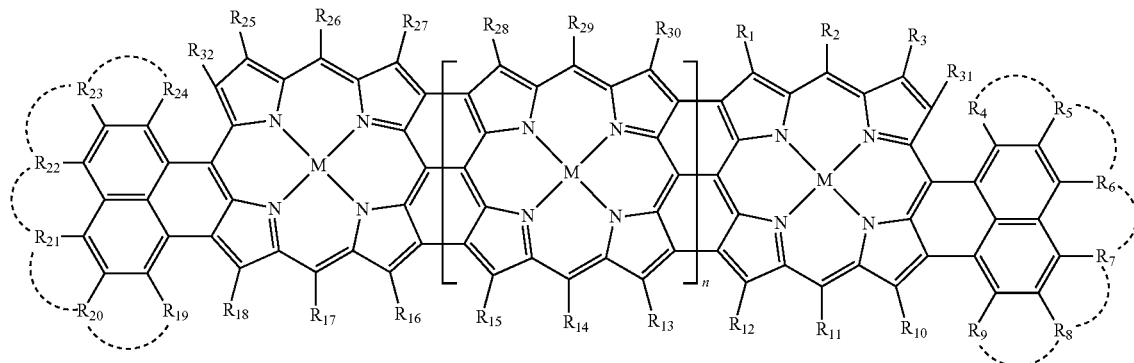

Formula IV
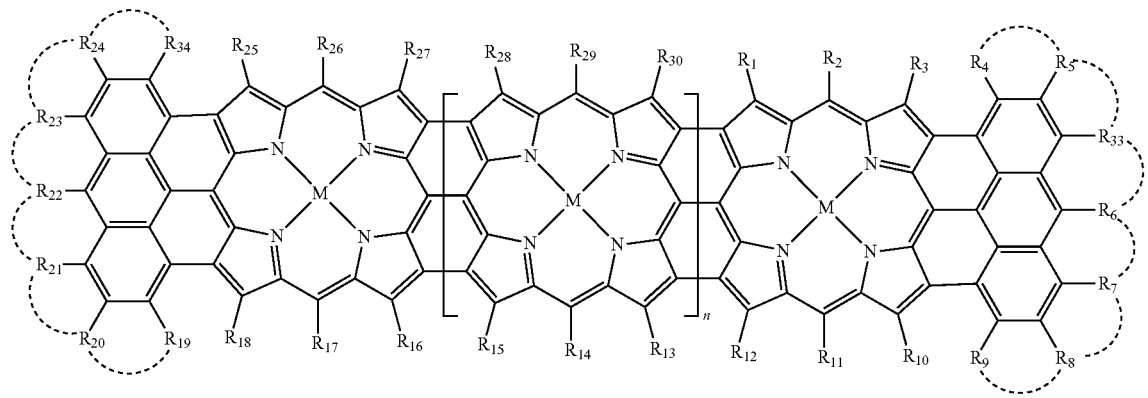
Formula V
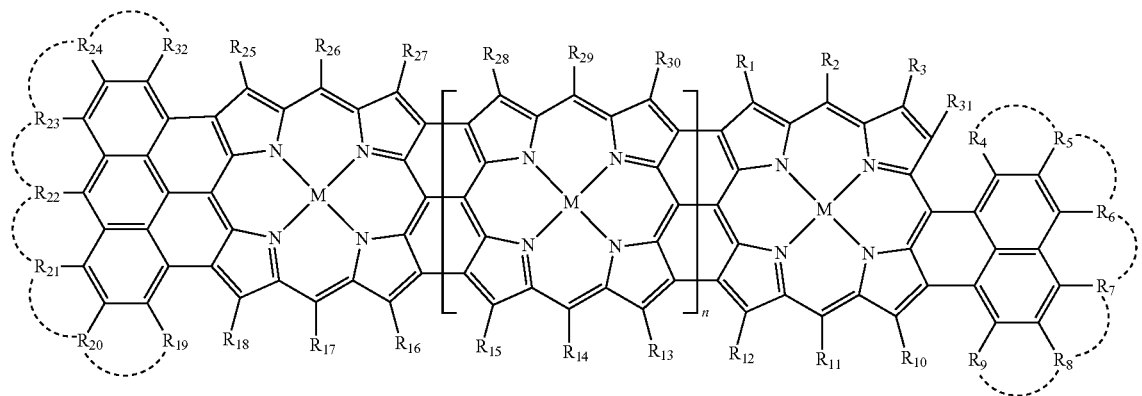
Formula VI
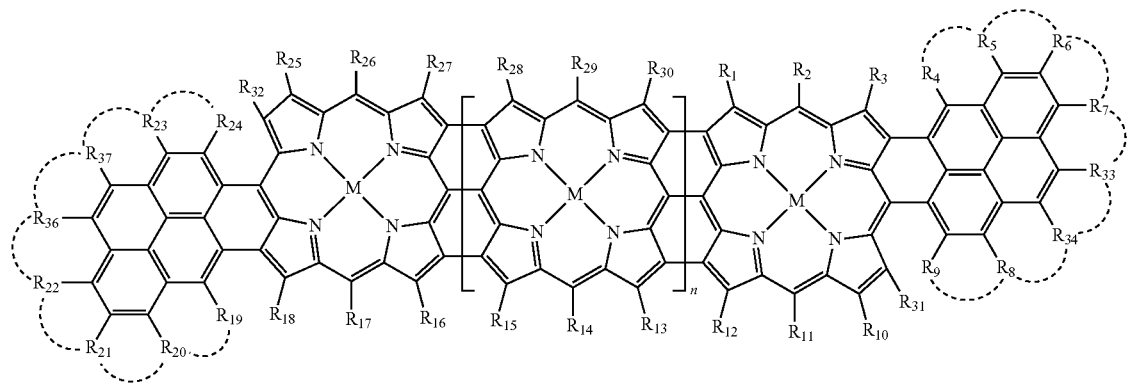
Formula VII
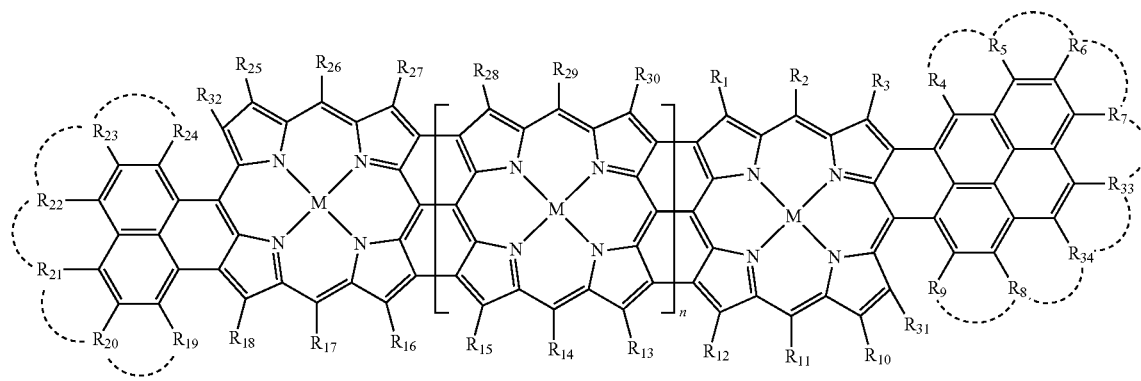

Formula VIII
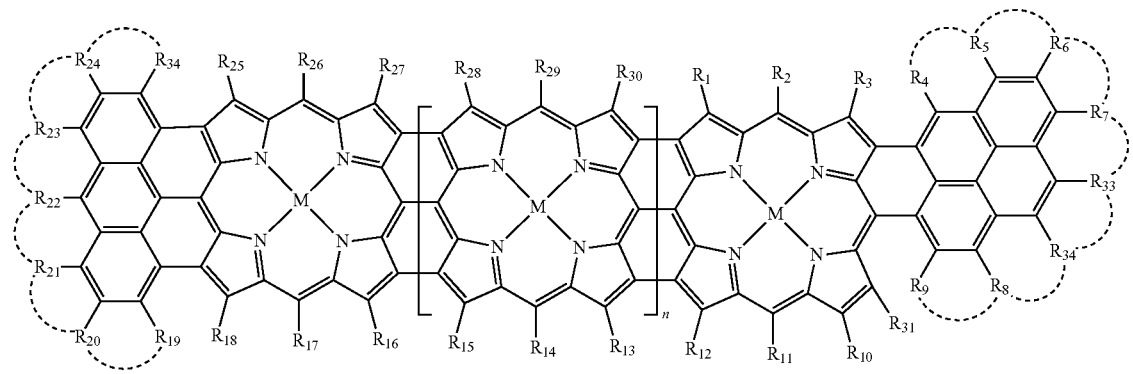
Formula IX
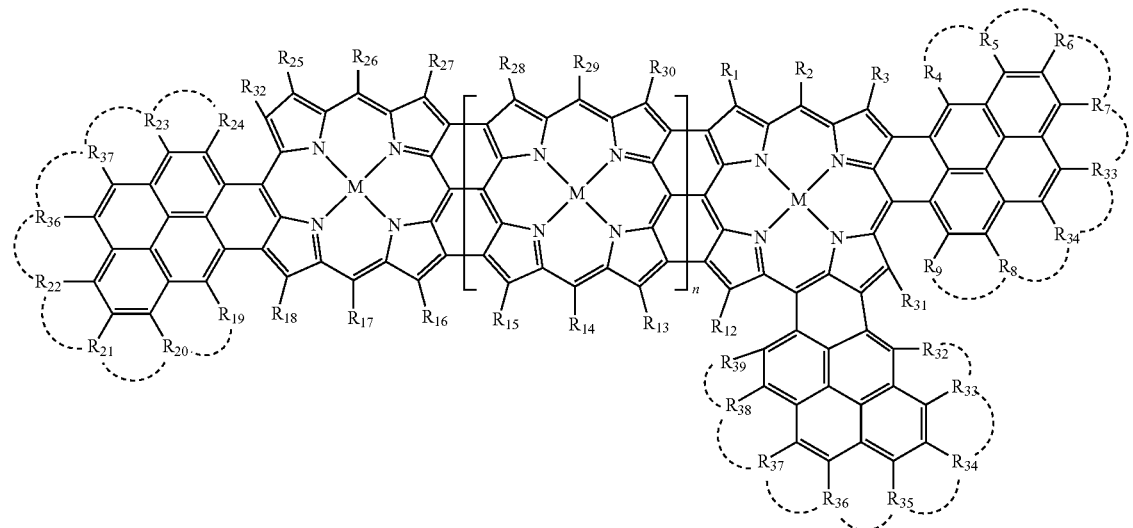
Formula X
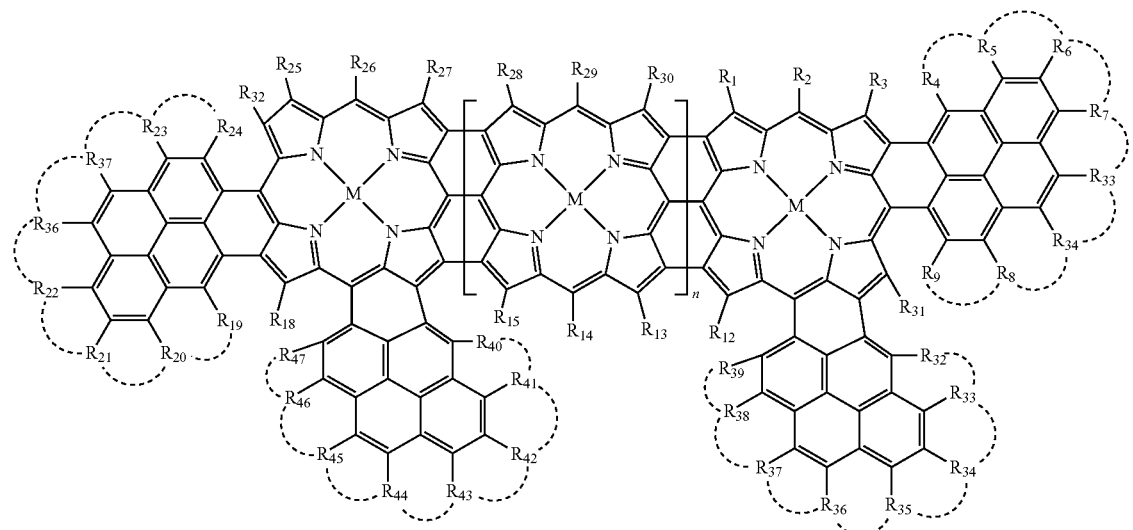

-continued
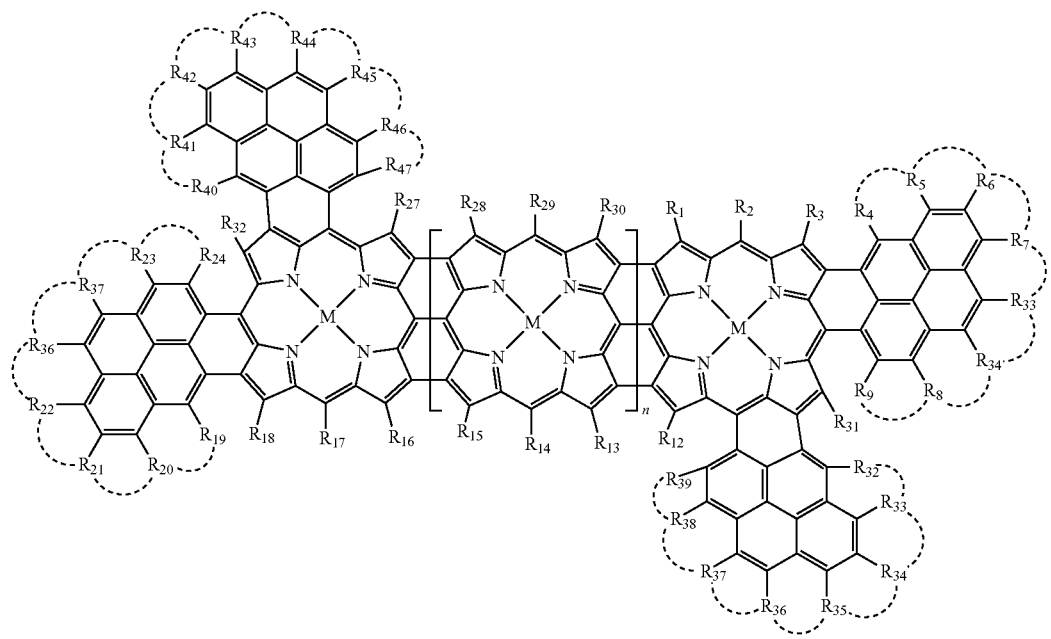
Formula XI
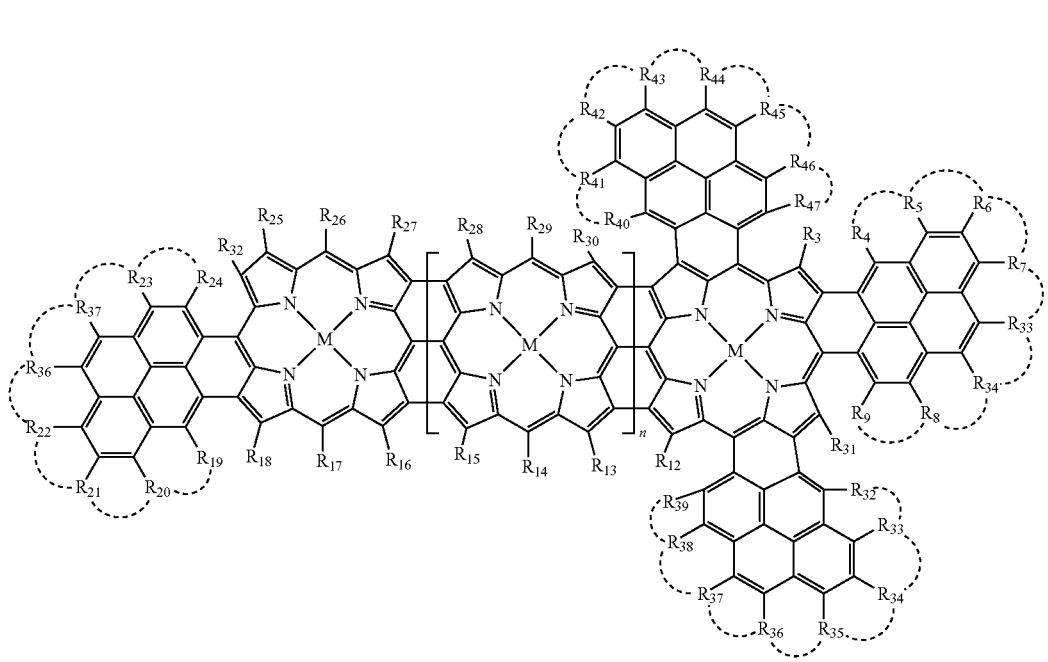
Formula XII

Formula XIII
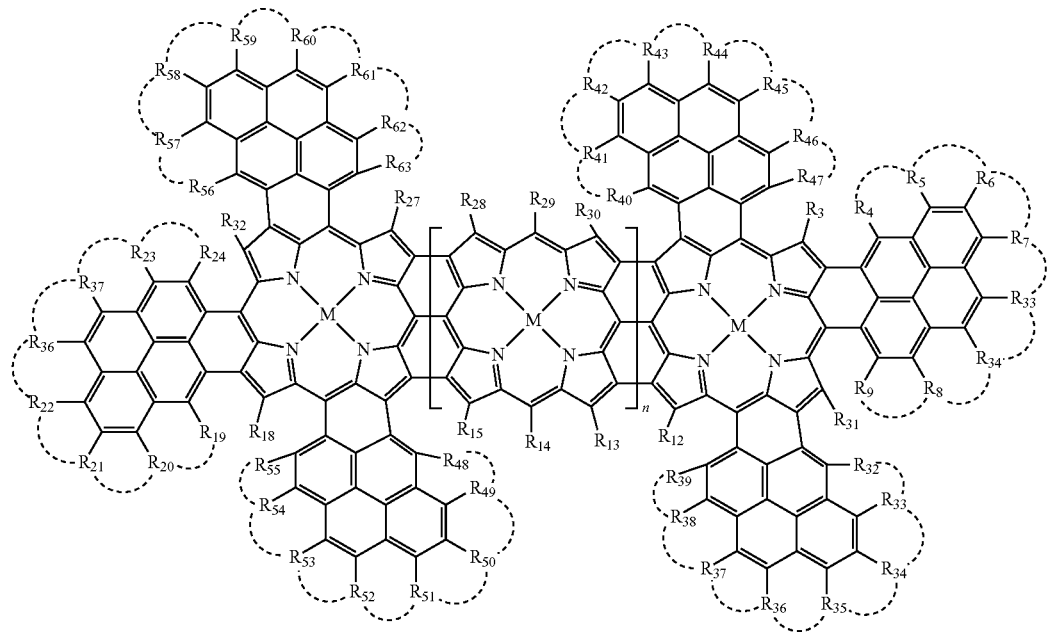
Formula XIV
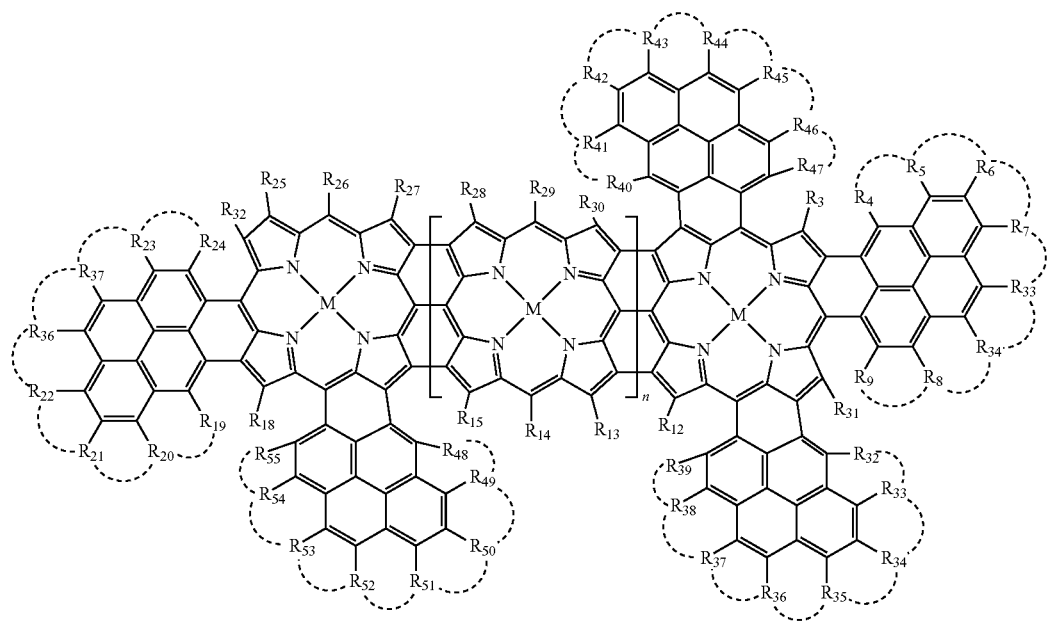
Formula XV
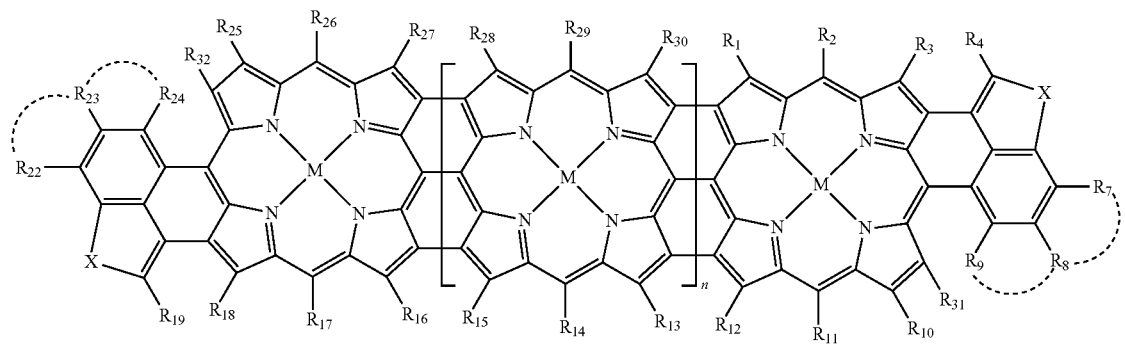

Formula XVI

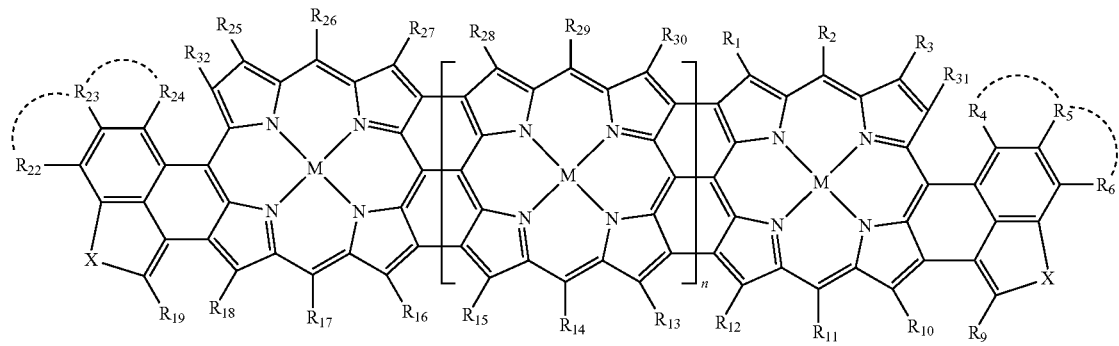

Formula XVII

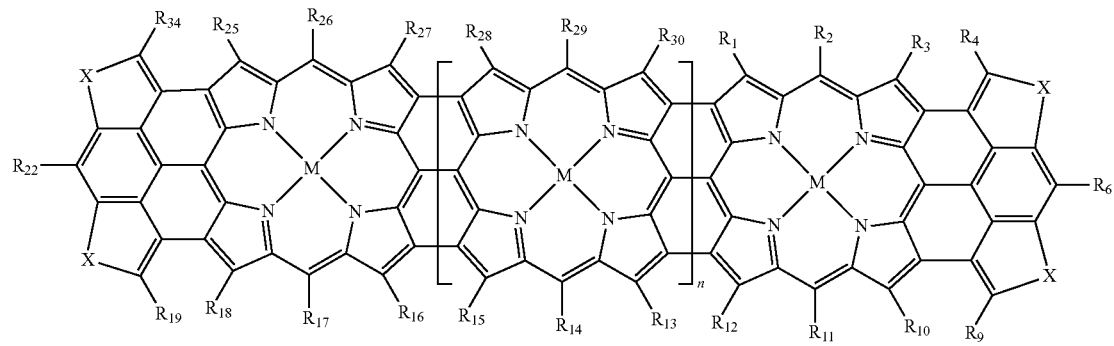

Formula XVIII

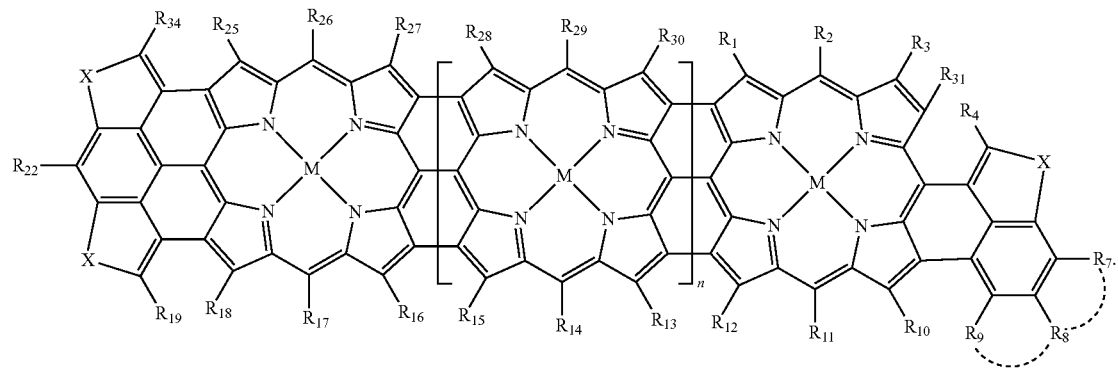

$R_1$-$R_{63}$ are independently selected from the group consisting of hydrogen, alkyl, fluoroalkyl, alkoxy, amino, cyano, alkenyl, alkynyl, aryl, and heteroaryl. Each dotted arc is a polycyclic aromatic substituent or a heterocyclic aromatic substituent. X may be dicoordinate, tricoordinate, tetracoordinate, or hexacoordinate. X is selected from the group consisting of O, S, Se, Te, N, P, As, Si, Ge, and B.

The dotted arc is a substituent that forms a closed ring, which may extend the conjugation of the pi-system. In one aspect, the substituent is selected from the group consisting of:

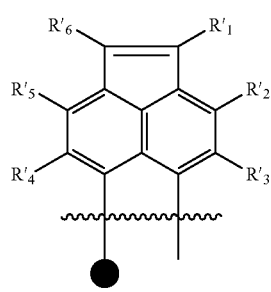

-continued
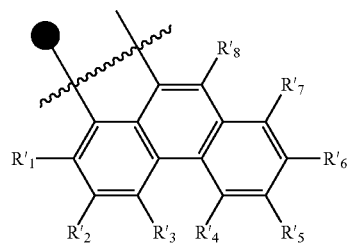
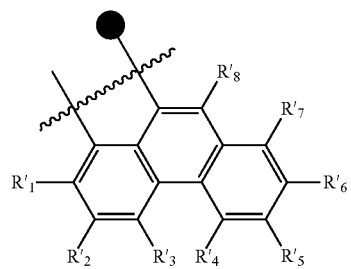
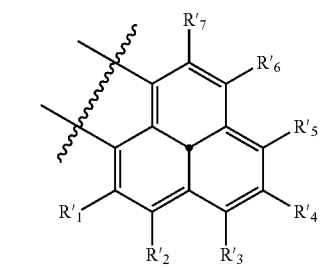
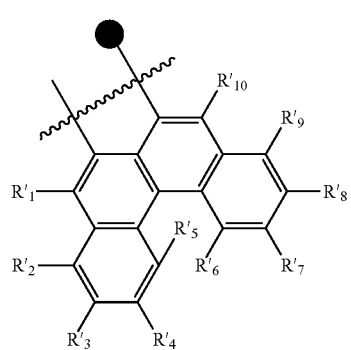
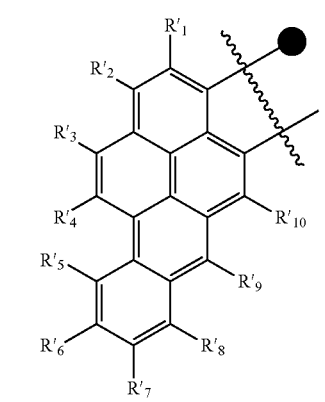
-continued
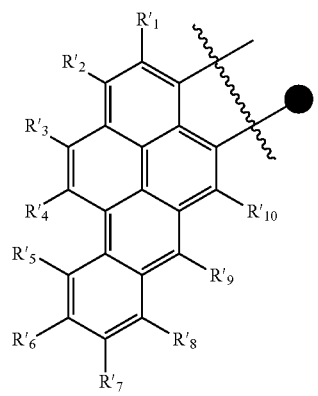
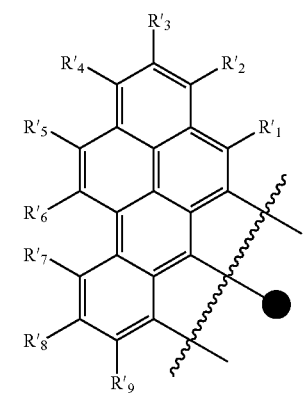
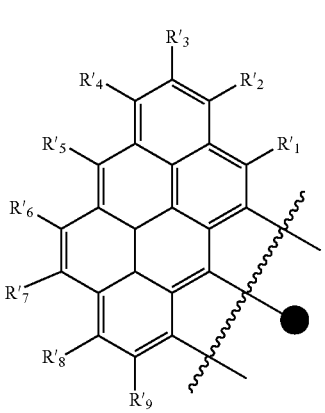
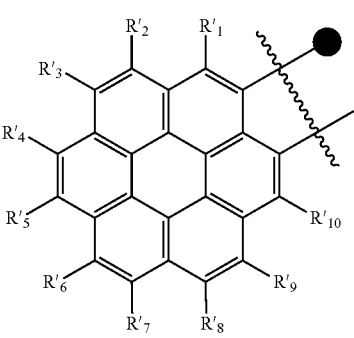

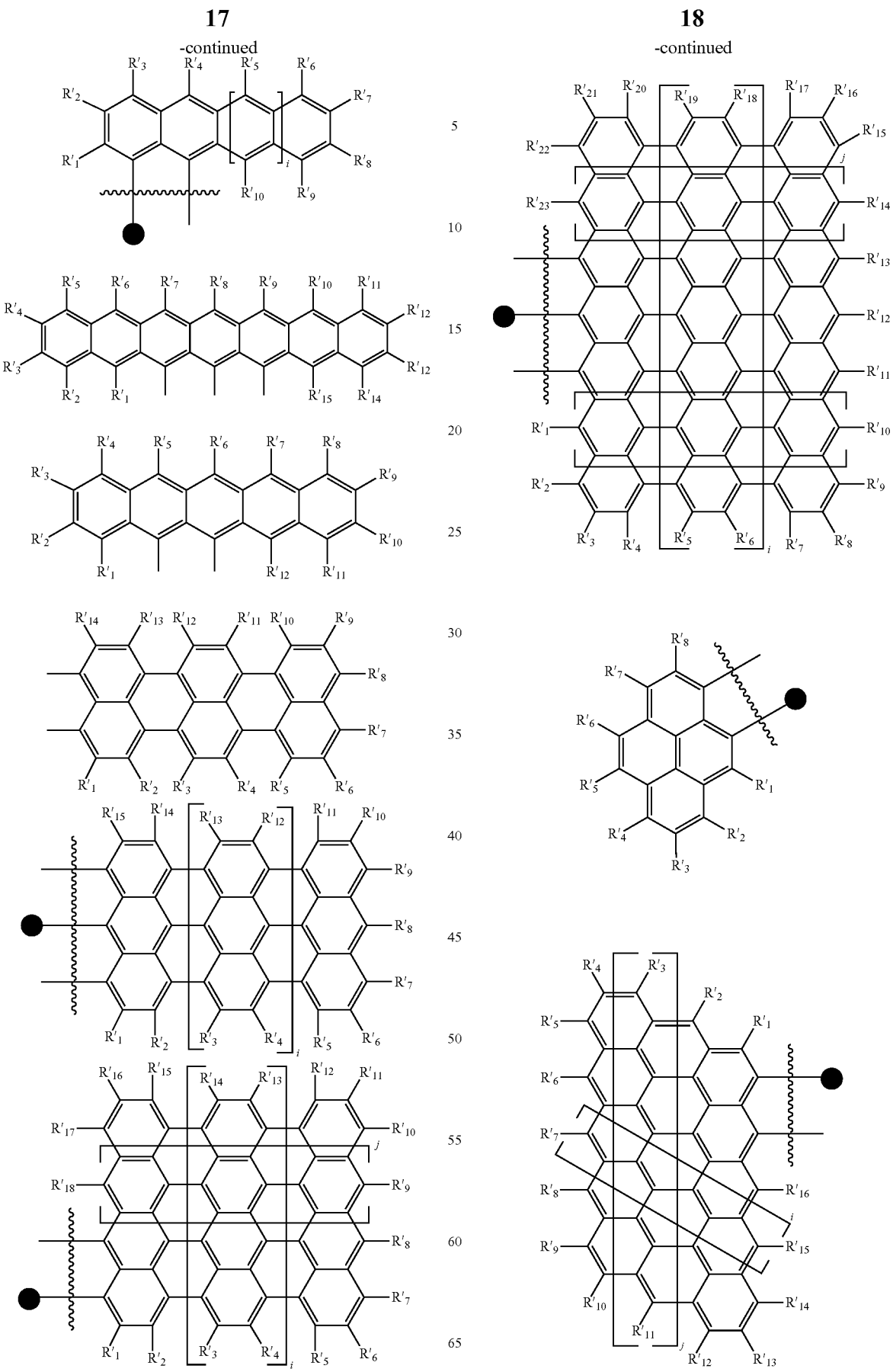

-continued

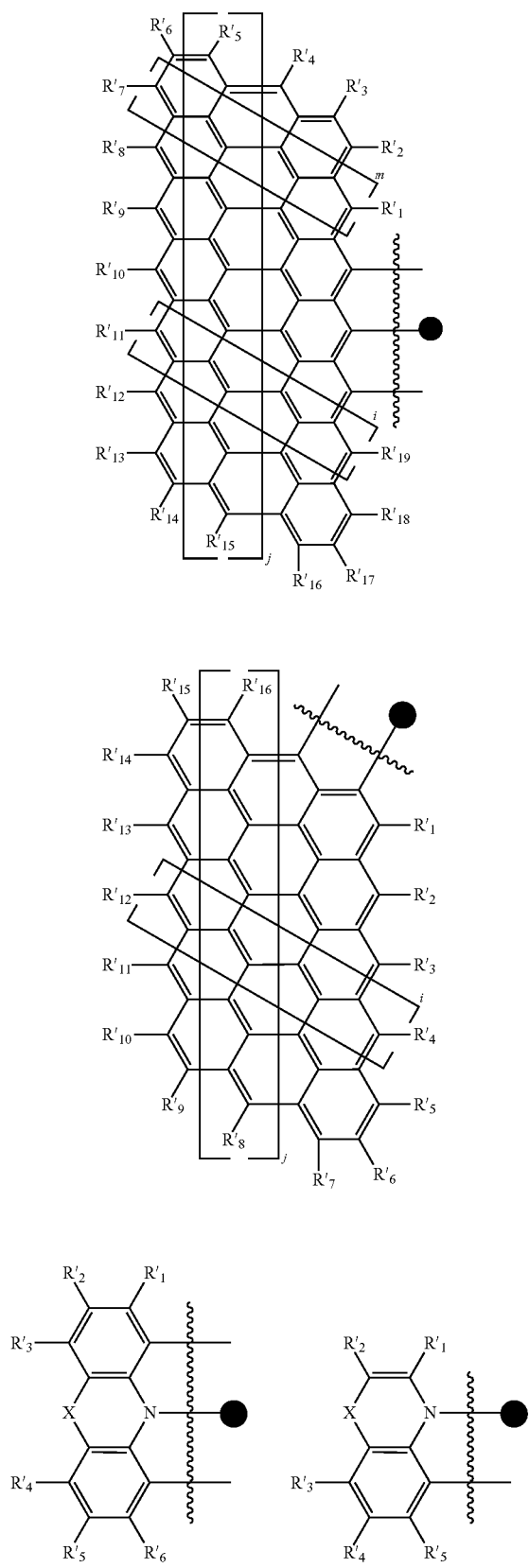

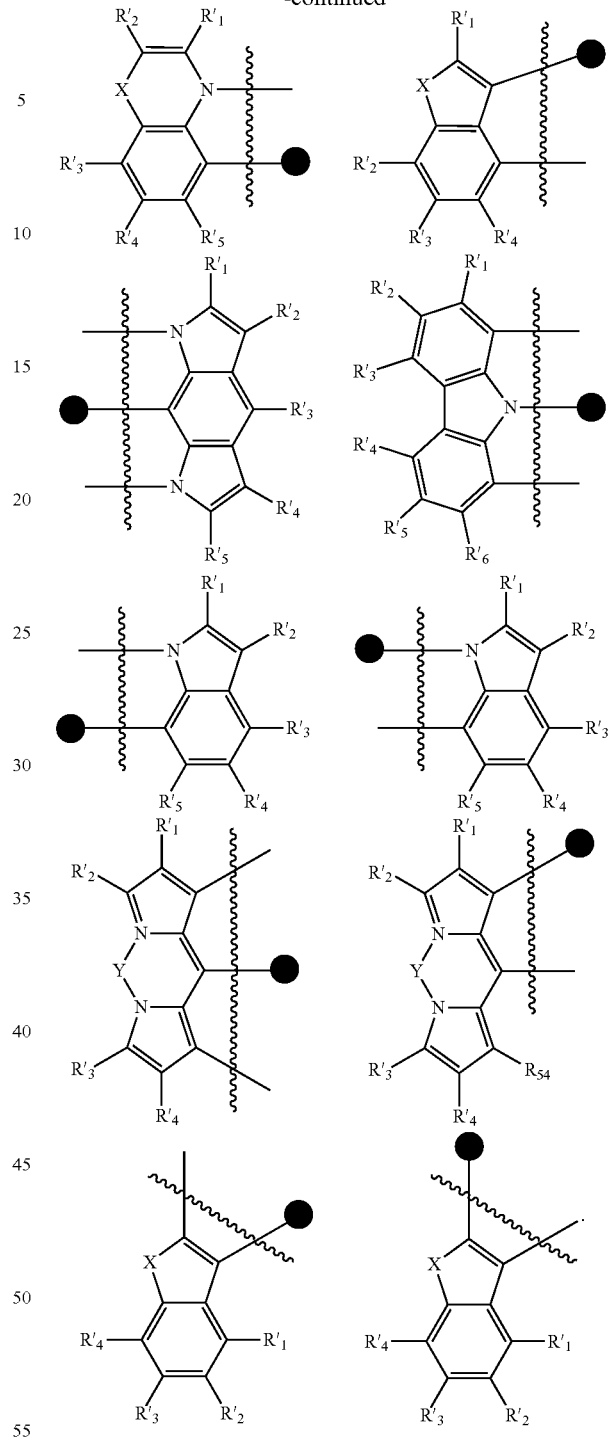

i, j, and m are each independently 0-100. The zig zag line represents the fusion points of the pi-extended unit to the porphyrin. The dot represents the point where the substituent is connected to the meso position of the porphyrin. X is O, S, Se, Te, N, P, As, Si, Ge, or B. Y is H, M, or X. $R'_1$-$R'_{23}$ are independently selected from hydrogen, hydroxyl, halogen, chalcogen, mercapto, alkyl, fluoroalkyl, alkoxy, amino, cyano, alkenyl, alkynyl, aryl, and heteroaryl.

Preferably, the dotted arc substituent is naphthalene, anthracene, or pyrene.

Specific examples of the porphyrin compounds are provided. In one aspect, the compound is selected from the group consisting of:

Compound 1
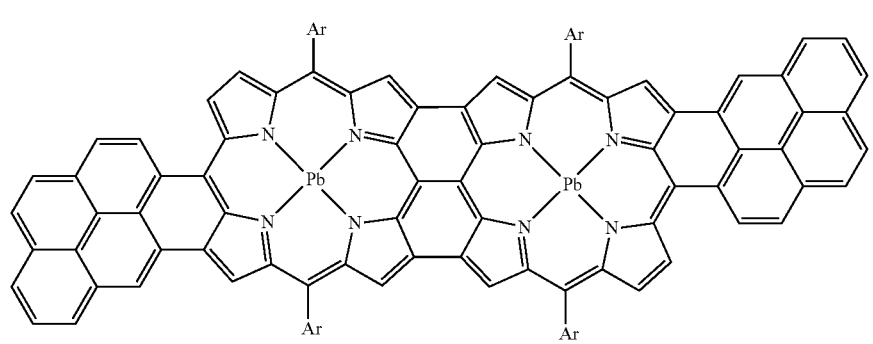
Compound 2
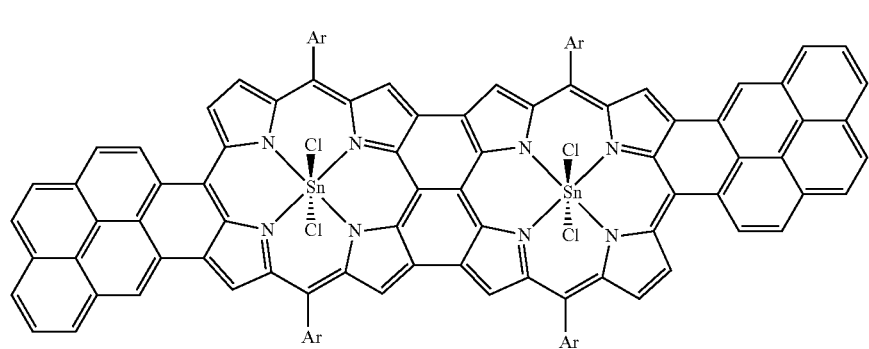
Compound 3
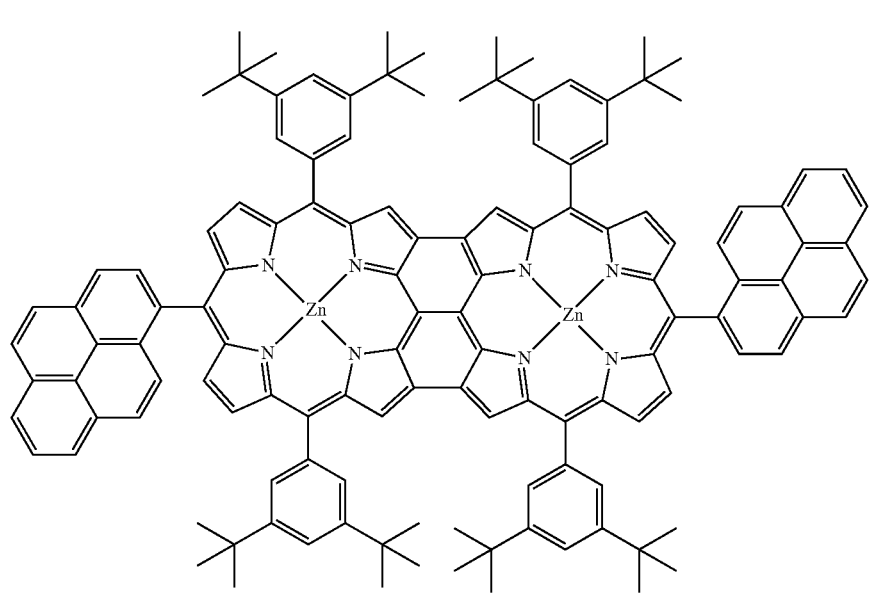

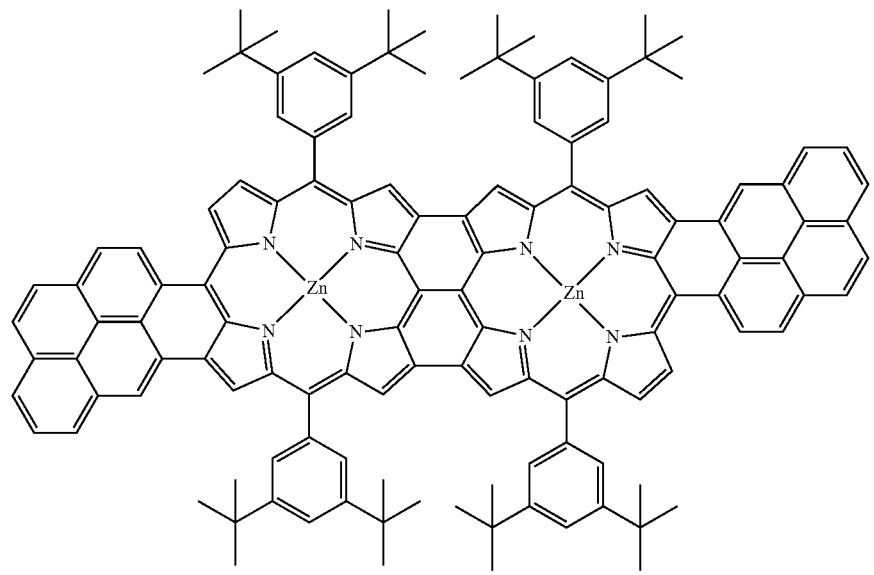
Compound 4
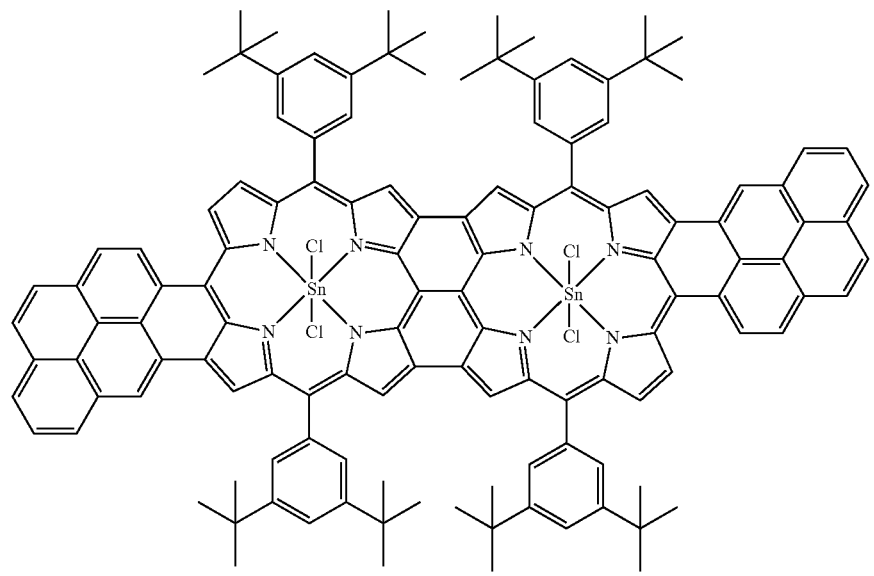
Compound 5

-continued
Compound 6
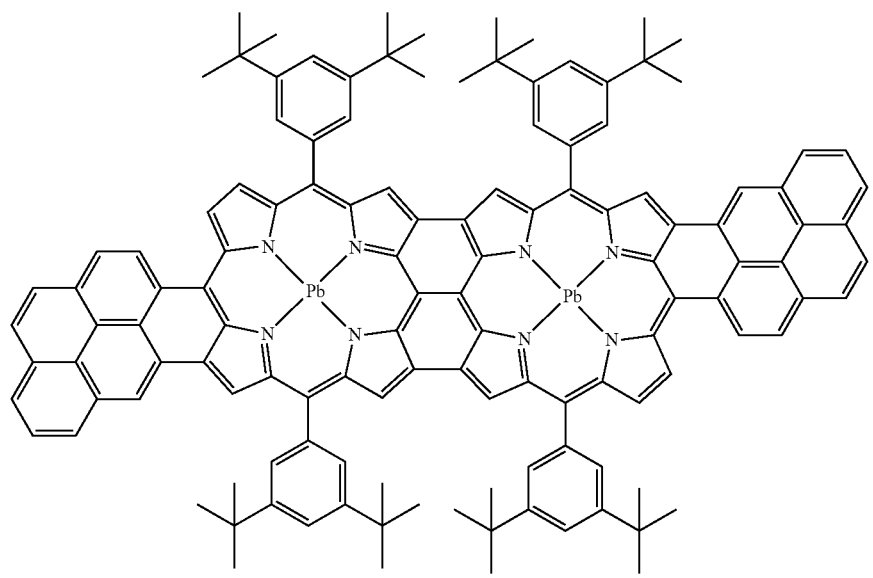
Compound 7
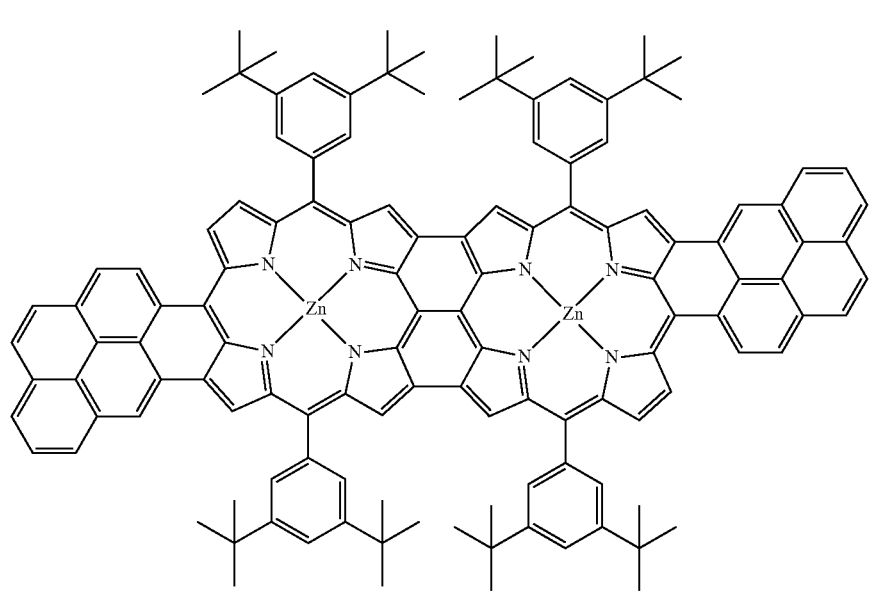
Compound 8
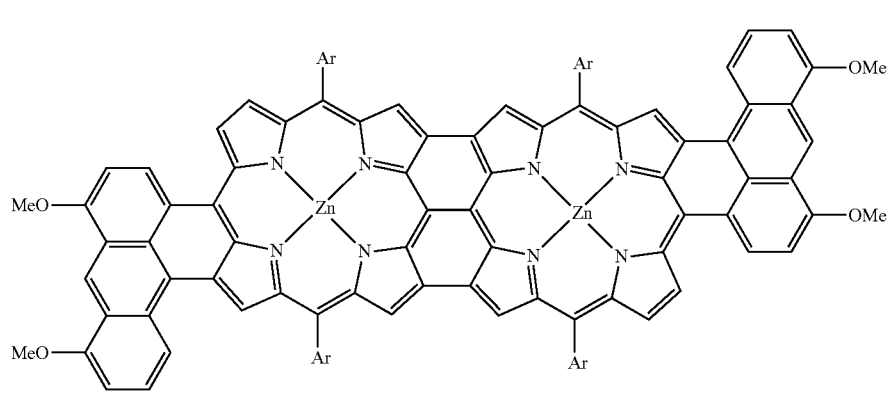

Compound 9

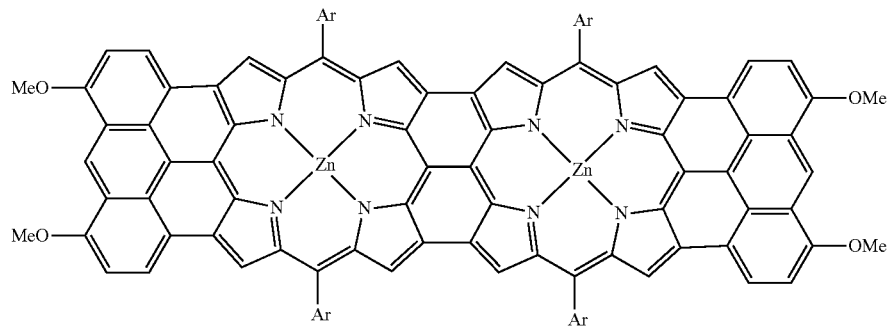

Compound 10

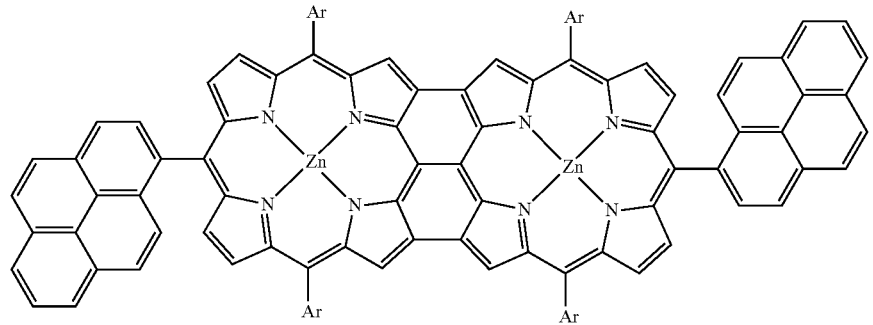

Compound 11

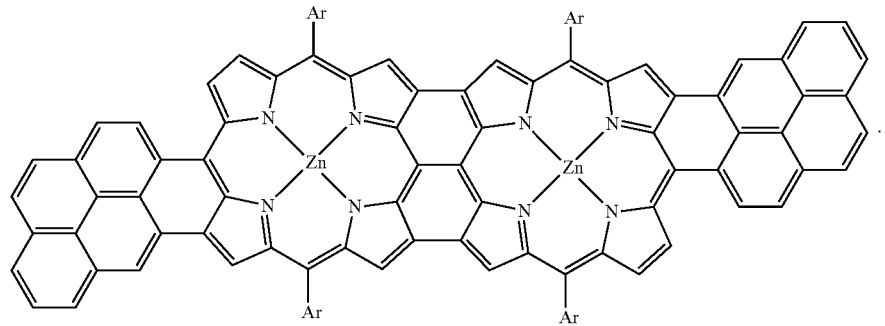

An organic device is also provided. The device comprises a first electrode, a second electrode, a first layer, disposed between the first electrode and the second electrode, and a second layer comprising a second organic compound disposed between the first electrode and the second electrode, wherein the second layer is in direct contact with the first layer.

The first layer comprises a first compound, wherein the first compound has the structure of Formula I, as described above.

$R_1$-$R_{24}$ are independently selected from the group consisting of hydrogen, hydroxyl, halogen, chalcogen, mercapto, alkyl, fluoroalkyl, alkoxy, amino, cyano, alkenyl, alkynyl, aryl, and heteroaryl. M is a dicoordinate, tricoordinate, tetracoordinate, pentacoordinate or hexacoordinate metal ion or 2 hydrogen atoms. n is 0-100. Preferably, n is 0-5.

In one aspect, at least one of $R_1$-$R_{24}$ is a fused polycyclic aromatic or a fused heterocyclic aromatic. Preferably, at least one of $R_1$-$R_{24}$ is a fused pyrene. More preferably, at least one of $R_1$-$R_9$ and $R_{13}$-$R_{21}$ is a fused pyrene.

In another aspect, the first layer is in contact with the first electrode and the device further comprises a layer of BCP disposed between and in contact with the second layer and the second electrode.

In one aspect, M is selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Ti, Si, Ge, Sn, Pb, P, As, Sb, Bi, Pr, Nd, Sm, Eu, Gd, Tb, Dy, Ho, Er, Tm, Yb, Lu, Th, U, Zn, ClAl, SnO, $SnCl_2$, Pb(OAc), and $Sn(OH)_2$. Preferably, M is Zn, Pb, Sn, ClAl, SnO, $SnCl_2$, Pb(OAc), and $Sn(OH)_2$.

In one aspect, the second compound is selected from the group consisting of $C_{60}$, $C_{70}$, $C_{84}$, $F_{16}$—CuPc, PTCBI, PTCDA, PCBM or PTCDI. Preferably, the second compound is $C_{60}$.

In one aspect, the device has an optical response at a wavelength greater than 1200 nm. In another aspect, the device has an optical response at a wavelength greater than 1500 nm.

In one aspect, the first layer is disposed using solution processing.

In another aspect, the first layer comprises more than one first compound.

In yet another aspect, the second compound is disposed in a layer having a thickness of about 80 nm to about 200 nm.

In one aspect, the first compound is disposed in combination with one or more of polystyrene, chlorobenzene, toluene, methylene chloride, dichloromethane, chloroform, chloronaphthalene, dichlorobenzene, and pyridine.

Specific example of devices comprising porphyrin compounds are provided. In one aspect, the first compound is selected from the group consisting of Formula II-Formula XVIII.

$R_1$-$R_{63}$ are independently selected from the group consisting of hydrogen, alkyl, fluoroalkyl, alkoxy, amino, cyano, alkenyl, alkynyl, aryl, and heteroaryl. Each dotted arc is a polycyclic aromatic substituent or a heterocyclic aromatic substituent. X may be dicoordinate, tricoordinate, tetracoordinate, or hexacoordinate. X is selected from the group consisting of O, S, Se, Te, N, P, As, Si, Ge, and B.

The dotted arc is a substituent that forms a closed ring that may extend the conjugation of the pi-system. In one aspect, the substituent is selected from the group consisting of:

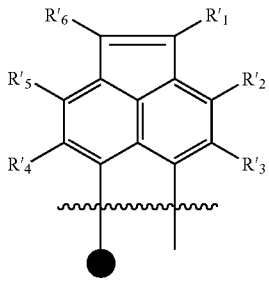
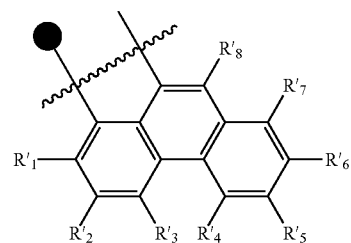
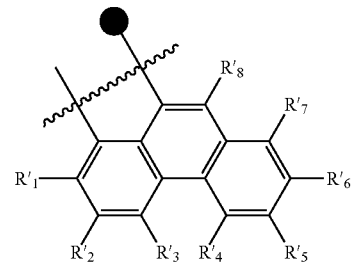
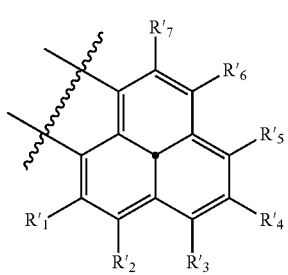
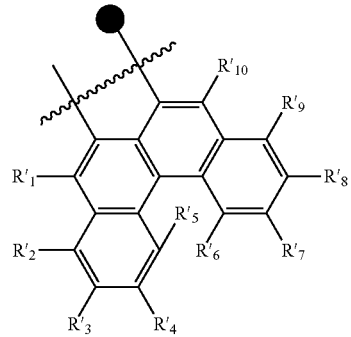
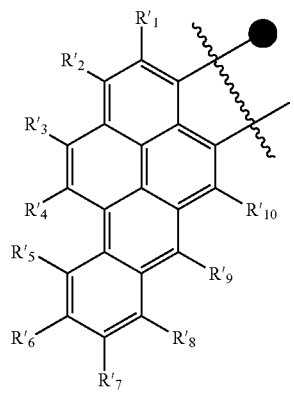
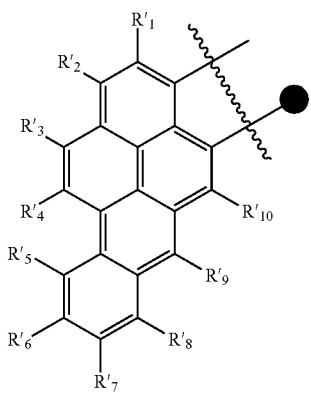
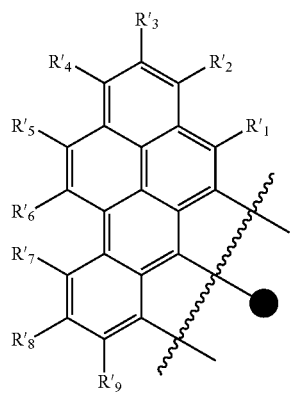
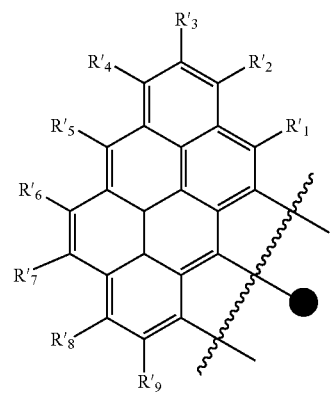
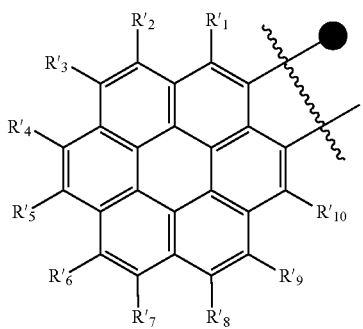
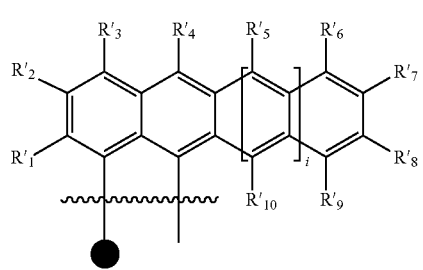

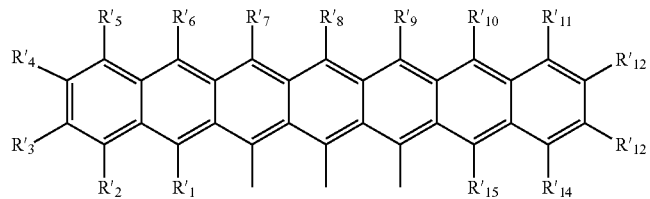
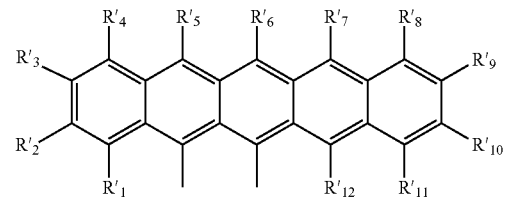
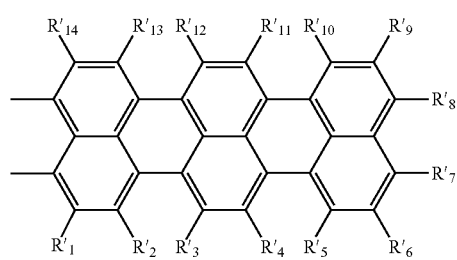
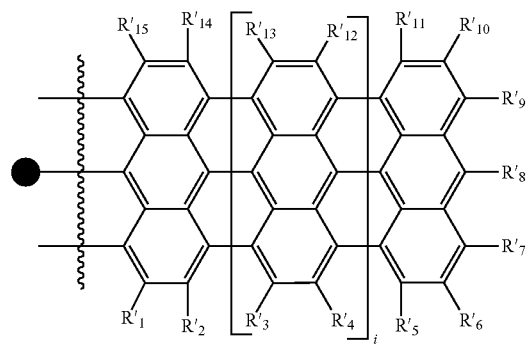
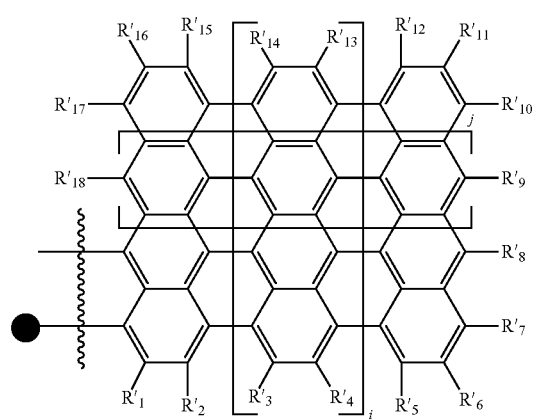
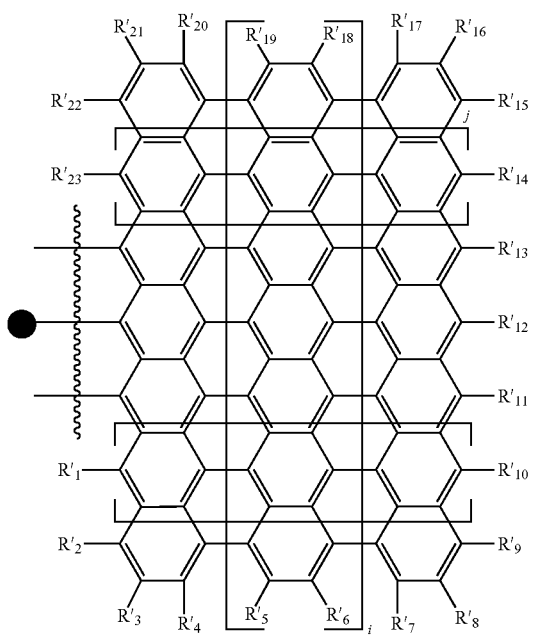

-continued
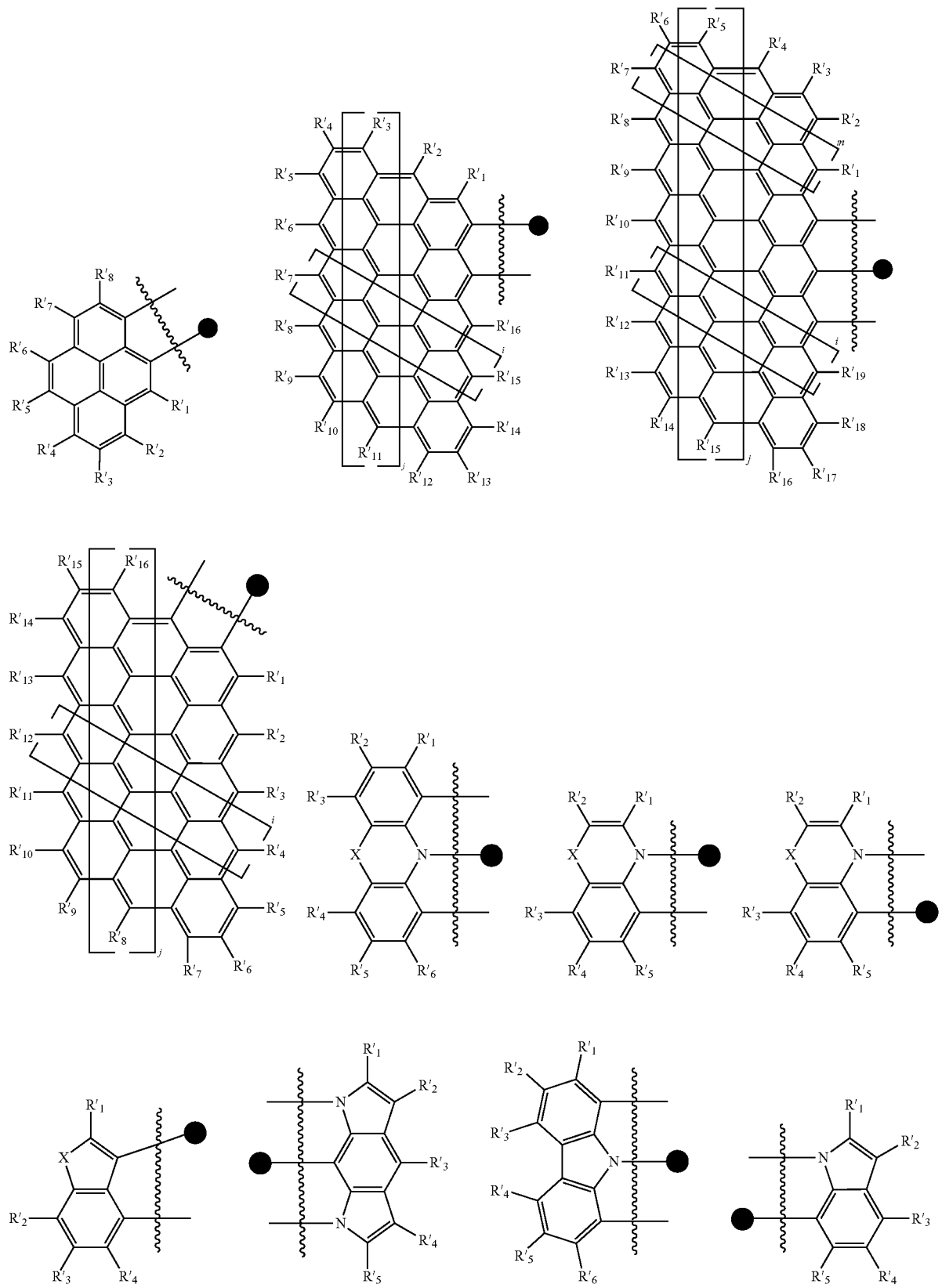

-continued

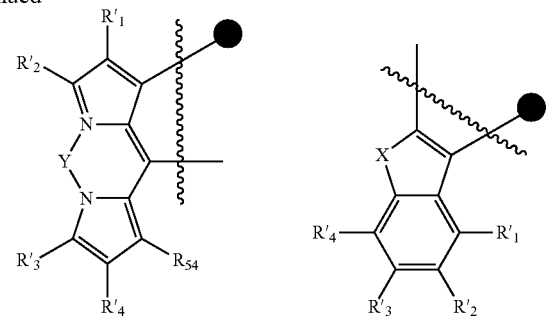
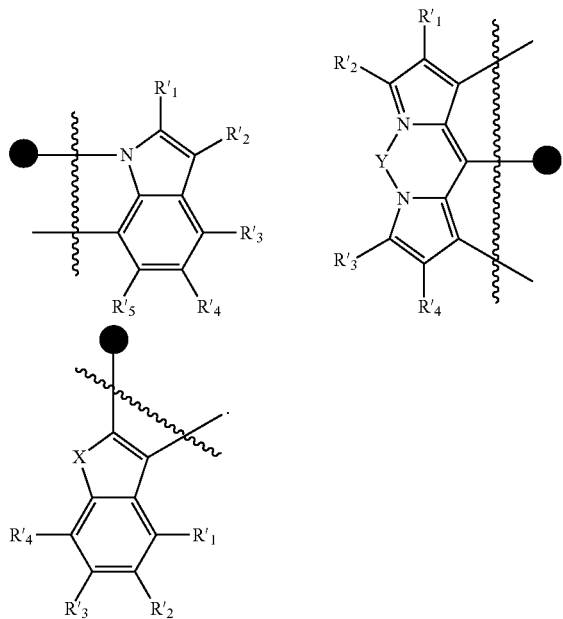

i, j, and m are each independently 0-100. The zig zag line represents the fusion points of the pi-extended unit to the porphyrin. The dot represents the point where the substituent is connected to the meso position of the porphryin. X is O, S, Se, Te, N, P, As, Si, Ge, or B. Y is H, M, or X. $R'_1$-$R'_{23}$ are independently selected from hydrogen, hydroxyl, halogen, chalcogen, mercapto, alkyl, fluoroalkyl, alkoxy, amino, cyano, alkenyl, alkynyl, aryl, and heteroaryl.

Preferably, the dotted arc is naphthalene, anthracene, or pyrene.

In another aspect, the first compound is selected from the group consisting of Compound 1-Compound 11.

In yet another aspect, the device is a consumer product.

plane is shown by the parallelogram, and projections of the b- and c-directions of the unit cell are labeled. c* denotes the direction perpendicular to the (001) plane and lies within the plane of the paper.

Figure 18:
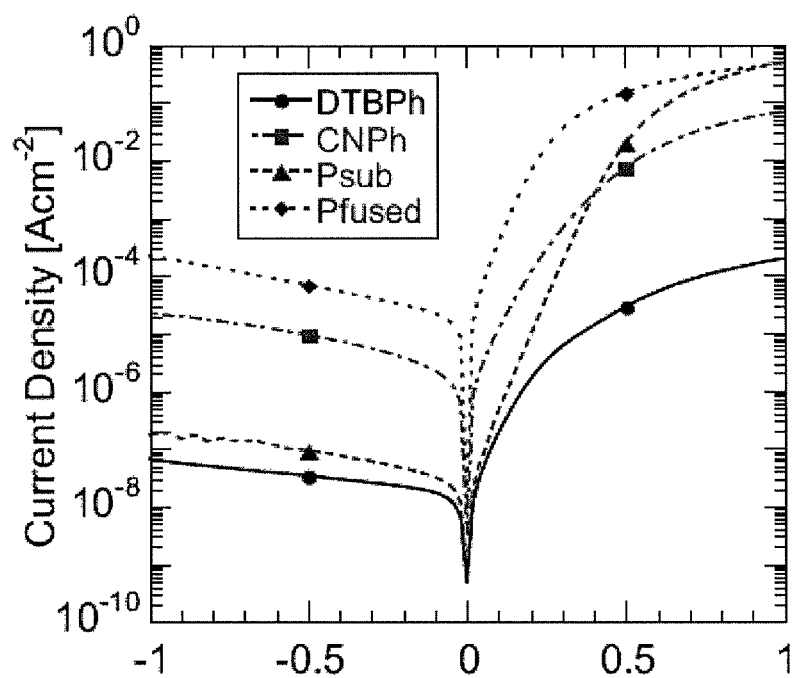

FIG. 18 shows current density vs. voltage characteristics of the porphyrin tape/$C_{60}$ photodetectors. Ideality factors and specific series resistances for detectors based on the several materials studied are DTBPh: n=1.31±0.11 and Rs=530±160 Ω-cm, CNPh: n=1.81±0.04 and Rs=5.8±2.1 Ω-cm, Psub: n=1.35±0.02 and Rs=0.90±0.1 Ω-cm, and Pfused: n=1.33±0.03 and Rs=1.4±0.1 Ω-cm.

Figure 19:
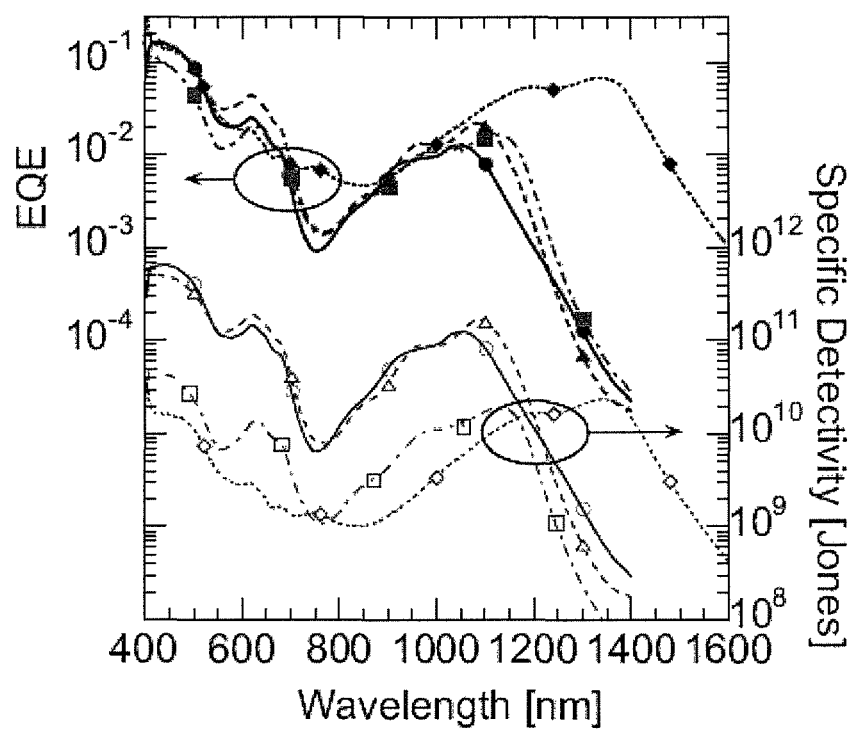

FIG. 19 shows external quantum efficiencies of devices fabricated from the several porphyrin-tape compounds are shown with the heavy lines (upper set). Specific detectivity of the same devices are shown in the lighter lines (lower set). Line types are: DTBPh, solid; CNPh, dot-dash; Psub, dashed; and Pfused, dotted.

Figure 20:
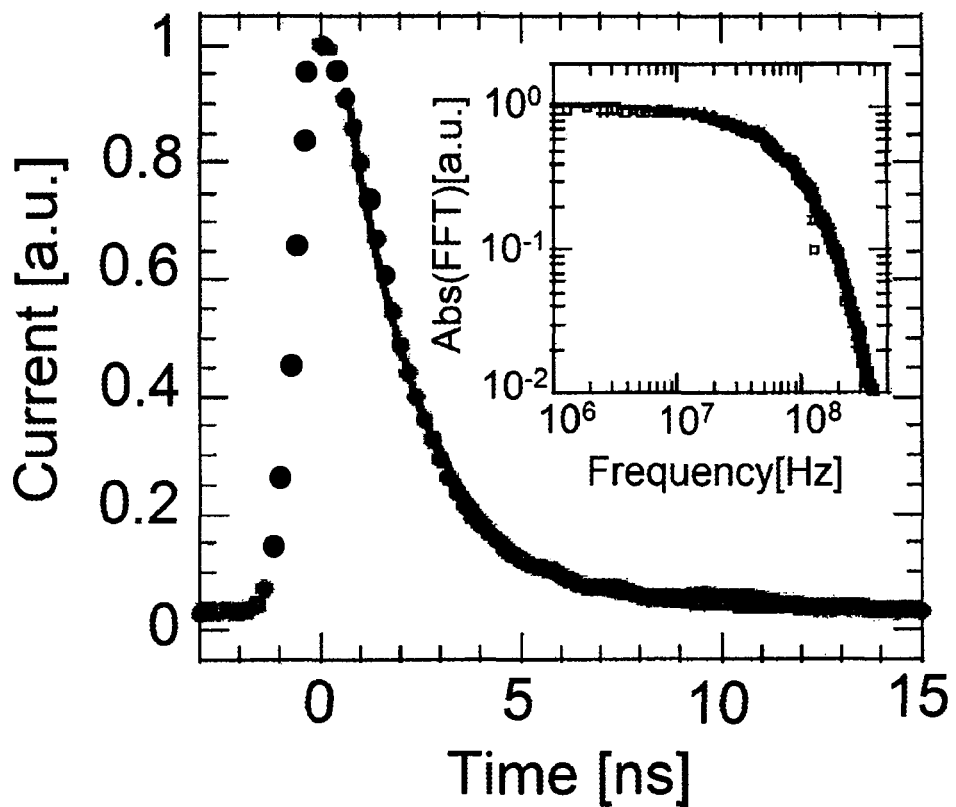

FIG. 20 shows the electrical response of a 0.3 mm diameter device biased at −1 V using a 1 ns pulse at λ=1064 nm. The fit corresponds to a decay time constant of 1.87±0.03 ns. Inset: Bode plot of the electrical response, indicating a 3 dB roll-off frequency of 56±7 MHz.

Figure 21:
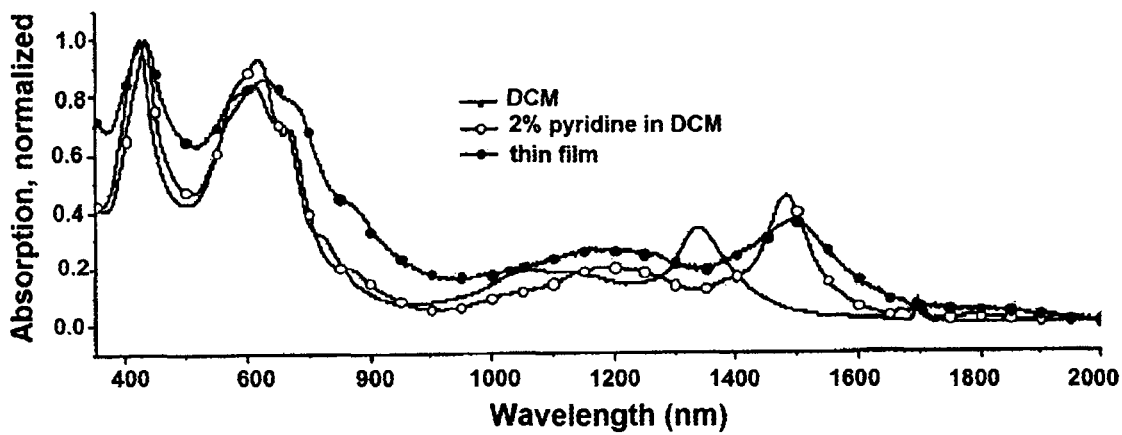

FIG. 21 illustrates absorption spectra of fused anthracene-porphyrin dimmer VI.

DETAILED DESCRIPTION

Porphyrin oligomers are provided herein, which may be used in a donor/acceptor configuration as a photodetector or photovoltaic material. Specifically, porphyrin tapes comprising fused polyaromatic hydrocarbons (PAHs) and fused heterocyclic aromatics are provided. Fused PAHs and fused heterocyclic aromatics may extend and broaden absorption, and modify the solubility, crystallinity, and film-forming properties of the porphyrin compounds.

Historically, organic photodetectors have been limited to wavelengths less than ~1000 nm. Difficulties in creating organic photodetectors can be traced to difficulties extending conjugation into larger molecules while maintaining sufficient exciton lifetime so that excitons have sufficient time to diffuse to a donor/acceptor interface where exciton dissociation can occur. Materials with infrared absorption will have a narrower HOMO/LUMO energy gap than those that absorb in the visible making pairing with an appropriate donor or acceptor more difficult.

Figure 1:
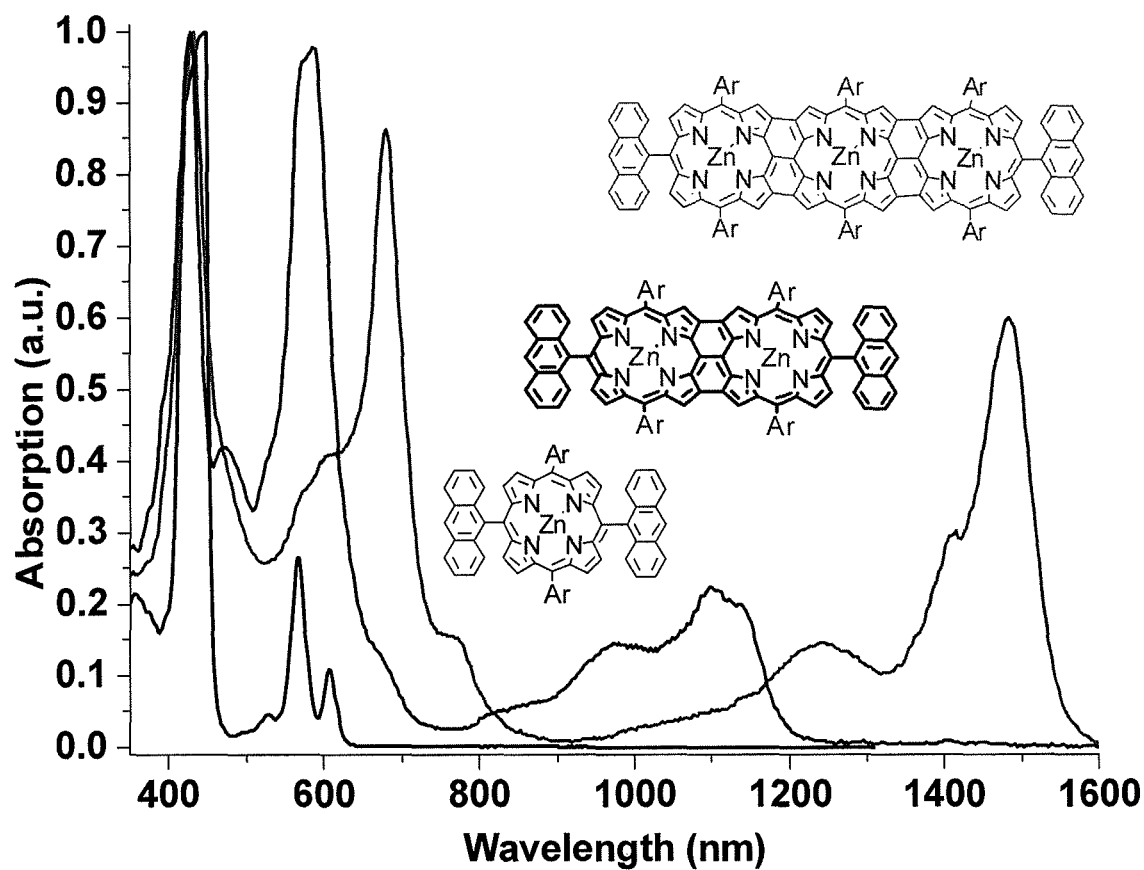
FIG. 1 shows monomer, dimer and trimer absorption features, showing how response wavelength can be increased by using longer oligomers.
Figure 2:
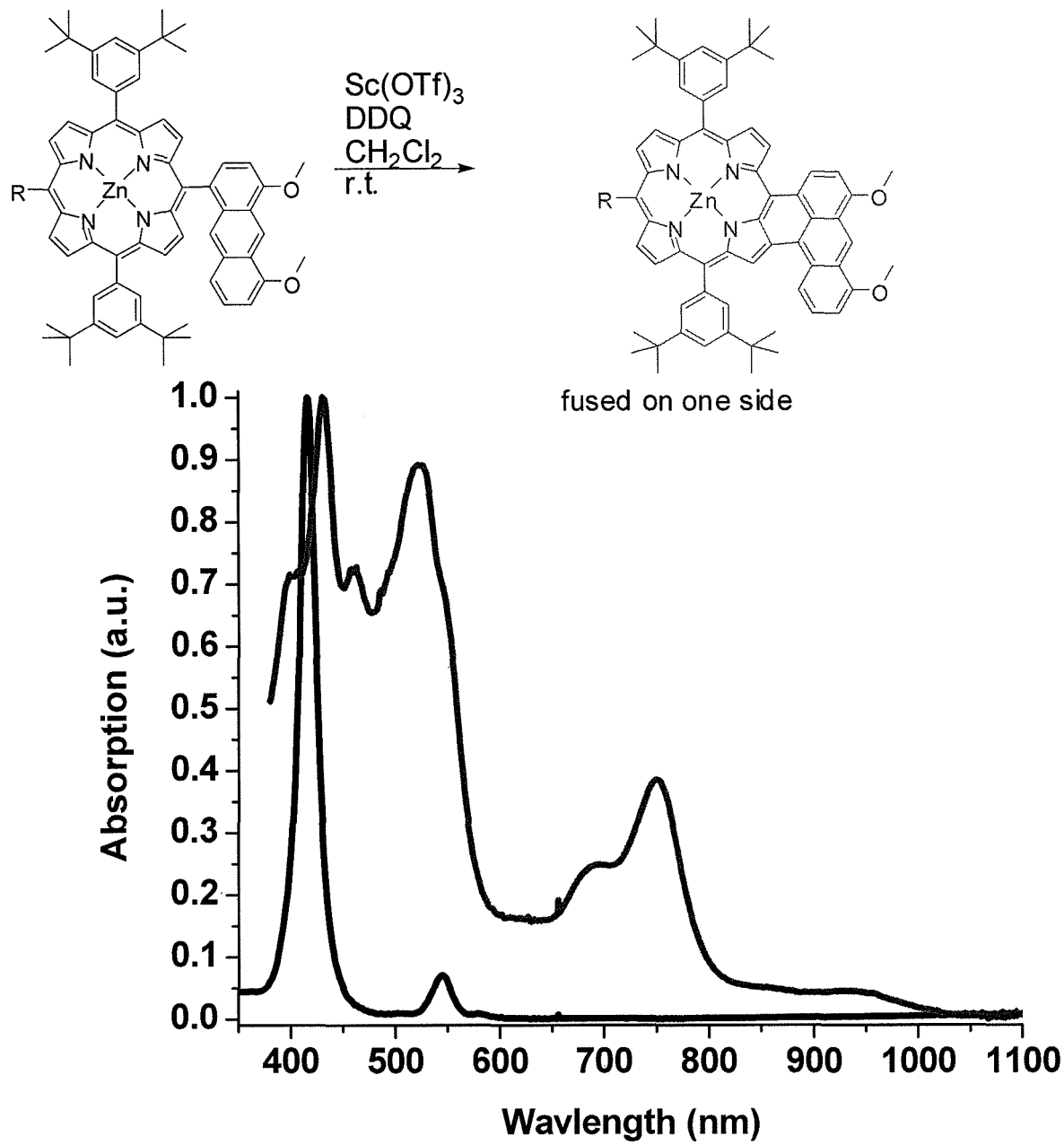
FIG. 2 shows the effect of fusing anthracene is shown. A two-sided fused molecule extends and broadens conjugation more than the one-sided fused molecule
Figure 3:
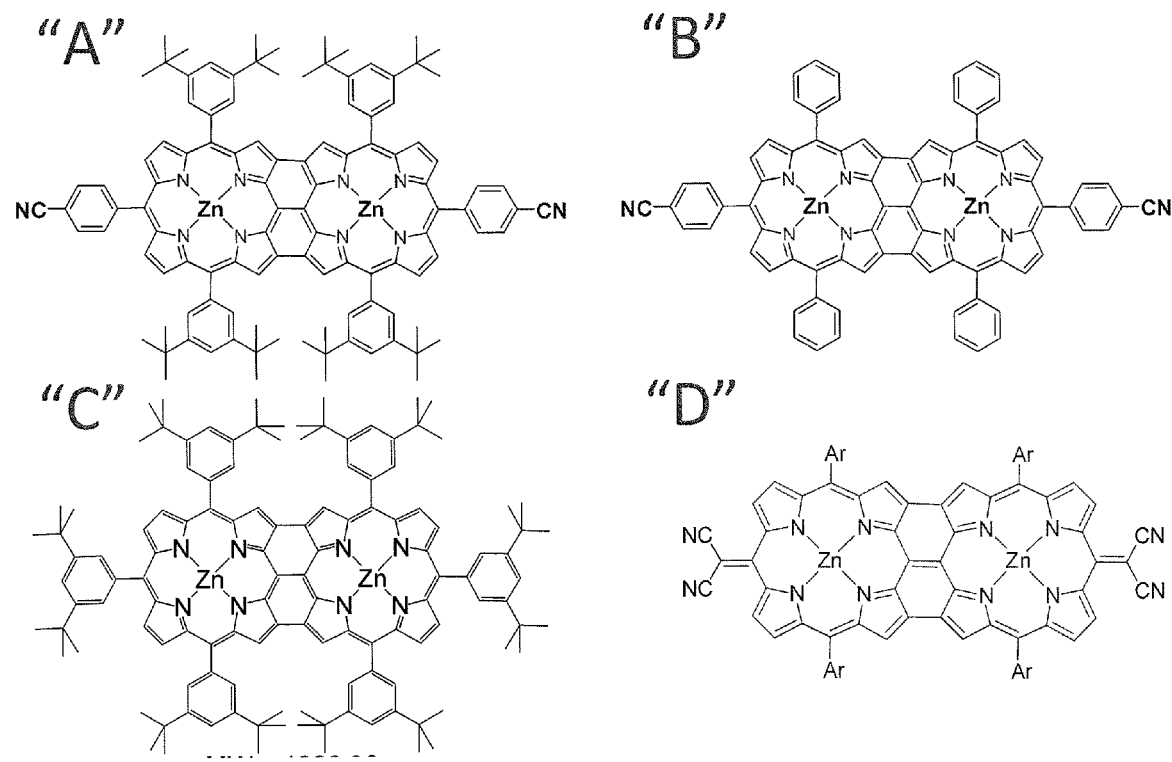
FIG. 3 shows four Zn-dimers with different end and side substituted variants. This chart is referenced in later charts.

Porphyrin molecules are well known visible absorbers. Oligomers of porphyrins can be made by fusing two porphyrins together with three carbon-carbon bonds between porphyrins (FIG. 1), extending conjugation and thus absorption out to ~1200 nm for a dimer, or 1500 nm for the trimer. A second method of extending conjugation is to fuse a polycyclic aromatic hydrocarbon (PAH), such as pyrene or anthracene to the ends of the porphyrin as seen in FIG. 2. This extends conjugation, increases the absorption wavelength, and broadens the absorption into wider bands. A third way of extending absorption is by modifying the core of the porphyrin. The core may contain two hydrogen atoms, a metal atom with valence of 2+ (i.e. Zn, Pb, Sn(II), etc), or a metal complex with an overall valence of 2+ (i.e. ClAl, Sn(IV)O, Sn(IV)Cl$_2$, etc), the metal can change the absorption energy and intensity. Also, different end structures and core metals will change the solubility in various solvents, propensity to crystallize, film-forming properties, and transport properties such as carrier mobility and exciton diffusion length.

The energetics of the porphyrin oligomers are similar to single porphyrins but with a narrower band gap and demonstrating shorter excited state lifetimes; however, we have shown traditional acceptors such as $C_{60}$, may be utilized. Different end and side groups (e.g. methoxy or cyano groups) will raise or lower the energetics, which may be used to change open circuit voltage and dark current in a detector.

Porphyrins are one of the most important biological molecules essential for life and responsible in nature for such oxidation-reduction reactions as photosynthesis in plants and respiration in animals. (Wasielewski, M. R., Chem. Rev. 1992, 435-461, and references therein; Harriman, A., Sauvage, J.-P., Chem. Soc. Rev. 1996, 24, 41-48, and references therein; Murakami, Y., Kikuchi, J.-i., Hisaeda, Y., Hayashida, O., Chem. Rev. 1996, 96, 721-758, and references therein). Synthetic porphyrins have broad applications as useful optoelectronic materials in different fields of organoelectronics (Applications: Past, Present and Future. The Porphyrin Handbook; Kadish, K. M., Smith, K. M. and Guilard, R., Eds.; Academic Press: San Diego, Calif., 2000; Vol. 6; Electron Transfer. The Porphyrin Handbook; Kadish, K. M., Smith, K. M. and Guilard, R., Eds.; Academic Press: San Diego, Calif., 2000; Vol. 8. Some most recent examples; Perez, M. D., Borek, C., Djurovich, P. I., Mayo, E. I., Lunt, R. R., Forrest, S. R., Thompson, M. E., Adv. Mater. 2009, 21, 1517-1520; Imahori, H., Umeyama, T., Ito, S., Acc. Chem. Res. 2009, ACS ASAP, 10.1021/ar900034t; Liu, Y., Feng, X., Shen, P., Zhou, W., Weng, C., Zhao, B., Tan, S., Chem. Comm. 2009, 2499-2501; and Che, C.-M., Chui, S. S.-Y., Xu, Z.-X., Roy, V. A. L., Yan. J. J., Fu, W.-F., Lai, P. T., Williams, I. D., Che. Asia. J. 2008, 3, 1092-1103), such as solar cells, photodetectors, as catalysts in a variety of reaction (Biochemistry and Binding: Activation of Small Molecules. The Porphyrin Handbook; Kadish, K. M., Smith, K. M. and Guilard, R., Eds.; Academic Press: San Diego, Calif., 2000; Vol. 4; Lu, Y., Yeung, N., Sieracki, N., Marshall, N. M., Nature, 2009, 855-862. (b) Doyle, M. P., Angew. Chem. Int. Ed. 2009, 48, 850-852; Thu, H-Y., Tong, G. S-M., Huang, J-S., Chan, S. L-F., Deng, Q-H., Che, C-M., Angew. Chem. Int. Ed. 2008, 47, 9747-9751), bioimaging agents and biologically active ingredients in medicine (Medical Aspects of Porphyrins. The Porphyrin Handbook; Kadish, K. M., Smith, K. M. and Guilard, R., Eds.; Academic Press: San Diego, Calif., 2003; Vol. 14). Advantages of usage of porphyrins as opto-electronic materials include efficiency of charge separation and charge transport even in thick films of assembled porphyrins (Huijser, A., Savenije, T. J., Meskers, S. C. J., Vermeulen, M. J., Siebbeles, L. D. A., J. Am. Chem. Soc. 2008, 130, 12496-12500; Winters, M. U., Dahlstedt, E. D., Blades, H. E., Wilson, C. J., Frampton, M. J., Anderson, H. L., Albinsson, B, J. Am. Chem. Soc. 2007, 129, 4291-4297; Siebbeles, L. D. A., Huijser, A., Savenije, T. J., J. Mater. Chem. 2009, 19, 6067-6072; Huijser, A., Suijkerbuijk, B. M. J. M., Klein Gebbink, R, J. M., Savenije, T. J., Siebbeles, L. D. A., J. Am. Chem. Soc. 2008, 130, 2485-2492), strong absorbance in the visible region, high chemical stability, ability to tune optoelectronic properties (Applications: Past, Present and Future. The Porphyrin Handbook; Kadish, K. M., Smith, K. M. and Guilard, R., Eds.; Academic Press: San Diego, Calif., 2000; Vol. 6; Electron Transfer. The Porphyrin Handbook; Kadish, K. M., Smith, K. M. and Guilard, R., Eds.; Academic Press: San Diego, Calif., 2000; Vol. 8; Perez, M. D., Borek, C., Djurovich, P. I., Mayo, E. I., Lunt, R. R., Forrest, S. R., Thompson, M. E., Adv. Mater. 2009, 21, 1517-1520; Imahori, H., Umeyama, T., Ito, S., Acc. Chem. Res. 2009, ACS ASAP, 10.1021/ar900034t; Liu, Y., Feng, X., Shen, P., Zhou, W., Weng, C., Zhao, B., Tan, S., Chem. Comm. 2009, 2499-2501; and Che, C.-M., Chui, S. S.-Y., Xu, Z.-X., Roy, V. A. L., Yan. J. J., Fu, W.-F., Lai, P. T., Williams, I. D., Che. Asia. J. 2008, 3, 1092-1103). Considerable attention has been paid recently to multi-porphyrin systems composed of porphyrin arrays (Beletskaya, I., Tyurin, V. S., Tsivadze, A. Yu., Guilard, R., Stern, C., Chem. Rev. 2009, 109, 1659-1713; Fukuzumi, S., Kojima, T., J. Mater. Chem. 2008, 18, 1427-1439). Oligomers of porphyrins made by fusing porphyrins together with three carbon-carbon bonds between porphyrin units (porphyrin tapes) represent highly conjugated systems with extended absorption into Near IR region (for example, 1200 nm for a dimer of zinc porphyrin, or 1500 nm for the trimer of zinc porphyrin) (Tsuda, A., Osuka, A., Science, 2001, 293, 79-82; Tsuda, A., Furuta, H., Osuka, A., J. Am. Chem. Soc. 2001, 123, 10304-10321; Cho, H. S., Jeong, D. H., Cho, S., Kim, D., Matsuzaki, Y., Tanaka, K., Tsuda, A., Osuka, A., J. Am. Chem. Soc. 2002, 124, 14642-14654; and Tsuda, A., Bull. Chem. Soc, Jpn., 2009, 82, 11-28).

A second way of extending absorption is by modifying the core of the porphyrin. The core may contain two hydrogen atoms, or a metal atom with valence of 2+ (i.e. Zn, Pb, Sn(II), etc), or a metal complex with an overall valence of 2+ (i.e. ClAl, Sn(IV)O, Sn(IV)Cl$_2$, etc), the metal changes the absorption energy and intensity. A new method of extending conjugation is to fuse a polycyclic aromatic hydrocarbon (PAH), such as pyrene or anthracene to the ends of the porphyrin as shown previously to occur with the formation of mono-fused porphyrins (Yamane, O., Sugiura, K-i., Miyasaka, H., Nakamura, K., Fujumoto, T., Nakamura, K., Kaneda, T., Sakata, Y., Yamashita, M., Chem. Lett. 2004, 33, 40-42; Tanaka, M., Hayashi, S., Eu, S., Umeyama, T., Matano, Y., Imahori, H., Chem. Comm. 2007, 2069-2071; and Davis, N. K. S., Pawlicki, M., Anderson, H. L., Org. Lett. 2008, 10, 3945-3947). This extends conjugation, increases the absorption wavelength and broadens the absorption into wider bands together with an increased intensity of the Q bands relative to that of the Soret band. However fusion of PAHs with porphyrins requires the presence of activating groups, such as methoxy or carboxy groups and does not occur with unsubstituted PAHs (Yamane, O., Sugiura, K-i., Miyasaka, H., Nakamura, K., Fujumoto, T., Nakamura, K., Kaneda, T., Sakata, Y., Yamashita, M., Chem. Lett. 2004, 33, 40-42; Tanaka, M., Hayashi, S., Eu, S., Umeyama, T., Matano, Y., Imahori, H., Chem. Comm. 2007, 2069-2071; and Davis, N. K. S., Pawlicki, M., Anderson, H. L., Org. Lett. 2008, 10, 3945-3947). Also to the best of our knowledge fusion was not shown to proceed with more than one aromatic ring to form end-capped porphyrins. On the other hand, porphyrin tapes have different oxidation-reduction properties and have narrower energy gaps (Cho, H. S., Jeong, D. H., Cho, S., Kim, D., Matsuzaki, Y., Tanaka, K., Tsuda, A., Osuka, A., J. Am. Chem. Soc. 2002, 124, 14642-14654). This could facilitate fusion reaction with PAHs as well as multiple fusion reactions could be possible within one porphyrin molecule without need to use activation groups. Herein, absorption and synthesis of a new class of hybrids of porphyrin tapes and PAHs composed by connecting both termini of tapes and PAHs with two or three carbon-carbon bonds are provided.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in many organic devices. For example, other optoelectronic devices such as OLEDs, organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Porphyrin oligomers and devices containing these compounds are provided. The porphyrin compounds are in a donor/acceptor configuration typical with more common small molecule organic photodetectors operating at visible wavelengths (i.e. copper phthalocyanine/$C_{60}$). The porphyrin oligomer may act as a donor and paired with an acceptor, such as $C_{60}$. One implementation is to deposit the detectors in a bottom illumination configuration. A glass substrate is used with a transparent conducting layer such as indium tin oxide (ITO), followed by a optional layer of PEDOT:PSS to aid in forming subsequent layers, followed by solution deposition of a soluble porphyrin or thermal evaporation of a sublimable porphyrin, thermal evaporation of an acceptor such as $C_{60}$ of thickness≈80-200 nm, and finally, evaporation of contacts such as BCP/silver or LiF/aluminum.

Porphyrin compounds are provided, the compounds having the structure:

Formula I

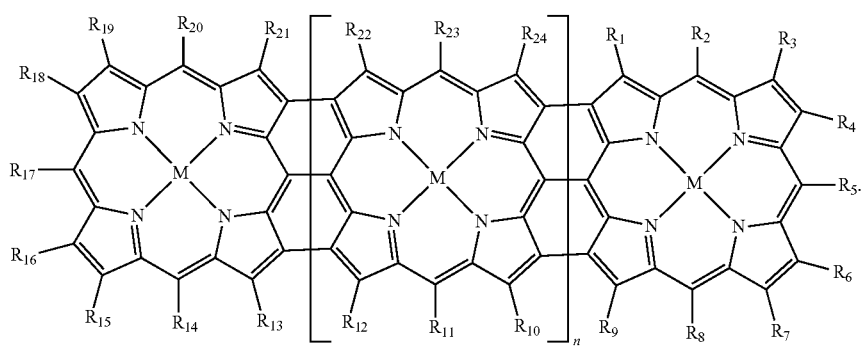

$R_1$-$R_{24}$ are independently selected from the group consisting of hydrogen, hydroxyl, halogen, chalcogen, mercapto, alkyl, fluoroalkyl, alkoxy, amino, cyano, alkenyl, alkynyl, aryl, and heteroaryl. One of $R_1$-$R_{24}$ is a fused polycyclic aromatic or a fused heterocyclic aromatic. M is a dicoordinate, tricoordinate, tetracoordinate, pentacoordinate or hexacoordinate metal ion or 2 hydrogen atoms. n is 0-100. Preferably, n is 0-5. When n is 5, the compounds exhibits a wavelength response at about 2500 nm. Without being bound by theory, it is believed that the excited state is localized on a relatively small section of the compound. Therefore, extending the porphoryin oligomer beyond five units may not change the wavelength response of the compound.

In one aspect, M is selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Ti, Si, Ge, Sn, Pb, P, As, Sb, Bi, Pr, Nd, Sm, Eu, Gd, Tb, Dy, Ho, Er, Tm, Yb, Lu, Th, U, Zn, ClAl, SnO, $SnCl_2$, Pb(OAc), and $Sn(OH)_2$. Preferably, M is Zn, Pb, Sn, ClAl, SnO, $SnCl_2$, Pb(OAc), and $Sn(OH)_2$.

In one aspect, one of $R_1$-$R_{24}$ is a fused pyrene. Preferably, one of $R_1$-$R_9$ and $R_{13}$-$R_{21}$ is a fused pyrene.

In one aspect, the compound is selected from the group consisting of:

Formula II

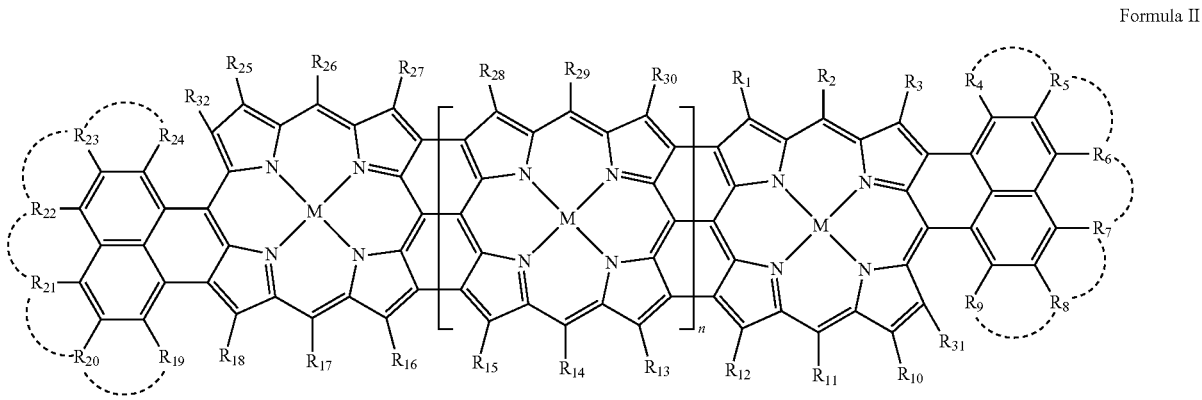

Formula III

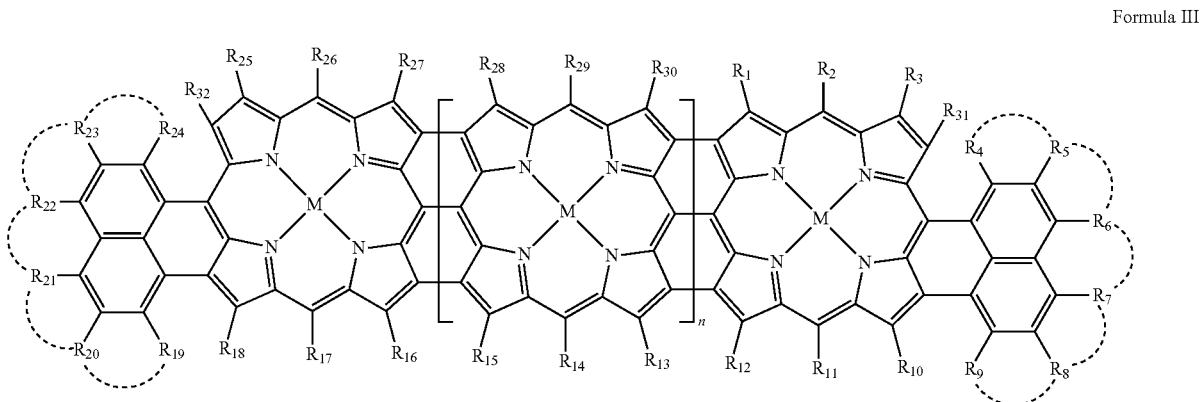

-continued
Formula IV
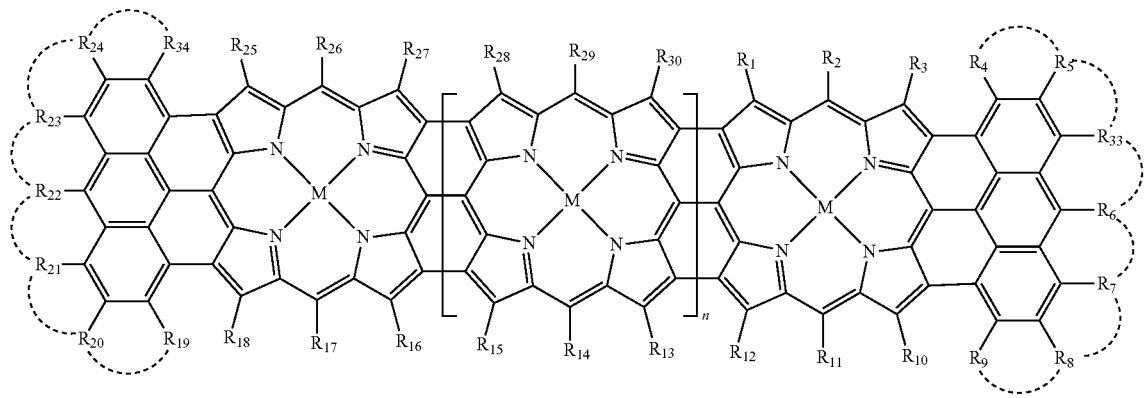
Formula V
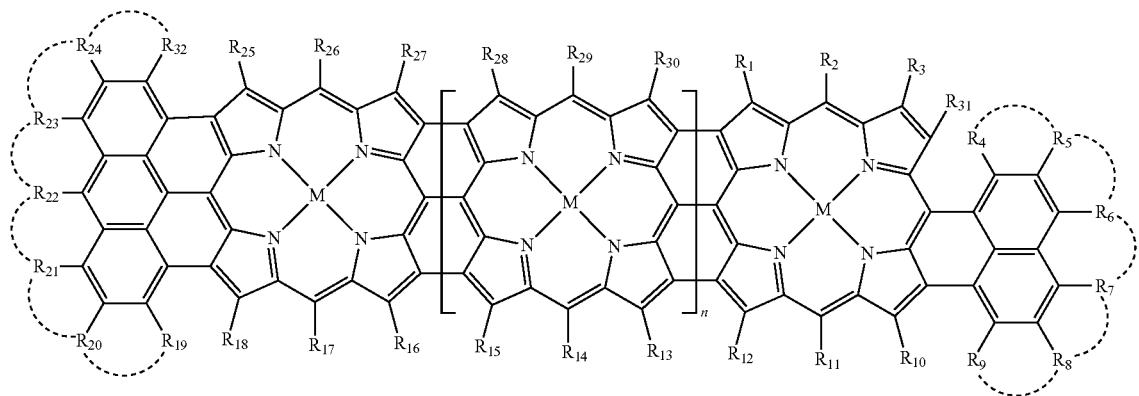
Formula VI
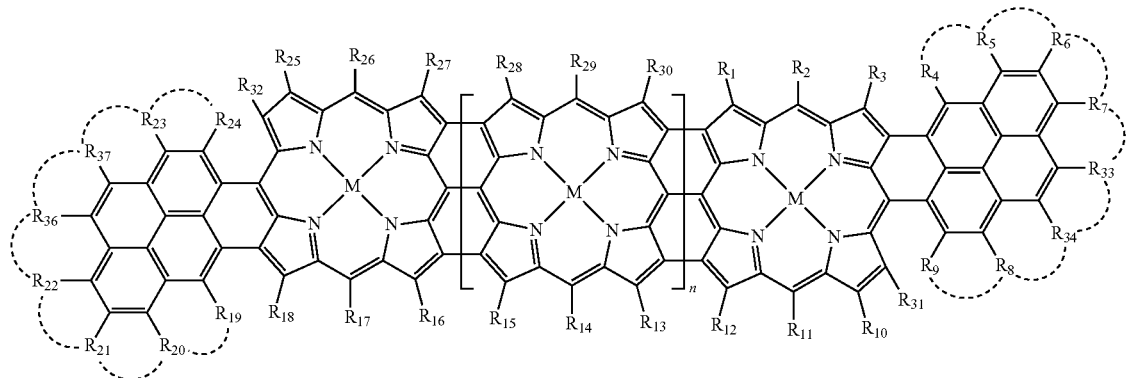
Formula VII
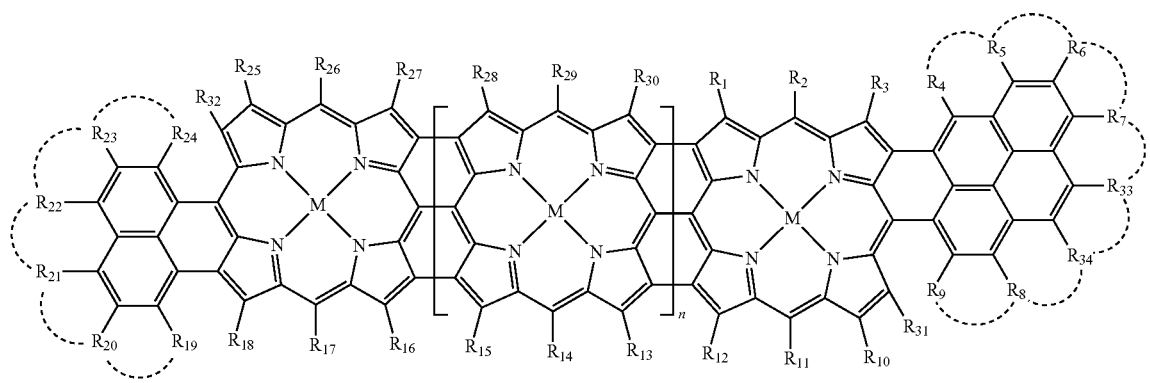

-continued
Formula VIII
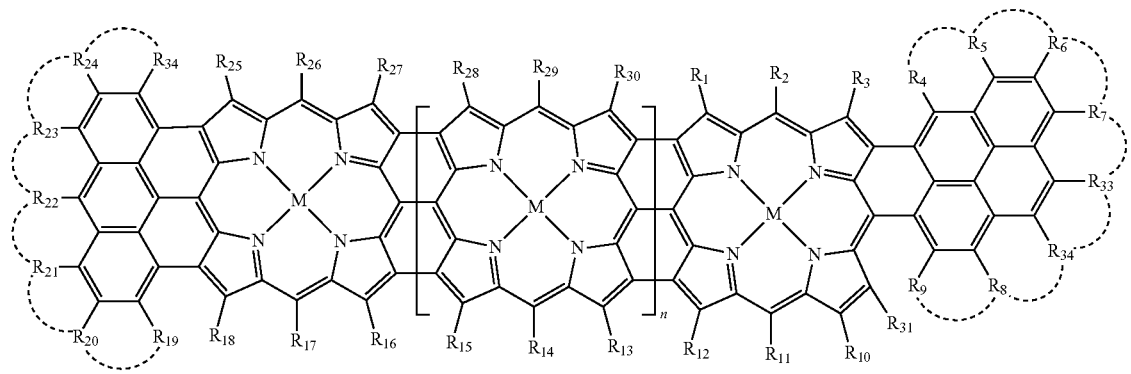
Formula IX
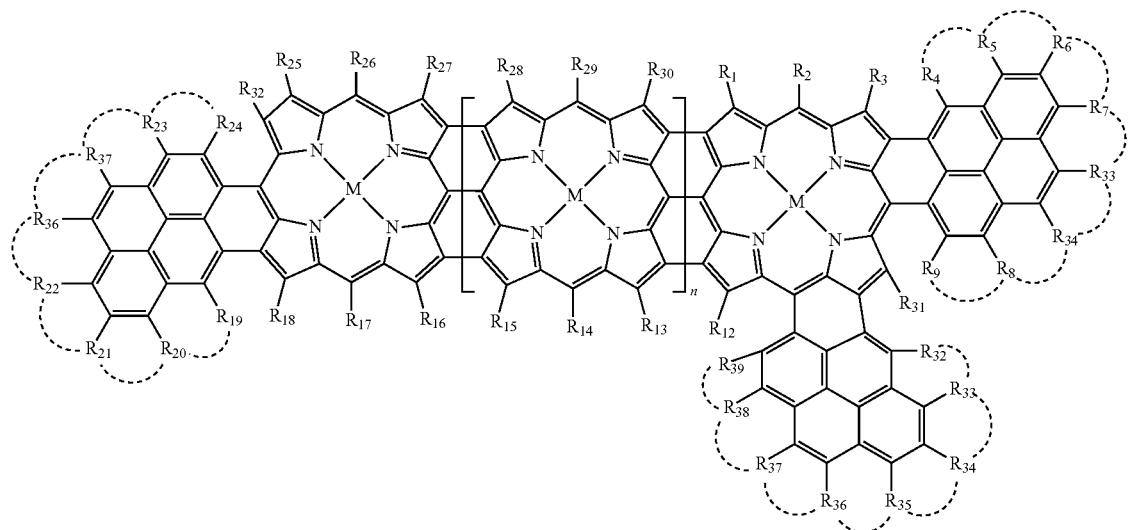
Formula X
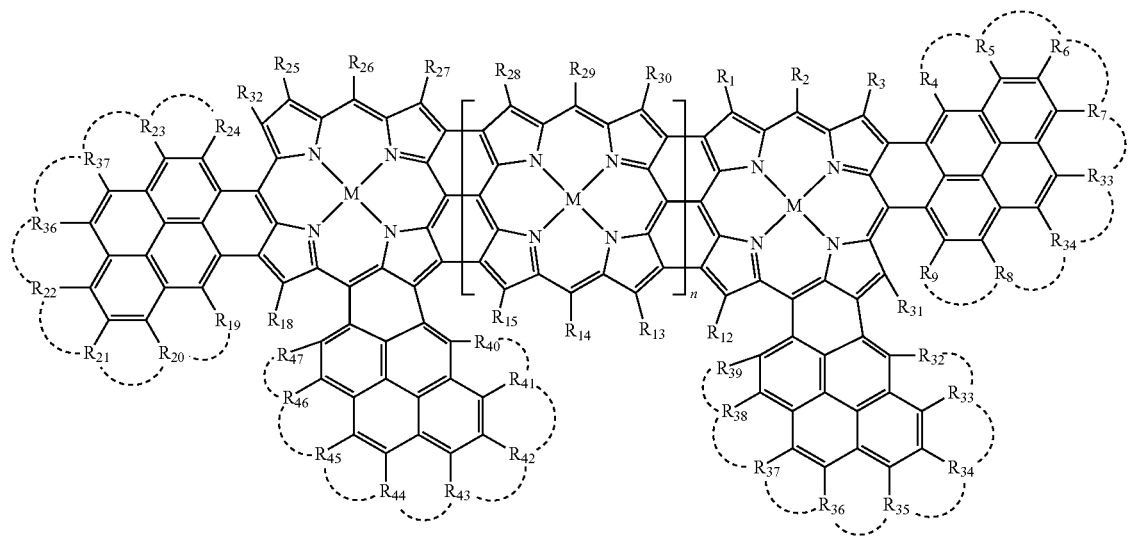

-continued
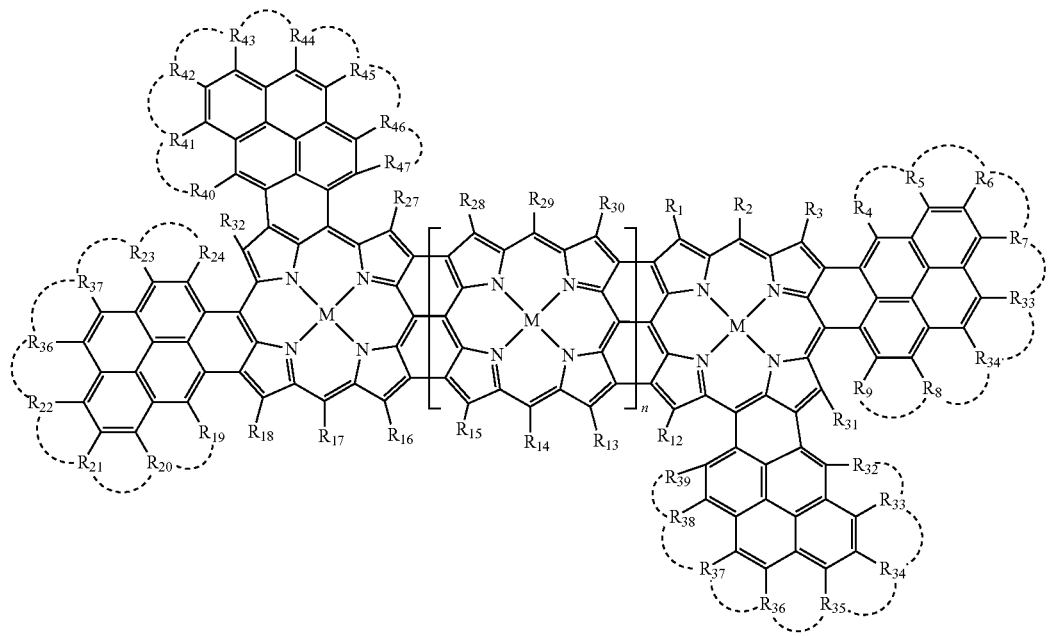
Formula XI
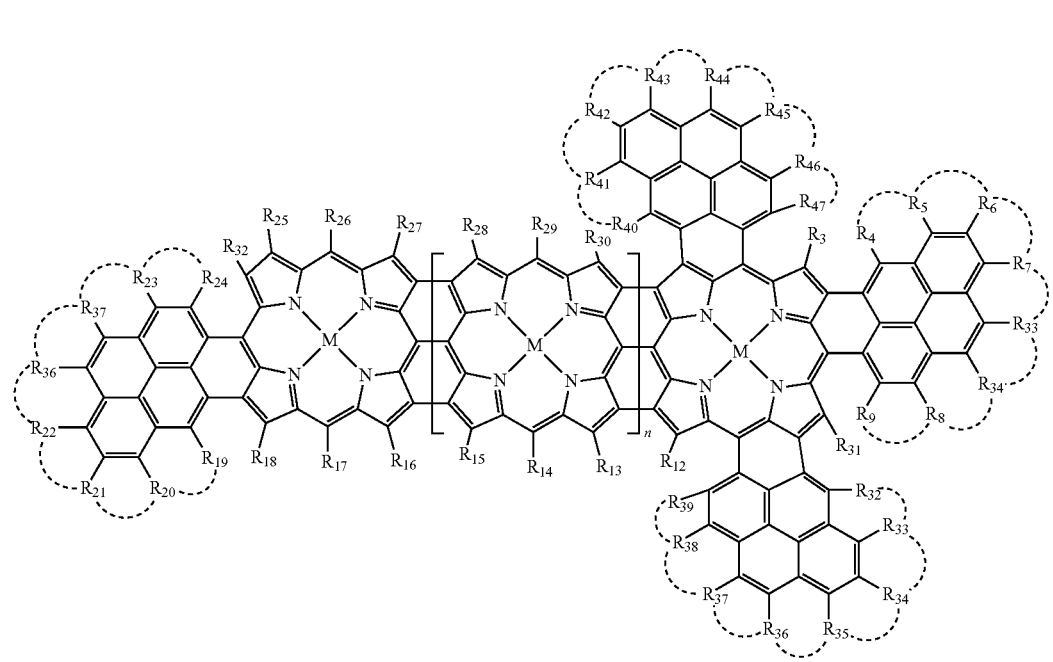
Formula XII

Formula XIII
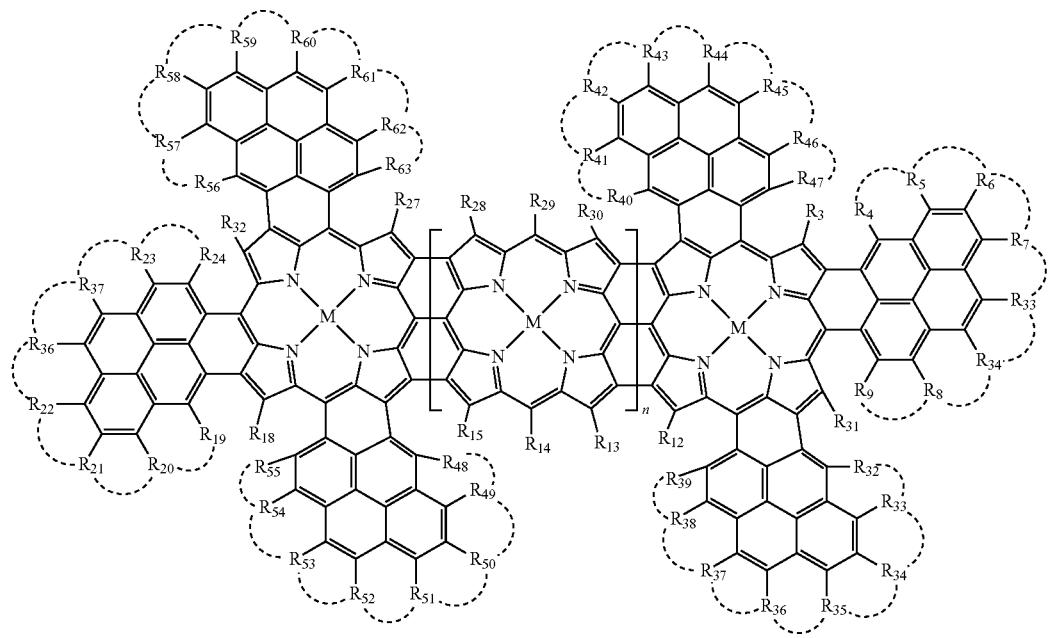
Formula XIV
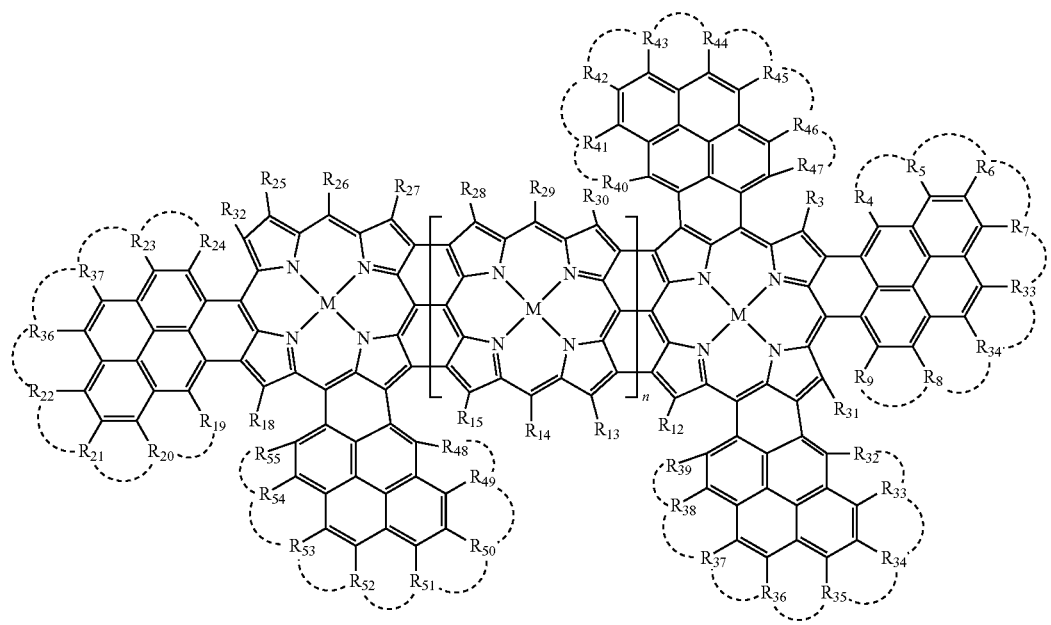
Formula XV
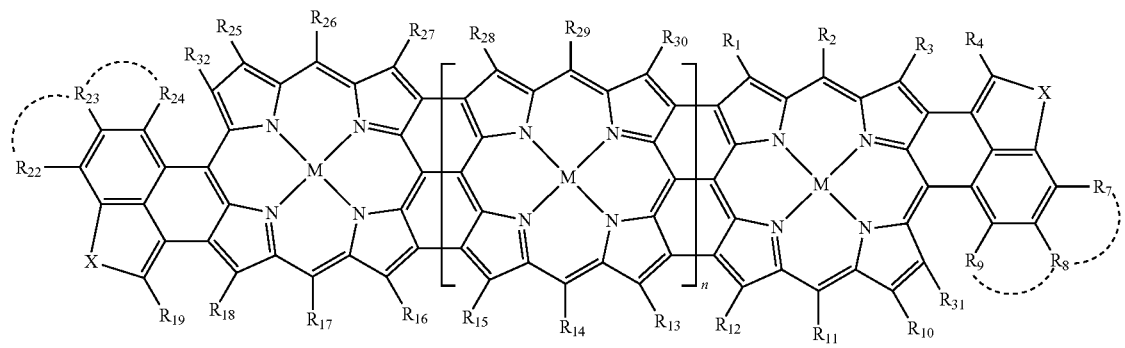

Formula XVI

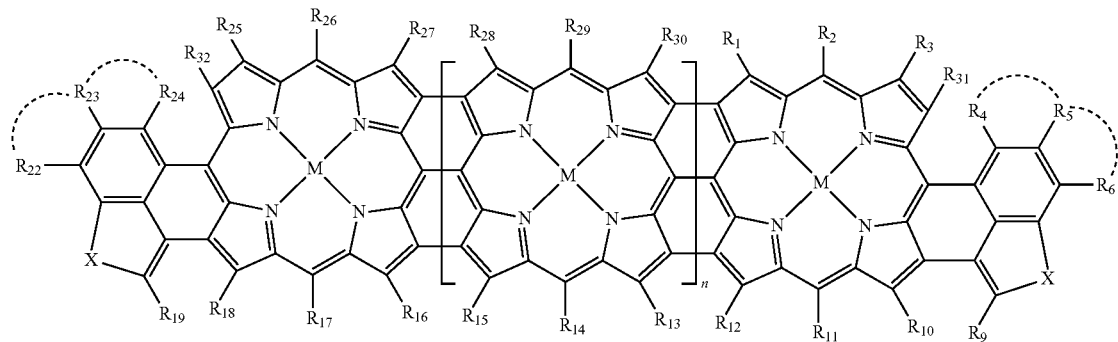

Formula XVII

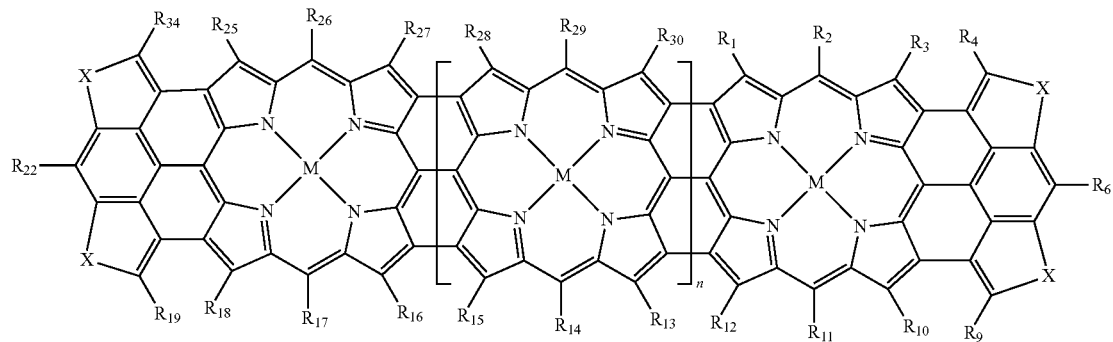

Formula XVIII

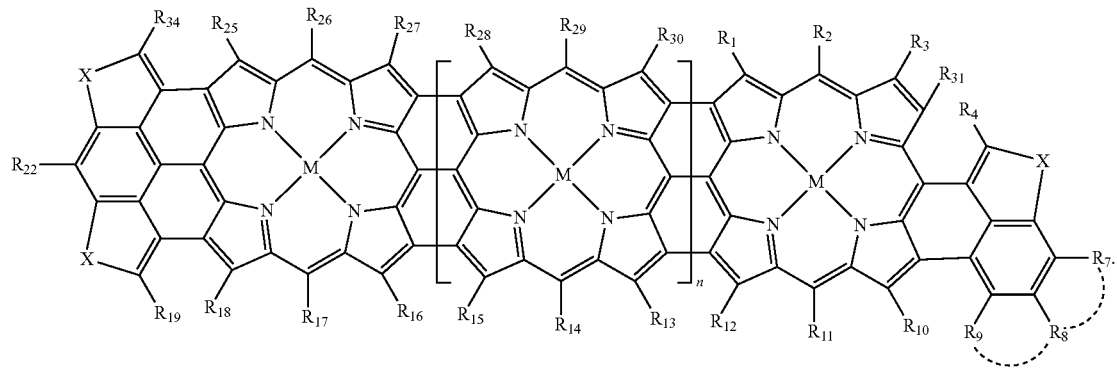

$R_1$-$R_{63}$ are independently selected from the group consisting of hydrogen, alkyl, fluoroalkyl, alkoxy, amino, cyano, alkenyl, alkynyl, aryl, and heteroaryl. Each dotted arc is a polycyclic aromatic substituent or a heterocyclic aromatic substituent. X may be dicoordinate, tricoordinate, tetracoordinate, or hexacoordinate. X is selected from the group consisting of O, S, Se, Te, N, P, As, Si, Ge, and B.

The dotted arc is a substituent that forms a closed ring, which may extend the conjugation of the pi-system. For example, the structure

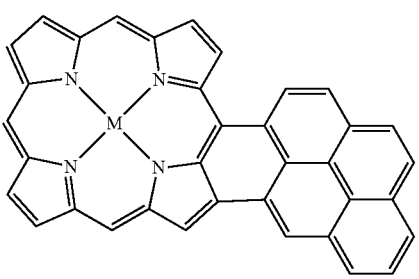

may be described as
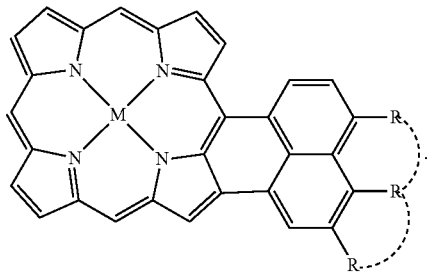
In another aspect, the dotted arc is a substituent selected from the group consisting of:
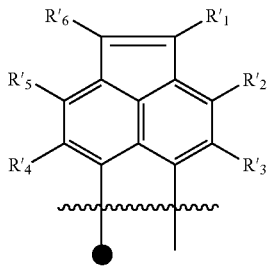
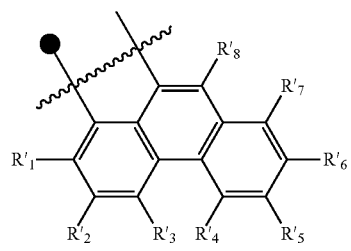
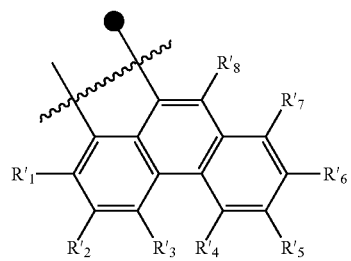
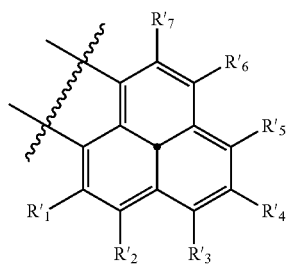
-continued
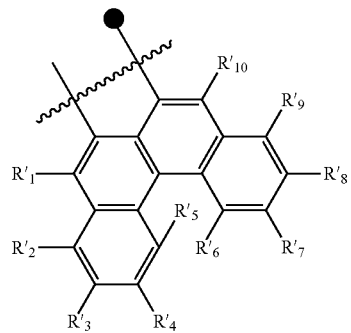
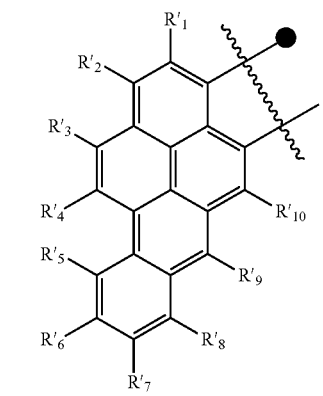
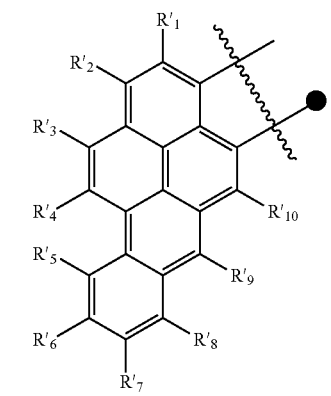
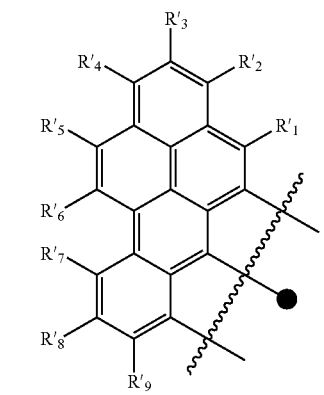

-continued
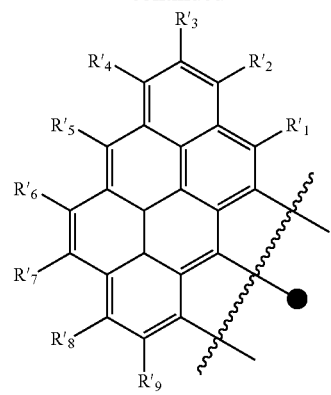
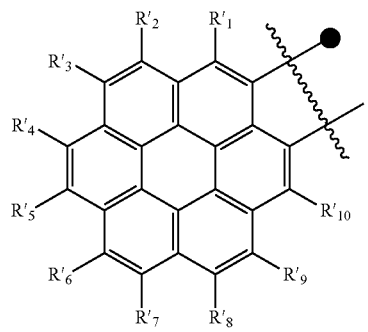
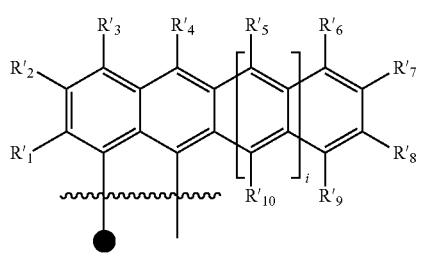
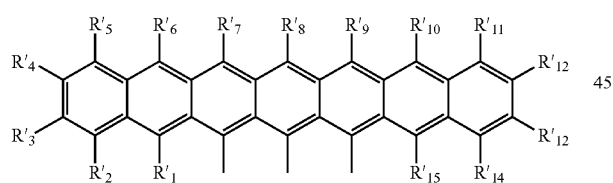
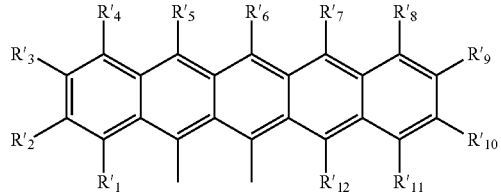
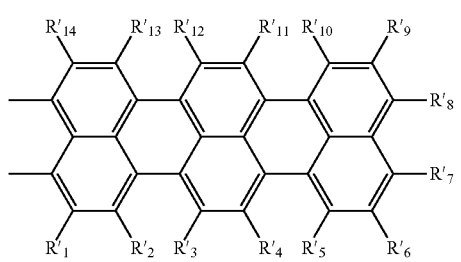
-continued
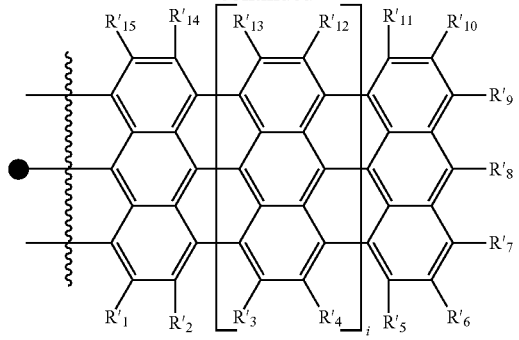
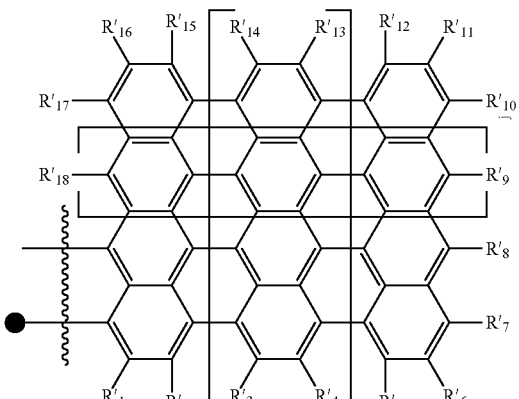
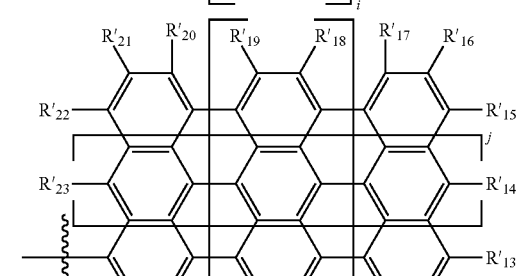
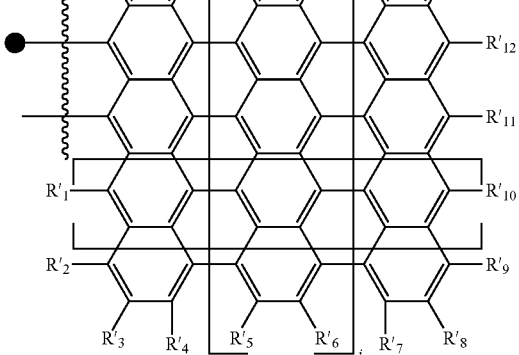
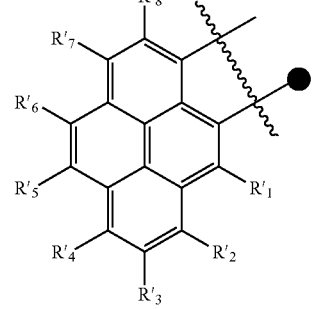

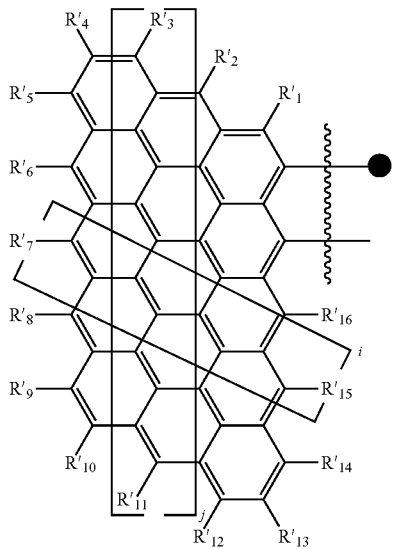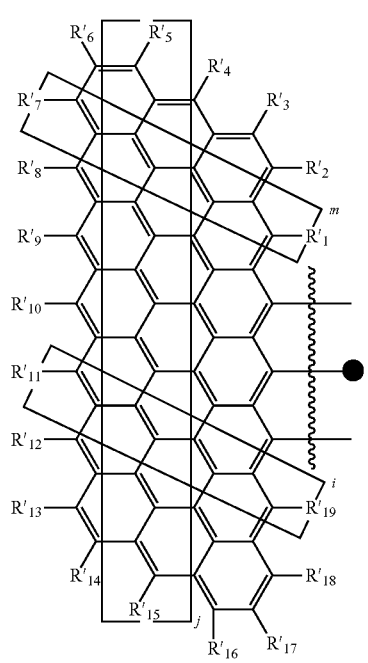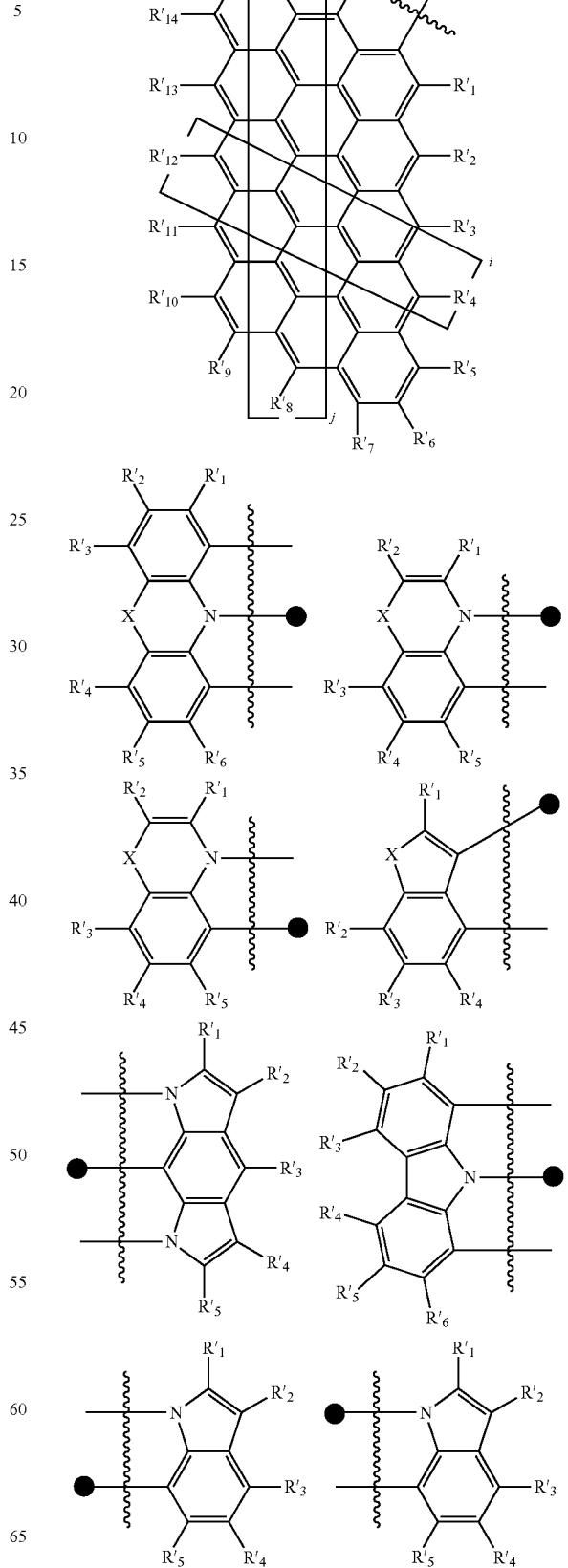

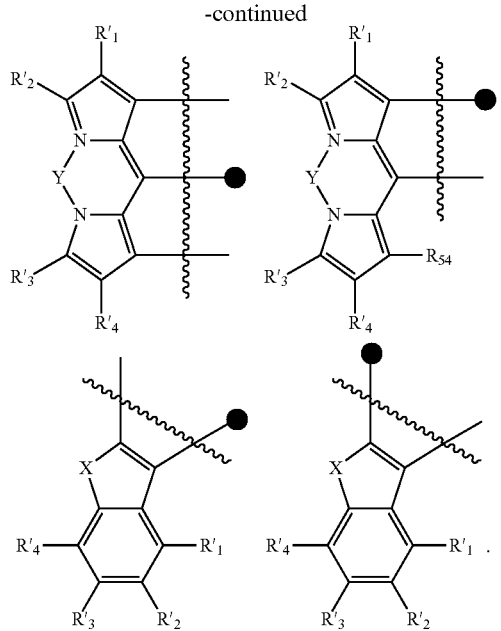

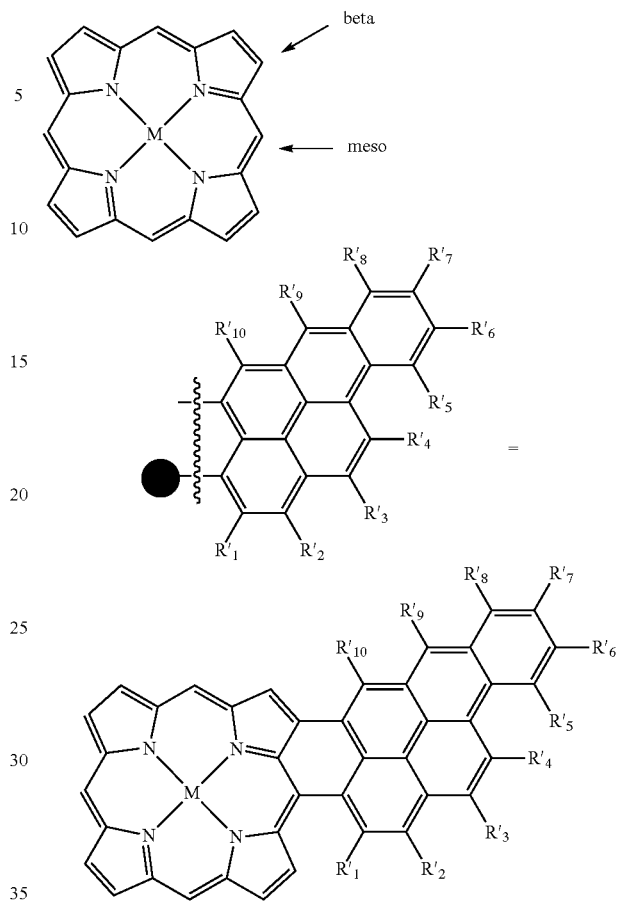

i, j, and m are each independently 0-100. The zig zag line represents the fusion points of the pi-extended unit to the porphyrin. The dot represents the point where the substituent is connected to the meso position of the porphryin. X is O, S, Se, Te, N, P, As, Si, Ge, or B. Y is H, M, or X. $R'_1$-$R'_{23}$ are independently selected from hydrogen, hydroxyl, halogen, chalcogen, mercapto, alkyl, fluoroalkyl, alkoxy, amino, cyano, alkenyl, alkynyl, aryl, and heteroaryl.

In the group of substituents provided above, the porphyrin tape is not shown explicitly. The "dot" in these images represents the point where the substituent is connected to the meso position of the porphryin. The "zig-zag" line delineates the fusion points of the pi-extended unit to the porphyrin. The following illustration is a non-limiting example depicting the "dot" indicating the positions of fusion of a polycyclic aromatic group fused to a porphyrin and the "zig zag" line indicating positions of connection with the meso position of the porphyrin ring.

Preferably, the dotted arc substituent is naphthalene, anthracene, or pyrene. Most preferably, the dotted arc is pyrene. Without being bound by theory, it is believed that fused pyrene results in twisting, which increases the solubility of the compound, this improving processability. Compounds with improved solubility may be particularly beneficial to make thin films.

Specific examples of the porphyrin compounds are provided. In one aspect, the compound is selected from the group consisting of:

Compound 1

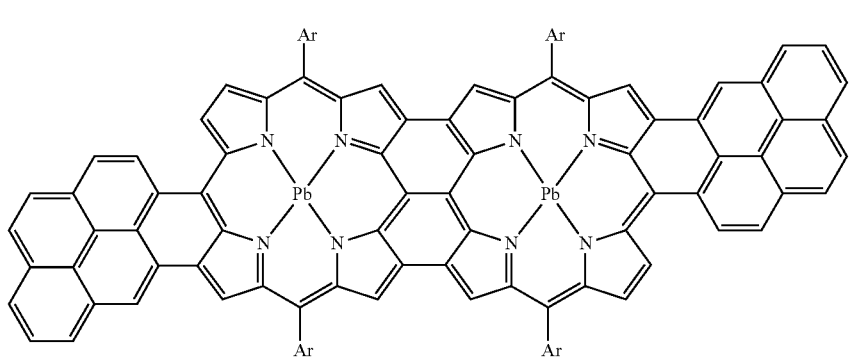

-continued
Compound 2
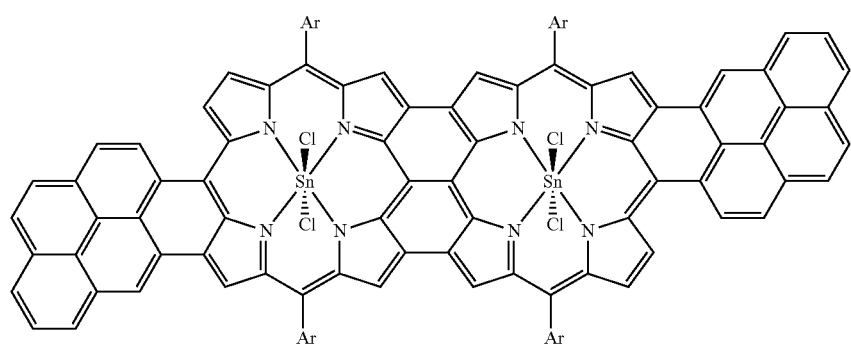
Compound 3
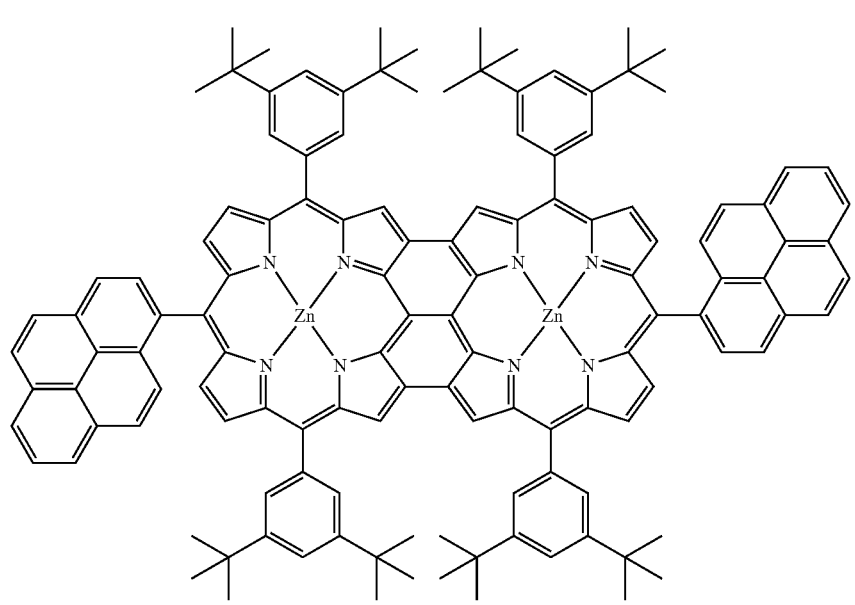
Compound 4
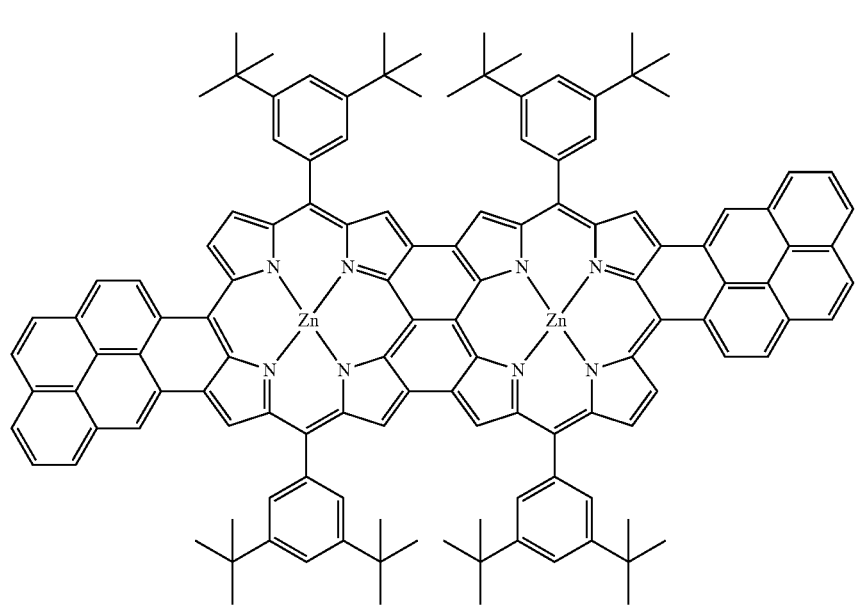

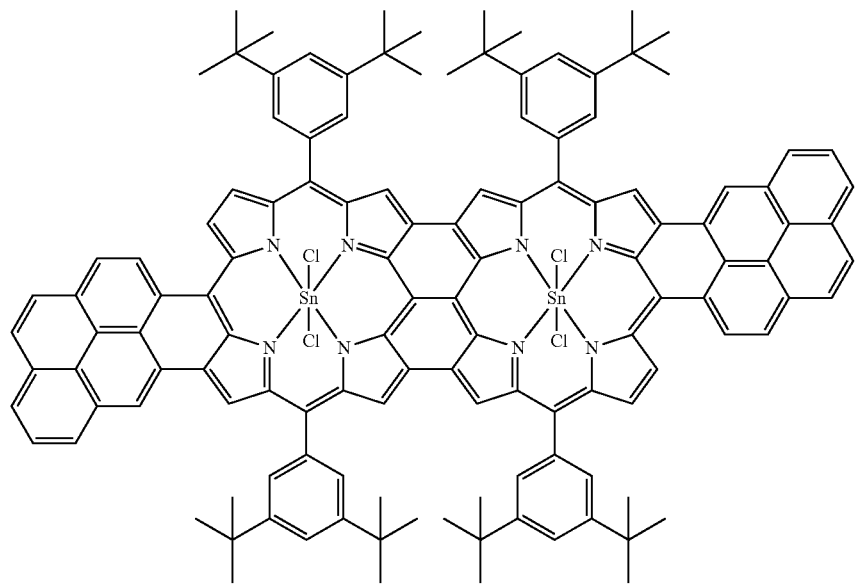
Compound 5
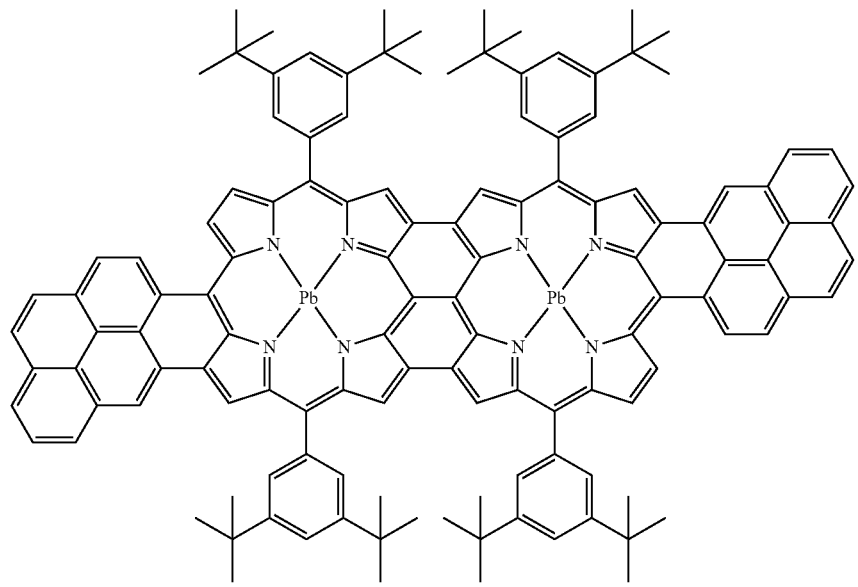
Compound 6

Compound 7
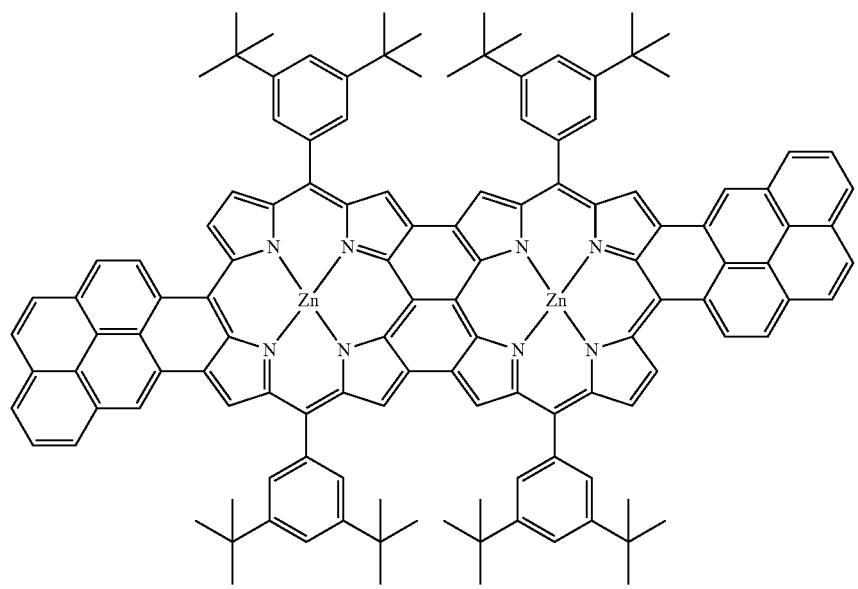
Compound 8
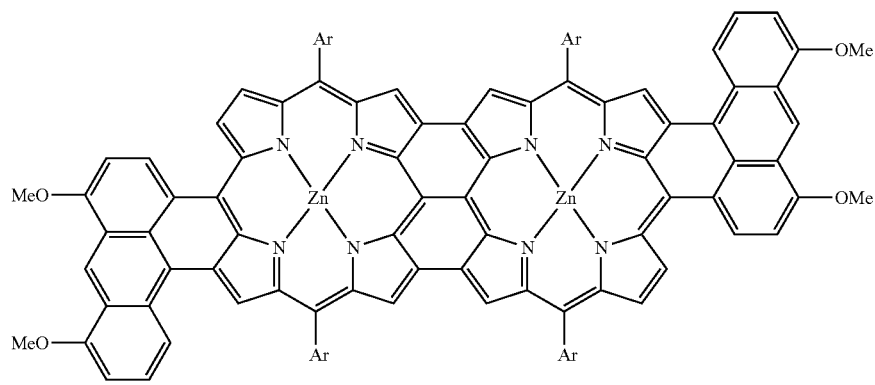
Compound 9
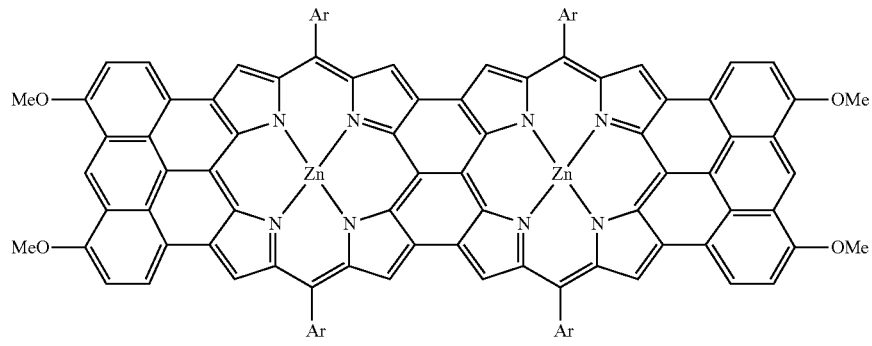
Compound 10
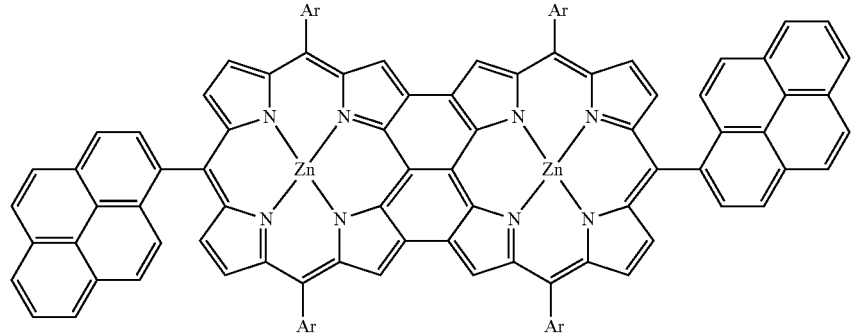

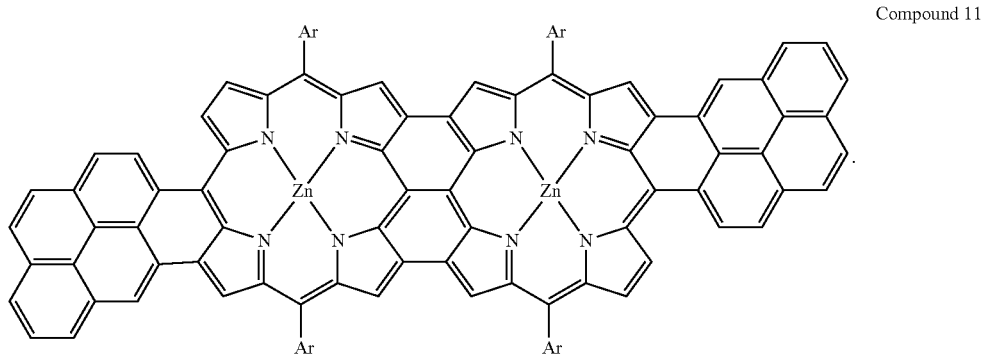

Compound 11

An organic device is also provided. The device comprises a first electrode, a second electrode, a first layer, disposed between the first electrode and the second electrode, and a second layer comprising a second organic compound disposed between the first electrode and the second electrode, wherein the second layer is in direct contact with the first layer.

The first layer comprises a first compound, wherein the first compound has the structure:

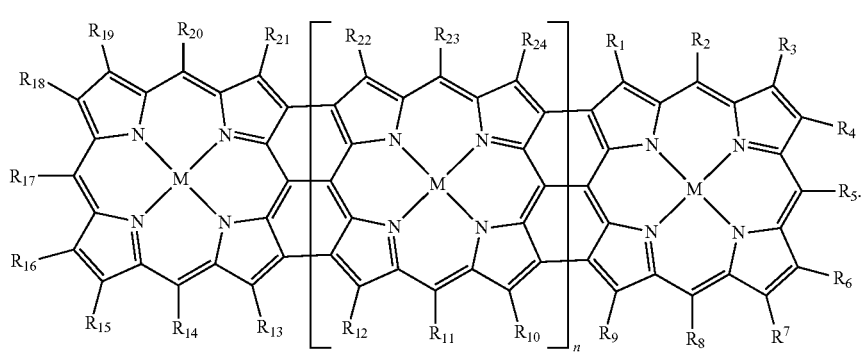

Formula I $R_1$-$R_{24}$ are independently selected from the group consisting of hydrogen, hydroxyl, halogen, chalcogen, mercapto, alkyl, fluoroalkyl, alkoxy, amino, cyano, alkenyl, alkynyl, aryl, and heteroaryl. M is a dicoordinate, tricoordinate, tetracoordinate, pentacoordinate or hexacoordinate metal ion or alternatively 2 hydrogen atoms. n is 0-100. Preferably, n is 0-5.

In one aspect, at least one of $R_1$-$R_{24}$ is a fused polycyclic aromatic or a fused heterocyclic aromatic. Preferably, at least one of $R_1$-$R_{24}$ is a fused pyrene. More preferably, at least one of $R_1$-$R_9$ and $R_{13}$-$R_{21}$ is a fused pyrene.

In another aspect, the first layer is in contact with the first electrode and the device further comprises a layer of BCP disposed between and in contact with the second layer and the second electrode.

In one aspect, M is selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, P, As, Sb, Bi, Pr, Nd, Sm, Eu, Gd, Tb, Dy, Ho, Er, Tm, Yb, Lu, Th, U, Zn, ClAl, SnO, $SnCl_2$, Pb(OAc), and Sn(OH)$_2$. Preferably, M is Zn, Pb, Sn, ClAl, SnO, $SnCl_2$, Pb(OAc), and Sn(OH)$_2$.

In one aspect, the second compound is selected from the group consisting of $C_{60}$, $C_{70}$, $C_{84}$, $F_{16}$—CuPc, PTCBI, PTCDA, PCBM or PTCDI. Preferably, the second compound is $C_{60}$.

In one aspect, the device has an optical response at a wavelength greater than 1200 nm. In another aspect, the device has an optical response at a wavelength greater than 1500 nm.

In one aspect, the first layer is disposed using solution processing.

In another aspect, the first layer comprises more than one first compound.

In yet another, the second compound is disposed in a layer having a thickness of about 80 nm to about 200 nm.

In one aspect, the first compound is disposed in combination with one or more of polystyrene, chlorobenzene, toluene, methylene chloride, dichloromethane, chloroform, chloronaphthalene, dichlorobenzene, and pyridine.

Specific example of devices comprising porphyrin compounds are provided. In one aspect, the first compound is selected from the group consisting of:

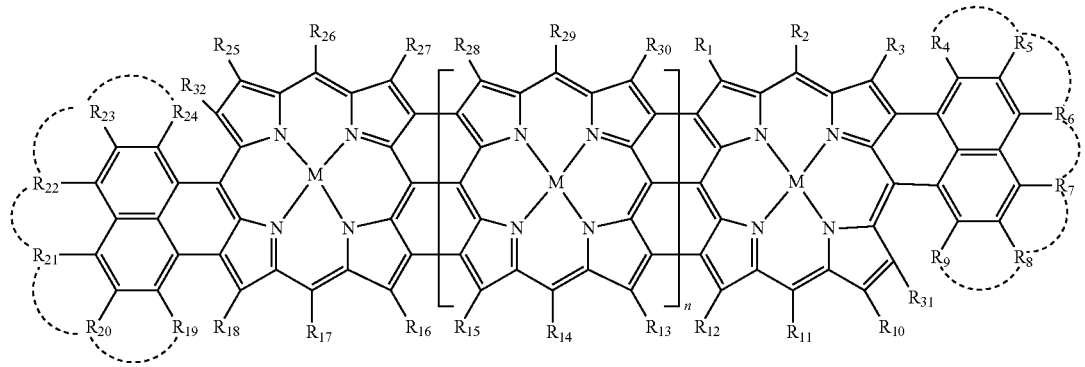
Formula II
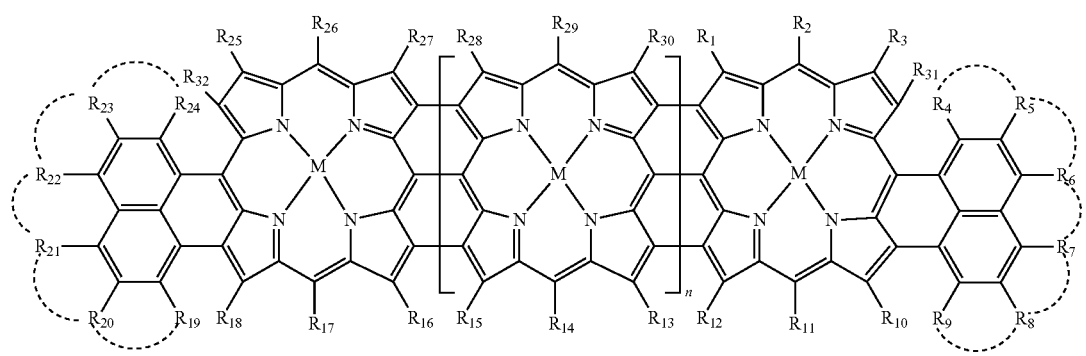
Formula III
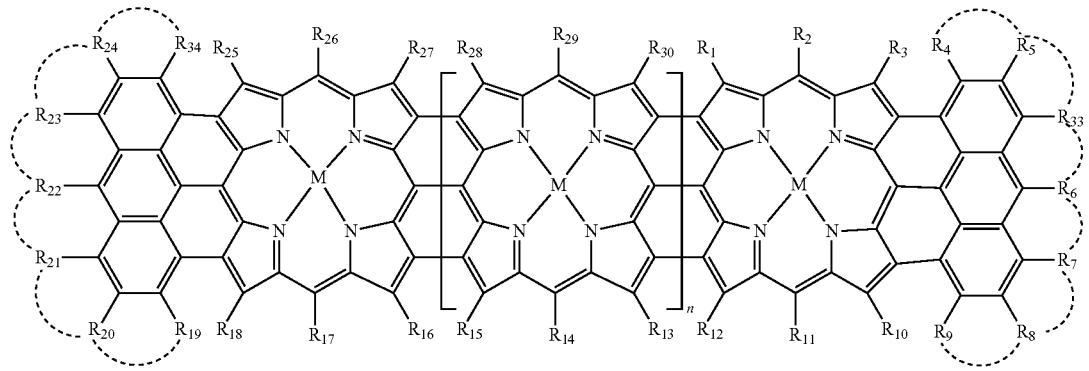
Formula IV
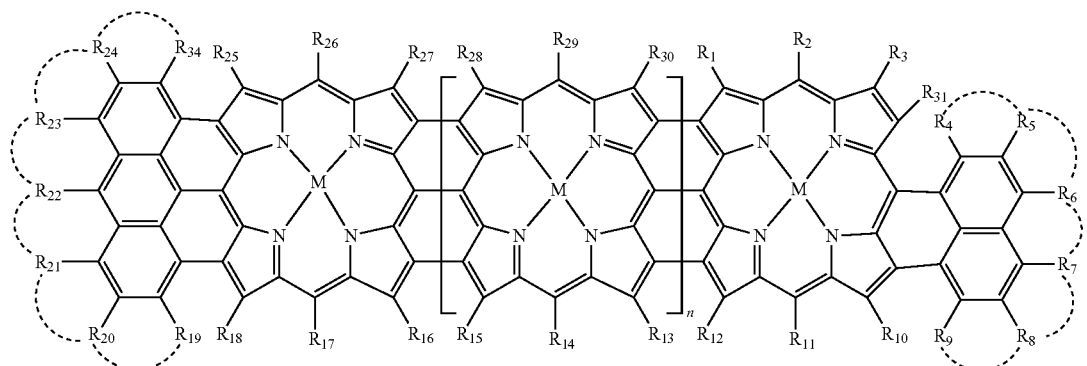
Formula V -continued
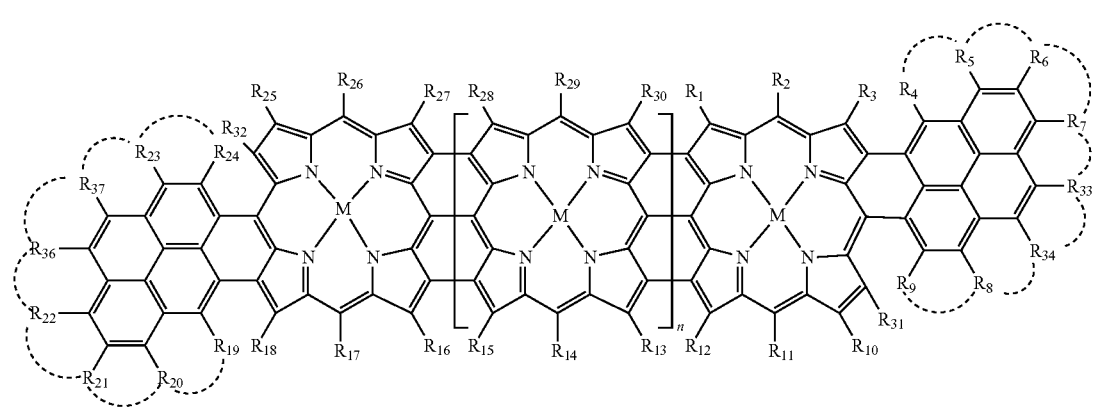
Formula VI
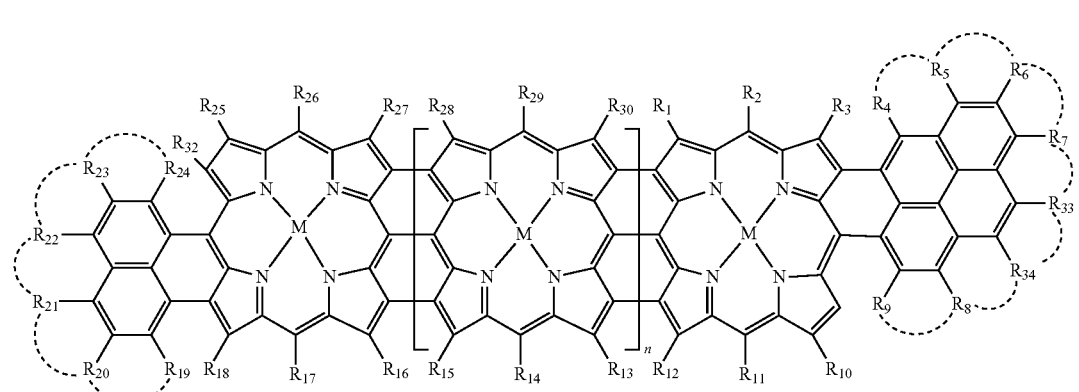
Formula VII
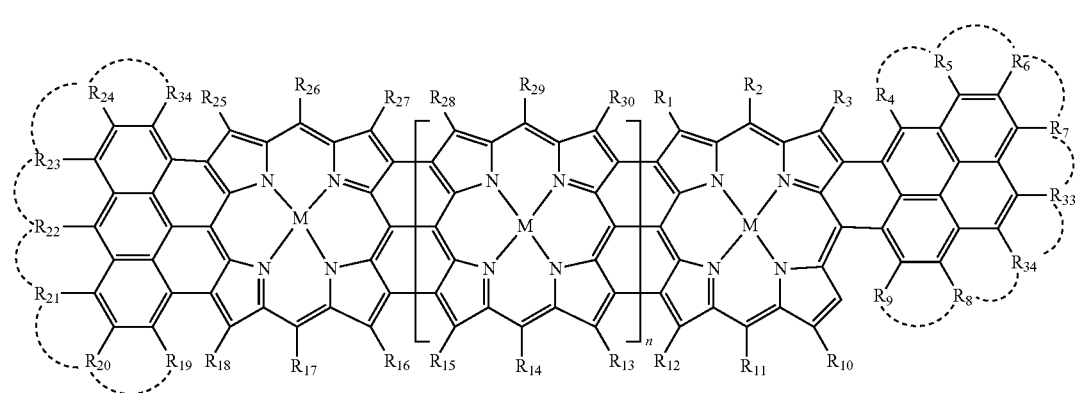
Formula VIII

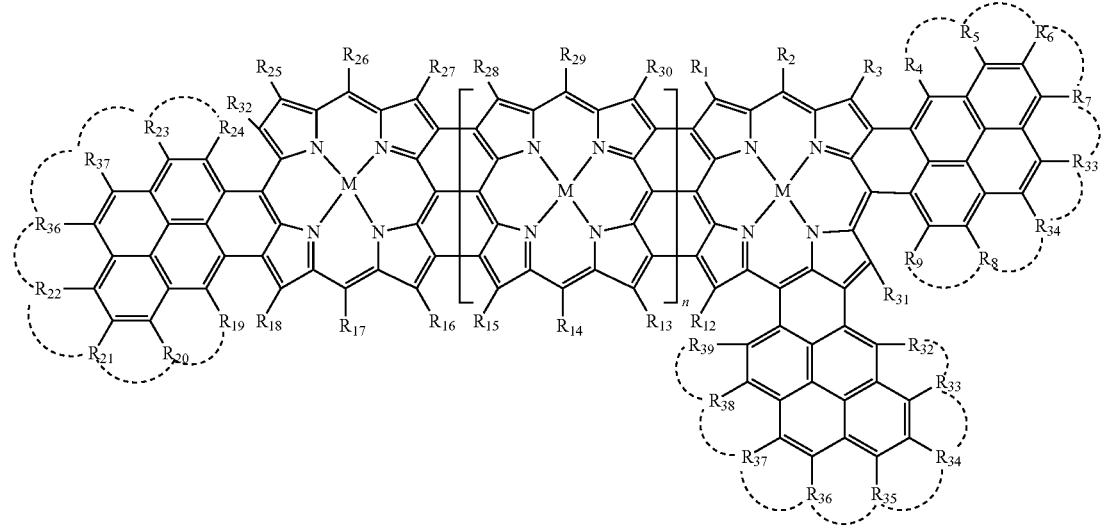
Formula IX
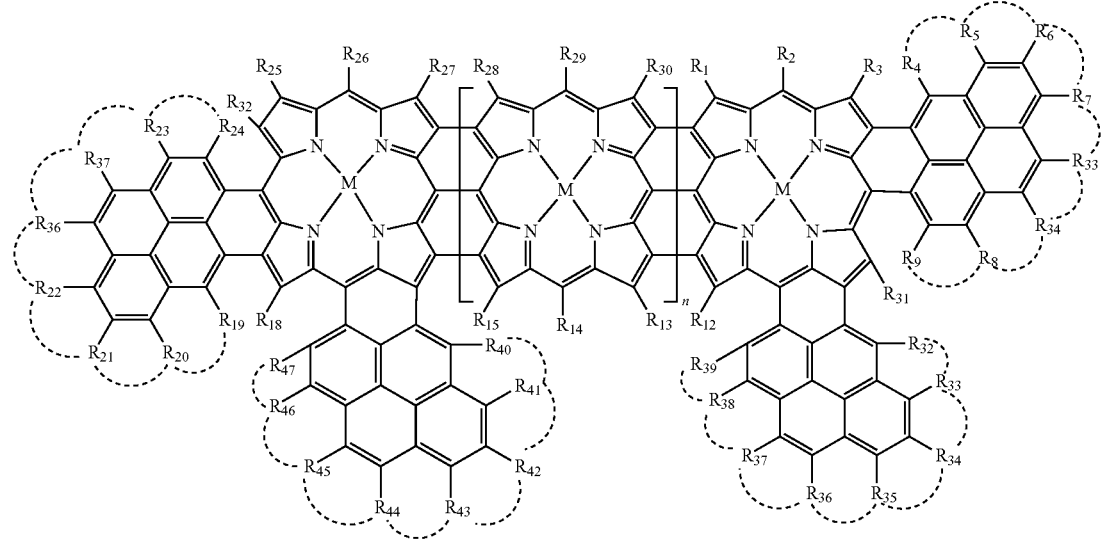
Formula X

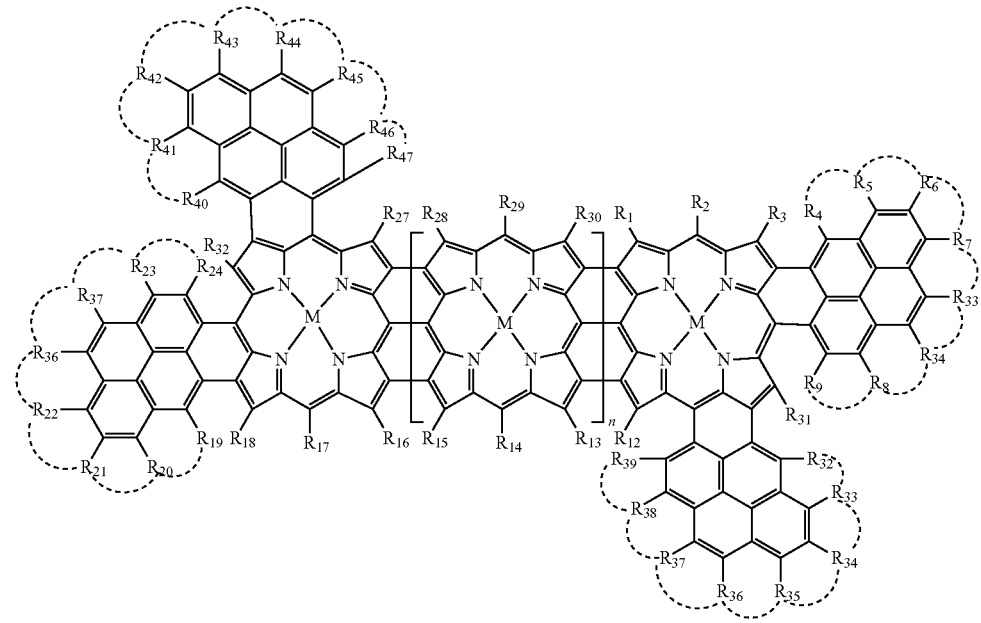
Formula XI
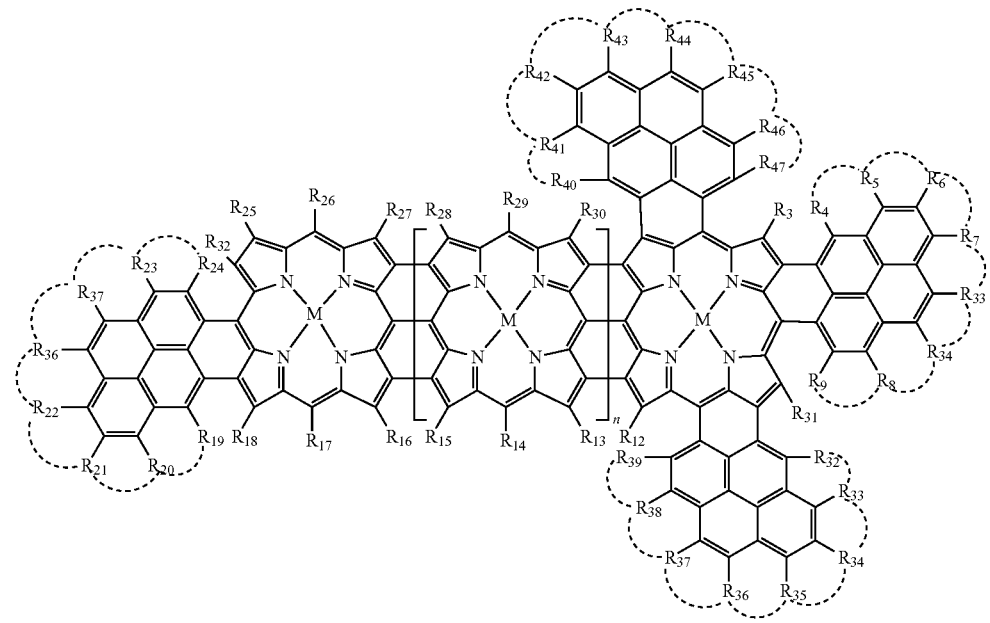
Formula XII

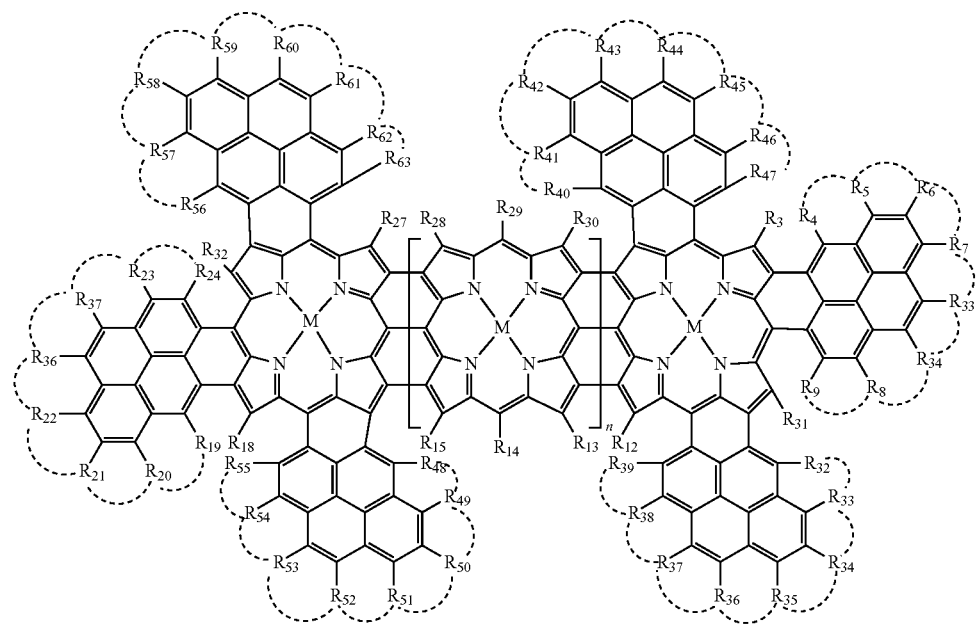
Formula XIII
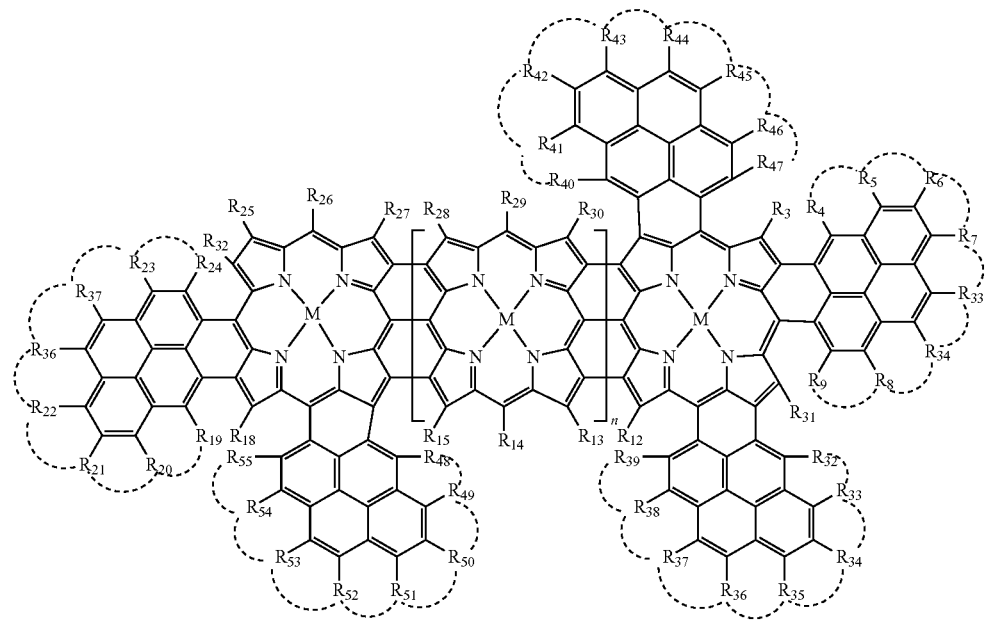
Formula XIV
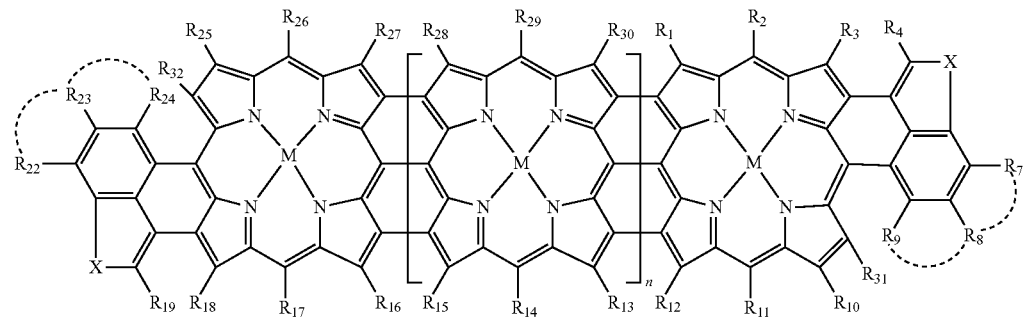
Formula XV

-continued

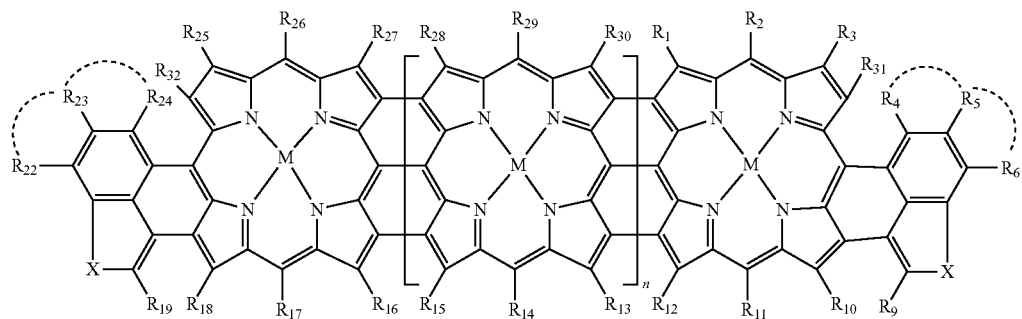
Formula XVI

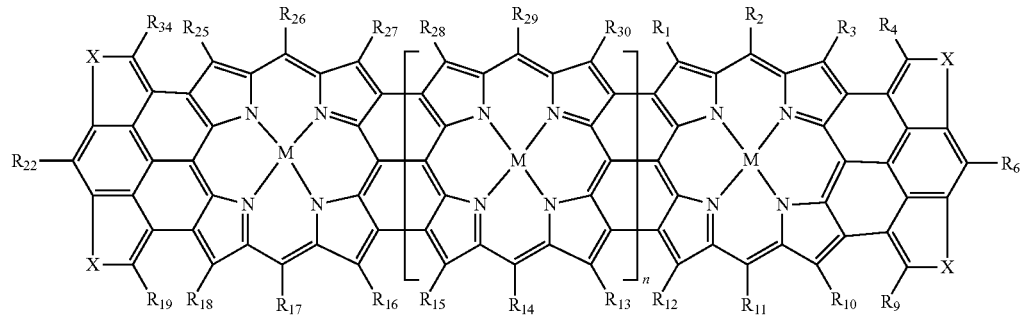
Formula XVII

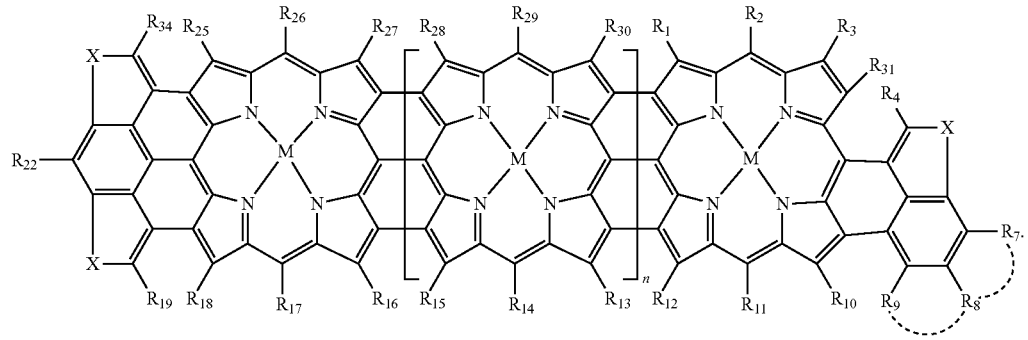
Formula XVIII $R_1$-$R_{63}$ are independently selected from the group consisting of hydrogen, alkyl, fluoroalkyl, alkoxy, amino, cyano, alkenyl, alkynyl, aryl, and heteroaryl. Each dotted arc is a polycyclic aromatic substituent or a heterocyclic aromatic substituent. X may be dicoordinate, tricoordinate, tetracoordinate, or hexacoordinate. X is selected from the group consisting of O, S, Se, Te, N, P, As, Si, Ge, and B.

The dotted arc is a substituent that forms a closed ring. As discussed above, the substituent may extend the conjugation of the pi-system. In one aspect, the dotted arc is a substituent selected from the group consisting of:

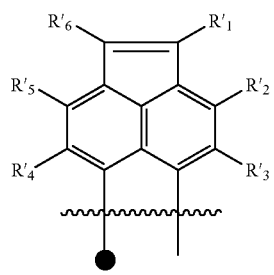

-continued

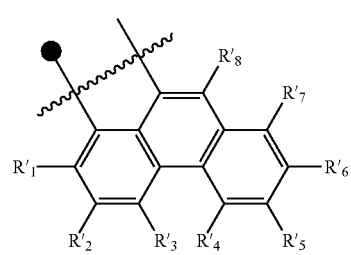

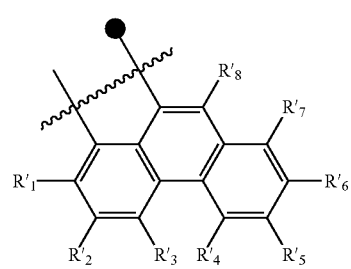

81
-continued
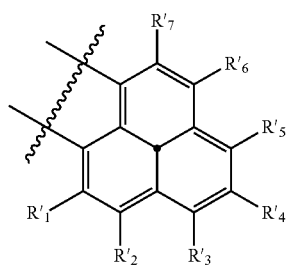
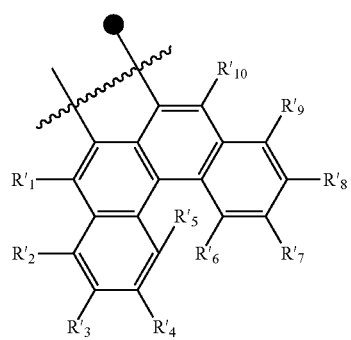
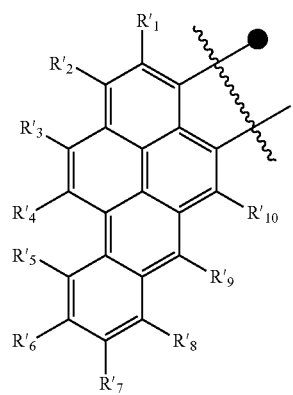
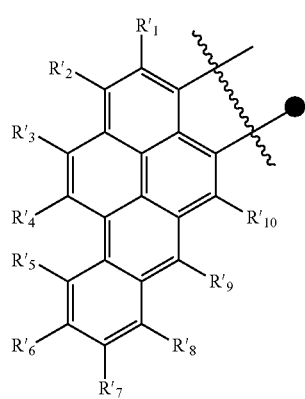
82
-continued
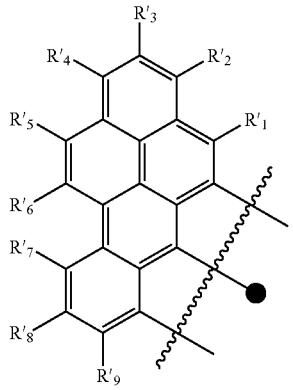
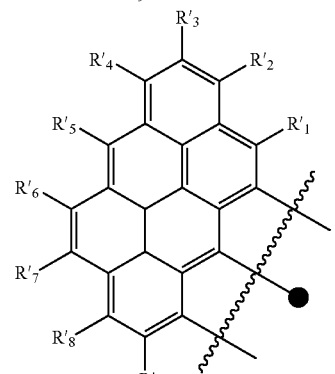
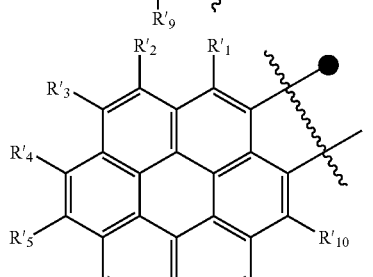
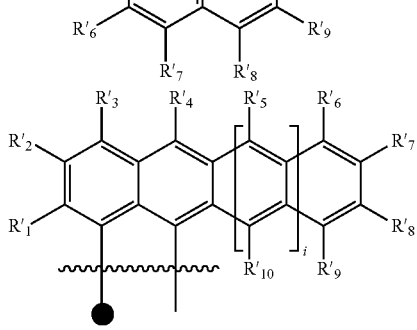
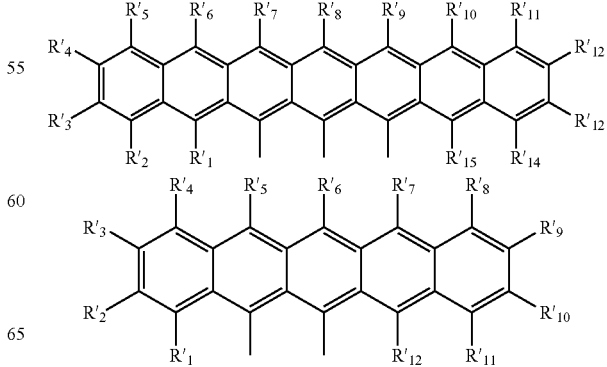

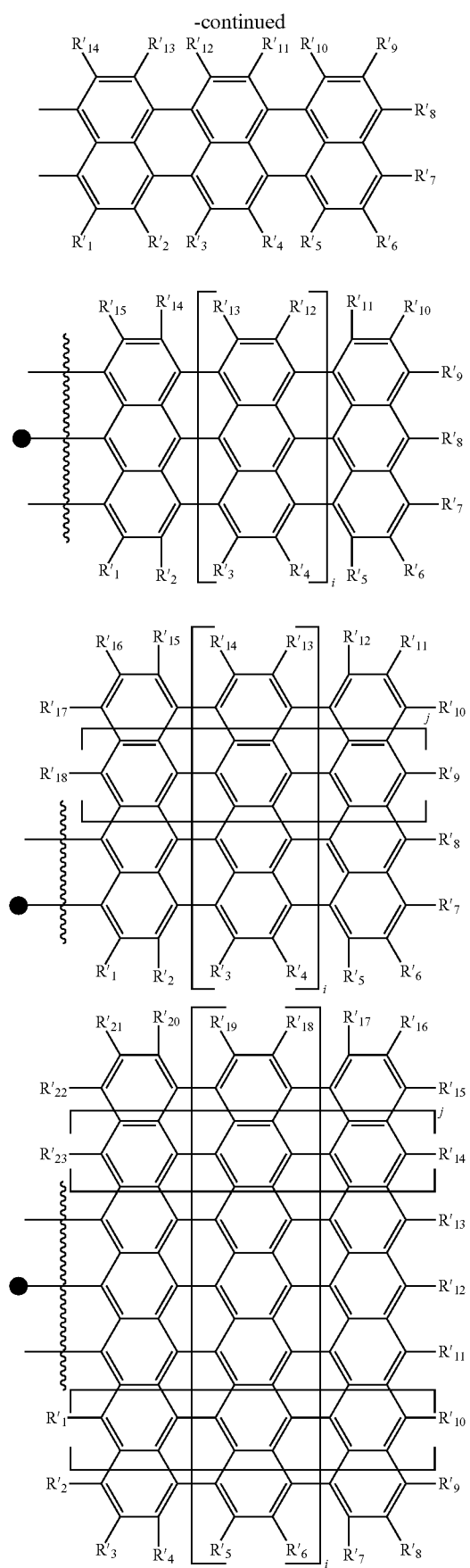
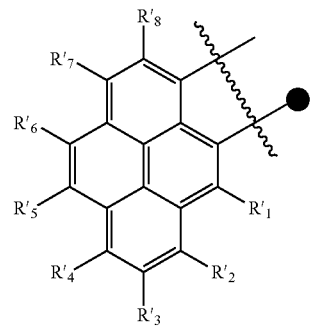
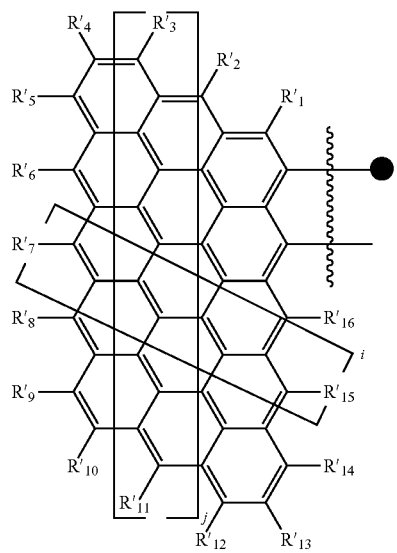
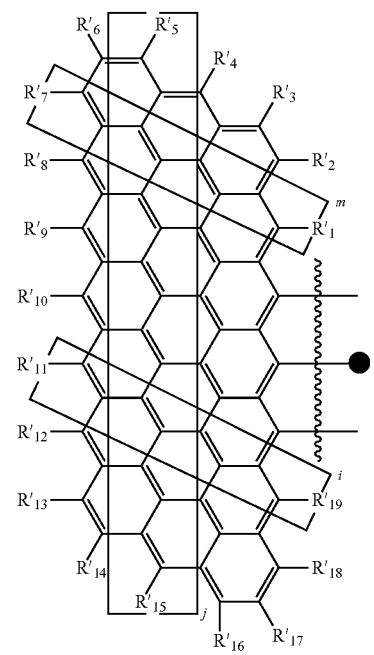

-continued

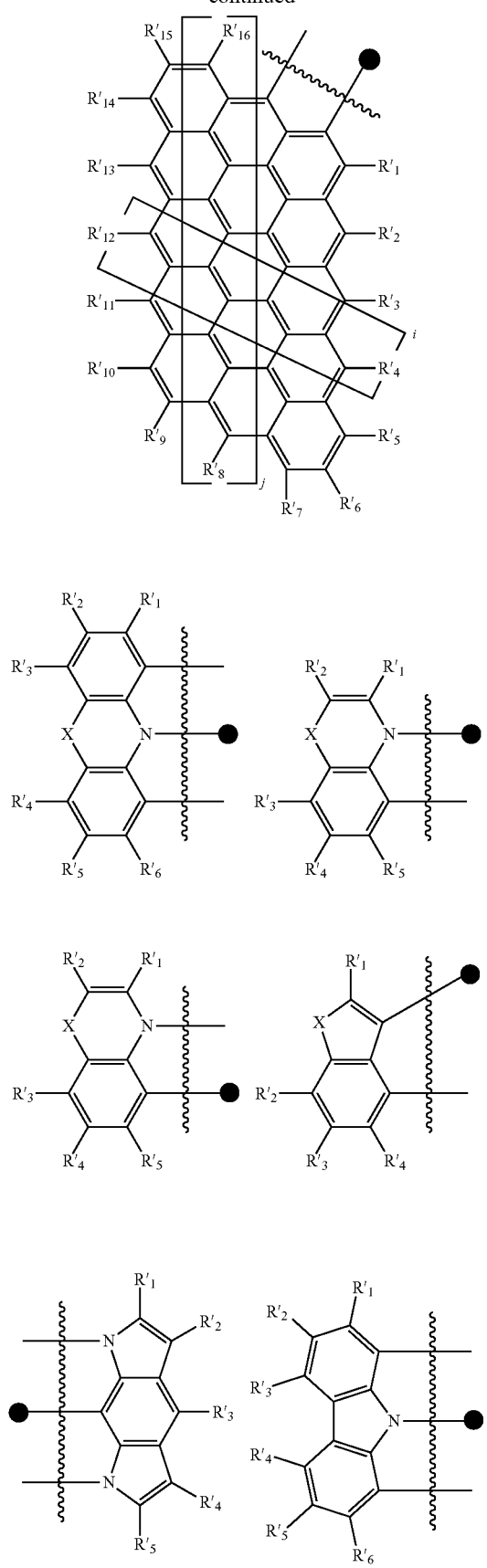

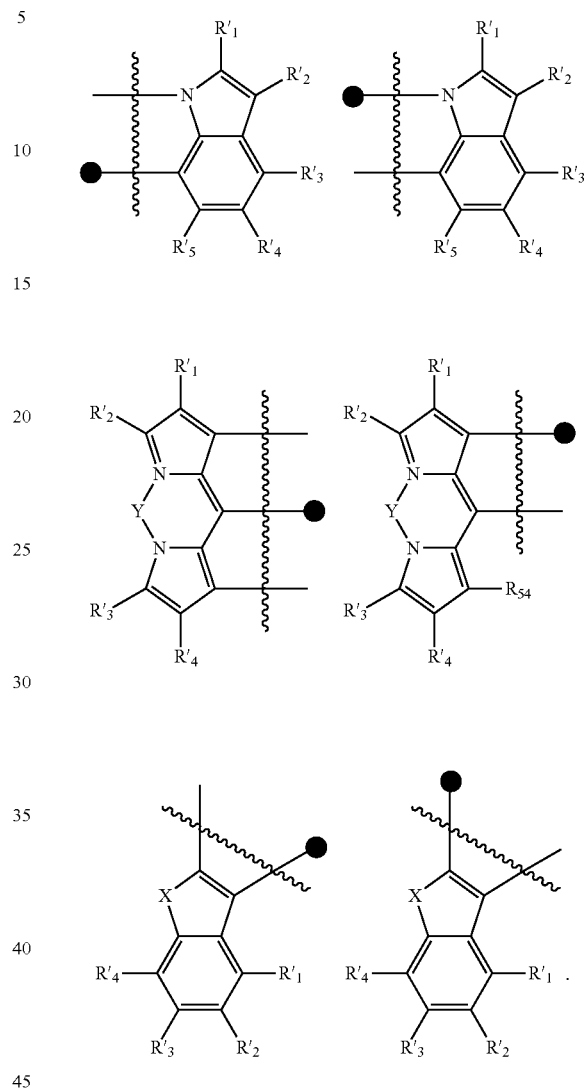

i, j, and m are each independently 0-100. The zig zag line represents the fusion points of the pi-extended unit to the porphyrin. The dot represents the point where the substituent is connected to the meso position of the porphyrin. X is O, S, Se, Te, N, P, As, Si, Ge, or B. Y is H, M, or X. $R'_1$-$R'_{23}$ are independently selected from hydrogen, hydroxyl, halogen, chalcogen, mercapto, alkyl, fluoroalkyl, alkoxy, amino, cyano, alkenyl, alkynyl, aryl, and heteroaryl. As discussed above, the porphyrin tape is not shown explicitly in the above listing of substituents. The "dot" in these images represents the point where the polycyclic aromatic group is connected to the meso position of the porphyrin. The "zig-zag" line delineates the fusion points of the pi-extended unit to the porphyrin.

Preferably, the dotted arc substituent is naphthalene, anthracene, or pyrene.

In another aspect, the first compound is selected from the group consisting of:

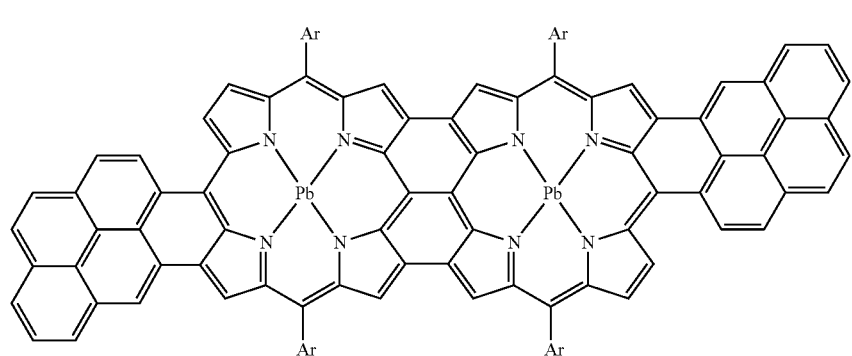
Compound 1
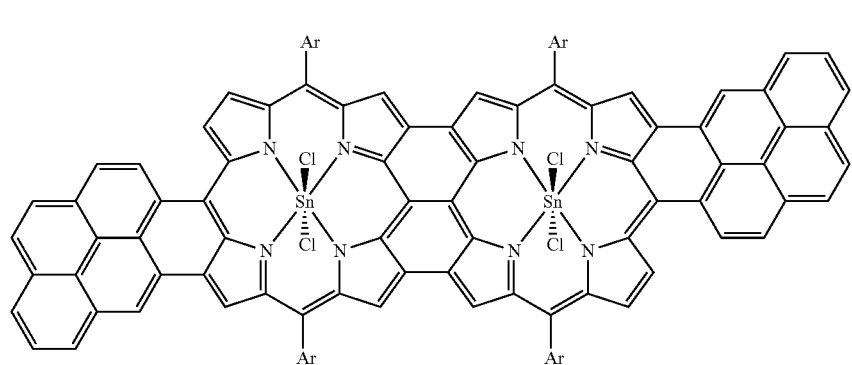
Compound 2
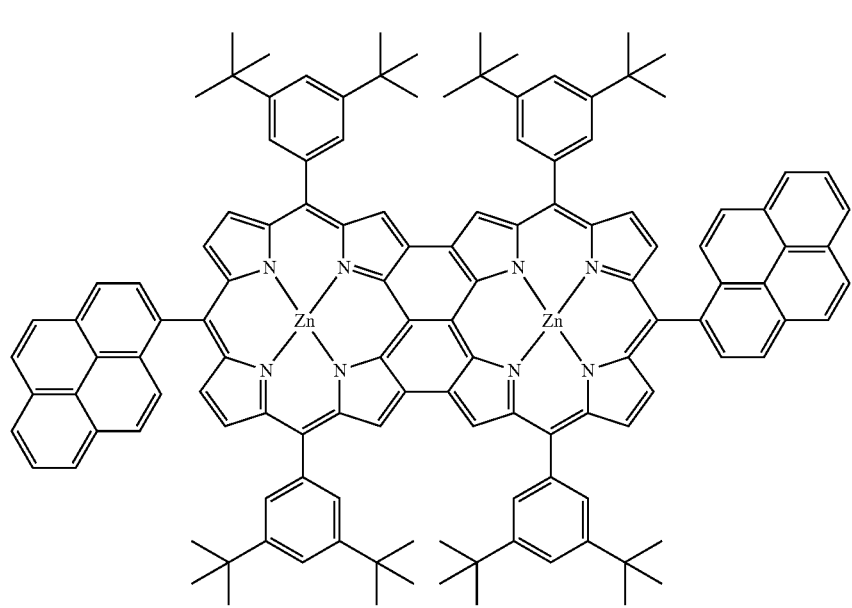
Compound 3

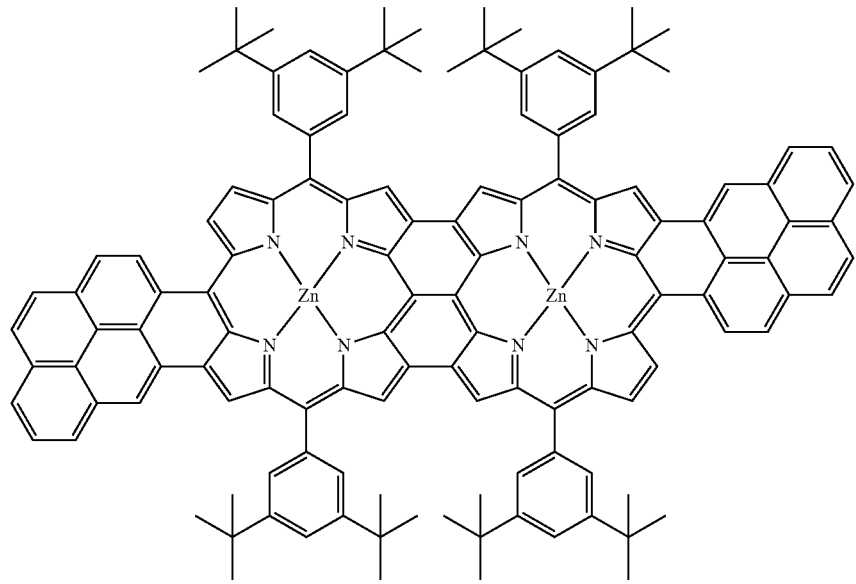
Compound 4
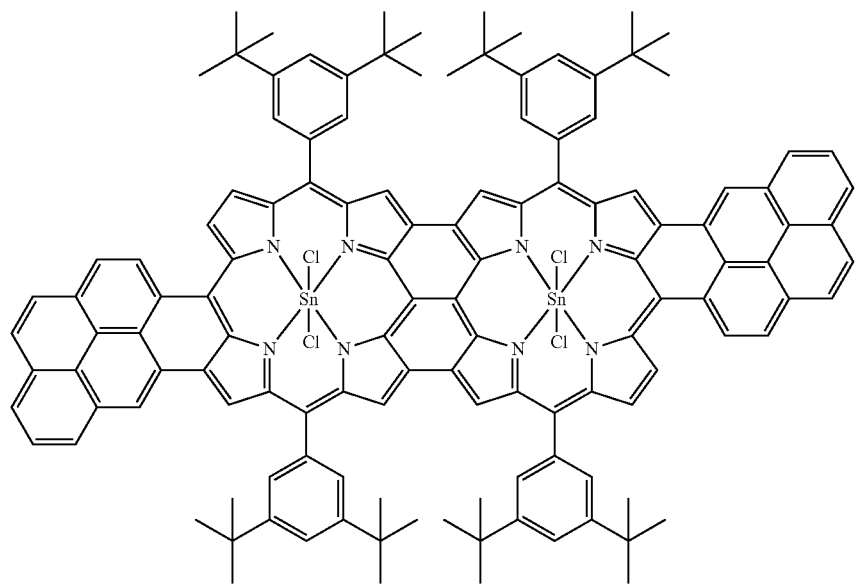
Compound 5

Compound 6
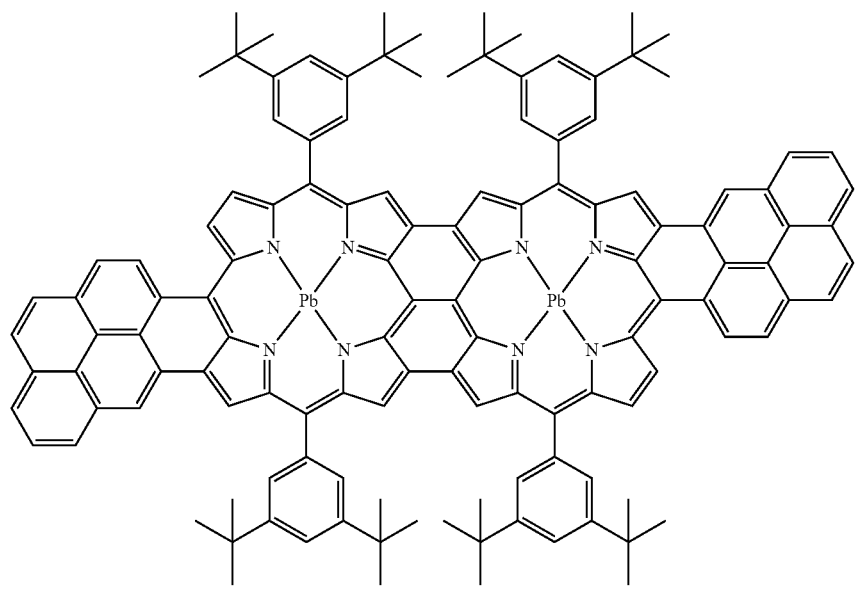
Compound 7
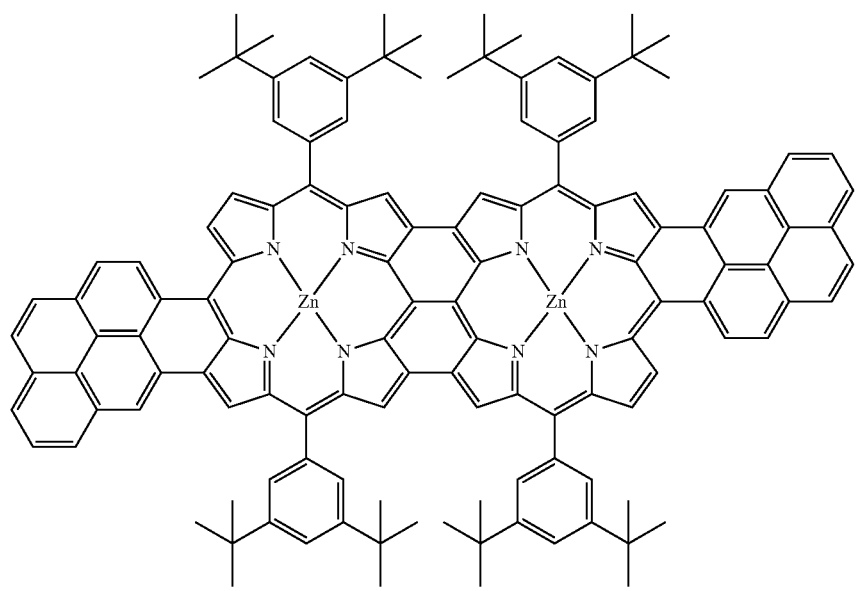
Compound 8
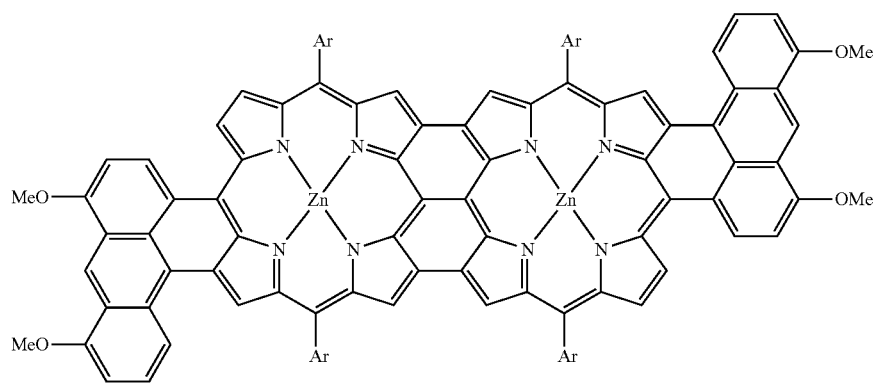

Compound 9

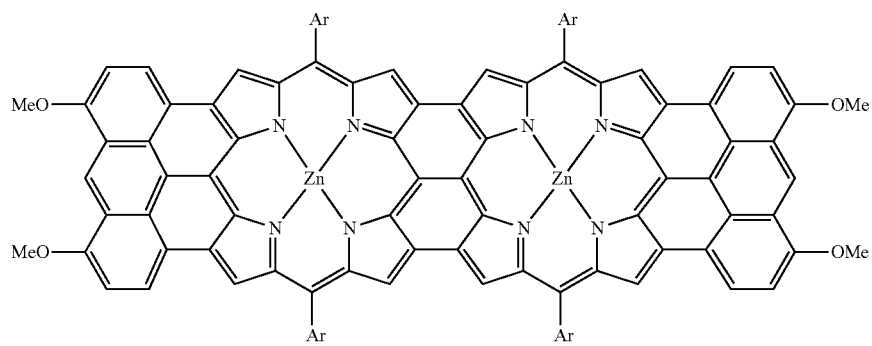

Compound 10

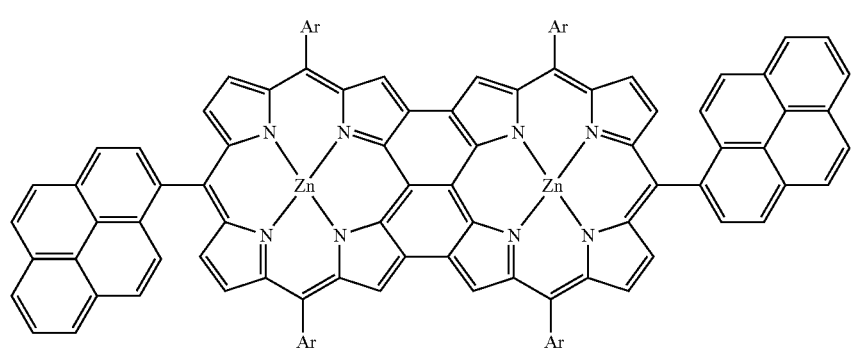

Compound 11

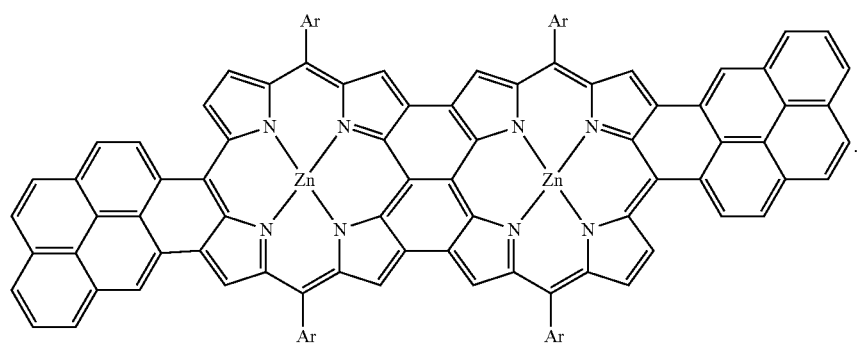

In yet another aspect, the device is a consumer product.

EXPERIMENTAL

Compound Examples

Example 1

Fusion of Pyrene Rings with Zinc Porphyrin Dimer. (See FIG. 12)

4,4,5,5-tetramethyl-2-(pyren-1-yl)-1,3,2-dioxaborolane. To a ca. 0.1 M solution of 1-bromopyrene in toluene 10 mol % of $Cl_2Pd(PPh_3)_2$, 5 equivalents of picolineborane and 10 equivalents of triethylamine was added. Reaction mixture was degassed with nitrogen and refluxed overnight. Reaction mixture was quenched with water, toluene was distilled off and the residue was subjected to column chromatography on silica gel (gradient elution with hexanes-ethyl acetate mixtures from 1:0 to 1000:5) to give 70-80% of 4,4,5,5-tetramethyl-2-(pyren-1-yl)-1,3,2-dioxaborolane. $^1$H-NMR ($CDCl_3$, 400 MHz): 1.51 (s, 12H), 8.02 (t, 1H, J=7.7 Hz), 8.07-8.24 (m, 6H), 8.56 (d, 1H, J=9.7 Hz), 9.09 (d, 1H, J=9.7 Hz). MALDI TOF: 328 (M+), requires 328.16 for $C_{22}H_{21}BO_2$.

Figure 12:
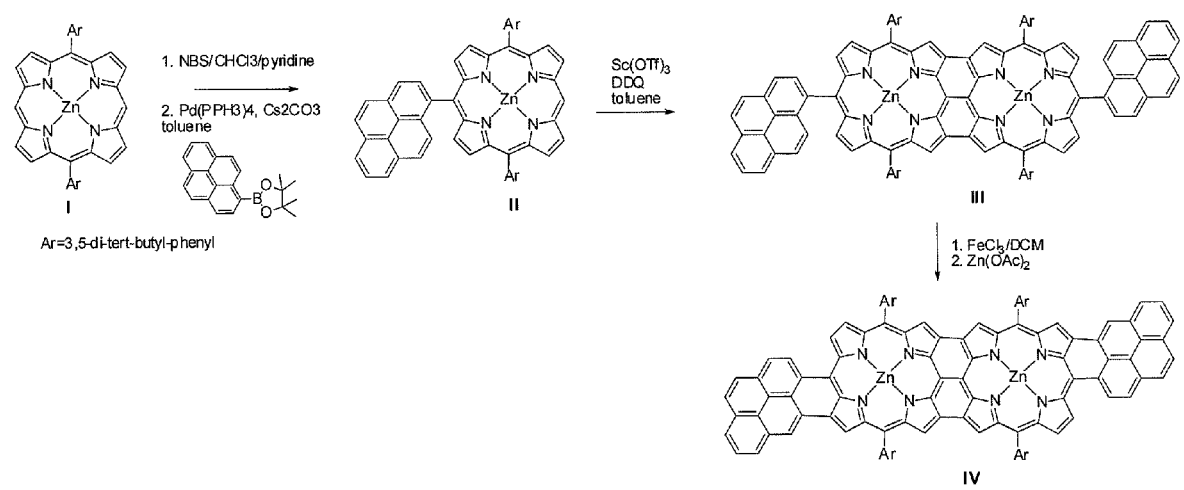
FIG. 12 shows the scheme for the synthesis of pyrene zinc porphyrin dimer and subsequent fusion of pyrene rings with porphyrin tape.

[10,20-Bis(3,5-di-tert-butylphenyl)-5-(1-pyrenyl)porphyrinato(2-)-κN[21],κN[22],κN[23],κN[24])zinc(II) (see FIG. 12). A) NBS (1.54 g, 8.7 mmol, 1.3 equiv.) was added to a stirred solution of porphyrin I (FIG. 12, compound I, 5 g, 6.7 mmol) in dichloromethane (300 mL) and pyridine (5 ml) at −10° C. (NaCl/ice bath) under nitrogen atmosphere. Reaction mixture was stirred at the same temperature for 10 min the was allowed to warm to 0° C. in 5 min (water bath) and was quenched with acetone (20 mL). Crude reaction mixture was passed through silica gel column, eluting with dichloromethane-pyridine mixture (100:1). All green-purple fractions were collected, solvents were evaporated, the residue was dissolved in dichloromethane-pyridine mixture (95:5, 100 mL) and 200 mL of methanol was added to precipitate brominated porphyrins. All crystals were collected by filtration after 30 min to give a mixture of mono and dibrominated porphyrins (ratio 2.3:1, 4.9 g, ca. 85%). This mixture was used for the next step without further separation. B) A mixture of the above mono and dibromoporphyrins (ratio of mono- to di-bromoporphyrins 2.3:1, 4 g, ca. 4.7 mmol), cesium carbonate (7.8 g, 24 mmol, 5 equiv.), Pd(PPh3)4 (271 mg, 5 mol %) and 1-pyrenyl-tetramethyldioxaborolane (2.32 g, 7.1 mmol) in toluene (700 mL) was degassed and reflux in nitrogen atmosphere for 12 h. Reaction mixture was cooled and passed consecutively through pad of celite, silica gel and neutral alumina washing with toluene. Toluene was distilled off in vacuum, the residue was separated by fractional crystallization from dichloromethane-methanol and column chromatography on silica gel eluting with mixture of hexanes and ethyl acetate to afford [10,20-Bis(3,5-di-tert-butylphenyl)-5-(1-pyrenyl)porphyrinato(2-)-$\kappa N^{21},\kappa N^{22},\kappa N^{23},\kappa N^{24}$] zinc(II) (see FIG. 12, compound II) 2.76 g, 2.9 mmol, 62%) and [10,20-Bis(3,5-di-tert-butylphenyl)-5,15-Bis(1-pyrenyl) porphyrinato(2-)-$\kappa N^{21},\kappa N^{22},\kappa N^{23},\kappa N^{24}$]zinc(II) (0.81 g, 0.71 mmol, 15%).

[10,20-Bis(3,5-di-tert-butylphenyl)-5-(1-pyrenyl)porphyrinato(2-)-$\kappa N^{21},\kappa N^{22},\kappa N^{23},\kappa N^{24}$]zinc(II) (see FIG. 12, compound II). $^1$H-NMR (CDCl$_3$, 400 MHz): 1.54 (s, 36H), 7.43 (d, 1H, J=9.3 Hz), 7.67 (d, 1H, J=9.3 Hz), 7.60 (s, 2H), 8.00-8.18 (m, 6H), 8.32 (t, 2H, J=7 Hz), 8.40 (d, 1H, J=9.1 Hz), 8.51 (d, 1H, J=7.7 Hz), 8.63 (d, 2H, J=4.6 Hz), 8.82 (d, 1H, J=7.7 Hz), 8.95 (d, 2H, J=4.6 Hz), 9.18 (d, 2H, J=4.5 Hz), 9.46 (d, 2H, J=4.5 Hz), 10.33 (s, 1H). MALDI TOF: 950 (M$^+$), requires 948.41 for C$_{64}$H$_{60}$N$_4$Zn.

[10,20-Bis(3,5-di-tert-butylphenyl)-5,15-Bis(1-pyrenyl) porphyrinato(2-)-$\kappa N^{21},\kappa N^{22},\kappa N^{23},\kappa N^{24}$]zinc(II). $^1$H-NMR (CDCl$_3$, 400 MHz): 1.47, 1.477 and 1.481 (s, 36H, rotamers), 7.50 (dd, 2H, J=9.3, 10.6 Hz), 7.71-7.74 (m, 4H, rotamers), 8.04-8.14 (m, 8H), 8.33 (t, 4H, J=7.2 Hz), 8.42 (d, 2H, J=9.1 Hz), 8.54 (d, 2H, J=7.7 Hz), 8.63 (dd, 4H, J=0.8, 4.7 Hz), 8.86 (dd, 2H, J=2.8, 7.7 Hz), 8.92 (d, 4H, J=4.7 Hz). MALDI TOF: 1150 (M$^+$), requires 1148.47 for C$_{80}$H$_{68}$N$_4$Zn.

{μ-[10,10'-Bis(1-pyrenyl)-5,5',15,15'-tetrakis(3,5-di-tert-butylphenyl)-18,18',20,20'-dicyclo-2,2'-biporphyrinato(4-)-$\kappa N^{21},\kappa N^{22},\kappa N^{23},\kappa N^{24}$, $\kappa N^{21'},\kappa N^{22'},\kappa N^{23'},\kappa N^{24'}$]}dizinc(II) (see FIG. 12, compound III). Porphyrin II (160 mg, 0.17 mmol), DDQ (191 mg, 0.82 mmol, 5 equiv.) and scandium (III) triflate (414 mg, 0.82 mmol, 5 equiv.) were dissolved in toluene (300 mL) under nitrogen atmosphere and the mixture was stirred at room temperature for 1 hour and heated at reflux for additional 2 h. After cooling to room temperature the mixture was passed consecutively through pad with silica gel (2 times) and pad with alumina (eluation with dichloromethane-pyridine mixture 100:1). Solvents were evaporated in vacuum, the residue was dissolved in dichloromethane-pyridine mixture (30 mL, 100:1) and the product was precipitated by addition of 200 mL of methanol. Yield 110 mg (0.058 mmol, 68%). $^1$H-NMR (5% pyridine-d$_5$ in CDCl$_3$, 400 MHz): 1.33 (s, 72H), 7.06 (s, 4H), 7.10 (d, 4H, J=4.5 Hz), 7.38 (d, 4H, J=4.5 Hz), 7.47-7.61 (m, 12H), 7.67 (t, 2H, J=9 Hz), 7.93 (t, 2H, J=8 Hz), 8.01 (d, 2H, J=7 Hz), 8.10 (d, 2H, J=9 Hz), 8.16 (d, 4H, J=8 Hz), 8.25 (d, 2H, J=7 Hz), 8.31 (t, 2H, J=8 Hz), 8.53 (s, 2H). $^{13}$C-NMR (5% pyridine-d$_5$ in CDCl$_3$, 75 MHz): 31.4, 34.6, 105.6, 117.8, 120.3, 122.1, 122.5, 124.1, 124.5, 124.8, 125.1, 125.9, 126.6, 126.7, 127.1, 127.4, 128.0, 128.1, 130.3, 130.6, 130.7, 131.0, 131.3, 131.9, 135.8, 136.9, 140.3, 148.2, 153.1, 153.36, 153, 44, 154.3. MALDI TOF: 1894.5 (M$^+$), requires 1895.77 for C$_{128}$H$_{114}$N$_8$Zn$_2$.

Figure 13:
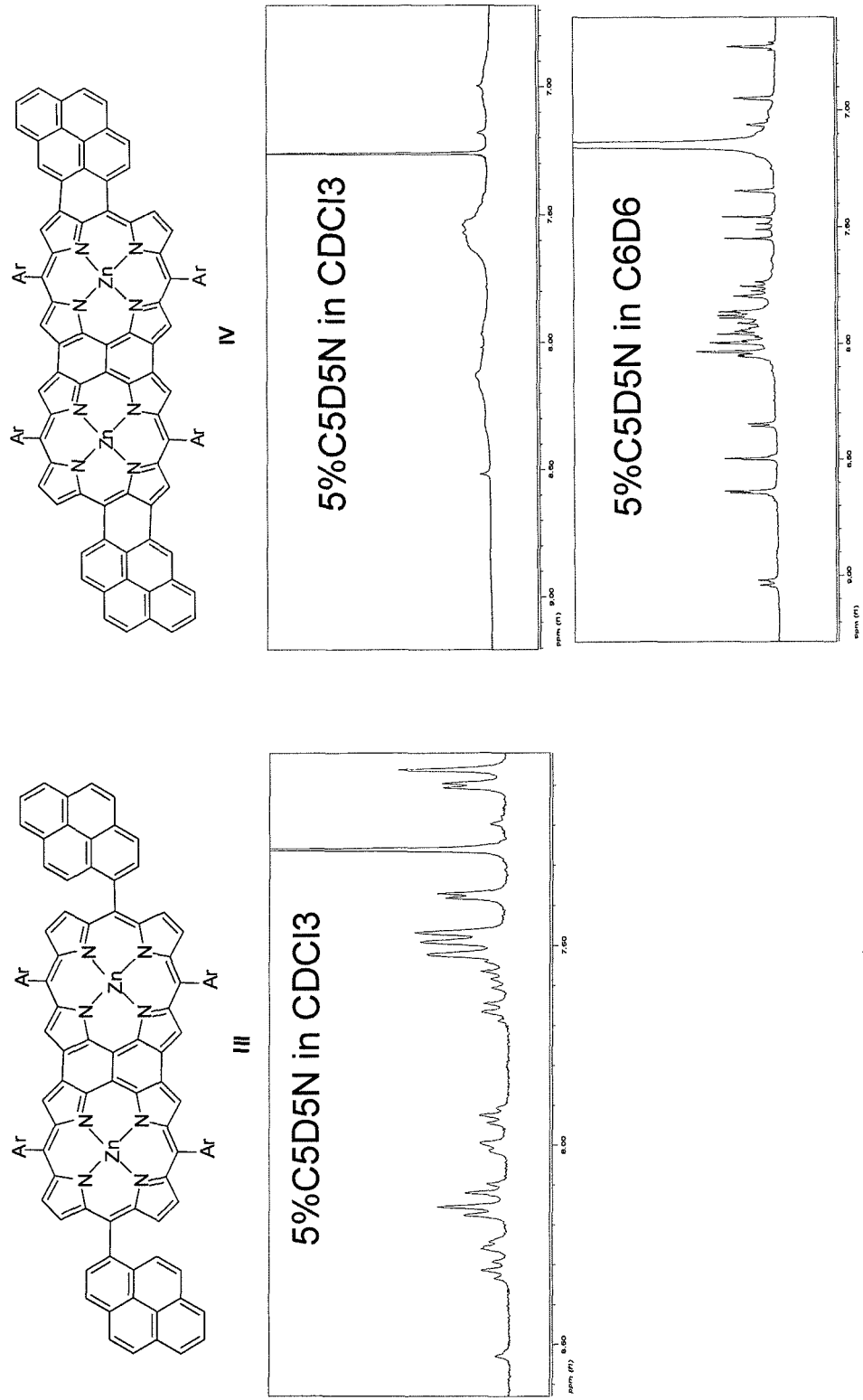
FIG. 13 shows the pronounced effect of aggregation in solution for fused product in comparison to starting porphyrin dimer is shown. $^1$H-NMR spectra for pyrene porphyrin dimer and porphyrin dimer with fused pyrene rings are shown in 5% pyridine-$d_5$/$CDCl_3$ (top) and in 5% pyridine-$d_5$/$C_6D_6$ (fused pyrene dimer, bottom).

{μ-[9,10,9'10'-Bis(1,10-pyrenyl)-5,5',15,15'-tetrakis(3,5-di-tert-butylphenyl)-18,18',20,20'-dicyclo-2,2'-biporphyrinato(4-)-$\kappa N^{21},\kappa N^{22},\kappa N^{23},\kappa N^{24},\kappa N^{21'},\kappa N^{22'},\kappa N^{23'},\kappa N^{24'}$]}dizinc(II) (see FIG. 12, compound IV). Zinc porphyrin dimer III (65 mg, 0.034 mmol) and anhydrous iron(III) chloride (120 mg, 0.74 mmol, ca. 20 equiv.) were stirred in anhydrous dichloromethane (50 mL) under nitrogen atmosphere for 2 h. Reaction mixture was quenched with pyridine (2 mL), washed with water and passed consecutively through pad with silica gel and neutral alumina eluting with dichloromethane to give solution of the crude free base fused porphyrin dimer (MALDI TOF: 1763 (M$^+$), requires 1764). Solution of zinc(II) acetate dihydrate (200 mg) in methanol (10 mL) was added to the solution of free-base dimer and the mixture was stirred for 2 h at room temperature. Reaction mixture was washed with water, passed consecutively through pad with silica gel and neutral alumina eluting with dichloromethane. The residue after evaporation of dichloromethane in vacuum was dissolved in dichloromethane (10 mL) and the product was precipitated by addition of methanol (100 mL). Yield 40-50 mg (62-77%). Fused pyrene-porphyrin dimer IV exhibits increased p-p stacking even in solution, so that $^1$H-NMR spectrum in 5% solution of pyridine-d$_5$ in CDCl$_3$ or CD$_2$Cl$_2$ consists of very broad signals in aromatic region and only broad signals of tert-butyl groups can be identified (see FIG. 13). However, aggregation can be avoided by using 5% solution of pyridine-d$_5$ in benzene-d$_6$ (see FIG. 13). $^1$H-NMR (5% pyridine-d$_5$ in CDCl$_3$, 400 MHz): tert-butyl protons 1.18 (s, 36H), 1.41 and 1.45 (s, 36H), aromatic protons as broad singlets 6.95, 7.00, 7.04, 7.54, 7.57, 7.60, 7.97, 8.13, 8.32. $^1$H-NMR (5% pyridine-d$_5$ in benzene-d$_6$, 400 MHz): some aromatic signals are overlapping with signal of benzene, 1.32 (s, 36H), 1.45 and 1.47 (s, 36H), 6.73 (s, 2H), 7.46-7.55 (m, 6H), 7.74-8.06 (m, 20H), 8.35 (d, 2H, J=4.5 Hz), 8.50 (s, 2H), 8.64 (d, 4H, J=2.7 Hz), 9.03 (d, 2H, J=8.3 Hz). MALDI TOF: 1890.1 (M$^+$), requires 1889.74 for C$_{128}$H$_{110}$N$_8$Zn$_2$.

Example 2

Double Fusion of 1-Substituted Anthracene Rings with Zinc Porphyrin Dimer. (See FIG. 14, Compound VI)

2-(4,5-dimethoxyanthracen-1-yl)-4,4,5,5-tetramethyl-1,3,2-dioxaborolane and 2-(4,5-dimethoxyanthracen-9-yl)-4,4,5,5-tetramethyl-1,3,2-dioxaborolane. To a solution of a mixture of 1-bromo- and 9-bromo-4,5-dimethoxyanthracenes (ratio of 1- and 9-bromo-isomers 3:1, 7.0 g, 22.1 mmol) in toluene (300 mL) 7 mol % of Cl$_2$Pd(PPh$_3$)$_2$ (1 g, 1.54 mmol), 5 equivalents of picolineborane and 10 equivalents of triethylamine was added. Reaction mixture was degassed with nitrogen and refluxed overnight. Reaction mixture was quenched with water, toluene was distilled off and the residue was subjected to column chromatography on silica gel (gradient eluation with hexanes-ethyl acetate mixtures from 1:0 to 1000:5) to give 2-(4,5-dimethoxyanthracen-1-yl)-4,4,5,5-tetramethyl-1,3,2-dioxaborolane (2.3 g, 6.3 mmol, 29%) and 2-(4,5-dimethoxyanthracen-9-yl)-4,4,5,5-tetramethyl-1,3,2-dioxaborolane (0.5 g, 1.4 mmol, 6.2%).

2-(4,5-dimethoxyanthracen-1-yl)-4,4,5,5-tetramethyl-1,3,2-dioxaborolane. $^1$H-NMR (CDCl$_3$, 250 MHz): 1.42 (s, 12H), 4.01 (s, 3H), 4.02 (s, 3H), 6.68 (dd, 2H, J=9.0, 8.0 Hz), 7.34 (t, 1H, J=9 Hz), 7.64 (d, 1H, J=9 Hz), 8.06 (d, 1H, J=8 Hz), 9.26 (s, 1H), 9.28 (s, 1H). MALDI TOF: 364 (M$^+$), requires 364.18 for C$_{22}$H$_{25}$BO$_4$.

2-(4,5-dimethoxyanthracen-9-yl)-4,4,5,5-tetramethyl-1,3,2-dioxaborolane. $^1$H-NMR (CDCl$_3$, 250 MHz): 1.54 (s, 12H), 4.03 (s, 6H), 6.68 (d, 2H, J=8 Hz), 7.37 (dd, 2H, J=8.0, 9.0 Hz), 7.93 (d, 2H, J=9 Hz), 9.37 (s, 1H). MALDI TOF: 364 (M$^+$), requires 364.18 for C$_{22}$H$_{25}$BO$_4$.

Figure 11:
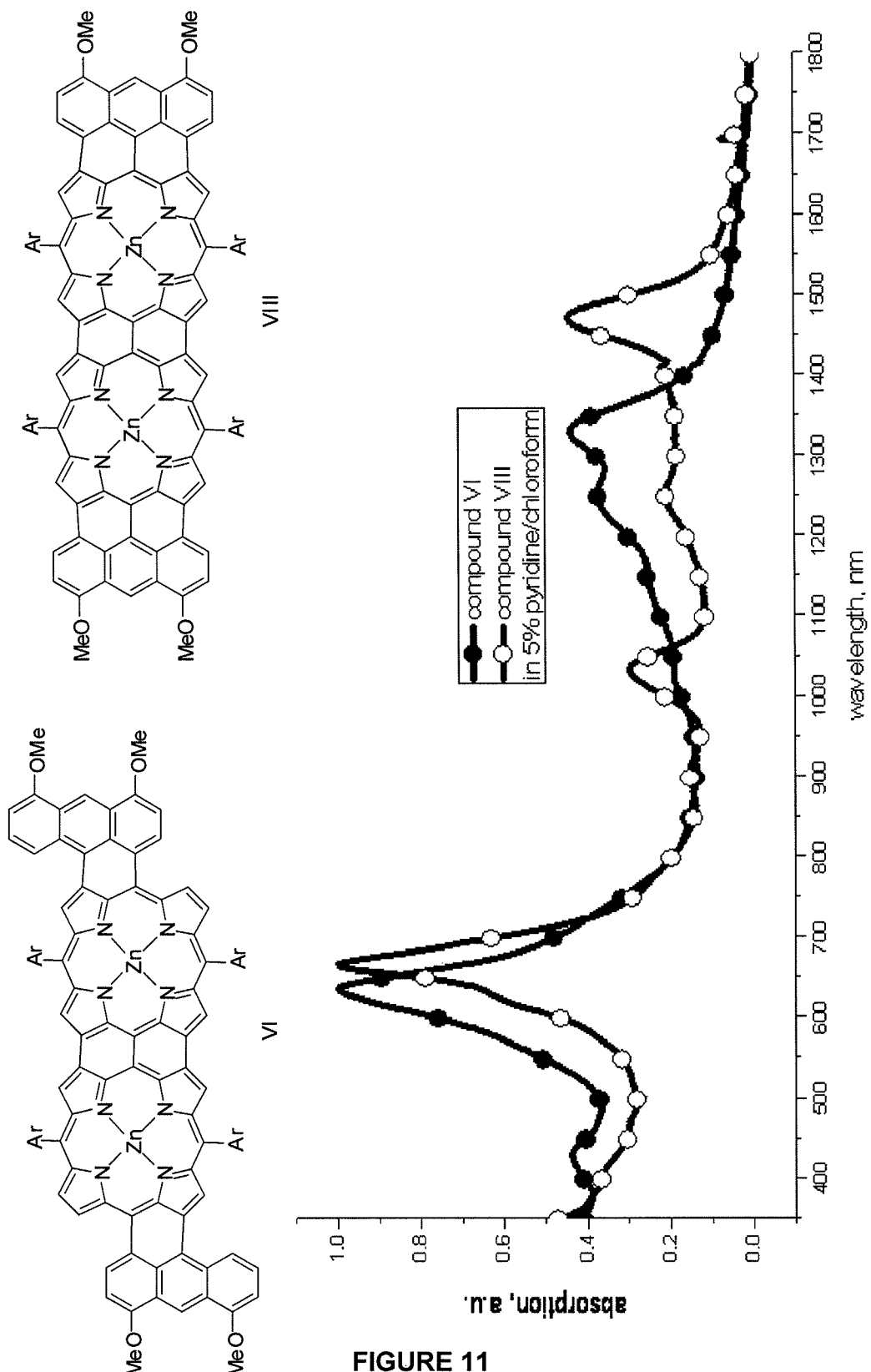
FIG. 11 Absorption spectra of anthracene fused porphyrin dimers.
Figure 14:
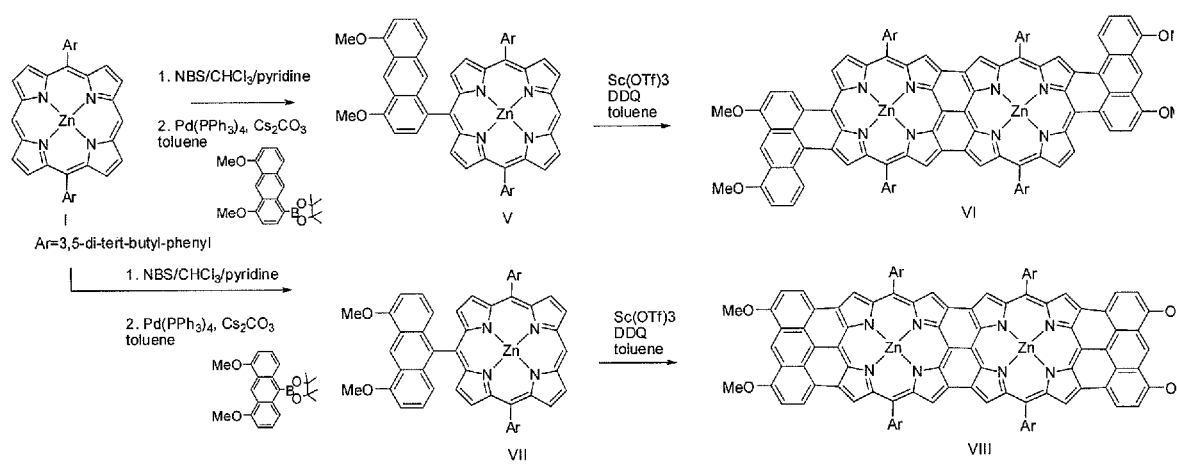
FIG. 14 shows the scheme for the synthesis of fused anthracene zinc porphyrin dimers.

[10,20-Bis(3,5-di-tert-butylphenyl)-5-(4,5-dimethoxyanthracen-1-yl)porphyrinato(2-)-κN$^{21}$,κN$^{22}$,κN$^{23}$,κN$^{24}$)zinc(II) (see FIG. 14, compound V). A mixture of the above mono and dibromoporphyrins (ratio of mono- to di-bromoporphyrins 10:1, 1.38 g, ca. 1.78 mmol), cesium carbonate (3 g, 8.9 mmol, 5 equiv.), Pd(PPh$_3$)$_4$ (620 mg, 30 mol %) and dimethoxyanthracen-1-yl-tetramethyldioxaborolane (0.95 g, 2.67 mmol, 1.5 equiv.) in toluene (500 ml) was degassed and reflux in nitrogen atmosphere for 2 h. Reaction mixture was cooled and passed consecutively through pad of celite, silica gel and neutral alumina washing with toluene. Toluene was distilled off in vacuum, the residue was separated by fractional crystallization from dichloromethane-methanol and column chromatography on silica gel eluting with mixture of hexanes and ethyl acetate to afford [10,20-Bis(3,5-di-tert-butylphenyl)-5-(4,5-dimethoxyanthracen-1-yl)porphyrinato(2-)-κN$^{21}$,κN$^{22}$,κN$^{23}$,κN$^{24}$)zinc(II) (FIG. 11, compound V) 1.35 g, 1.37 mmol, 77%) and [10,20-Bis(3,5-di-tert-butylphenyl)-5,15-Bis(4,5-dimethoxyanthracen-1-yl)porphyrinato(2-)-κN$^{21}$,κN$^{22}$,κN$^{23}$,κN$^{24}$)zinc(II).

[10,20-Bis(3,5-di-tert-butylphenyl)-5-(4,5-dimethoxyanthracen-1-yl)porphyrinato(2-)-κN$^{21}$,κN$^{22}$,κN$^{23}$,κN$^{24}$)zinc(II) (see FIG. 14, compound V). $^1$H-NMR (5% pyridine-d$_5$ in CDCl$_3$, 400 MHz): 1.50 (d, 36H, J=1 Hz), 4.05 (s, 3H), 4.33 (s, 3H), 6.39 (d, 1H, J=8.8 Hz), 6.47 (d, 1H, J=7.1 Hz), 6.91 (dd, 1H, J=7.1, 8.8 Hz), 7.36 (s, 1H), 7.74 (t, 2H, J=2 Hz), 8.02 (t, 2H, J=2 Hz), 8.10 (t, 2H, J=2 Hz), 8.14 (d, 1H, J=8 Hz), 8.68 (d, 2H, J=4.6 Hz), 8.82 (d, 2H, J=4.6 Hz), 9.06 (d, 2H, J=4.5 Hz), 9.33 (d, 2H, J=4.5 Hz), 9.49 (s, 1H), 10.14 (s, 1H). $^{13}$C-NMR (5% pyridine-d$_5$ in CDCl$_3$, 75 MHz): 31.0, 33.00, 33.02, 36.2, 56.1, 56.3, 100.0, 100.7, 104.6, 114.1, 116.6, 118.9, 119.1, 119.9, 122.4, 122.5, 123.7, 126.4, 128.3, 128.5, 129.5, 129.9, 130.4, 130.5, 130.7, 130.9, 131.4, 135.5, 140.4, 146.1, 146.2, 147.4, 148.0, 148.2, 148.7, 153.5, 153.6. MALDI TOF: 985.6 (M$^+$), requires 984.43 for C$_{64}$H$_{64}$N$_4$O$_2$Zn.

{μ-[10,10'-Bis(4,5-dimethoxyanthracen-1,9-yl)-5,5',15,15'-tetrakis(3,5-di-tert-butylphenyl)-18,18',20,20'-dicyclo-2,2'-biporphyrinato(4-)-κN$^{21}$,κN$^{22}$,κN$^{23}$,κN$^{24}$, κN$^{21'}$,κN$^{22'}$,κN$^{23'}$,κN$^{24'}$]}zinc(II) (see FIG. 14, compound VI). Porphyrin V (50 mg, 0.051 mmol), DDQ (115 mg, 0.51 mmol, 10 equiv.) and scandium(III) triflate (249 mg, 0.51 mmol, 10 equiv.) were dissolved in toluene (50 mL) under nitrogen atmosphere and the mixture was stirred at room temperature for 1 h and heated at reflux for additional 8 h. After cooling to room temperature the mixture was passed consecutively through pad with silica gel (2 times) and pad with alumina (eluation with dichloromethane-pyridine mixture 100:1). Solvents were evaporated in vacuum, the residue was dissolved in dichloromethane-pyridine mixture (30 ml, 100:1) and the product was precipitated by addition of 200 mL of methanol. Yield 47 mg (0.23 mmol, 94%). Fused anthracene-porphyrin dimer VI exhibits increased aggregation in solution, so that $^1$H-NMR spectrum in 5% solution of pyridine-d$_5$ in CDCl$_3$ consists of broad signals in aromatic region and only broad signals of tert-butyl groups can be identified. $^1$H-NMR (5% pyridine-d$_5$ in CDCl$_3$, 400 MHz): tert-butyl protons 1.43, 1.44 and 1.47 (s, 72H), broad singlets of methoxy group 3.97, 4.08 and 4.17, aromatic protons as broad signals 6.60 (m), 6.67 (d, J=8 Hz), 6.78 (d, J=7 Hz), 6.85 (s), 6.99 (t, J=9 Hz), 7.04 (s), 7.07 (d, J=8 Hz), 7.12 (d, J=9 Hz), 7.49 (s), 7.67 (s). $^{13}$C-NMR (5% pyridine-d$_5$ in CDCl$_3$, 75 MHz): 29.3, 31.1 (broad), 34.6 (broad), 52.2 (broad), 55.3 (broad), 122.2, 123.1, 123.2, 123.3, 125.5, 125.53, 126.0, 127.2, 127.7, 127.74, 127.9, 128.0, 128.3, 128.4, 128.5, 128.7, 129.8, 134.5, 135.5, 137.6, 138.5. MALDI TOF: 1963 (M$^+$), requires 1963.78 for C$_{128}$H$_{118}$N$_8$O$_4$Zn$_2$. Absorption spectrum can be seen in FIG. 11.

Example 3

Triple Fusion of 9-Substituted Anthracene Rings with Zinc Porphyrin Dimer. (See FIG. 14, Compound VIII)

[10,20-Bis(3,5-di-tert-butylphenyl)-5-(4,5-dimethoxyanthracen-9-yl)porphyrinato(2-)-κN$^{21}$,κN$^{22}$,κN$^{23}$,κN$^{24}$)zinc(II) (see FIG. 14, Compound VII). A) NBS (3.6 g, 20 mmol, 2.3 equiv.) was added to a stirred solution of porphyrin I (see FIG. 12, compound 1.5 g, 6.7 mmol) in dichloromethane (300 mL) and pyridine (5 mL) at −10° C. (NaCl/ice bath) under nitrogen atmosphere. Reaction mixture was stirred at the same temperature for 10 min the was allowed to warm to 0° C. in 5 min (water bath) and was quenched with acetone (20 mL). Crude reaction mixture was passed through silica gel column, eluting with dichloromethane-pyridine mixture (100:1). All green-purple fractions were collected, solvents were evaporated, the residue was dissolved in dichloromethane-pyridine mixture (95:5, 100 mL) and 200 mL of methanol was added to precipitate brominated porphyrins. All crystals were collected by filtration after 30 min to give dibrominated porphyrin (4.6 g, 5.03 mmol, 75%). B) The above dibromoporphyrin (0.82 g, 0.9 mmol), cesium carbonate (1.64 g, 5 mmol, 5.6 equiv.), Pd(PPh$_3$)$_4$ (205 mg, 20 mol %) and dimethoxyanthracen-9-yl-tetramethyldioxaborolane (0.49 g, 1.35 mmol, 1.5 equiv.) in toluene (400 mL) was degassed and heated to reflux for 10 min. After that Pd$_2$(dba)$_3$ (164 mg, 20 mol %) and tri-tert-butylphosphine (4 ml of 10% wt solution in hexanes) were added and reaction mixture continued to reflux in nitrogen atmosphere for 2 h. Reaction mixture was cooled and passed consecutively through pad of celite, silica gel and neutral alumina washing with toluene. Toluene was distilled off in vacuum, the residue was separated by fractional crystallization from dichloromethane-methanol and column chromatography on silica gel eluting with mixture of hexanes and ethyl acetate to afford [10,20-

Bis(3,5-di-tert-butylphenyl)-5-(4,5-dimethoxyanthracen-9-yl)porphyrinato(2-)-$\kappa N^{21},\kappa N^{22},\kappa N^{23},\kappa N^{24}$)zinc(II) (see FIG. 14, compound VII) 127 mg, 0.13 mmol, 14%). $^1$H-NMR (5% pyridine-$d_5$ in CDCl$_3$, 400 MHz): 1.48 (s, 36H), 4.16 (s, 6H), 6.39 (d, 2H, J=9 Hz), 6.62 (d, 2H, J=7 Hz), 6.73 (dd, 2H, J=7, 9 Hz), 7.71 (t, 2H, J=2 Hz), 8.03 (d, 4H, J=2 Hz), 8.24 (d, 2H, J=4.6 Hz), 8.74 (d, 2H, J=4.6 Hz), 9.04 (d, 2H, J=4.4 Hz), 9.32 (d, 2H, J=4.4 Hz), 9.73 (s, 1H), 10.15 (s, 1H). $^{13}$C-NMR (5% pyridine-$d_5$ in CDCl$_3$, 75 MHz): 31.7, 34.9, 55.6, 100.8, 105.6, 115.9, 116.3, 120.3, 121.2, 121.3, 123.6, 123.7, 125.1, 129.9, 131.1, 131.3, 132.3, 132.4, 135.8, 136.2, 136.8, 142.2, 148.1, 149.4, 149.7, 149.9, 150.4, 150.7, 155.7. MALDI TOF: 985 (M$^+$), requires 984.43 for $C_{64}H_{64}N_4O_2Zn$.

{μ-[10,10'-Bis(4,5-dimethoxyanthracen-1,8,9-yl)-5,5',15,15'-tetrakis(3,5-di-tert-butylphenyl)-18,18',20,20'-dicyclo-2,2'-biporphyrinato(4-)-$\kappa N^{21},\kappa N^{22},\kappa N^{23},\kappa N^{24}, \kappa N^{21'},\kappa N^{22'}, \kappa N^{23'},\kappa N^{24'}$]}dizinc(II) (see FIG. 14, compound VI). Porphyrin VII (20 mg, 0.051 mmol), DDQ (36 mg, 0.16 mmol, 8 equiv.) and scandium(III) triflate (79 mg, 0.16 mmol, 8 equiv.) were dissolved in toluene (20 mL) under nitrogen atmosphere and the mixture was stirred at room temperature for 1 h and heated at reflux for additional 8 h. After cooling to room temperature the mixture was passed consecutively through pad with silica gel (2 times) and pad with alumina (eluation with dichloromethane-pyridine mixture 100:1). Yield 19 mg (quant.). Fused anthracene-porphyrin dimer VIII exhibits increased aggregation in solution, so that $^1$H-NMR spectrum in 5% solution of pyridine-$d_5$ in CDCl$_3$ consists of broad signals in aromatic region and could not be resolved. MALDI TOF: 1959 (M$^+$), requires 1957.75 for $C_{128}H_{114}N_8O_4Zn_2$. Absorption spectrum can be seen in FIG. 11.

Example 4
Double Fusion of 3-Substituted Benzothienyl Rings with Zinc Porphyrin Dimer

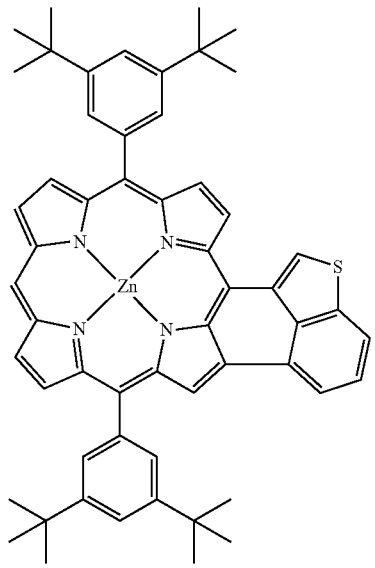

[10,20-Bis(3,5-di-tert-butylphenyl)-5-(3-benzothienyl) porphyrinato(2-)-$\kappa N^{21},\kappa N^{22}, \kappa N^{23},\kappa N^{24}$)zinc(II). A mixture of the above mono and dibromoporphyrins (ratio of mono- to di-bromoporphyrins 6:4, 1.0 g, ca. 1.1 mmol), cesium carbonate (3 g, 8.9 mmol), Pd(PPh$_3$)$_4$ (120 mg, 10 mol %), pyridine (4 mL) water (2 mL) and 3-benzothienylboronic acid (0.39 g, 2.2 mmol, 2 equiv.) in toluene (400 mL) was degassed and reflux in nitrogen atmosphere for 7 h. Reaction mixture was cooled and passed consecutively through pad of celite, silica gel and neutral alumina washing with toluene. Toluene was distilled off in vacuum, the residue was crystallized by addition of methanol to dichloromethane solution. Yield of mono and bis-substituted 3-benzothienyl porphyrins 1 g, used for the next step without further purification.

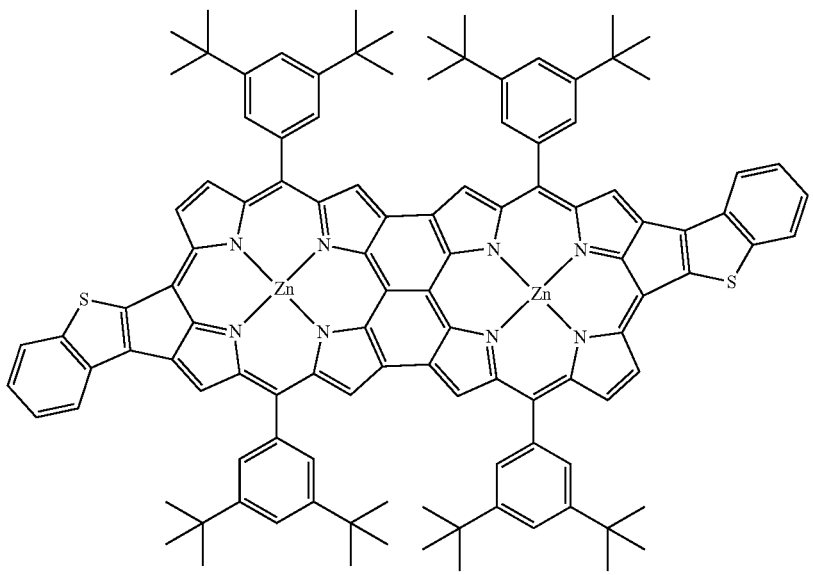

{μ-[9,10,9',10'-Bis(2,3-benzothienyl)-5,5',15,15'-tetrakis(3,5-di-tert-butylphenyl)-18,18',20,20'-dicyclo-2,2'-biporphyrinato(4-)-κN$^{21}$, κN$^{22}$, κN$^{23}$, κN$^{24}$, κN$^{21'}$, κN$^{22'}$, κN$^{23'}$, κN$^{24'}$]}dizinc(II). A mixture of above benzothienyl-substituted porphyrins (1.0 g, 0.68 mmol), DDQ (770 mg, 3.4 mmol, 5 equiv.) and scandium(III) triflate (1670 mg, 3.4 mmol, 5 equiv.) were dissolved in toluene (500 mL) under nitrogen atmosphere and the mixture was stirred at room temperature for 1 h and heated at reflux for additional 1 h. After cooling to room temperature the mixture was subjected to column chromatography eluting with a mixture of hexanes-dichloromethane-pyridine. Solvents were evaporated in vacuum, the residue was dissolved in dichloromethane-pyridine mixture (30 mL, 100:1) and the product was precipitated by addition of 200 mL of methanol. Yield 170 mg (0.1 mmol, 15%). Fused anthracene-porphyrin dimer VI exhibits increased aggregation in solution, so that $^1$H-NMR spectrum in 5% solution of pyridine-d5 in CDCl$_3$ consists of broad signals in aromatic region and only broad signals of tert-butyl groups can be identified. UV/VIS (2% C$_5$H$_5$N in CH$_2$Cl$_2$) λ, nm: 1485, 1186, 768, 670, 617, 433. (MALDI TOF: 1833.3 (M$^+$), requires 1832.67 (100%) for C$_{128}$H$_{118}$N$_8$O$_4$Zn$_2$*C$_5$H$_5$N.

conc. hydrochloric acid (0.2 mL) was added and the reaction mixture was vigorously stirred for 1 min. Reaction mixture was quenched with pyridine (0.5 mL), washed with water and passed consecutively through pad with silica gel and neutral alumina eluting with dichloromethane to give solution of the free base fused porphyrin dimer (MALDI TOF (100% int): 1763 (M+), requires 1764). Solution of lead(II) acetate trihydrate (100 mg) in pyridine (4 mL) was added to the solution of free-base dimer and the mixture was heated to reflux for 3 h. After that the reaction mixture was cooled to room temperature and passed consecutively through pad with silica gel and neutral alumina eluting with dichloromethane. The residue after evaporation of solvents in vacuum was dissolved in dichloromethane (1 mL) and the product was precipitated by addition of methanol (10 mL). Yield 43 mg (0.020 mmol, 76%). $^1$H-NMR (5% pyridine-d$_5$ in benzene-d$_6$, 400 MHz, recorded at 75° C.) consists of broad signals due to: 1.33 (br. s, 36H), 1.53 (br. s, 36H), 7.04 (br. t, 2H, J=4.5 Hz), 7.63 (br.

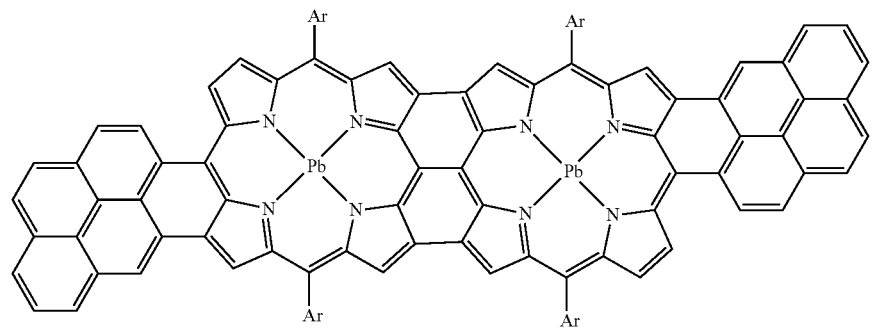

{μ-[9,10,9',10'-Bis(1,10-pyrenyl)-5,5',15,15'-tetrakis(3,5-di-tert-butylphenyl)-18,18',20,20'-dicyclo-2,2'-biporphyrinato(4-)-κN$^{21}$,κN$^{22}$,κN$^{23}$,κN$^{24}$, κN$^{21'}$,κN$^{22'}$,κN$^{23'}$, κN$^{24'}$]}dilead(II). Fully fused zinc porphyrin dimer III (50 mg, 0.026 mmol) was dissolved in dichloromethane (10 mL), t, 2H, J=4.5 Hz), 7.69-8.23 (m), 8.57 (br. s, 2H), 8.92 (br. s, 2H). MALDI TOF (100% int): 2174.73 (M+), requires 2175.84 for C$_{128}$H$_{110}$N$_8$Pb$_2$. UV/VIS NIR (1% C$_5$H$_5$N in CH$_2$Cl$_2$), λ (ε): 1459 (63583), 1241 (26596), 634 (141820), 476 (33718), 426 (36312).

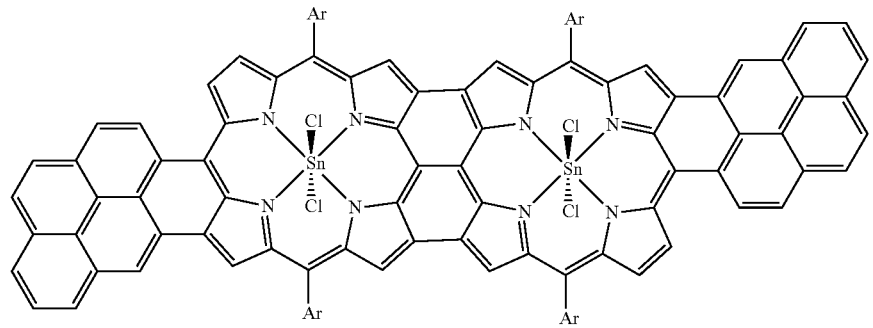

{μ-[9,10,9'10'-Bis(1,10-pyrenyl)-5,5',15,15'-tetrakis(3,5-di-tert-butylphenyl)-18,18',20,20'-dicyclo-2,2'-biporphyrinato(4-)-$\kappa N^{21},\kappa N^{22},\kappa N^{23},\kappa N^{24}$, $\kappa N^{21'},\kappa N^{22'},\kappa N^{23'}$, $\kappa N^{24'}$] }tetrachloroditin(II). Fully fused zinc porphyrin dimer III (50 mg, 0.026 mmol) was dissolved in dichloromethane (10 mL), conc. hydrochloric acid (0.2 mL) was added and the reaction mixture was vigorously stirred for 1 min. Reaction mixture was quenched with pyridine (0.5 mL), washed with water and passed consecutively through pad with silica gel and neutral alumina eluting with dichloromethane to give solution of the free base fused porphyrin dimer (MALDI TOF (100% int): 1763 (M+), requires 1764). Solution of tin(II) chloride trihydrate (200 mg) in pyridine (5 mL) was added to the solution of free-base dimer in chloroform (100 mL) and the mixture was heated to reflux for 2 h. After that the reaction mixture was cooled to room temperature, washed with water (100 mL) and passed consecutively through pad with silica gel eluting with dichloromethane. The residue after evaporation of solvents in vacuum was dissolved in dichloromethane (10 mL) and the product was precipitated by addition of methanol (50 mL). Yield 35 mg (0.016 mmol, 63%). $^1$H-NMR (5% pyridine-$d_5$ in benzene-$d_6$, 400 MHz, recorded at 75° C.) consists of broad signals due to aggregation. MALDI TOF (100% int): 2066.9 (100%, M+-2Cl), 2139.1 (M+), requires 2067.63 for $C_{128}H_{110}N_8Sn2Cl_2$ (M−2Cl), 2139.57 for $C_{128}H_{110}N_8Sn_2Cl_4$(M+).

Device Examples

While few examples have been demonstrated, near-infrared (NIR) organic photodetectors with response at wavelengths ($\lambda$) beyond the cutoff of Si (i.e. $\lambda$>1100 nm) are interesting for use in imaging and other detection applications. (A. Rogalski, *Infrared Physics & Technology* 2002, 43, 187). In previous work, polymer photodetectors with response at $\lambda$>1000 nm have been demonstrated, but the optical sensitivity is generally due to a long absorption tail having an external quantum efficiency (EQE) less than a few percent. (Y. J. Xia, L. Wang, X. Y. Deng, D. Y. Li, X. H. Zhu, Y. Cao, *Applied Physics Letters* 2006, 89; L. Wen, B. C. Duck, P. C. Dastoor, S. C. Rasmussen, *Macromolecules* 2008, 41, 4576; and E. Perzon, F. L. Zhang, M. Andersson, W. Mammo, O. Inganas, M. R. Andersson, *Advanced Materials* 2007, 19, 3308). Organic materials systems with a large NIR photoresponse are rare for several reasons. A type-II (staggered) heterojunction must be formed between the donor and acceptor materials with a sufficient energy offset to dissociate photogenerated excitons; as the energy-gap is decreased, finding molecular combinations with suitable energy alignments becomes increasingly difficult. In addition, exciton lifetimes generally decrease with energy gap due to exciton-phonon induced recombination (i.e. internal conversion). (H. S. Cho, D. H. Jeong, S. Cho, D. Kim, Y. Matsuzaki, K. Tanaka, A. Tsuda, A. Osuka, *Journal of the American Chemical Society* 2002, 124, 14642; D. Tittelbachhelmrich, R. P. Steer, *Chemical Physics* 1995, 197, 99). These difficulties have motivated the development of hybrid organic-inorganic devices using polymeric and small-molecule materials in conjunction with II-VI quantum dots (with EQE<1% at $\lambda$>1000 nm) (X. M. Jiang, R. D. Schaller, S. B. Lee, J. M. Pietryga, V. I. Klimov, A. A. Zakhidov, *Journal of Materials Research* 2007, 22, 2204) or single walled carbon nanotubes (EQE≈2% at $\lambda$=1150 and 1300 nm) (M. S. Arnold, J. D. Zimmerman, C. K. Renshaw, X. Xu, R. R. Lunt, C. M. Austin, S. R. Forrest, *Nano Letters* 2009, 9, 3354). Here, we demonstrate a NIR having EQE≈6.5% at $\lambda$=1350 nm using photodetectors based on triplylinked porphyrin-tape dimers. These porphyrin tapes are representative of a promising new class of materials that can be modified to exhibit even longer wavelength response by spatially extending the conjugation of the electron system (H. S. Cho, D. H. Jeong, S. Cho, D. Kim, Y. Matsuzaki, K. Tanaka, A. Tsuda, A. Osuka, *Journal of the American Chemical Society* 2002, 124, 14642).

Figure 4:
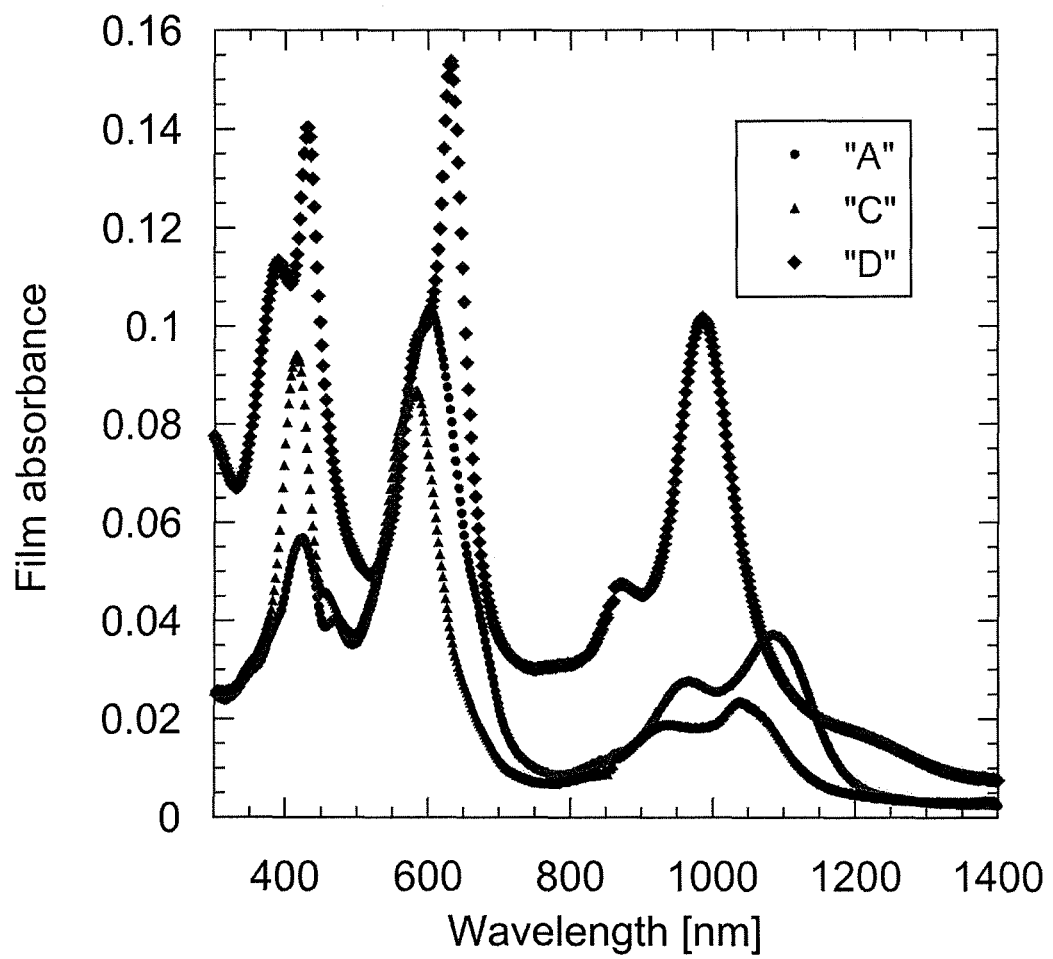
FIG. 4 shows film absorbance of A, C, and D (see FIG. 3). Various changes to the end substitutions has little effect on absorption wavelength.
Figure 5:
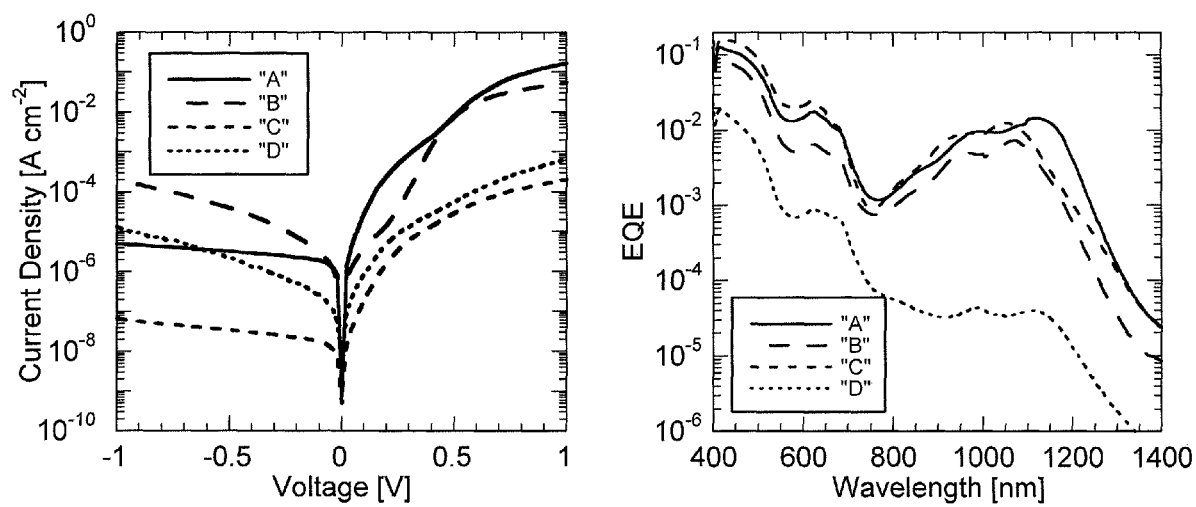
FIG. 5 shows typical I-V and EQE data for "A", "B", "C", and "D" (see FIG. 3). Devices with "A", "B" and "C" have a 1:10 polystyrene:dimer ratio to help with film forming and increase device yield. All devices are cast on ITO/PEDOT and have ~1000 Å of $C_{60}$, 100 Å BCP, and 1000 Å Ag.
Figure 15:
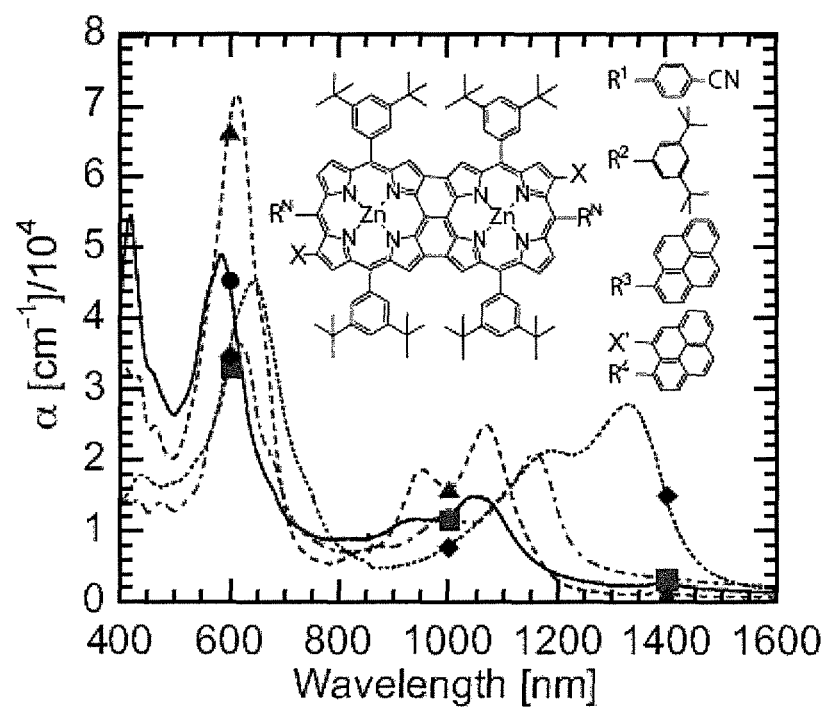
FIG. 15 shows absorption coefficients (α) of the four molecules studied: DTBPh, solid line, (circles); CNPh, long-dashed line (squares); Psub, short-dashed line (triangles); and Pfused, dotted line (diamonds). Inset: Chemical structures of molecules studied. All donors use the same porphyrin-dimer base, and differ only in their end terminations. For CNPh, R=R1, X=H; DTBPh, R=R2, X=H; Psub, R=R3, X=H; and Pfused, R=R4 where X', is the second bond to the pyrene.
Figure 16:
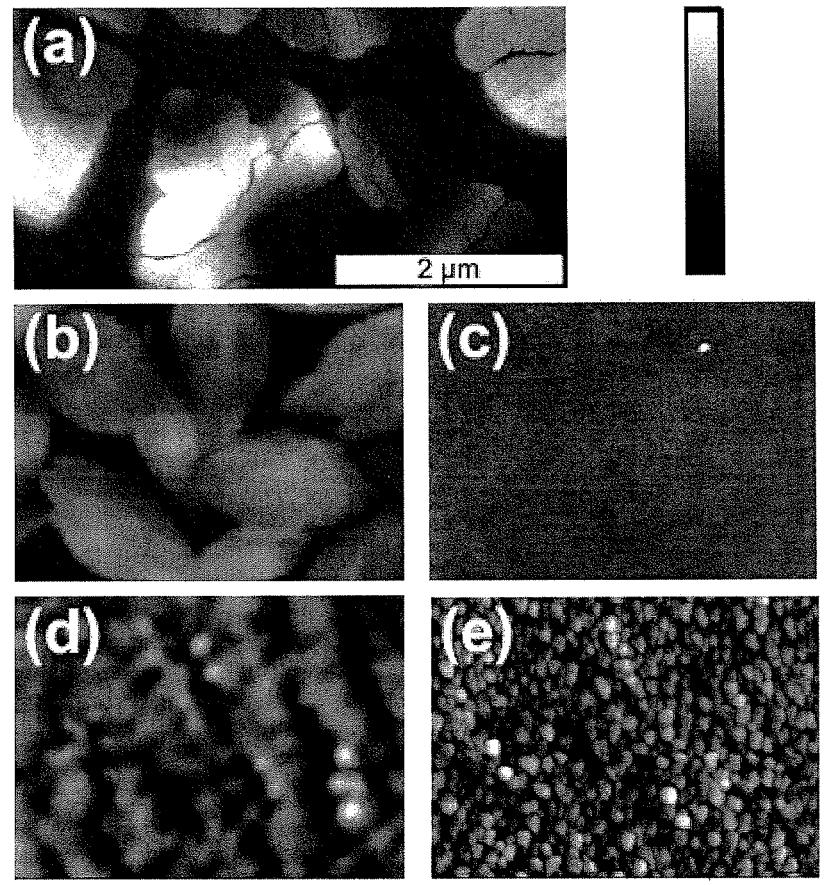
FIG. 16 shows atomic force micrographs of films deposited by doctor blading a 0.5 wt/vol % solution in chlorobenzene of (a) CNPh, (b) CNPh with 1 vol % pyridine, (c) DTBPh, (d) Psub, and (e) Pfused with 1% pyridine. The vertical scale range of the respective micrographs are 110 nm, 80 nm, 20 nm 20 nm, and 40 nm. The RMS roughnesses of the films are 20 nm, 9.0 nm 0.5 nm, 2.7 nm, and 5.3 nm, respectively.

The molecules provided consist of a base of two Zn-metallated porphyrins, triply-linked at the meso-meso and both β-β positions, with four side groups of 3,5-di-tert-butylphenyl, but differ in the end-terminations of singly bonded 4-cyanophenyl (CNPh), 3,5-di-tertbutyl-phenyl (DTBPh), pyrene (Psub), and doubly-bonded pyrene (Pfused) (see inset, FIG. 15). The triply-fused porphyrin tapes were synthesized as described previously. (A. Tsuda, H. Furuta, A. Osuka, Angewandte ChemieInternational Edition 2000, 39, 2549; M. Kamo, A. Tsuda, Y. Nakamura, N. Aratani, K. Furukawa, T. Kato, A. Osuka, *Organic Letters* 2003, 5, 2079; F. Y. Cheng, S. Zhang, A. Adronov, L. Echegoyen, F. Diederich, *Chemistrya European Journal* 2006, 12, 6062). Psub was converted to Pfused by a procedure similar to that reported by Osuka, et. al. (K. Kurotobi, K. S. Kim, S. B. Noh, D. Kim, A. Osuka, Angewandte ChemieInternational Edition 2006, 45, 3944). The compounds absorb throughout the visible and into the NIR, with Q-band absorption peaks between wavelengths of $\lambda$ 1050 nm and 1350 nm, and have corresponding absorption coefficients of $\leq$1.5-3×10$^4$ cm$^{-1}$, as shown in FIG. 4. Films for materials characterization were deposited on bare, or poly (3,4-ethylenedioxythiophene) poly(styrenesulfonate) (PE-DOT-PSS) coated quartz substrates using a film casting knife (i.e. a doctor blade). An atomic force microscope (AFM) was used to measure surface morphology. CNPh was soluble (5-10 mg/ml) in pure chlorobenzene, and as shown in FIG. 16(a), formed large crystalline domains with >20 nm root mean square (RMS) roughness that proved too rough for device fabrication. The addition of 1 (vol) % pyridine to CNPh enhanced its solubility, thereby decreasing the RMS roughness to 9.0 nm, and changed the film morphology from large, cracked oak leaf-shaped grains to almond-shaped grains as shown in FIG. 16(b). Both DBTPh and Psub were more soluble than CNPh (>10 mg/ml) in chlorobenzene, and formed films with 0.5 nm and 2.7 nm RMS roughness, respectively (FIGS. 16(c) and (d)). The solubility of Pfused was <2.5 mg/ml in chlorobenzene, resulting in a thin (and hence overly transparent) film; the addition of 1 (vol) % pyridine increased solubility and resulted in films with a RMS roughness of 5.3 nm.

Figure 17:
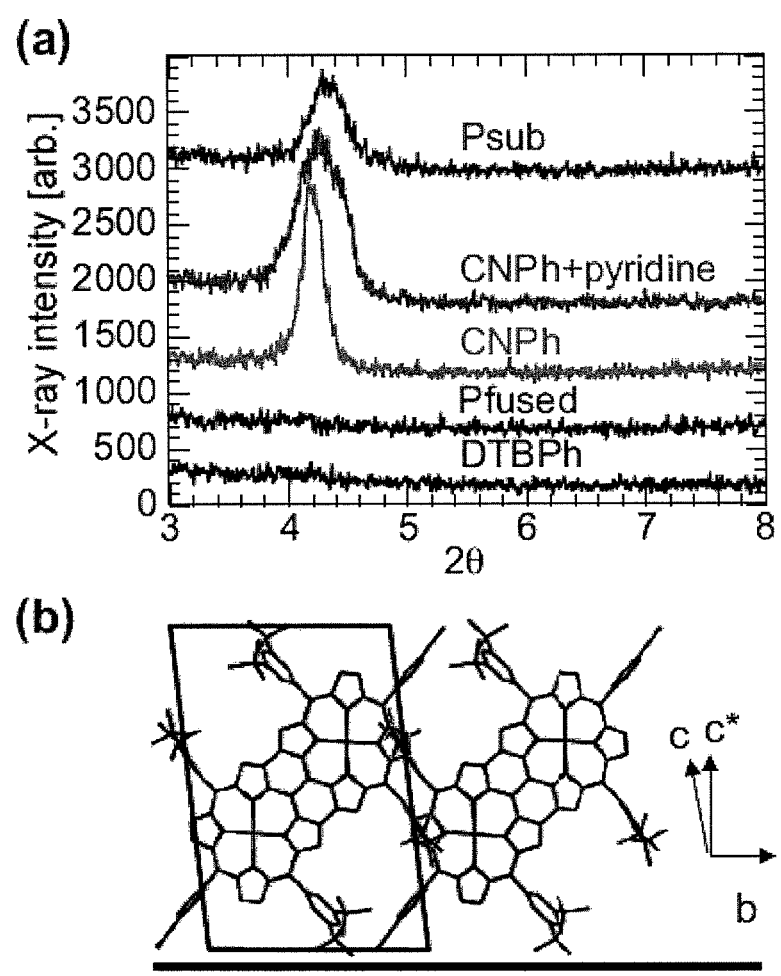
FIG. 17 (a) shows X-ray diffraction intensity of films consisting of the various porphyrin tape molecules indicated. (b) shows the orientation if the molecules with respect to the substrate surface (black horizontal line). The (001) plane is parallel to the substrate surface, the projection of the (100)

X-ray diffraction peaks (see FIG. 17a) were observed at 2θ=4.21±0.1° for CNPh cast from chlorobenzene, 4.28±0.1° for CNPh cast from chlorobenzene with 1 (vol) % pyridine, and 4.34±0.1° for Psub, corresponding to the distance between the (001) planes of 20.96±0.50 Å, 20.62±0.48 Å, and 20.32±0.47 Å, respectively. These closely match the calculated (001) interplanar spacing of 20.2 Å and 20.0 Å for CNPh and Psub, respectively, as seen in the calculated crystal structure shown in FIG. 17(b). The lone (001) diffraction peak indicates that the molecules crystallize with their (001)-planes parallel to the substrate surface. The addition of pyridine increases the fullwidth half-maximum (FWHM) of the CNPh diffraction peak from 0.214±0.004° (2θ) to 0.463+0.010° (2θ), corresponding to Scherrer broadening due to mean crystallite sizes of 43±2 nm (~20 molecular layers) and 18±1 nm (~9 molecular layers), respectively. (A. Guinier, Xray diffraction in crystals, imperfect crystals, and amorphous bodies, W.H. Freeman, San Francisco, 1963). The FWHM for Psub is 0.354±0.010° (2θ), corresponding to a crystallite size of 24±1 nm (~12 molecular layers). No diffraction peaks are observed for DTBPh or Pfused, indicating that the films are amorphous. The reduction and oxidation potentials of Psub and Pfused were measured against a ferrocene/ferricinium reference. The reduction (oxidation) potentials for Psub and Pfused are −1.10 V (−0.01 V) and −0.97 V (−0.13 V), respectively. Reduction (oxidation) potentials for DTBPh, CNPh, and C60 have previously been measured at −1.07 V (+0.03 V) and −1.07 V (0.01V), and −0.86 V, respectively. (L. A. Fendt, H. Fang, M. E. Plonska-Brzezinska, S. Zhang, F. Cheng, C. Braun, L. Echegoyen, F. Diederich, European Journal of Organic Chemistry 2007, 4659; S. A. Lerke, B. A. Parkinson, D. H. Evans, P. J. Fagan, Journal of the American Chemical Society 1992, 114, 7807). Devices were fabricated on pre-cleaned PEDOT-PSS-coated indium tin oxide (ITO)-on-glass substrates using the same conditions as for the morphological studies, followed by sequential vacuum thermal evaporation (VTE) of $C_{60}$, bathocuproine (BCP), and the Ag cathodes. Rectification ratios of $>2\times10^3$ at ±1 V were observed for CNPh, DTBPh, and Pfused, and $>2\times10^6$ for Psub devices. Ideality factors of n≈1.3 were observed for all devices except those based on CNPh, where n≈1.8, as shown in FIG. 18. An ideality of n<1.5 is typical of drift-diffusion, and a ideality between n=1.5 and n=2 is characteristic of defect assisted generation-recombination in the bulk or at the donor-acceptor heterointerface. Defect-related traps may arise from the presence of impurities or morphological disorder. (N. Li, B. E. Lassiter, R. R. Lunt, G. Wei, S. R. Forrest, Applied Physics Letters 2009, 94, 3). When converting Psub to Pfused, the process of forming the additional bond to the pyrene end group decreases the reduction potential of Psub, therefore decreasing the interfacial gap (i.e. the energy difference between the highest occupied molecular orbital, or HOMO, of the porphyrin tape molecule, and the lowest unoccupied molecular orbital, or LUMO, of $C_{60}$) by 0.12 eV, leading to a calculated 11-fold increase in interface-generated dark current (B. P. Rand, D. P. Burk, S. R. Forrest, Physical Review B 2007, 75, 11) compared with an observed difference of approximately three orders of magnitude. These differences suggest that an increased generation-recombination rate from defects is present in the CNPh and Pfused materials, as compared to DTBPh and Psub. Alternatively, the bulky end groups of Psub and DTBPh reduce the interaction between the donor and acceptor systems resulting in a reduced geminate recombination rate and thus a lower dark current in respect to the CNPh and Pfused with the less bulky end groups. (M. D. Perez, C. Borek, S. R. Forrest, M. E. Thompson, Journal of the American Chemical Society 2009, 131, 9281).

Spectrally resolved EQE for the several devices are shown in FIG. 19. Peak efficiencies of 1.2±0.1%, 1.6±0.1%, 2.1±0.1%, and 6.5±0.3% at wavelengths of λ=1045 nm, 1130 nm, 1090 nm, and 1345 nm are observed for TBPh-, CNPh-, Psub-, and Pfused-based devices, respectively. A transfer matrix model was used to determine the internal quantum efficiency (IQE) from the EQE data and the optical properties of the device structures. (P. Peumans, A. Yakimov, S. R. Forrest, Journal of Applied Physics 2003, 93, 3693). In a structure consisting of a 20±4 nm-thick film of Pfused, 125 nm of C60, 10 nm of BCP, and 100 nm of Ag, 19±5% of the incident radiation at λ=1350 nm light is absorbed, while the observed EQE was 5.9%. This results in IQE=31±8%, indicating that excitons are collected from an active region thickness of 6.2±1.6 nm. Films cast from solutions of 0.25, 0.5, and 1 mg/ml in chlorobenzene resulted in thicknesses of 20±4 nm, 60±12 nm, and 120±24 nm, resulting in EQE=5.3±0.6%, 6.2±0.4%, and 4.5±0.4% at λ=1350 nm, respectively. The weak dependence on donor-layer thickness is consistent with a diffusion length smaller than the thinnest film.

The specific detectivity is calculated using: $D^* = \Re A^{1/2}/S_N$, where $\Re$ is the responsivity, A is the detector active area, and $S_N$ is the RMS noise current spectral density. (S. M. Sze, Physics of Semiconductor Devices, Wiley, New York 1981, xii). Peak specific detectivities at zero bias, where thermal noise dominates, of $D^* = 1.6 \pm 0.1 \times 10^{11}$ Jones at λ=1090 nm for Psub-, and $2.3 \pm 0.1 \times 10^{10}$ Jones at λ=1350 nm for Pfused-based devices were obtained, as shown in FIG. 19. These detectivities are significantly less than for InGaAs detectors (~$10^{13}$ Jones) that are sensitive within the same wavelength range, but are comparable to those obtained using cooled PbS detectors. (A. Rogalski, Infrared Physics & Technology 2002, 43, 187; J. G. Webster, The measurement, instrumentation, and sensors handbook, CRC Press published in cooperation with IEEE Press, Boca Raton, Fla. 1999).

Figure 6:
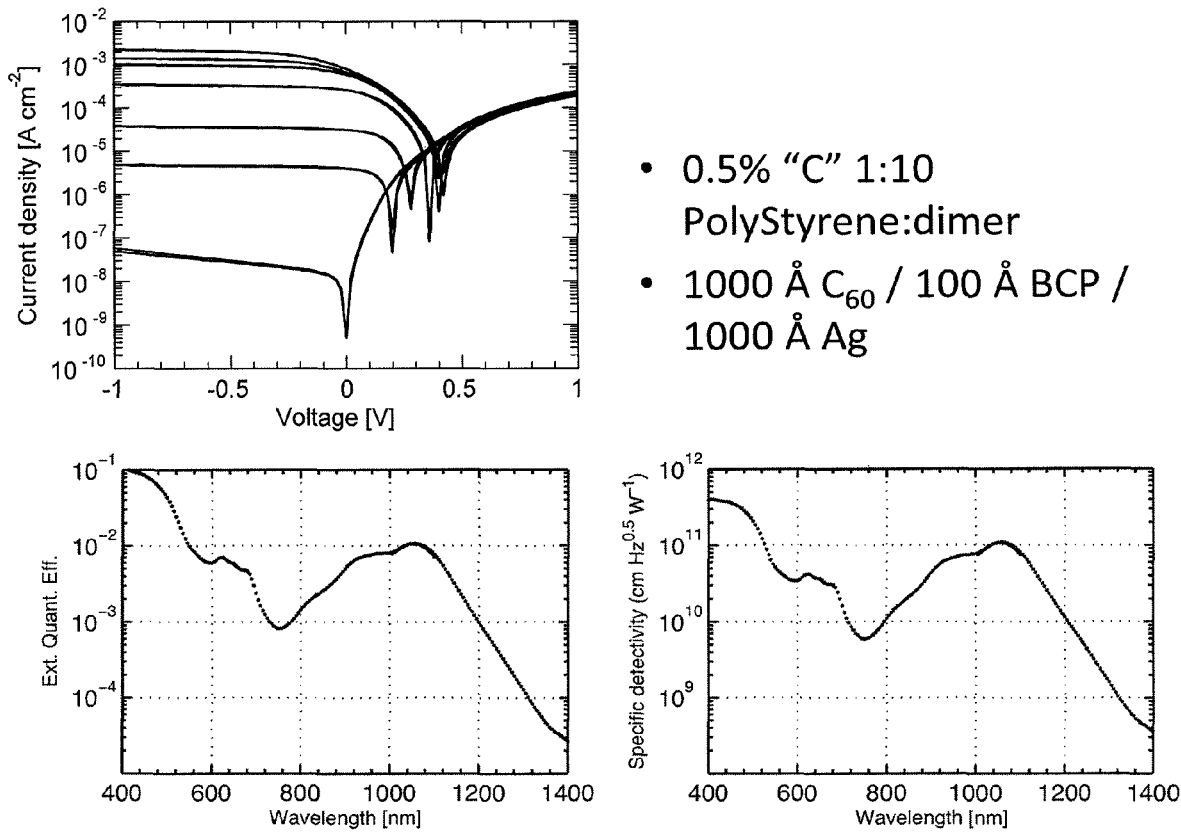
FIG. 6 shows typical illuminated IV, EQE, and specific detectivity (D*) for molecule "C".
Figure 7:
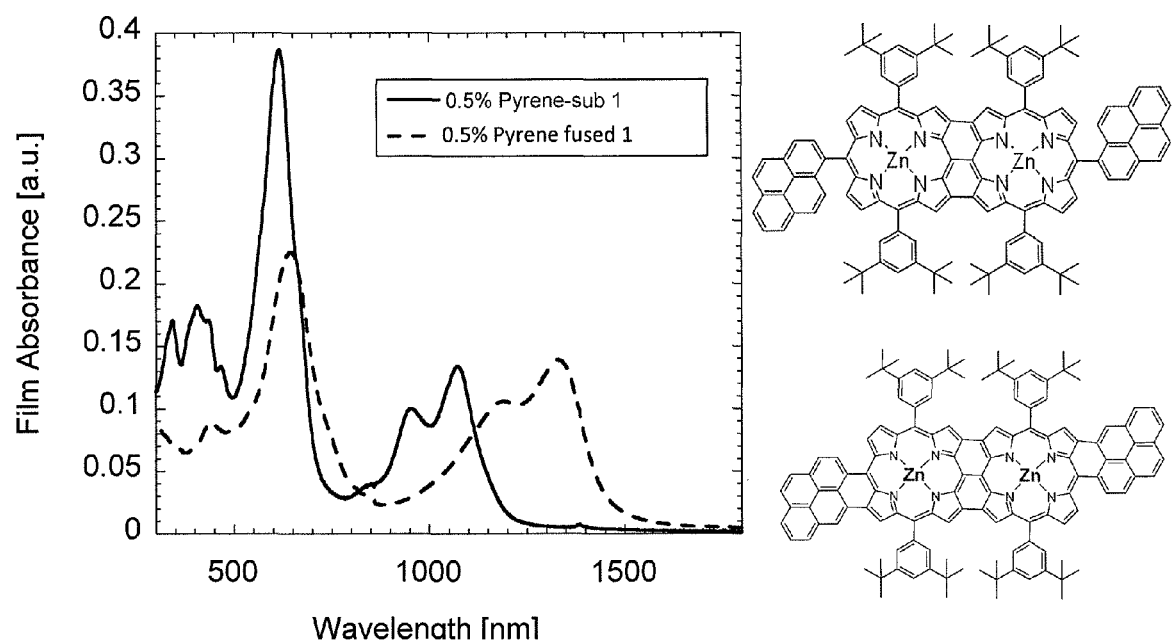
FIG. 7 shows film absorbance (left) of pyrene substituted and pyrene fused dimers. Substituted dimer is shown at top right, and the fused dimer is shown at bottom right.
Figure 8:
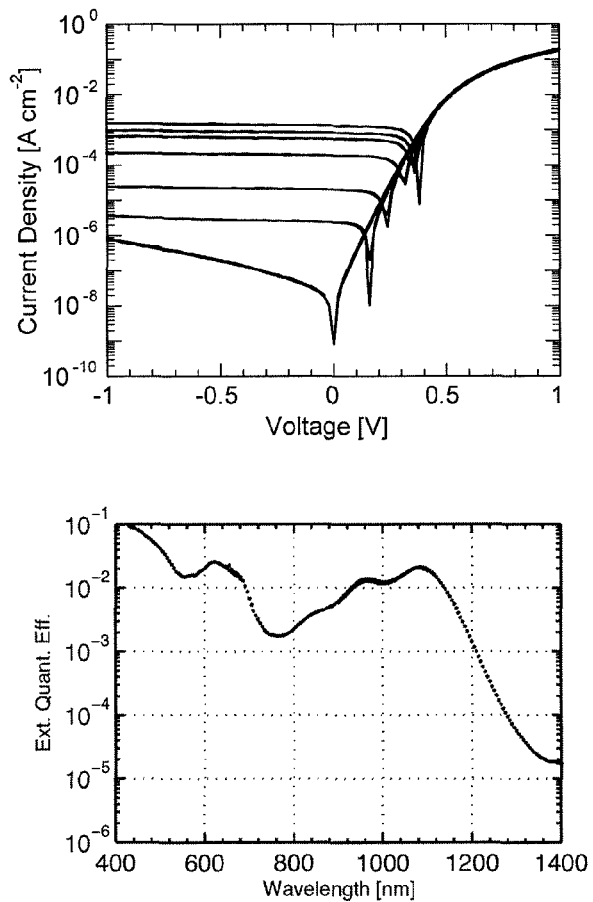
FIG. 8 shows illuminated IV, EQE, and D* data for pyrene substituted dimer with 1000 Å $C_{60}$ (film is approximately the same thickness as shown in FIG. 7). Film was cast from chlorobenzene.
Figure 9:
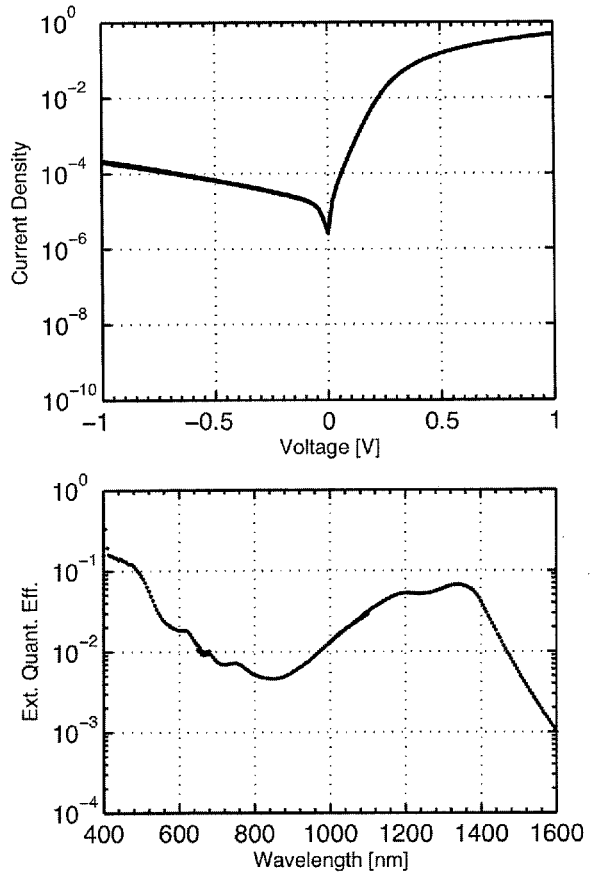
FIG. 9 shows illuminated IV, EQE, and D* data for pyrene fused dimer with 1250 Å $C_{60}$ (film is the same thickness as shown in FIG. 7.) Film was cast from 99% chlorobenzene+ 1% pyridine.
Figure 10:
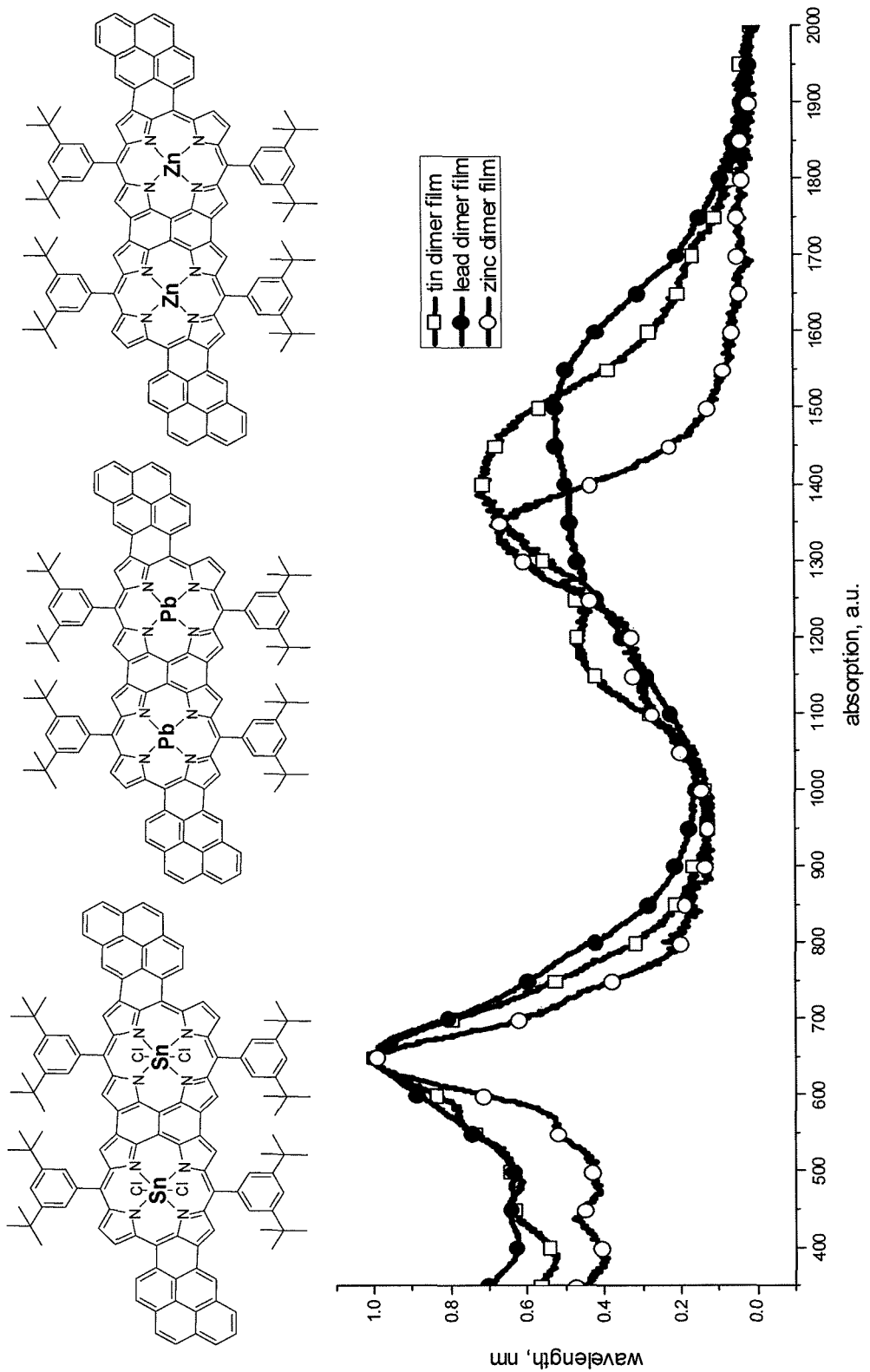
FIG. 10 shows the effect of different core metallizations is shown. $SnCl_2$ and Pb both extend the wavelength response.

The electrical response to optical excitation using an external 50Ω load was used to probe photogenerated carrier extraction and device bandwidth, with results shown in FIG. 6. For Psub-based detectors, the response decay time constant is 2.09±0.02 ns at V=0, decreasing asymptotically to τ=1.87±0.03 ns at −1 V. This corresponds to 3 dB roll-off frequency of 56±7 MHz as shown in FIG. 20, inset. At −1V, the response times of Pfused-, DTBPh-, and CNPh-based devices are τ=2.15±0.02 ns, 2.30±0.02 ns, and 3.17±0.02 ns, respectively. The capacitances of the devices are between C=20.4 and 21.6 nF/cm2, indicating fully depleted active regions that should have resistance-capacitance (RC) time constants of ~0.8 ns across a 50Ω load, assuming series resistance is negligible. Here, τ was found to decrease when either the $C_{60}$ and/or the porphyrin dimer thickness was increased, thus decreasing capacitance, indicating that parasitic series resistance introduces a limit to the device bandwidth.

Therefore, these porphyrin tape molecules may be promising for use in NIR photodetector applications. By extending the conjugation length in this broad class of materials, the absorption is extended from the near visible deep into the NIR. The detector performance is influenced by the functionalizing substituent molecule that, in turn, affects the film crystal structure and morphology. Detectors based on the Pfused, have a peak EQE=6.5%, $D^* = 2.3 \pm 0.1 \times 10^{10}$ Jones, and a response time of τ=2.12±0.02 ns at λ=1350 nm.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the structure:

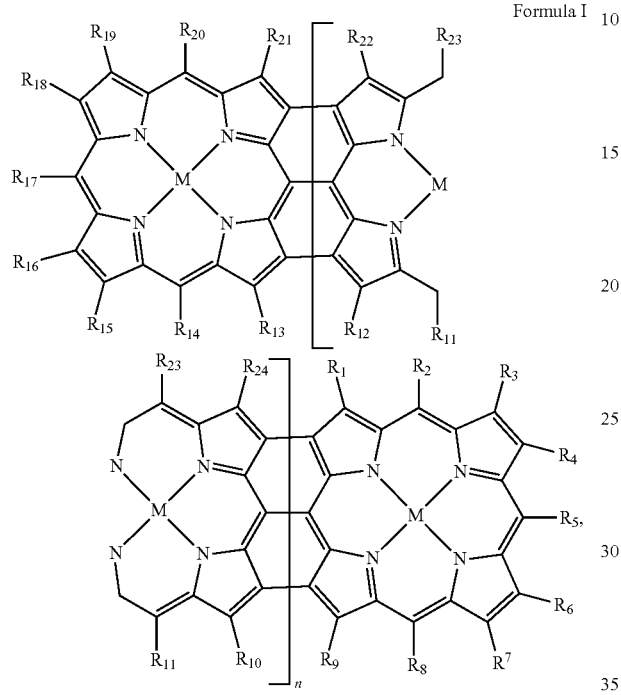

Formula I wherein $R_1$-$R_{24}$ are independently selected from the group consisting of hydrogen, hydroxyl, halogen, chalcogen, mercapto, alkyl, fluoroalkyl, alkoxy, amino, cyano, alkenyl, alkynyl, aryl, and heteroaryl;

wherein-at least two of $R_1$-$R_{24}$ are each a fused polycyclic aromatic group or a fused heterocyclic aromatic group, wherein each fused polycyclic aromatic group and fused heterocyclic aromatic group are fused to the fused porphyrin of Formula I, wherein when the at least two $R_1$-$R_{24}$ are adjacent, the at least two $R_1$-$R_{24}$ correspond to the same fused polycyclic aromatic group or the fused heterocyclic aromatic group;

wherein M is a dicoordinate, tricoordinate, tetracoordinate, pentacoordinate or hexacoordinate metal ion or 2 hydrogen atoms; and wherein n is 0-100.

2. The compound of claim 1, wherein M is selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Ti, Si, Ge, Sn, Pb, P, As, Sb, Bi, Pr, Nd, Sm, Eu, Gd, Tb, Dy, Ho, Er, Tm, Yb, Lu, Th, U, Zn, ClAl, SnO, $SnCl_2$, Pb(OAc), and $Sn(OH)_2$.

3. The compound of claim 1, wherein M is Zn, Pb, Sn, ClAl, SnO, $SnCl_2$, Pb(OAc), or $Sn(OH)_2$.

4. The compound of claim 1, wherein one of $R_1$-$R_{24}$ is a fused pyrene.

5. The compound of claim 1, wherein one of $R_1$-$R_9$ and $R_{13}$-$R_{21}$ is a fused pyrene.

6. The compound of claim 1, wherein n is 0-5.

7. The compound of claim 1, wherein the compound is selected from the group consisting of:

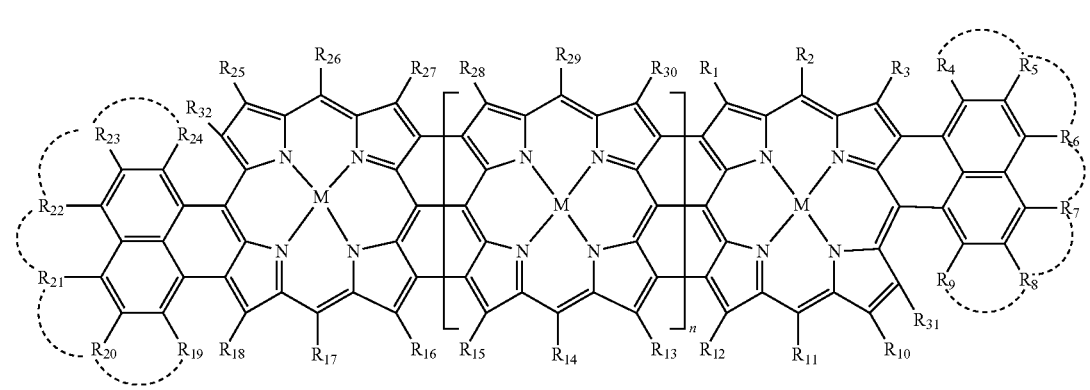

Formula II

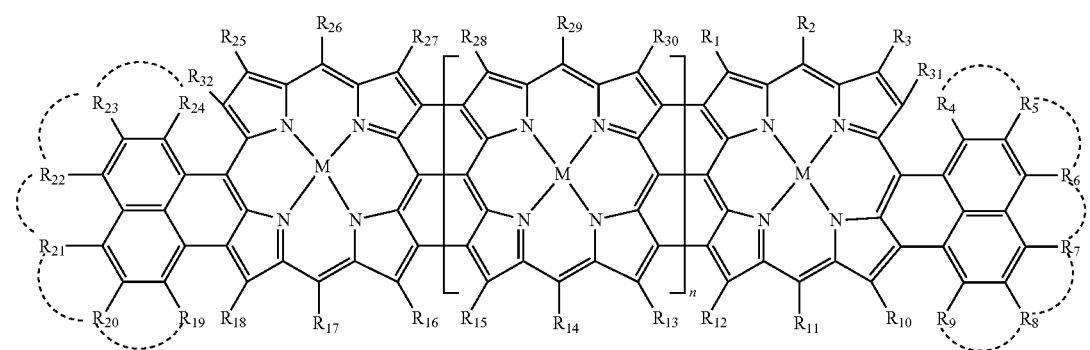

Formula III

-continued
Formula IV
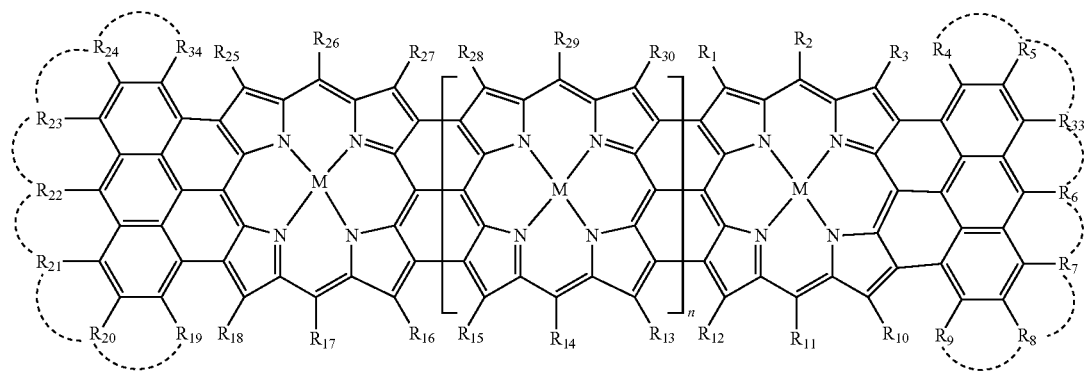
Formula V
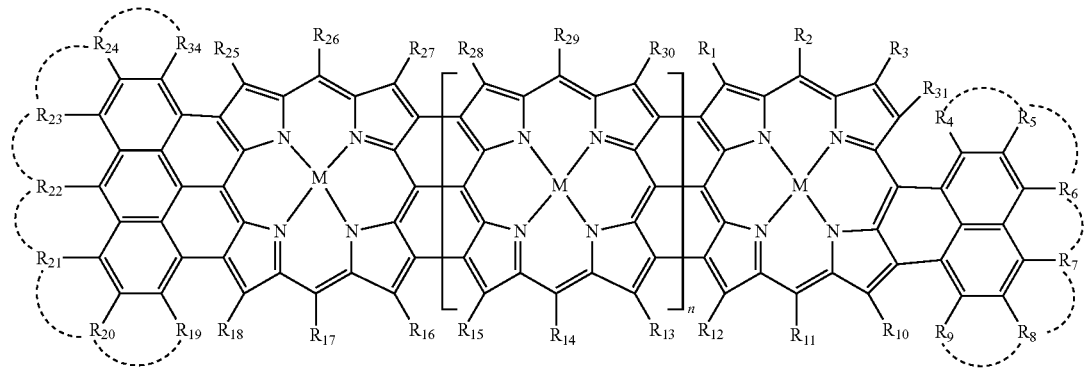
Formula VI
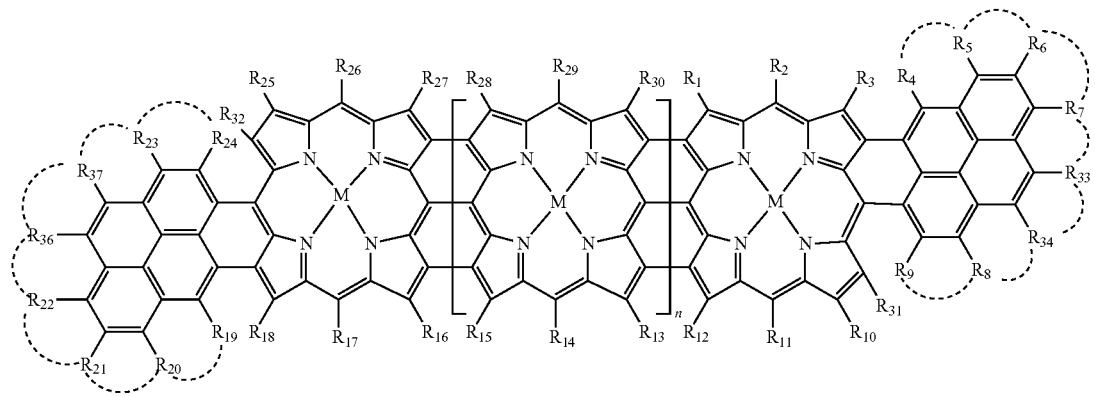
Formula VII
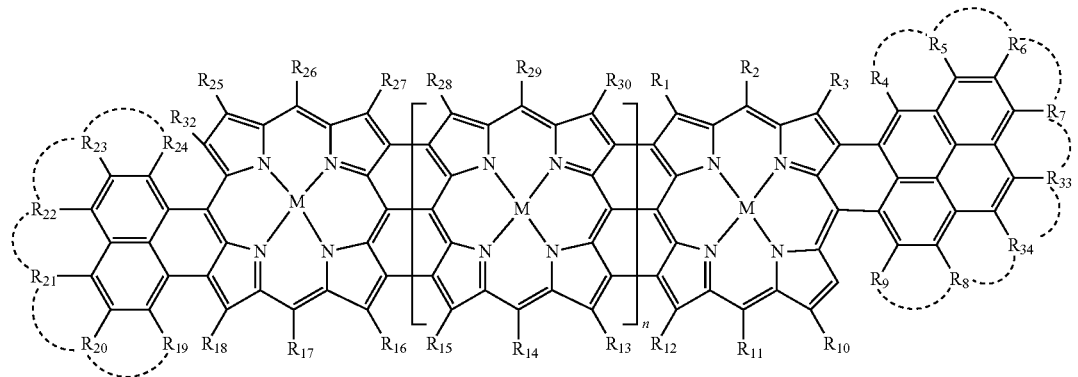

-continued
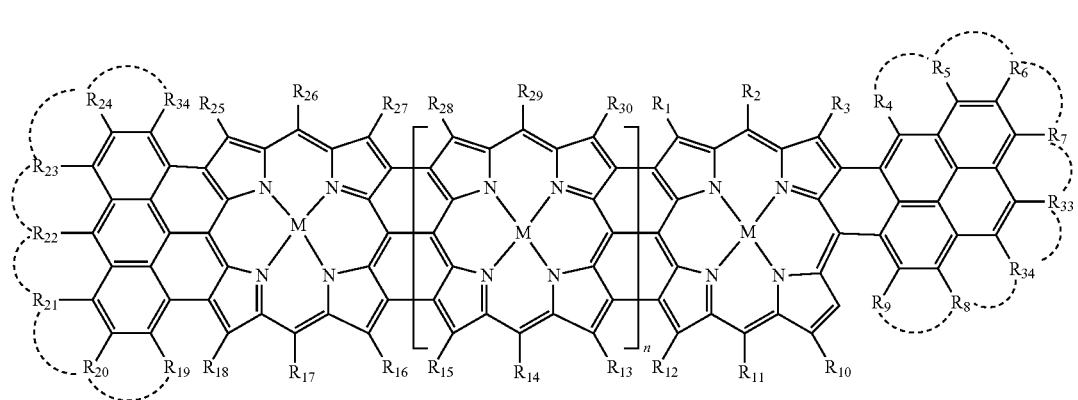
Formula VIII
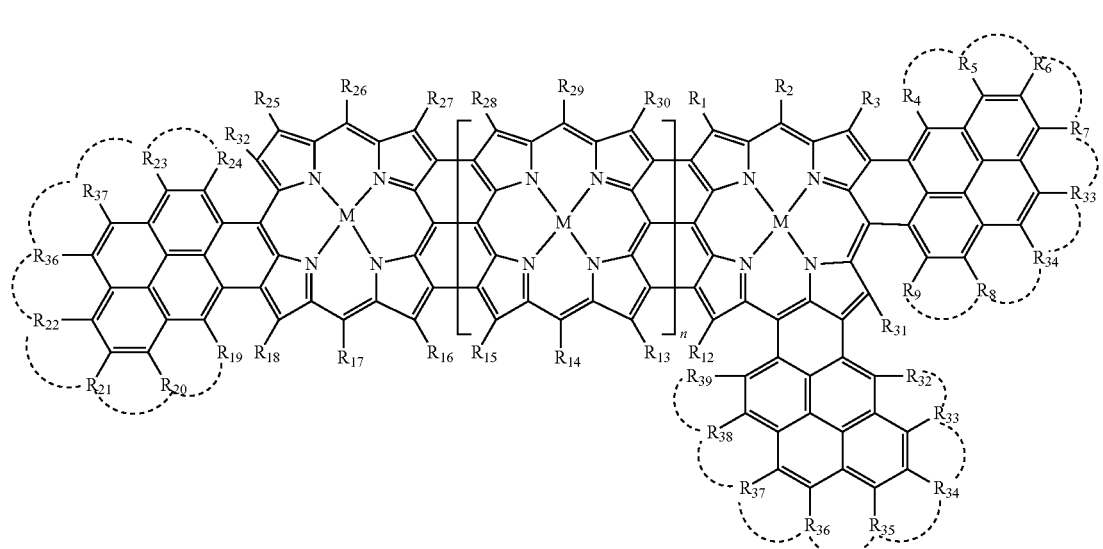
Formula IX
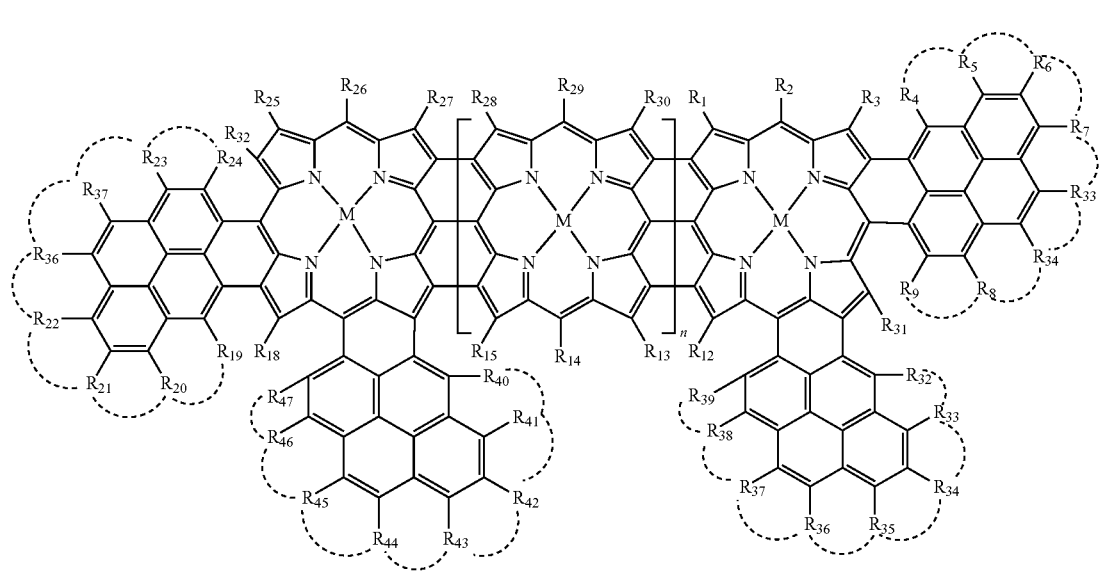
Formula X

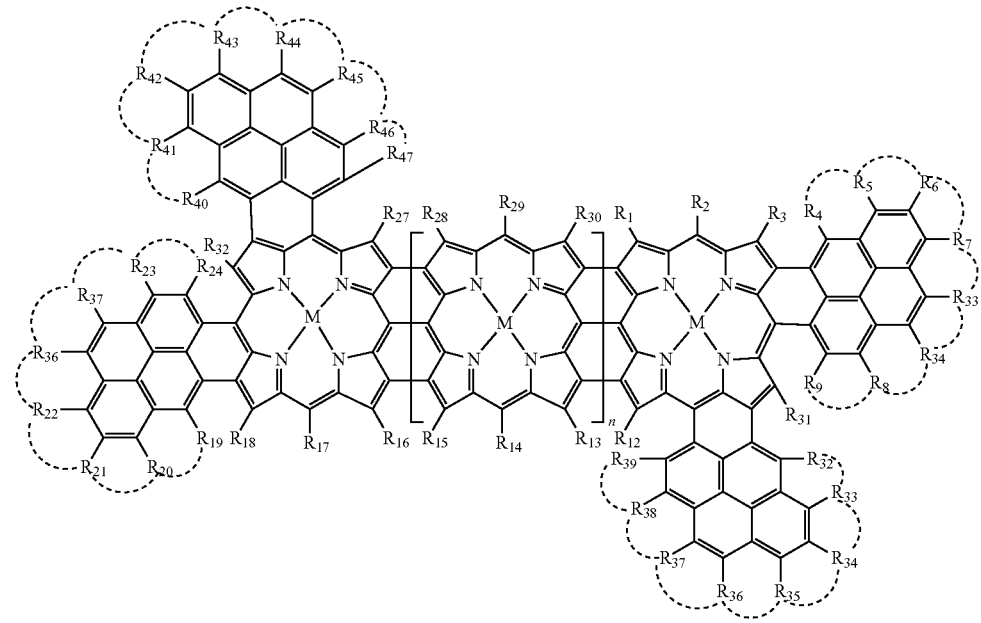
Formula XI
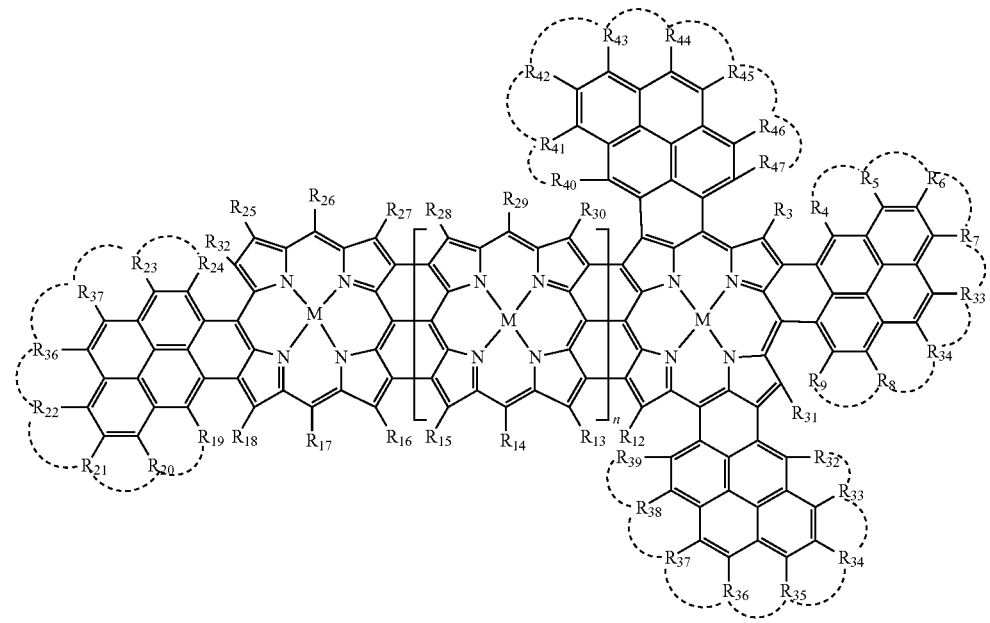
Formula XII

-continued
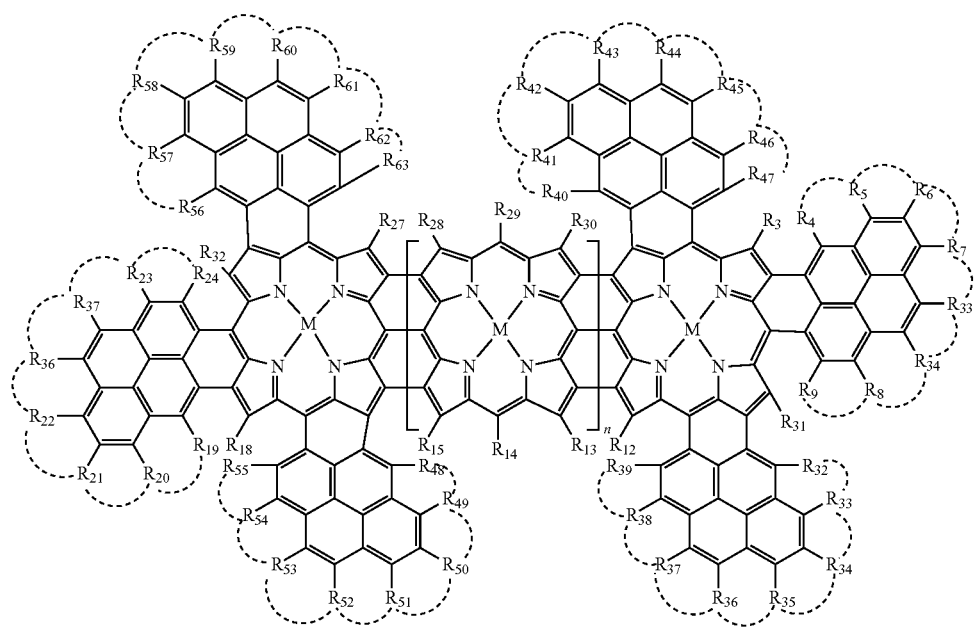
Formula XIII
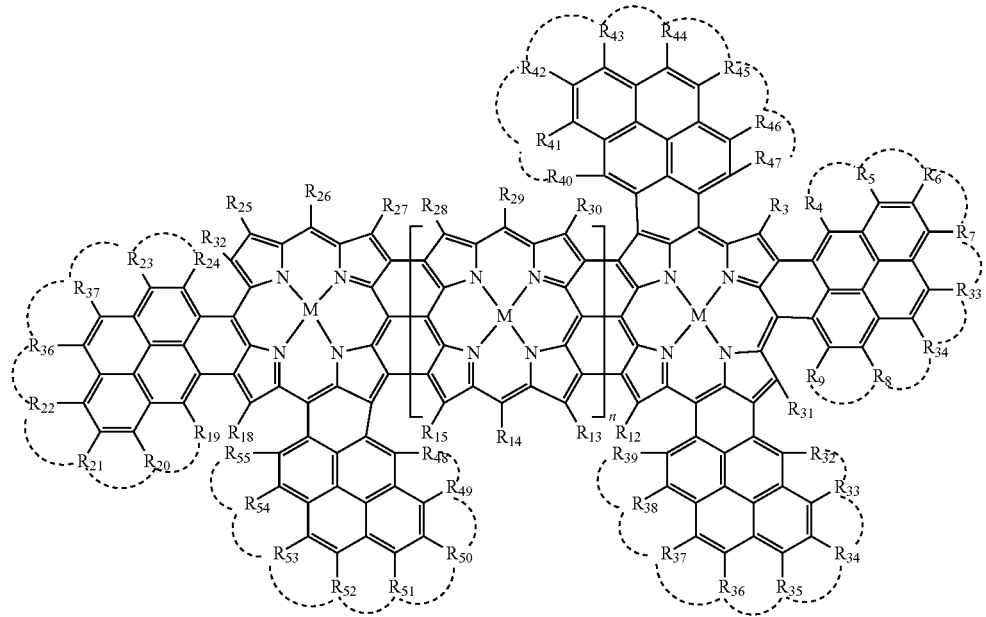
Formula XIV
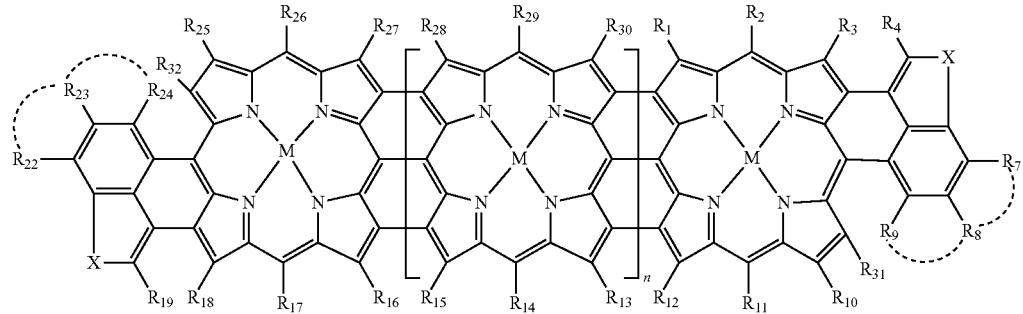
Formula XV -continued

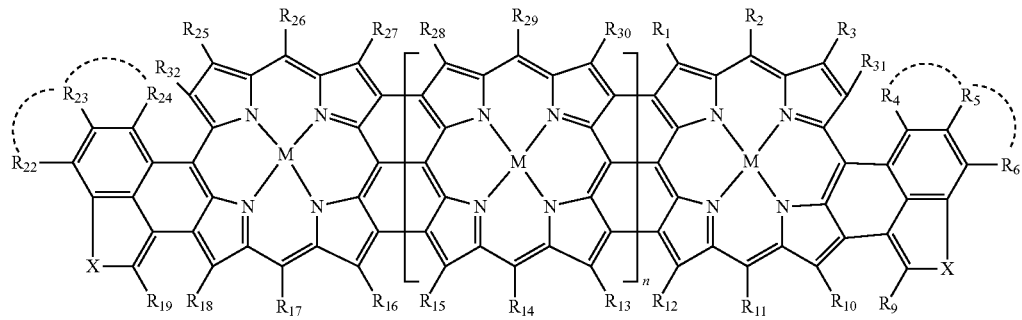
Formula XVI

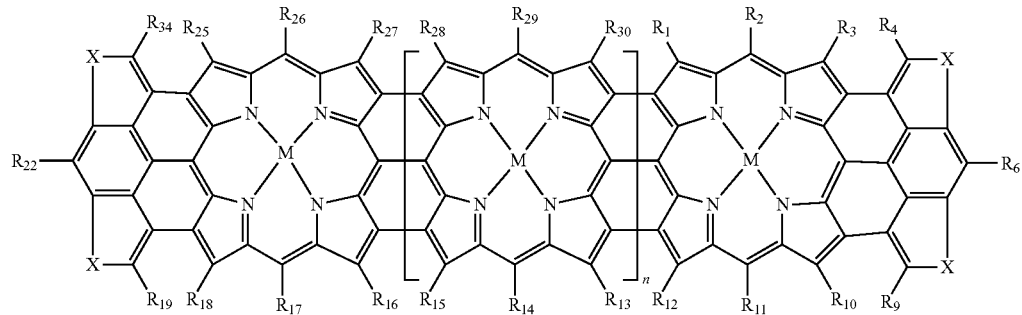
Formula XVII

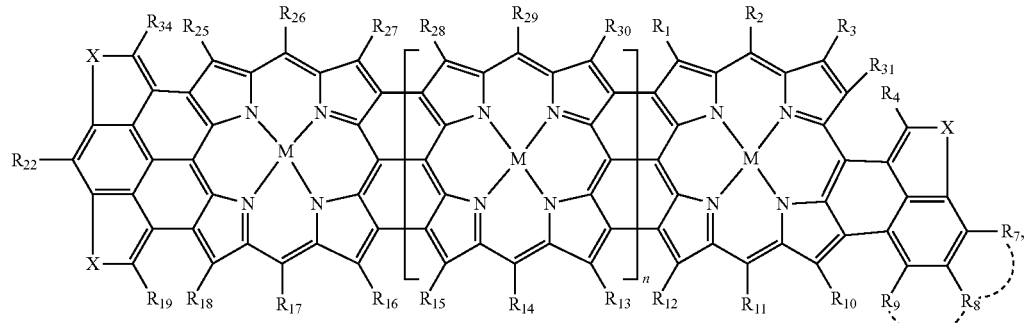
Formula XVIII wherein $R_1$-$R_{63}$ are independently selected from the group consisting of hydrogen, alkyl, fluoroalkyl, alkoxy, amino, cyano, alkenyl, alkynyl, aryl, and heteroaryl;
wherein each dotted arc is a polycyclic aromatic substituent or a heterocyclic aromatic substituent;
wherein X may be dicoordinate, tricoordinate, tetracoordinate, or hexacoordinate; and
wherein X is selected from the group consisting of O, S, Se, Te, N, P, As, Si, Ge, and B.

8. The compound of claim 7, wherein the dotted arc substituent is selected from the group consisting of:

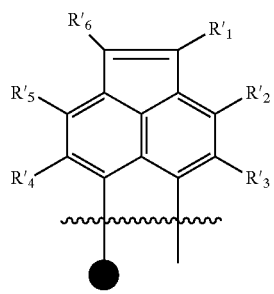

-continued

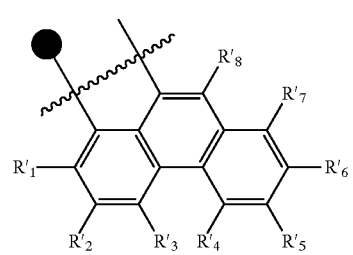

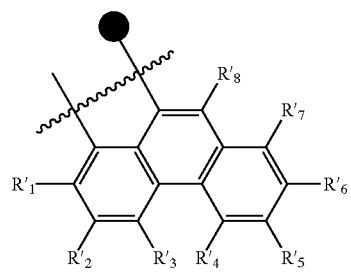

119
-continued
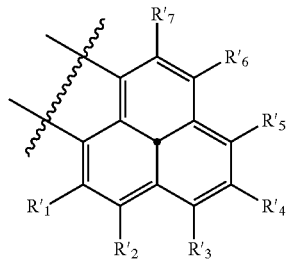
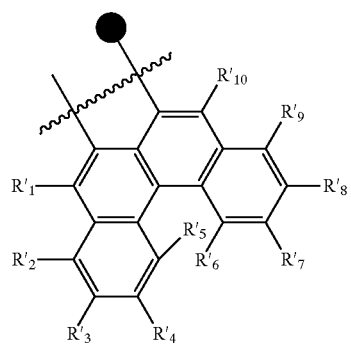
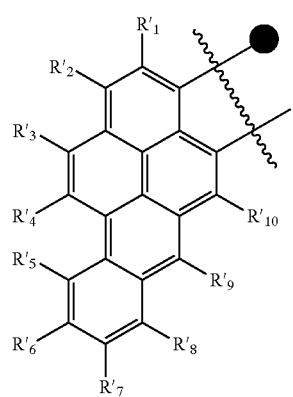
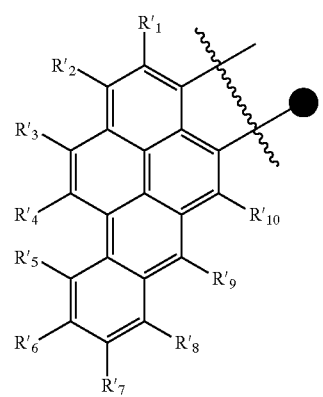
120
-continued
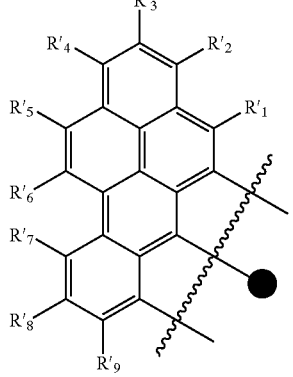
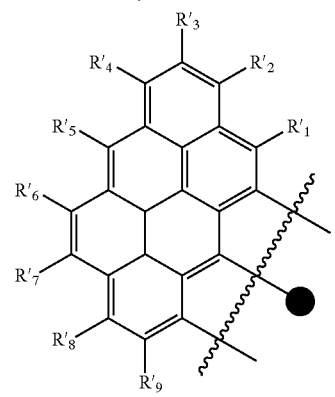
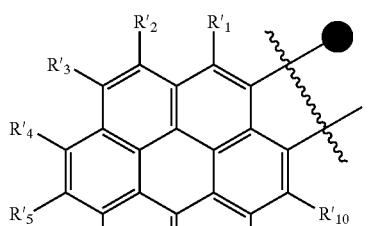
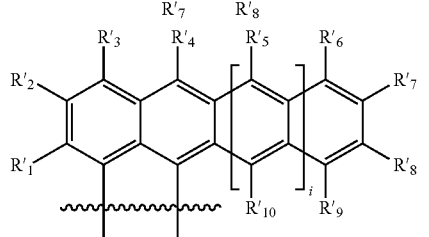
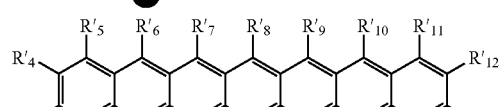
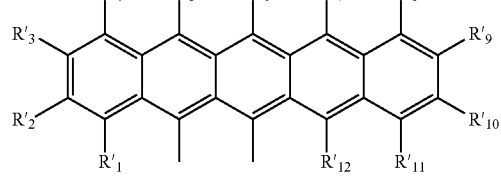

121
-continued
122
-continued
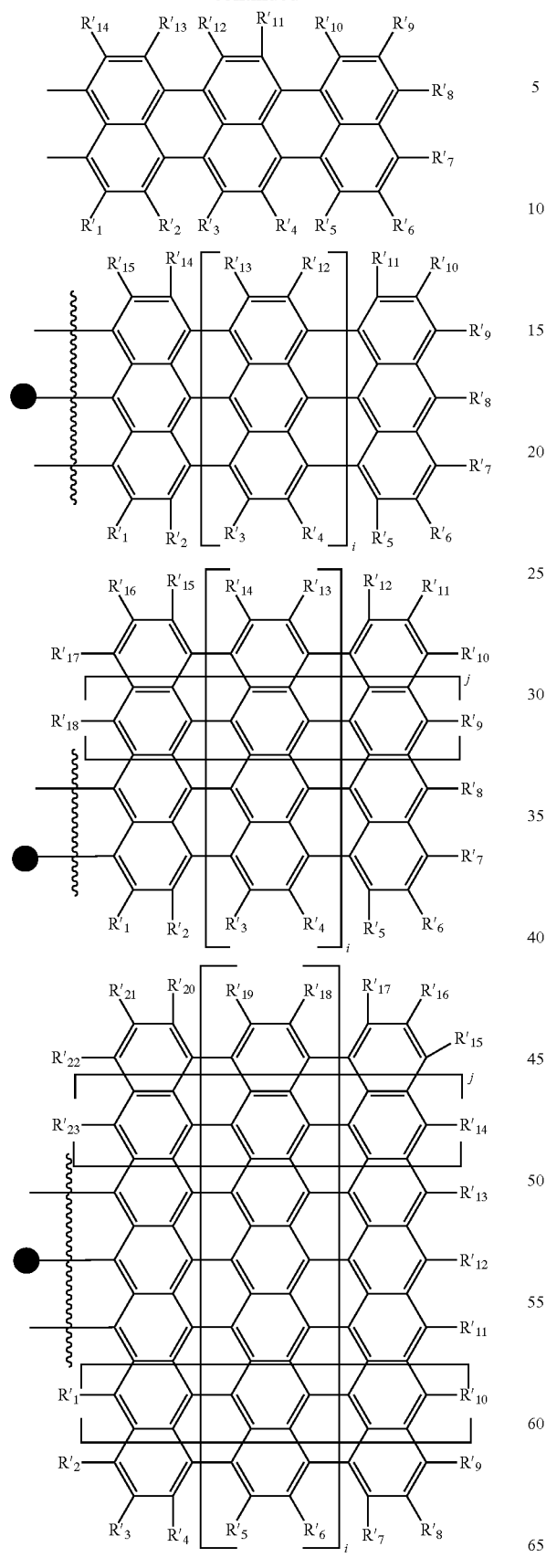
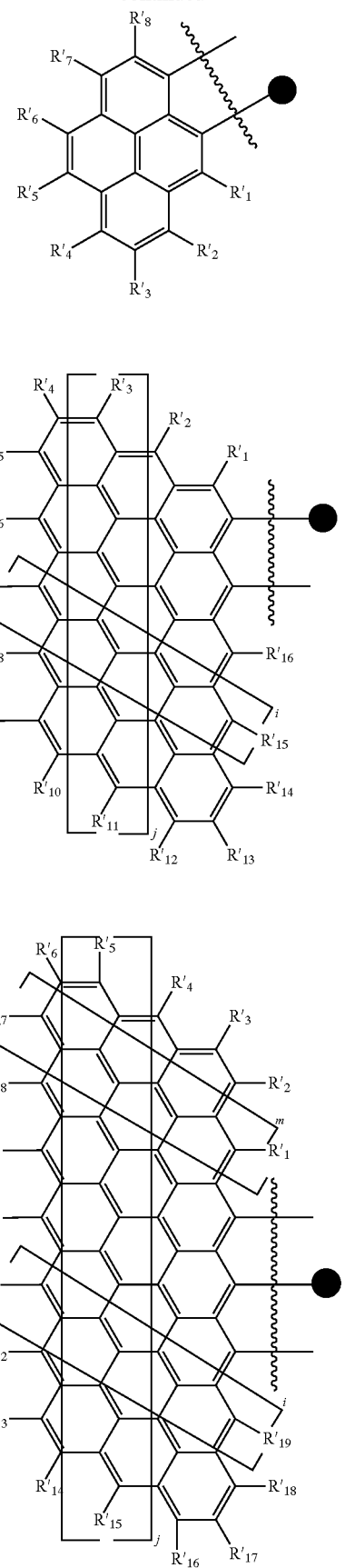

123
-continued

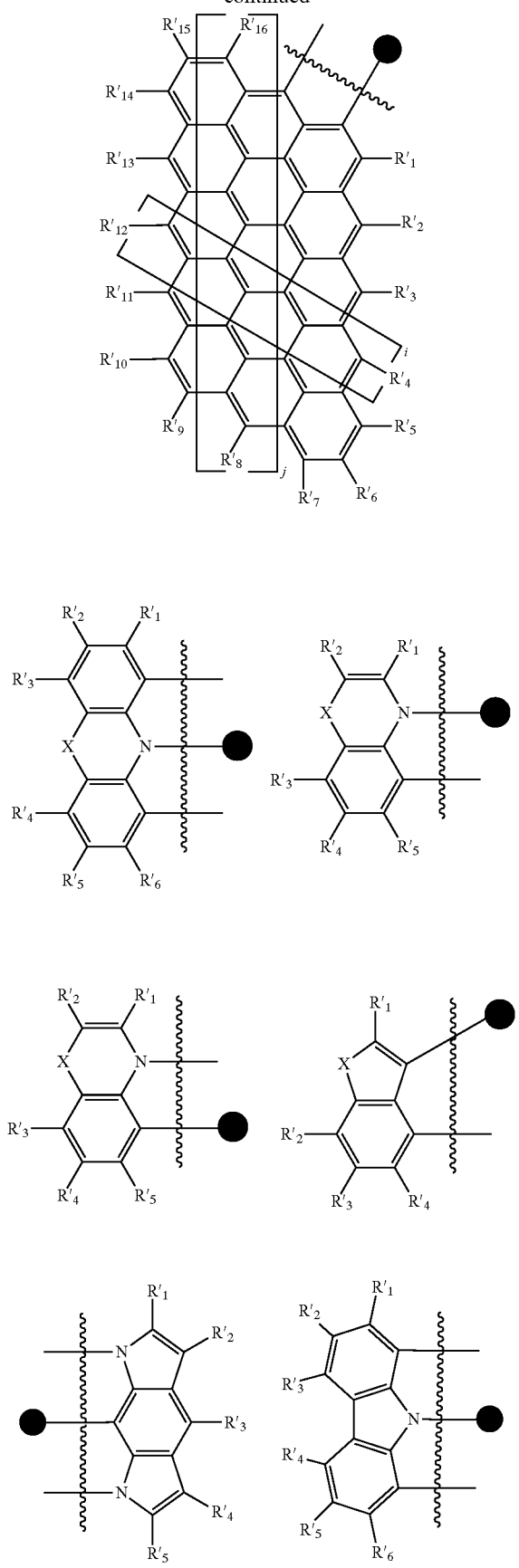

124
-continued

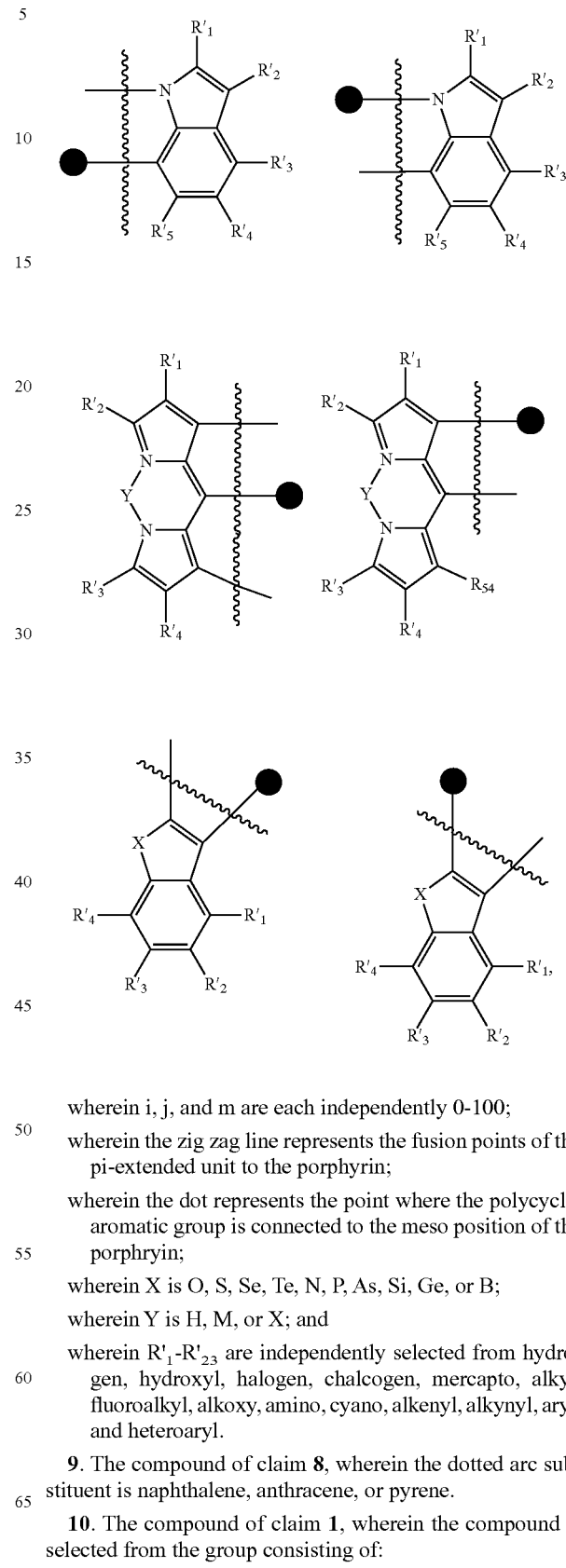

wherein i, j, and m are each independently 0-100;

wherein the zig zag line represents the fusion points of the pi-extended unit to the porphyrin;

wherein the dot represents the point where the polycyclic aromatic group is connected to the meso position of the porphryin;

wherein X is O, S, Se, Te, N, P, As, Si, Ge, or B;

wherein Y is H, M, or X; and wherein $R'_1$-$R'_{23}$ are independently selected from hydrogen, hydroxyl, halogen, chalcogen, mercapto, alkyl, fluoroalkyl, alkoxy, amino, cyano, alkenyl, alkynyl, aryl, and heteroaryl.

9. The compound of claim 8, wherein the dotted arc substituent is naphthalene, anthracene, or pyrene.

10. The compound of claim 1, wherein the compound is selected from the group consisting of:

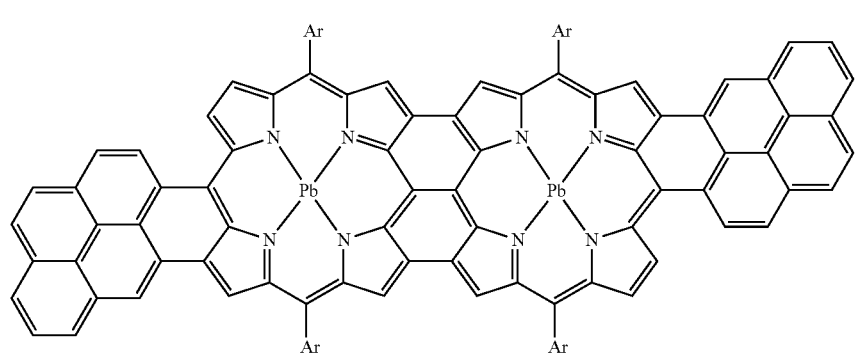
Compound 1
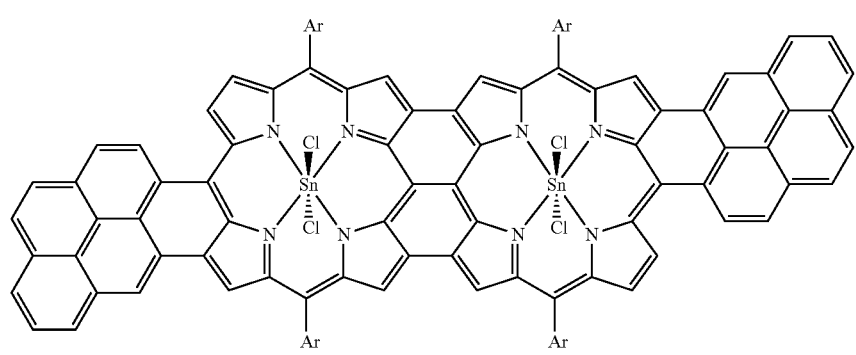
Compound 2
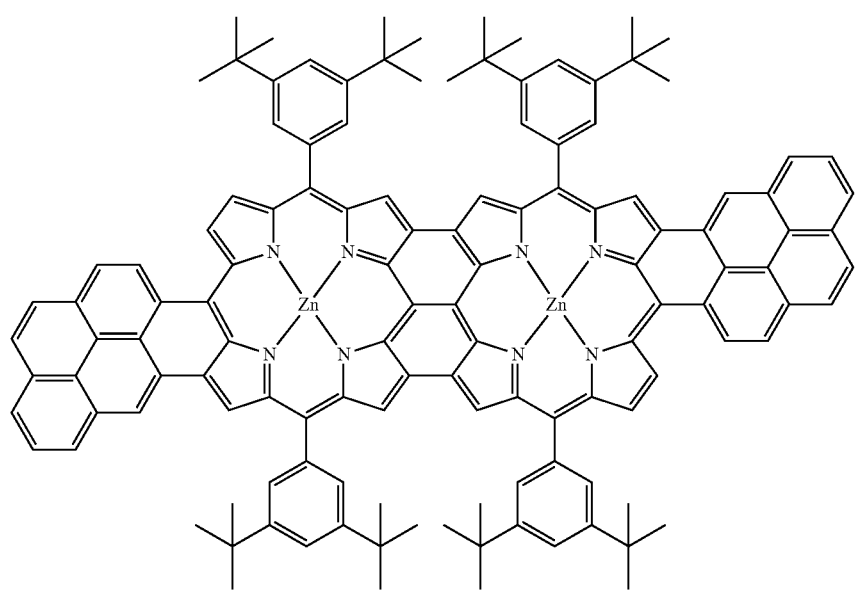
Compound 4

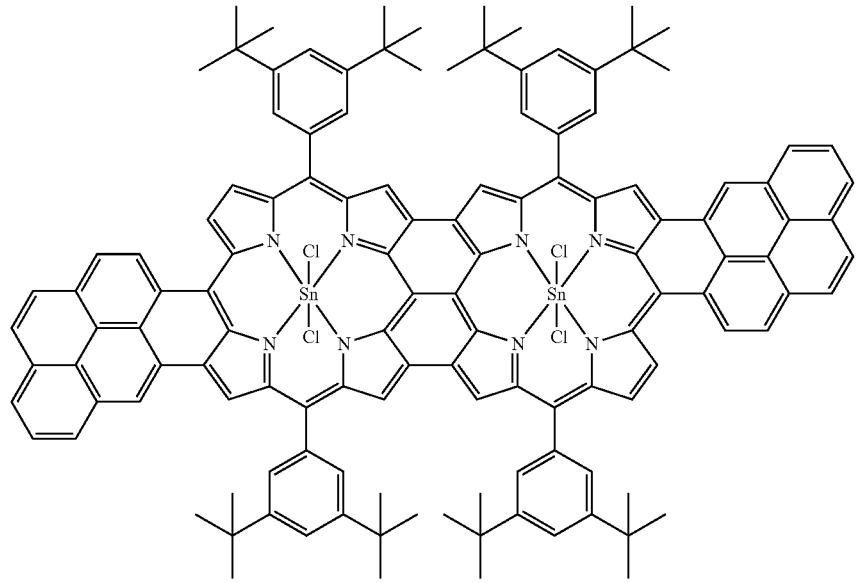
Compound 5
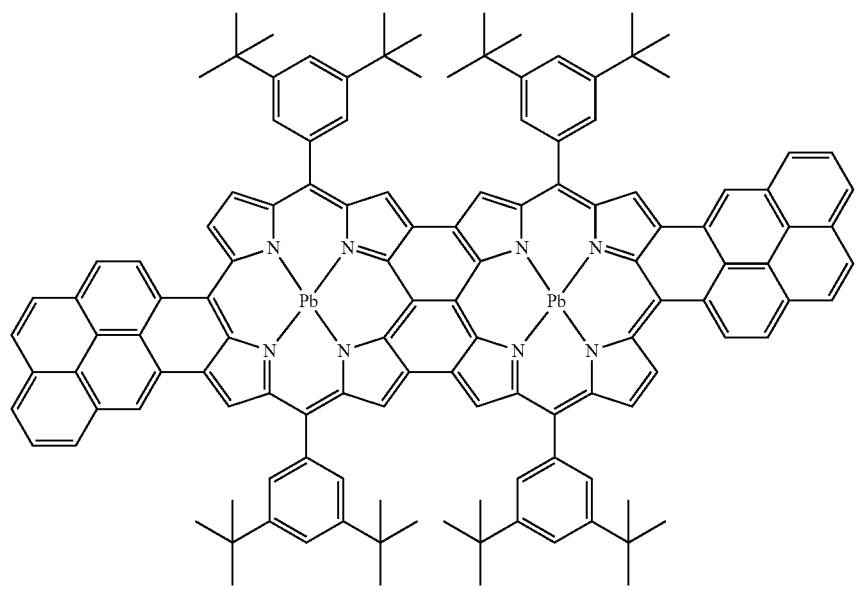
Compound 6

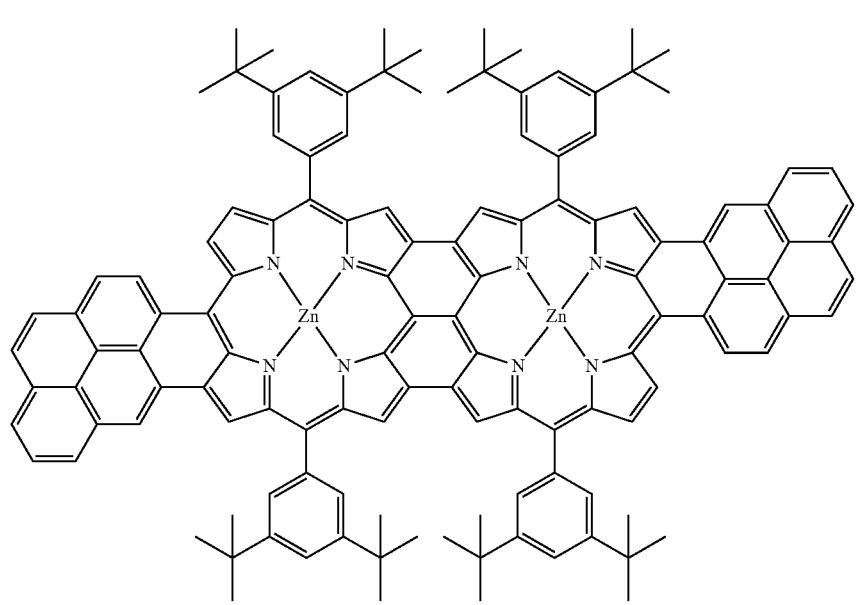
Compound 7
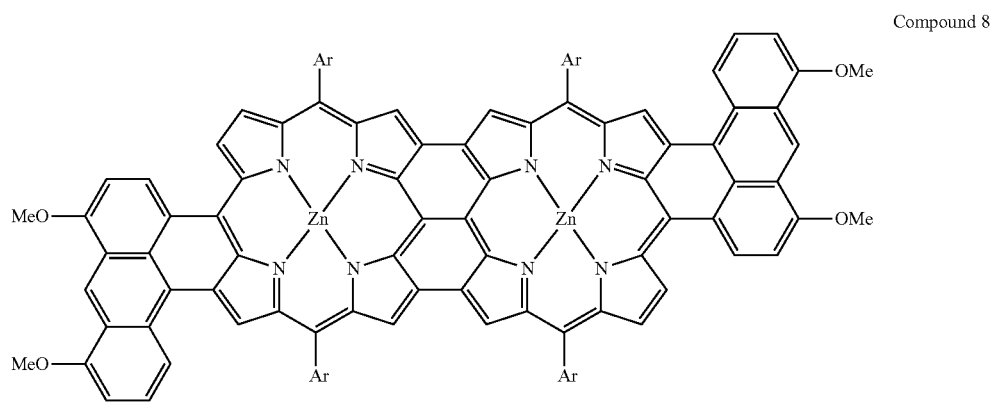
Compound 8
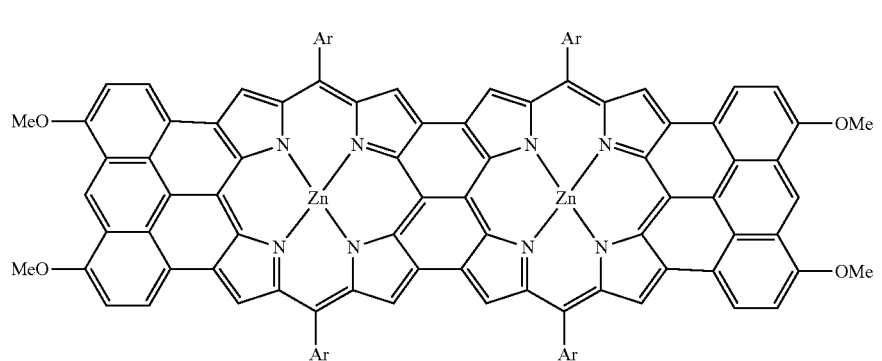
Compound 9

Compound 11

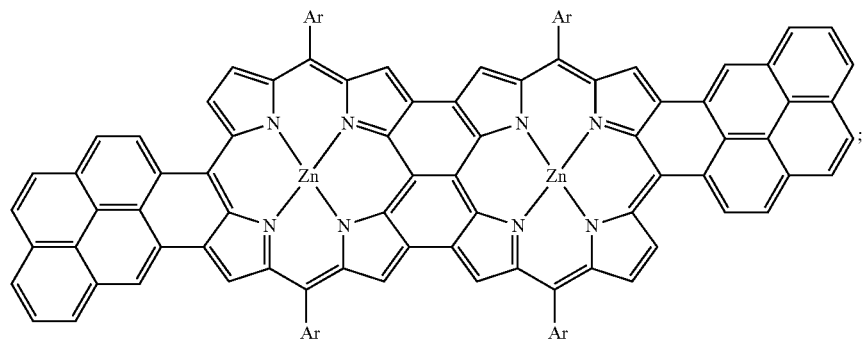

wherein Ar is aryl or heteroaryl.

11. An organic device, comprising:
a first electrode;
a second electrode; and
a first layer, disposed between the first electrode and the second electrode, wherein the first layer comprises a first compound, wherein the first compound has the structure:

Formula I

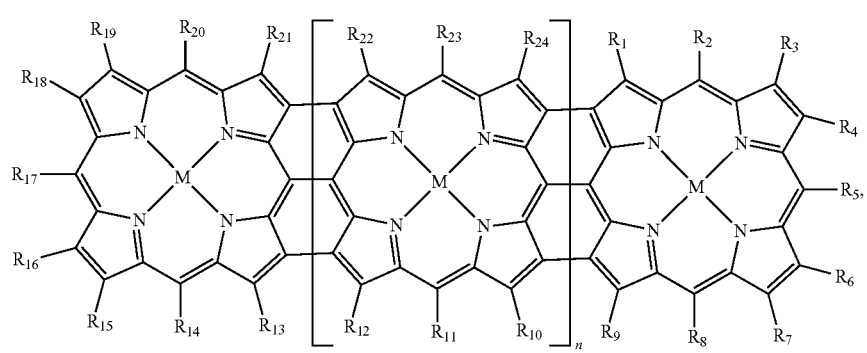

wherein $R_1$-$R_{24}$ are independently selected from the group consisting of hydrogen, hydroxyl, halogen, chalcogen, mercapto, alkyl, fluoroalkyl, alkoxy, amino, cyano, alkenyl, alkynyl, aryl, and heteroaryl;
wherein M is a dicoordinate, tricoordinate, tetracoordinate, pentacoordinate or hexacoordinate metal ion or 2 hydrogen atoms;
wherein at least two of $R_1$-$R_{24}$ are each a fused polycyclic aromatic group or a fused heterocyclic aromatic group, wherein each fused polycyclic aromatic group and fused heterocyclic aromatic group are fused to the fused porphyrin of Formula I, wherein when the at least two $R_1$-$R_{24}$ are adjacent, the at least two $R_1$-$R_{24}$ correspond to the same fused polycyclic aromatic group or the fused heterocyclic aromatic group;
wherein n is 0-100; and
a second layer comprising a second organic compound disposed between the first electrode and the second electrode, wherein the second layer is in direct contact with the first layer.

12. The device of claim 11, wherein at least one of $R_1$-$R_{24}$ is a fused pyrene.

13. The device of claim 11, wherein at least one of $R_1$-$R_9$ and $R_{13}$-$R_{21}$ is a fused pyrene.

14. The device of claim 11, wherein the first layer is in contact with the first electrode and the device further comprises a layer of BCP disposed between and in contact with the second layer and the second electrode.

15. The device of claim 11, wherein M is selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, P, As, Sb, Bi, Pr, Nd, Sm, Eu, Gd, Tb, Dy, Ho, Er, Tm, Yb, Lu, Th, U, Zn, ClAl, SnO, $SnCl_2$, Pb(OAc), and $Sn(OH)_2$.

16. The device of claim 11, wherein the second compound is selected from the group consisting of $C_{60}$, $C_{70}$, $C_{84}$, $F_{16}$-CuPc, PTCBI, PTCDA, PCBM or PTCDI.

17. The device of claim 11, wherein the second compound is $C_{60}$.

18. The device of claim 11, wherein the device has an optical response at a wavelength greater than 1200 nm.

19. The device of claim 11, wherein the device has an optical response at a wavelength greater than 1500 nm.

20. The device of claim 11, wherein M is Zn, Pb, Sn, ClAl, SnO, $SnCl_2$, Pb(OAc), and $Sn(OH)_2$.

21. The device of claim 11, wherein the first layer is disposed using solution processing.

22. The device of claim 11, wherein the first layer comprises more than one first compound.

23. The device of claim 11, wherein the second compound is disposed in a layer having a thickness of about 80 nm to about 200 nm.

24. The device of claim 11, wherein the first compound is disposed in combination with one or more of polystyrene, chlorobenzene, toluene, methylene chloride, dichloromethane, chloroform, chloronaphthalene, dichlorobenzene, and pyridine.

25. The device of claim 11, wherein the first compound is selected from the group consisting of:

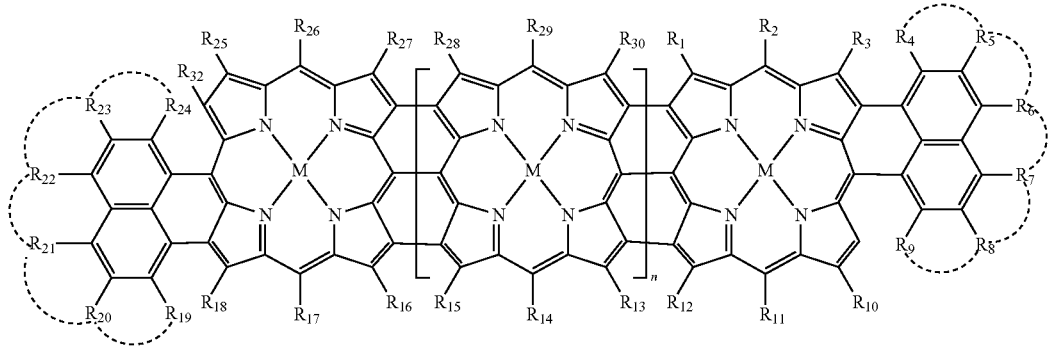
Formula II
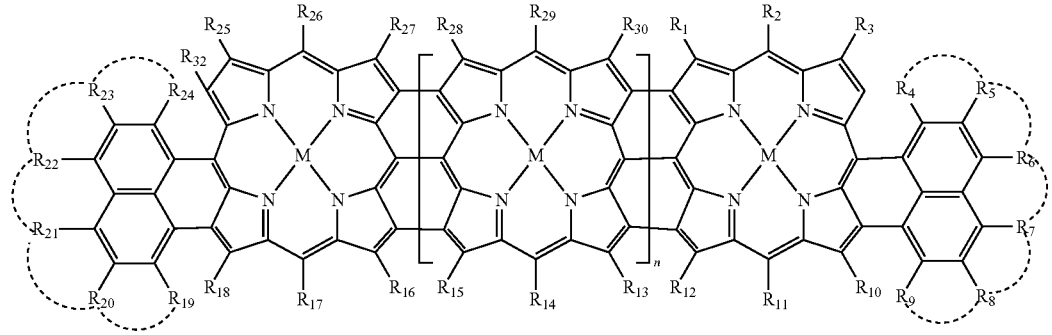
Formula III
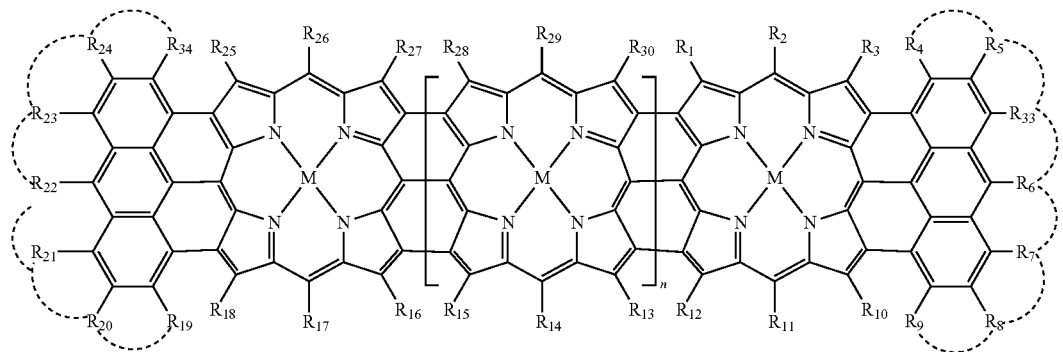
Formula IV
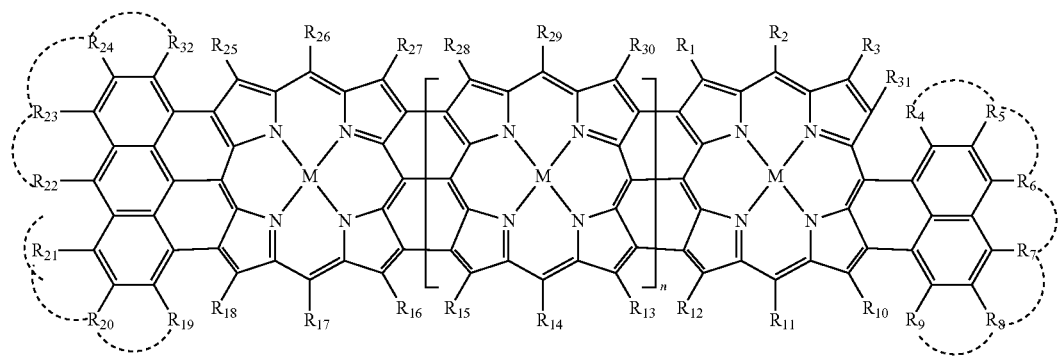
Formula V -continued
Formula VI
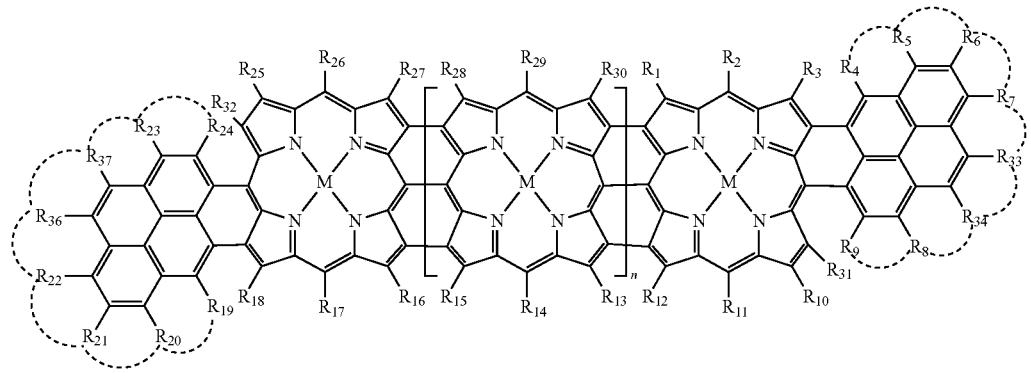
Formula VII
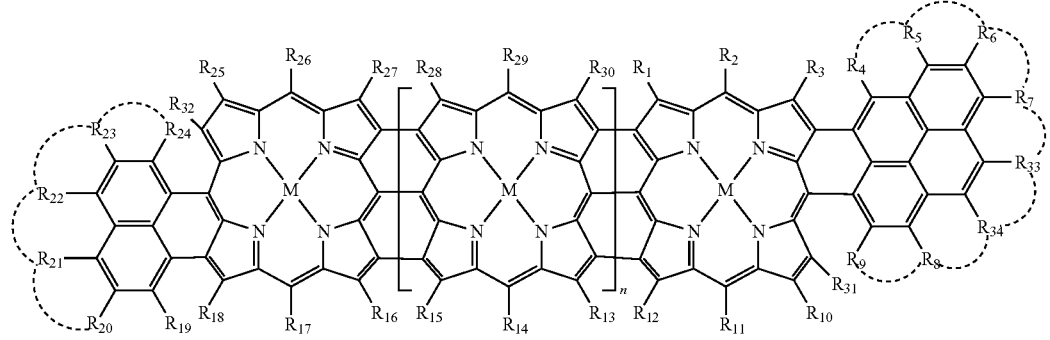
Formula VIII
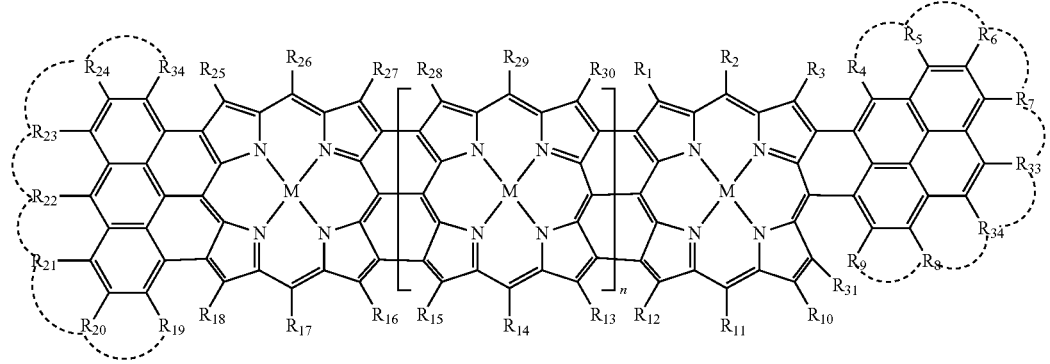
Formula IX
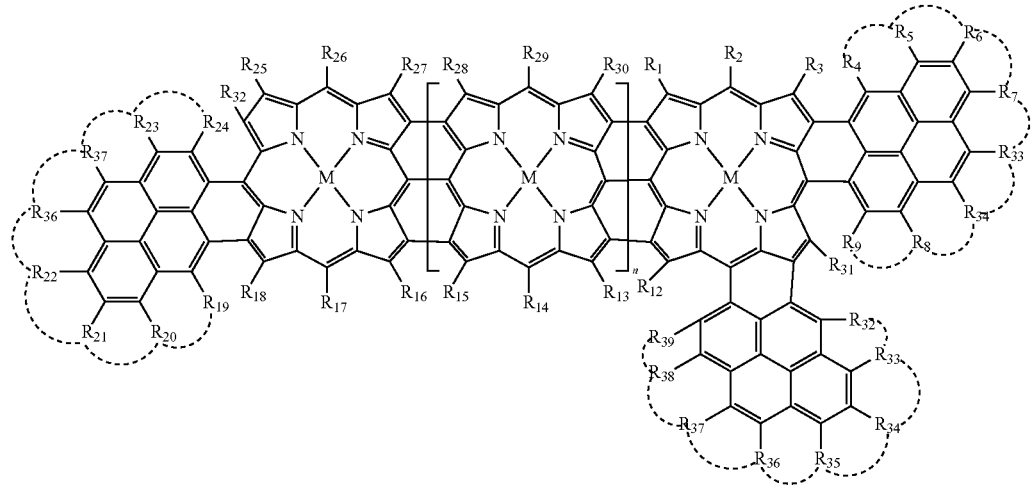

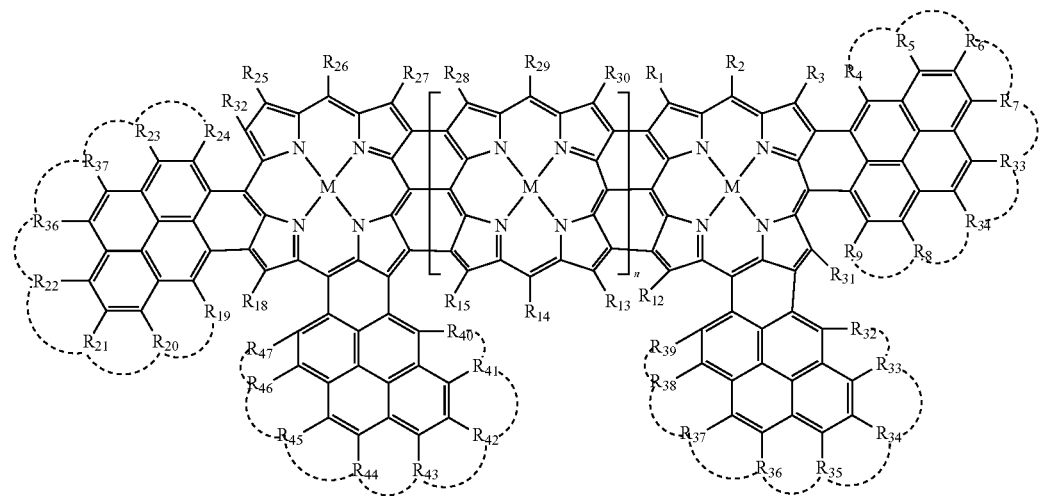
Formula X
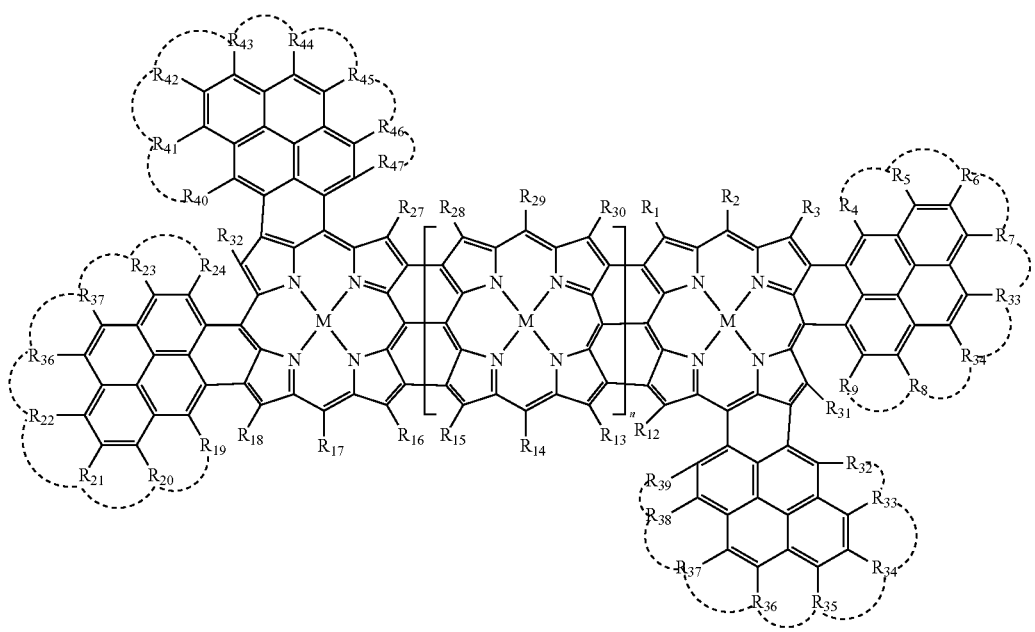
Formula XI

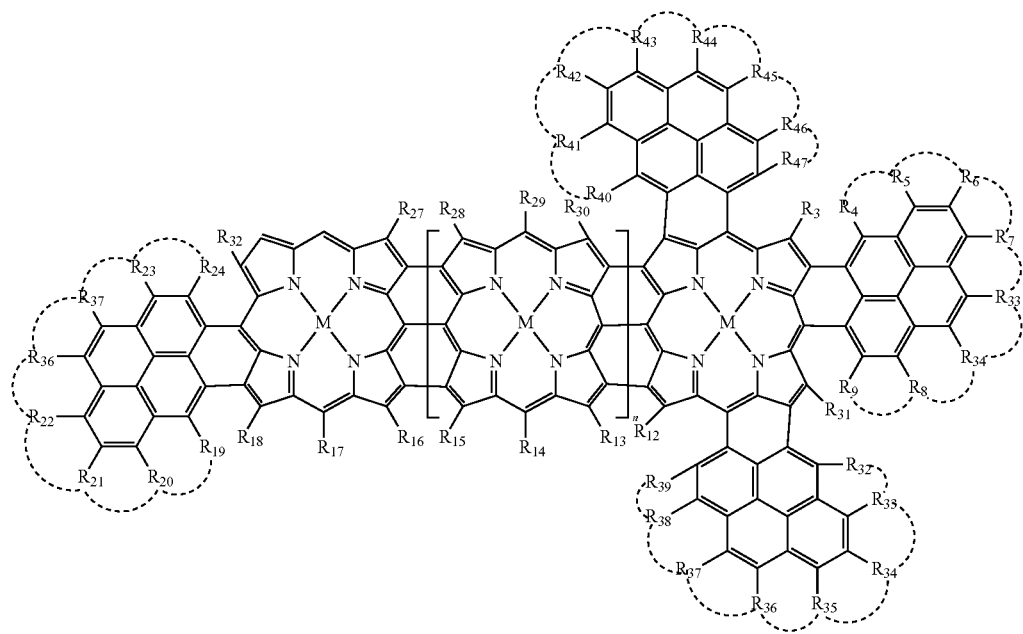
Formula XII
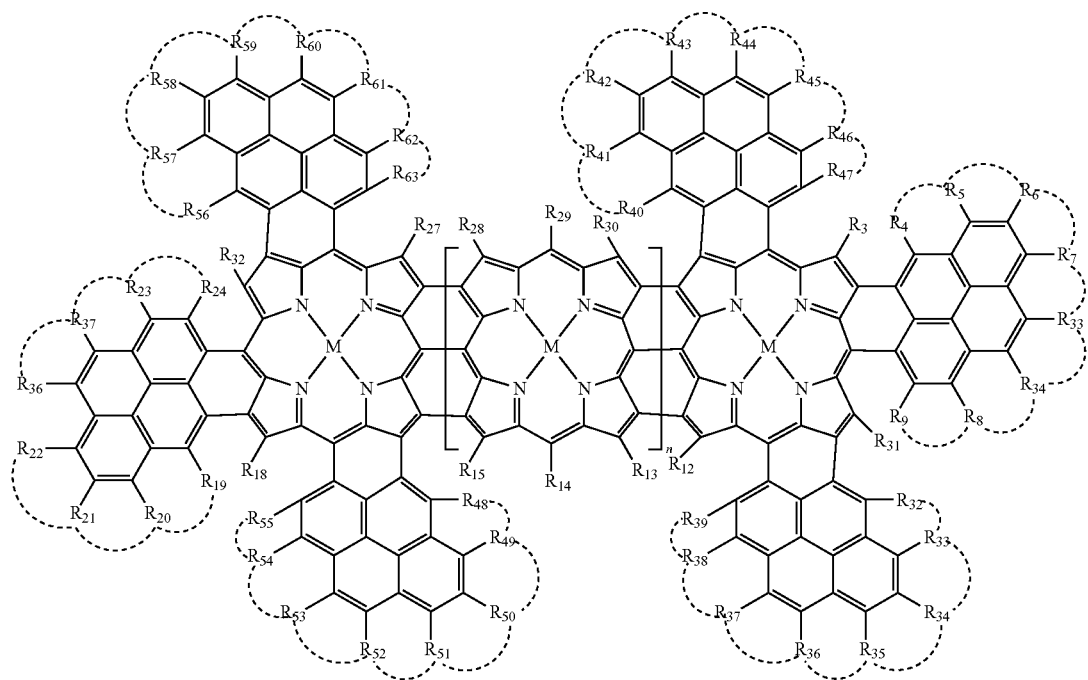
Formula XIII

Formula XIV
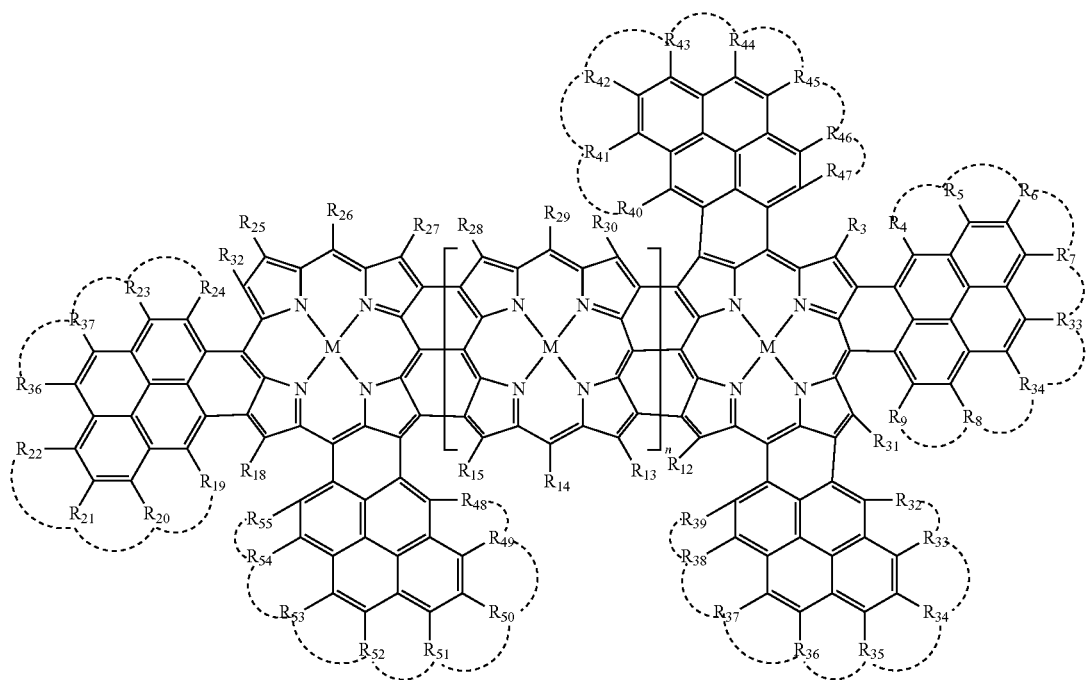
Formula XV
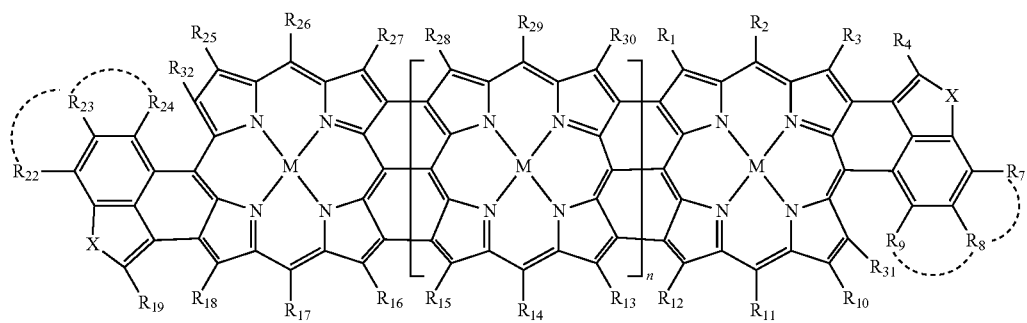
Formula XVI
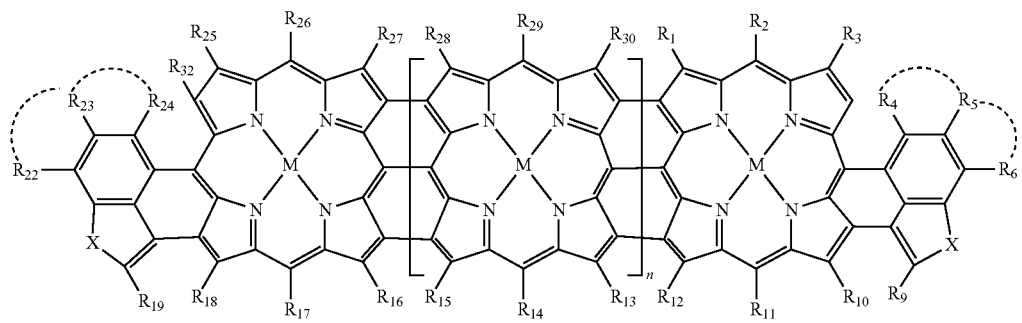
Formula XVII
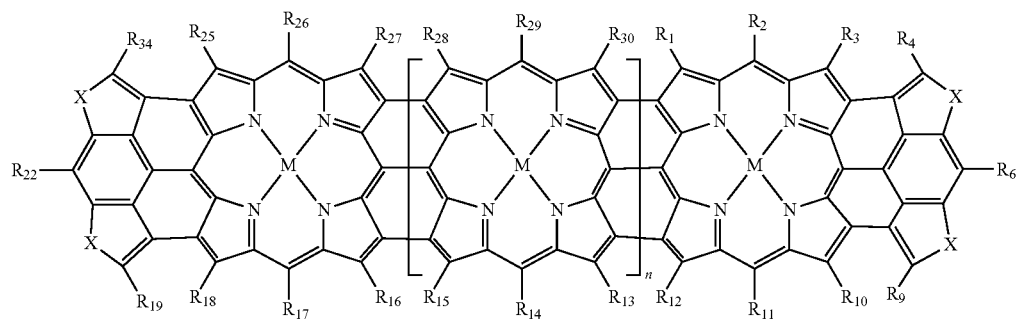

Formula XVIII

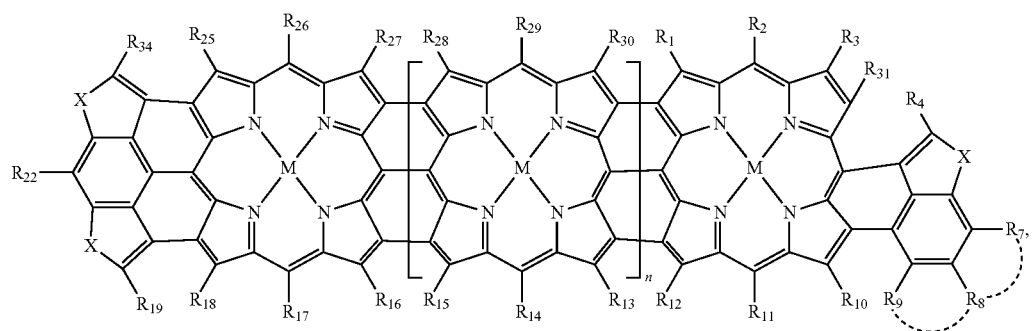

wherein $R_1$-$R_{63}$ are independently selected from the group consisting of hydrogen, alkyl, fluoroalkyl, alkoxy, amino, cyano, alkenyl, alkynyl, aryl, and heteroaryl;

wherein each dotted arc is a polycyclic aromatic substituent or a heterocyclic aromatic substituent;

wherein X may be dicoordinate, tricoordinate, tetracoordinate, or hexacoordinate; and wherein X is selected from the group consisting of O, S, Se, Te, N, P, As, Si, Ge, and B.

26. The device of claim 25, wherein the dotted arc substituent is selected from the group consisting of:

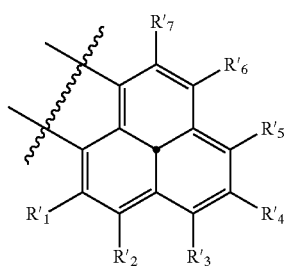

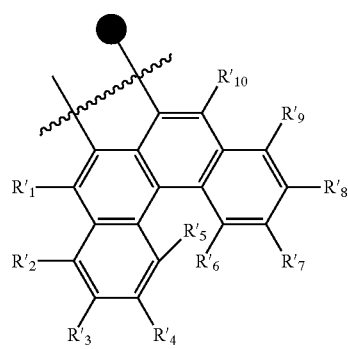

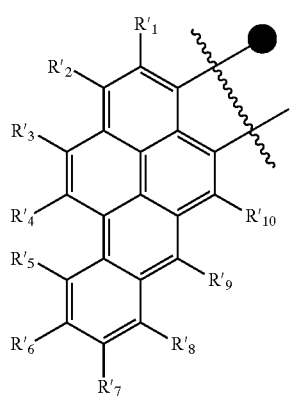

145
-continued
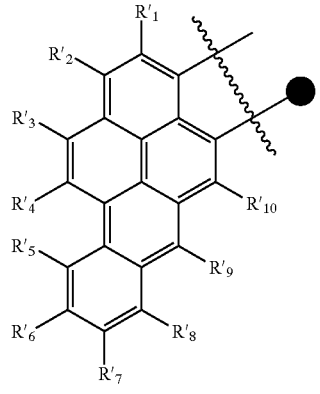
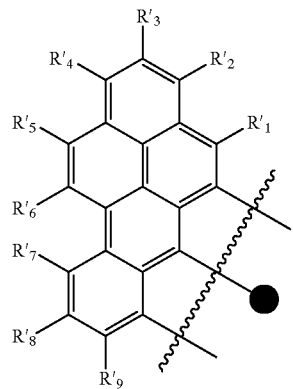
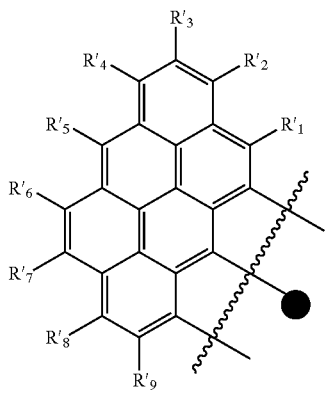
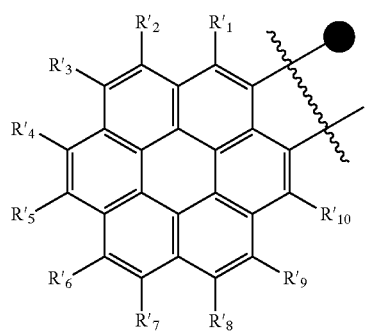
146
-continued
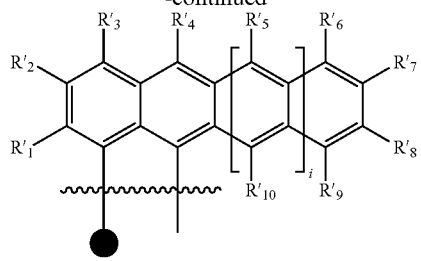
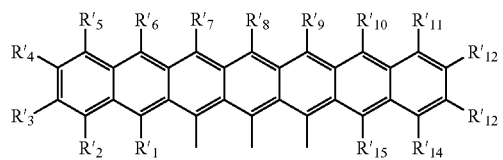
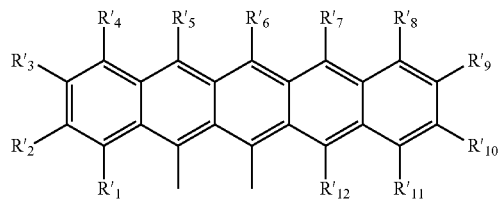
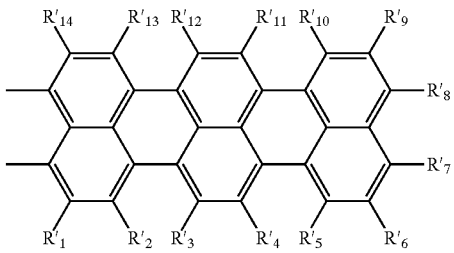
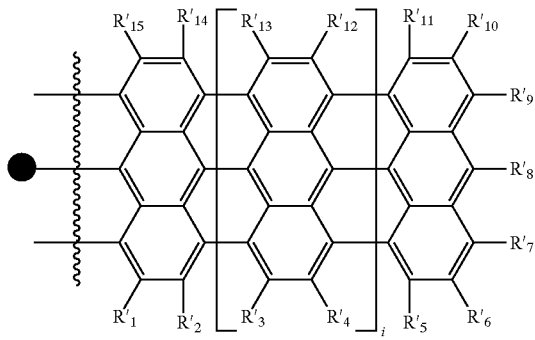
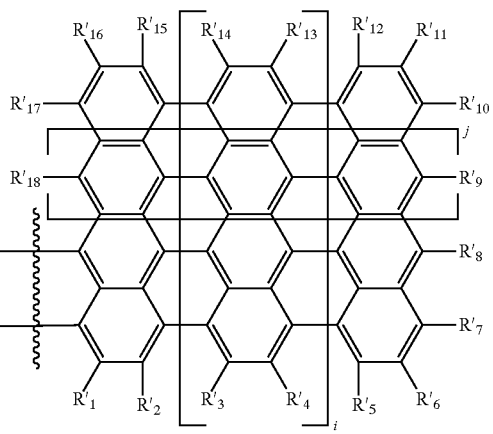

147
-continued
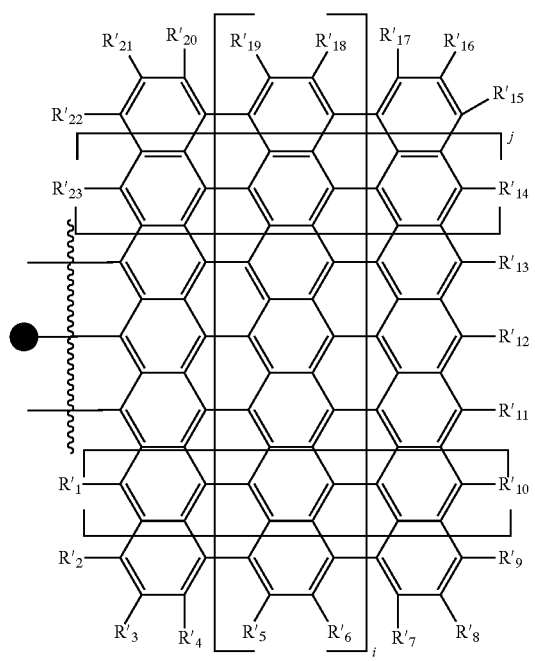
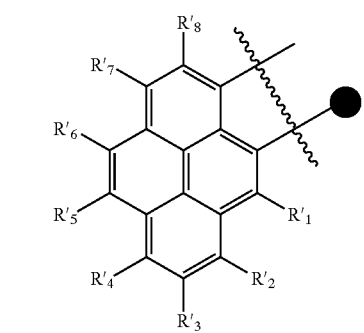
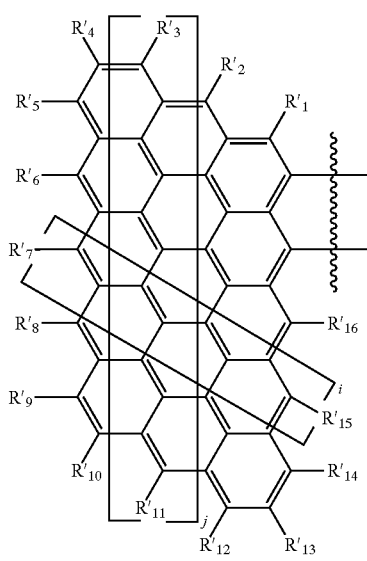
148
-continued
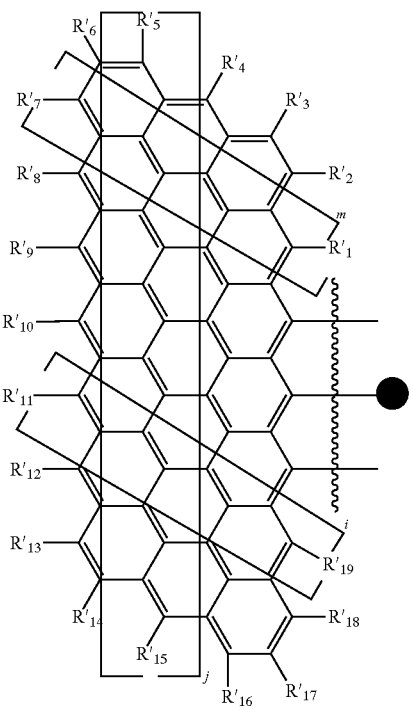
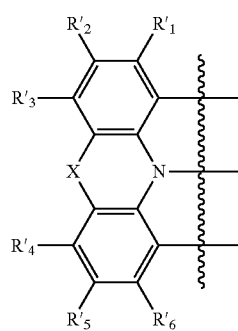
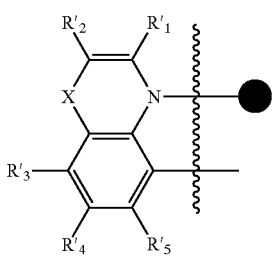

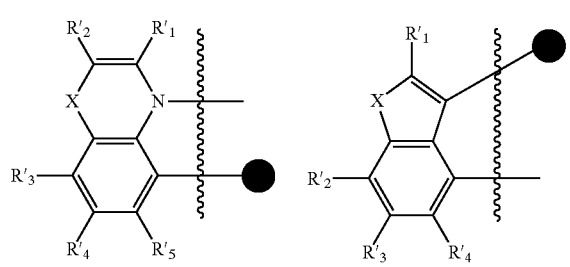
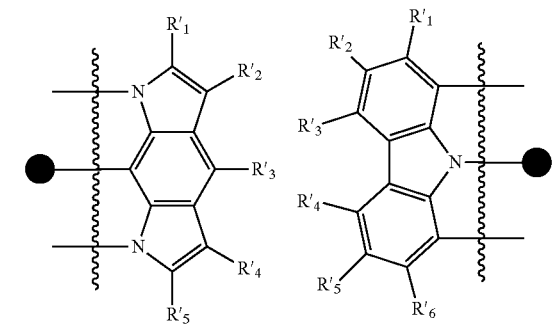
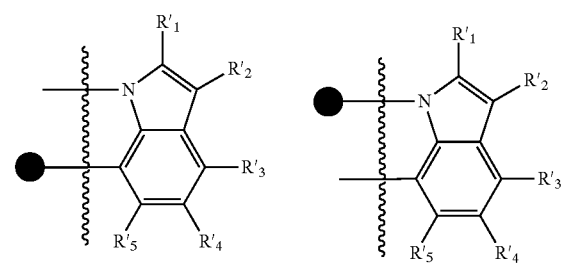

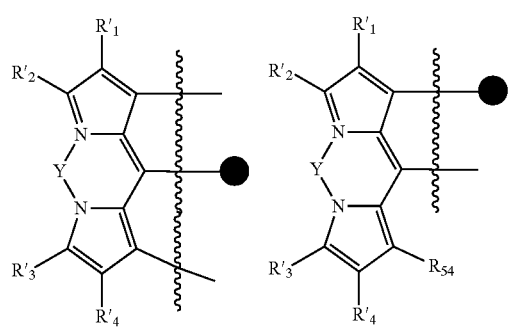
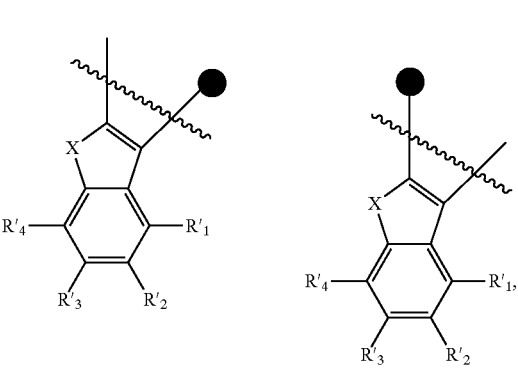

wherein i, j, and m are each independently 0-100;
wherein the zig zag line represents the fusion points of the pi-extended unit to the porphyrin;
wherein the dot represents the point where the polycyclic aromatic group is connected to the meso position of the porphryin;
wherein X is O, S, Se, Te, N, P, As, Si, Ge, or B;
wherein Y is H, M, or X; and
wherein R'$_1$-R'$_{23}$ are independently selected from hydrogen, hydroxyl, halogen, chalcogen, mercapto, alkyl, fluoroalkyl, alkoxy, amino, cyano, alkenyl, alkynyl, aryl, and heteroaryl.

27. The device of claim 25, wherein the dotted arc substituent is naphthalene, anthracene, or pyrene.

28. The device of claim 11, wherein the first compound is selected from the group consisting of:

Compound 1

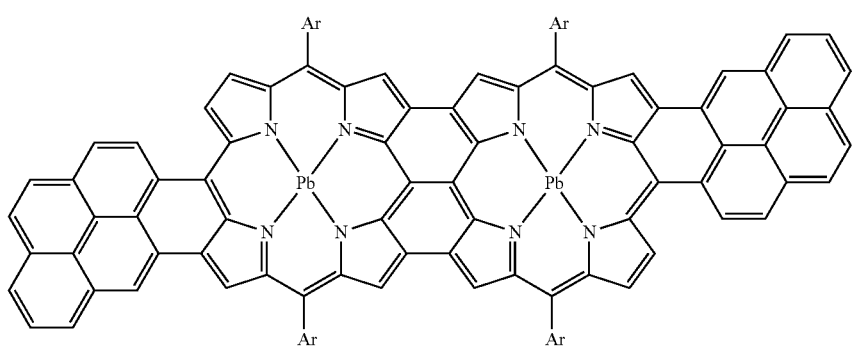

Compound 2
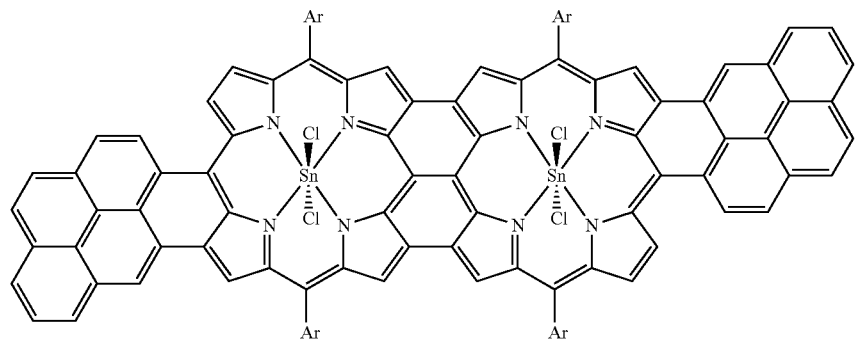
Compound 4
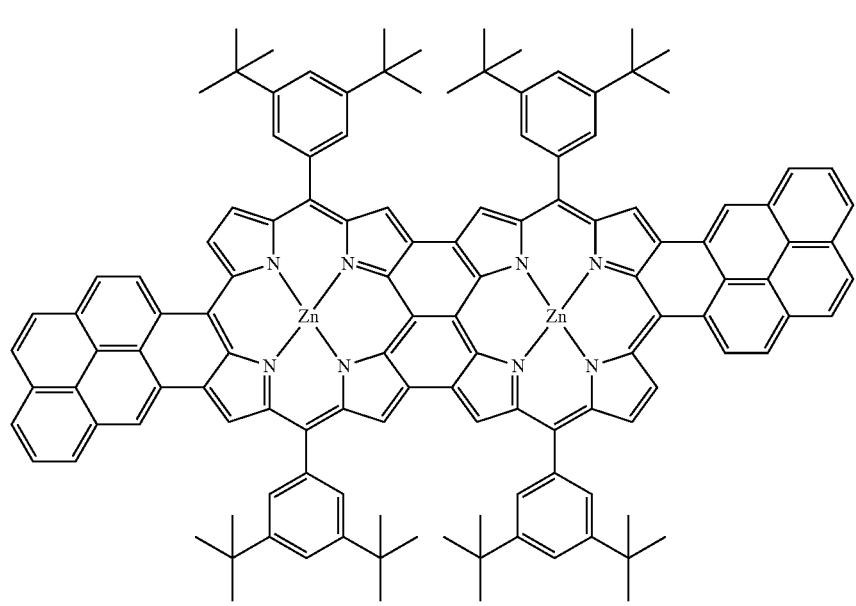
Compound 5
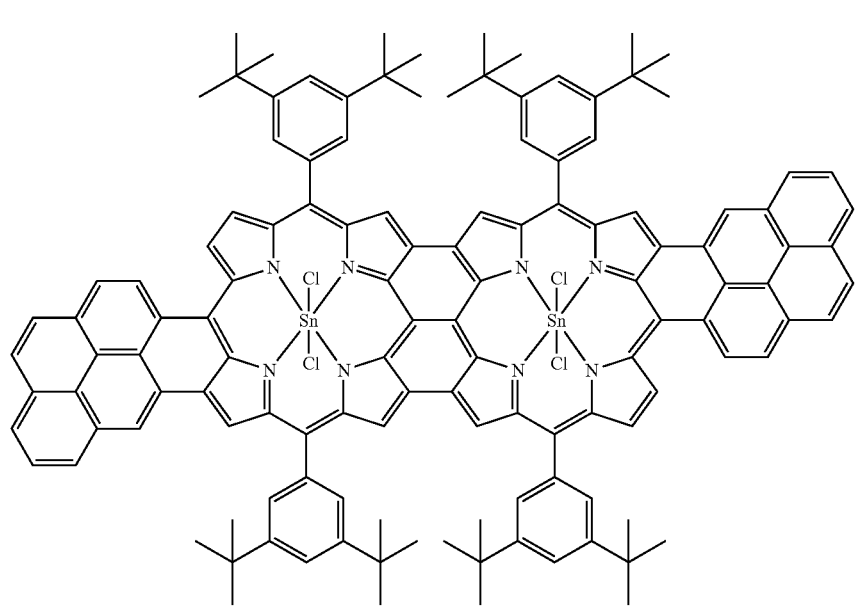

Compound 6
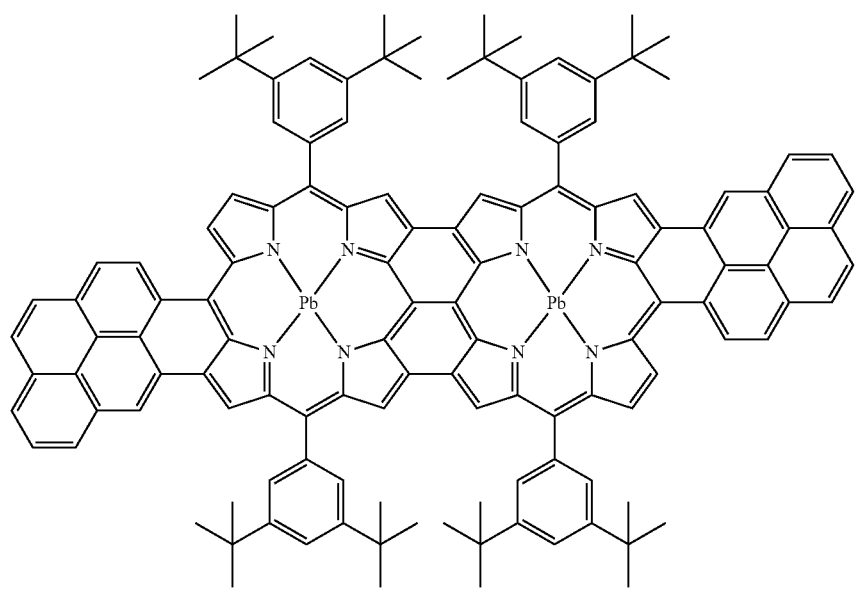
Compound 7
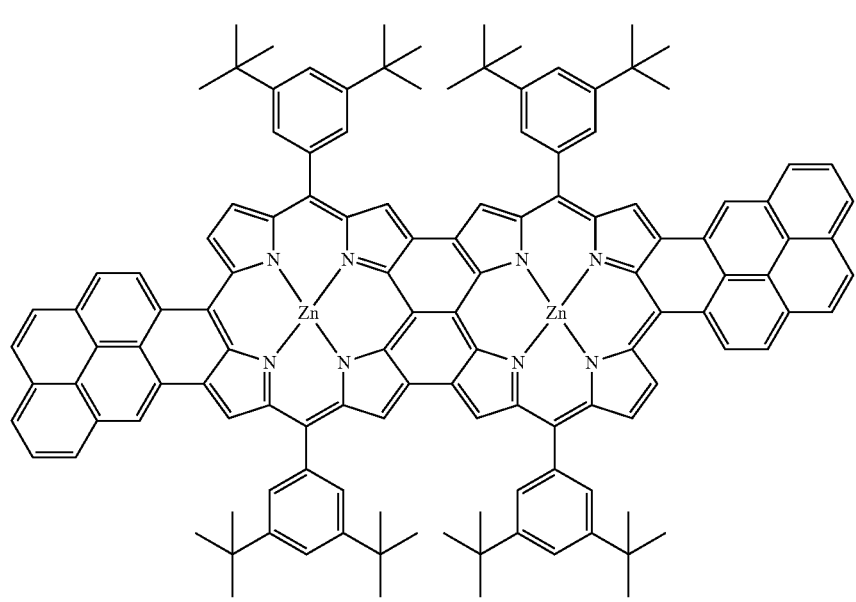
Compound 8
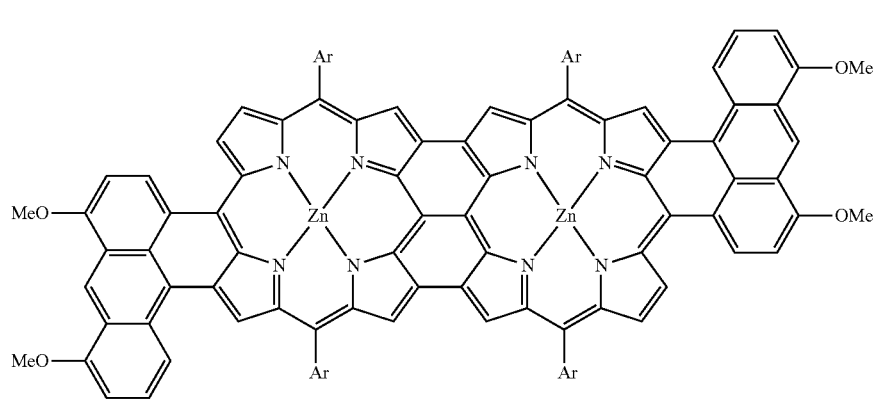

-continued
Compound 9
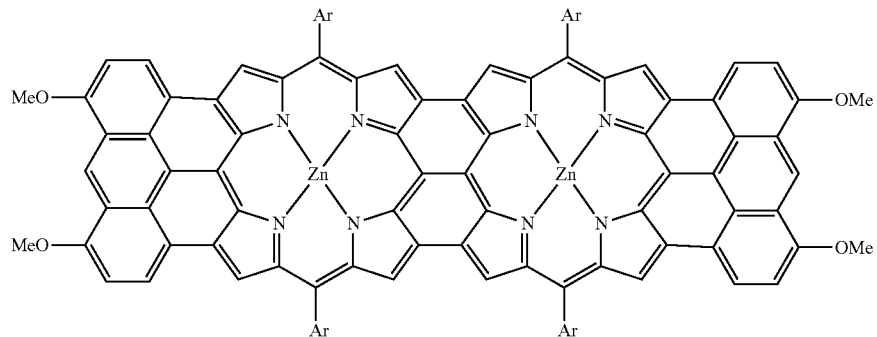
Compound 11
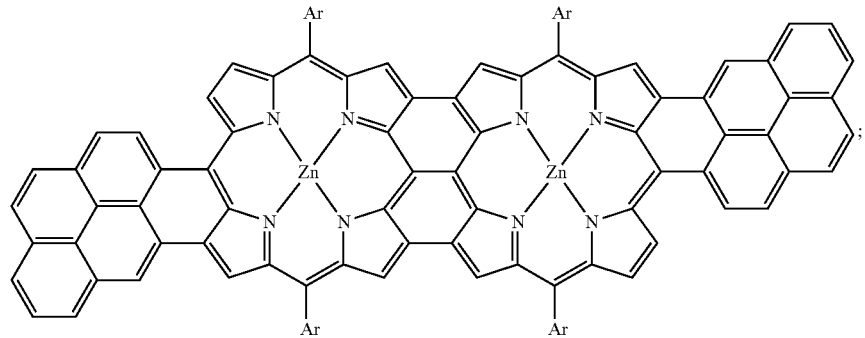
wherein Ar is aryl or heteroaryl.
29. The device of claim 11, wherein the device is a consumer product.
* * * * *